US009835640B2

(12) United States Patent
Raicu et al.

(10) Patent No.: US 9,835,640 B2
(45) Date of Patent: Dec. 5, 2017

(54) AUTOMATED STORAGE MODULES FOR DIAGNOSTIC ANALYZER LIQUIDS AND RELATED SYSTEMS AND METHODS

(71) Applicant: Abbott Laboratories, Abbott Park, IL (US)

(72) Inventors: Razvan Raicu, Coppell, TX (US); Robert P. Luoma, II, Colleyville, TX (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 15/042,968

(22) Filed: Feb. 12, 2016

(65) Prior Publication Data

US 2016/0238625 A1    Aug. 18, 2016

Related U.S. Application Data

(60) Provisional application No. 62/115,959, filed on Feb. 13, 2015, provisional application No. 62/214,029, filed on Sep. 3, 2015.

(51) Int. Cl.
*G01N 35/02* (2006.01)
*B65G 1/06* (2006.01)
(Continued)

(52) U.S. Cl.
CPC ............. *G01N 35/026* (2013.01); *B65G 1/06* (2013.01); *G01N 35/0099* (2013.01);
(Continued)

(58) Field of Classification Search
CPC .......................................... G01N 2035/00435
See application file for complete search history.

(56) References Cited

U.S. PATENT DOCUMENTS 2,814,226 A    11/1957  Lojczyc
5,233,844 A     8/1993  Knippscheer et al.
(Continued)

FOREIGN PATENT DOCUMENTS

EA    2728362    5/2014
EP    0408804    1/1991
(Continued)

OTHER PUBLICATIONS

U.S. Patent and Trademark Office, "Non-Final Office Action," issued in connection with U.S. Appl. No. 15/042,963, dated Nov. 4, 2016, 30 pages.

(Continued)

*Primary Examiner* — P. Kathryn Wright
(74) *Attorney, Agent, or Firm* — Hanley, Flight & Zimmerman, LLC

(57) ABSTRACT

Example automated storage modules for analyzer liquids are described herein. An example apparatus includes a refrigerated storage module having a plurality of shelves (to store a plurality of carriers) and a loading bay having an array of slots to receive one or more of the carriers. The loading bay is accessible by a user for manual loading or unloading of the carriers. The example apparatus includes a first carrier transporter coupled to the storage module to transfer the carriers between the shelves and a first transfer location and a second carrier transporter movable along a track connecting the storage module to an automated diagnostic analyzer. The second carrier transporter is to transfer a first carrier between the first transfer location and a slot in the loading bay and a second carrier between the first transfer location and a second transfer location accessible by the automated diagnostic analyzer.

19 Claims, 59 Drawing Sheets

(51) Int. Cl.
  *G01N 35/00* (2006.01)
  *G01N 35/10* (2006.01)
  *G01N 35/04* (2006.01)
  *B01L 9/06* (2006.01)

(52) U.S. Cl.
  CPC ....... *G01N 35/025* (2013.01); *G01N 35/1011* (2013.01); *G01N 35/1081* (2013.01); *B01L 9/06* (2013.01); *G01N 2035/00435* (2013.01); *G01N 2035/00445* (2013.01); *G01N 2035/0405* (2013.01); *G01N 2035/0412* (2013.01); *G01N 2035/0462* (2013.01); *G01N 2035/0465* (2013.01)

(56) References Cited

U.S. PATENT DOCUMENTS

| | | |
|---|---|---|
| 5,417,922 A | 5/1995 | Markin et al. |
| 5,427,743 A | 6/1995 | Markin |
| 5,582,796 A | 12/1996 | Carey et al. |
| 5,589,137 A | 12/1996 | Markin et al. |
| 5,590,052 A | 12/1996 | Kopf-Sill et al. |
| 5,591,642 A | 1/1997 | Jones |
| 5,599,501 A | 2/1997 | Carey et al. |
| 5,628,962 A | 5/1997 | Kanbara et al. |
| 5,635,137 A | 6/1997 | Manz et al. |
| 5,637,275 A | 6/1997 | Carey et al. |
| 5,665,315 A | 9/1997 | Robert et al. |
| 5,670,114 A | 9/1997 | Sakazume et al. |
| 5,722,553 A | 3/1998 | Hovatter |
| 5,795,784 A | 8/1998 | Arnquist et al. |
| 5,855,847 A | 1/1999 | Oonuma et al. |
| 5,856,194 A | 1/1999 | Arnquist et al. |
| 5,863,506 A | 1/1999 | Farren |
| 5,885,529 A | 3/1999 | Babson et al. |
| 5,885,530 A | 3/1999 | Babson et al. |
| 5,902,549 A | 5/1999 | Mimura et al. |
| 5,940,178 A | 8/1999 | Barber et al. |
| 5,980,830 A | 11/1999 | Savage et al. |
| 5,983,734 A | 11/1999 | Mathur et al. |
| 6,060,022 A | 5/2000 | Pang et al. |
| 6,068,437 A | 5/2000 | Boje et al. |
| 6,074,615 A | 6/2000 | Lewis et al. |
| 6,146,592 A | 11/2000 | Kawashima et al. |
| 6,164,215 A | 12/2000 | Cook et al. |
| 6,193,933 B1 | 2/2001 | Sasaki et al. |
| 6,257,091 B1 | 7/2001 | Cohen et al. |
| 6,306,658 B1 | 10/2001 | Turner et al. |
| 6,331,437 B1 | 12/2001 | Cohen et al. |
| 6,335,166 B1 | 1/2002 | Ammann et al. |
| 6,343,690 B1 | 2/2002 | Britton et al. |
| 6,383,452 B1 | 5/2002 | Miyake et al. |
| 6,498,037 B1 | 12/2002 | Carey et al. |
| 6,555,062 B1 | 4/2003 | Lewis et al. |
| 6,588,625 B2 | 7/2003 | Luoma, II et al. |
| 6,599,476 B1 | 7/2003 | Watson et al. |
| 6,604,903 B2 | 8/2003 | Osborne et al. |
| 6,723,288 B2 | 4/2004 | Devlin, Sr. et al. |
| 6,729,104 B2 | 5/2004 | Marshall |
| 6,733,728 B1 | 5/2004 | Mimura et al. |
| 6,797,518 B1 | 9/2004 | Jacobs et al. |
| 6,808,522 B2 | 10/2004 | Richards et al. |
| 6,827,113 B2 | 12/2004 | Downs et al. |
| 6,866,825 B2 | 3/2005 | Chiou et al. |
| 6,919,795 B2 | 7/2005 | Roseen |
| 6,974,294 B2 | 12/2005 | Pressman et al. |
| 6,983,884 B2 | 1/2006 | Auchinleck |
| 7,029,922 B2 | 4/2006 | Miller |
| 7,141,213 B1 | 11/2006 | Pang et al. |
| 7,148,476 B2 | 12/2006 | Andersson et al. |
| 7,163,660 B2 | 1/2007 | Lehmann |
| 7,169,356 B2 | 1/2007 | Gebrian et al. |
| 7,169,357 B2 | 1/2007 | Motegi et al. |
| 7,250,303 B2 | 7/2007 | Jakubowicz et al. |
| 7,322,170 B2 | 1/2008 | Tomalesky et al. |
| 7,338,803 B2 | 3/2008 | Mizzer et al. |
| 7,354,774 B2 | 4/2008 | Hughes et al. |
| 7,361,309 B2 | 4/2008 | Vann et al. |
| 7,364,698 B2 | 4/2008 | Fujita et al. |
| 7,381,370 B2 | 6/2008 | Chow et al. |
| 7,401,094 B1 | 7/2008 | Kesler |
| 7,409,809 B1 | 8/2008 | Degen et al. |
| 7,421,831 B2 | 9/2008 | Neeper et al. |
| 7,431,883 B2 | 10/2008 | Bell |
| 7,458,483 B2 | 12/2008 | Luoma, II |
| 7,494,623 B2 | 2/2009 | Tansey, III |
| 7,498,174 B2 | 3/2009 | Tansey, III |
| 7,547,516 B2 | 6/2009 | Light, II |
| 7,553,453 B2 | 6/2009 | Gu et al. |
| 7,556,778 B2 | 7/2009 | Kawahara et al. |
| 7,569,189 B2 | 8/2009 | Jacobs et al. |
| 7,618,587 B2 | 11/2009 | Kawate |
| 7,622,078 B2 | 11/2009 | Pagés Pinyol |
| 7,648,321 B2 | 1/2010 | Neeper et al. |
| 7,661,551 B2 | 2/2010 | Gebrian et al. |
| 7,666,355 B2 | 2/2010 | Alavie et al. |
| 7,670,553 B2 | 3/2010 | Babson |
| 7,678,330 B2 | 3/2010 | Ostrovsky et al. |
| 7,688,207 B2 | 3/2010 | Fritchie et al. |
| 7,704,457 B2 | 4/2010 | Patton |
| 7,727,718 B2 | 6/2010 | Chomczynski |
| 7,731,414 B2 | 6/2010 | Vincent et al. |
| 7,731,903 B2 | 6/2010 | Sattler et al. |
| 7,749,441 B2 | 7/2010 | Hanawa et al. |
| 7,776,263 B2 | 8/2010 | East |
| 7,790,114 B2 | 9/2010 | Fukuda et al. |
| 7,799,283 B2 | 9/2010 | Jacobs et al. |
| 7,807,448 B2 | 10/2010 | Glezer et al. |
| 7,811,521 B2 | 10/2010 | Sando et al. |
| 7,823,745 B2 | 11/2010 | Esser et al. |
| 7,829,800 B2 | 11/2010 | Thiel et al. |
| 7,830,518 B2 | 11/2010 | Kanayama |
| 7,842,509 B2 | 11/2010 | Matsuo et al. |
| 7,845,149 B2 | 12/2010 | Owen et al. |
| 7,875,245 B2 | 1/2011 | Favuzzi et al. |
| 7,876,442 B2 | 1/2011 | Tokunaga et al. |
| 7,906,318 B2 | 3/2011 | Nakajima et al. |
| 7,910,062 B2 | 3/2011 | Yu et al. |
| 7,916,280 B2 | 3/2011 | Ueno et al. |
| 7,916,298 B2 | 3/2011 | Yamamoto |
| 7,931,863 B2 | 4/2011 | Kitagawa et al. |
| 7,939,021 B2 | 5/2011 | Smith et al. |
| 7,947,225 B2 | 5/2011 | Itoh |
| 7,947,237 B2 | 5/2011 | Belz et al. |
| 7,957,935 B2 | 6/2011 | Nishida et al. |
| 7,962,292 B2 | 6/2011 | Matsuo et al. |
| 7,981,662 B2 | 7/2011 | Ueno et al. |
| 7,998,432 B2 | 8/2011 | Rousseau |
| 8,003,049 B2 | 8/2011 | Fujimoto |
| 8,035,485 B2 | 10/2011 | Fritchie |
| 8,035,811 B2 | 10/2011 | Silbergleit et al. |
| 8,038,942 B2 | 10/2011 | Pang et al. |
| 8,043,559 B2 | 10/2011 | Biancalani et al. |
| 8,064,061 B2 | 11/2011 | Yamamoto et al. |
| 8,071,029 B2 | 12/2011 | Wakamiya et al. |
| 8,076,126 B2 | 12/2011 | Jakubowicz et al. |
| 8,100,266 B2 | 1/2012 | Lackner et al. |
| 8,110,397 B2 | 2/2012 | Green |
| 8,142,740 B2 | 3/2012 | Self et al. |
| 8,153,061 B2 | 4/2012 | Walters et al. |
| 8,168,443 B2 | 5/2012 | Yu et al. |
| 8,180,573 B2 | 5/2012 | Ariyoshi |
| 8,196,371 B2 | 6/2012 | Yuyama |
| 8,196,375 B2 | 6/2012 | Kohanski et al. |
| 8,222,048 B2 | 7/2012 | Fritchie et al. |
| 8,231,830 B2 | 7/2012 | Wakamiya et al. |
| 8,252,232 B2 | 8/2012 | Neeper et al. |
| 8,268,248 B2 | 9/2012 | Steuerwald et al. |
| 8,273,304 B2 | 9/2012 | Coassin et al. |
| 8,277,729 B2 | 10/2012 | Matsuo et al. |
| 8,278,108 B2 | 10/2012 | Wada et al. |
| 8,288,164 B2 | 10/2012 | Mishima et al. |
| 8,298,498 B2 | 10/2012 | Safar et al. |
| 8,298,834 B2 | 10/2012 | Glezer et al. |

(56) References Cited

U.S. PATENT DOCUMENTS

| | | |
|---|---|---|
| 8,318,499 B2 | 11/2012 | Fritchie et al. |
| 8,354,078 B2 | 1/2013 | Shohmi et al. |
| 8,367,022 B2 | 2/2013 | Warhurst et al. |
| 8,367,023 B2 | 2/2013 | Bae et al. |
| 8,372,356 B2 | 2/2013 | Warhurst et al. |
| 8,383,411 B2 | 2/2013 | Kawamura |
| 8,396,669 B2 | 3/2013 | Cocks et al. |
| 8,425,839 B2 | 4/2013 | Wakamiya et al. |
| 8,430,321 B2 | 4/2013 | Tokunaga et al. |
| 8,440,140 B2 | 5/2013 | Nagai et al. |
| 8,454,909 B2 | 6/2013 | Martinell Gispert-Sauch |
| 8,460,528 B2 | 6/2013 | Pollack et al. |
| 8,460,935 B2 | 6/2013 | Kurono et al. |
| 8,476,066 B2 | 7/2013 | Takata et al. |
| 8,529,847 B2 | 9/2013 | Arras et al. |
| 8,530,229 B2 | 9/2013 | Ochsenbein et al. |
| 8,544,665 B2 | 10/2013 | Bogle et al. |
| 8,545,756 B2 | 10/2013 | Holtlund et al. |
| 8,545,760 B2 | 10/2013 | Yamamoto et al. |
| 8,550,697 B2 | 10/2013 | Vincent et al. |
| 8,557,605 B2 | 10/2013 | Stöcker et al. |
| 8,562,909 B2 | 10/2013 | Schacher |
| 8,580,210 B2 | 11/2013 | Katsumi et al. |
| 8,606,525 B2 | 12/2013 | Jacobs |
| 8,628,971 B2 | 1/2014 | Fritchie et al. |
| 8,652,422 B2 | 2/2014 | Mabuchi et al. |
| 8,663,559 B2 | 3/2014 | Shibata et al. |
| 8,669,115 B2 | 3/2014 | Pagoria et al. |
| 8,672,219 B2 | 3/2014 | Furrer |
| 8,679,421 B2 | 3/2014 | Sano et al. |
| 8,679,425 B2 | 3/2014 | Ueda et al. |
| 8,683,712 B2 | 4/2014 | Kim et al. |
| 8,685,750 B2 | 4/2014 | Schoeneck |
| 8,691,149 B2 | 4/2014 | Fritchie et al. |
| 8,696,990 B2 | 4/2014 | Meller et al. |
| 8,700,345 B2 | 4/2014 | Okabayashi |
| 8,703,056 B2 | 4/2014 | Sakairi et al. |
| 8,715,574 B2 | 5/2014 | Fritchie et al. |
| 8,728,395 B2 | 5/2014 | Suzuki et al. |
| 8,730,459 B2 | 5/2014 | Nogami et al. |
| 8,735,142 B2 | 5/2014 | Charbonnet et al. |
| 8,741,229 B2 | 6/2014 | Kondou |
| 8,753,574 B2 | 6/2014 | Tan et al. |
| 8,757,864 B2 | 6/2014 | Yamakawa et al. |
| 8,789,344 B2 | 7/2014 | Monti |
| 8,790,577 B2 | 7/2014 | Mizumoto et al. |
| 8,808,624 B2 | 8/2014 | Matsumoto et al. |
| 8,815,153 B2 | 8/2014 | Sato |
| 8,834,791 B2 | 9/2014 | Katsumi et al. |
| 8,840,848 B2 | 9/2014 | Kraihanzel |
| 8,841,117 B2 | 9/2014 | Nagai et al. |
| 8,845,963 B2 | 9/2014 | Glezer et al. |
| 8,852,506 B2 | 10/2014 | Hamada et al. |
| 8,852,530 B2 | 10/2014 | Oonuma et al. |
| 8,852,952 B2 | 10/2014 | Pollack et al. |
| 8,859,289 B2 | 10/2014 | Marty et al. |
| 8,871,147 B2 | 10/2014 | Wakamiya et al. |
| 8,894,946 B2 | 11/2014 | Nielsen et al. |
| 8,906,618 B2 | 12/2014 | O'Keefe et al. |
| 8,906,671 B2 | 12/2014 | Yamazaki et al. |
| 8,920,722 B2 | 12/2014 | Kitagawa et al. |
| 8,920,726 B2 | 12/2014 | Matsumoto et al. |
| 8,926,901 B2 | 1/2015 | Mototsu |
| 8,926,921 B2 | 1/2015 | Rousseau et al. |
| 8,932,543 B2 | 1/2015 | Bui et al. |
| 8,936,752 B2 | 1/2015 | Kuwano |
| 8,936,753 B2 | 1/2015 | Yamamoto et al. |
| 8,951,803 B2 | 2/2015 | Mototsu et al. |
| 8,961,876 B2 | 2/2015 | Tanoshima et al. |
| 8,968,653 B2 | 3/2015 | Fukuma et al. |
| 8,968,656 B2 | 3/2015 | Hamada |
| 8,974,733 B2 | 3/2015 | Haga |
| 8,978,517 B2 | 3/2015 | Meyers et al. |
| 8,986,927 B2 | 3/2015 | Lee et al. |
| 8,992,833 B2 | 3/2015 | Blecka et al. |
| 8,992,856 B2 | 3/2015 | De Gier |
| 8,996,317 B2 | 3/2015 | Ariyoshi |
| 8,999,241 B2 | 4/2015 | Katsumi et al. |
| 9,005,916 B2 | 4/2015 | Shibata |
| 9,029,159 B2 | 5/2015 | Furrer et al. |
| 9,034,575 B2 | 5/2015 | Gisler et al. |
| 9,040,002 B2 | 5/2015 | Yu et al. |
| 9,044,750 B2 | 6/2015 | Ding |
| 9,050,594 B2 | 6/2015 | Williams et al. |
| 9,052,299 B2 | 6/2015 | Jones et al. |
| 9,061,282 B2 | 6/2015 | Icke et al. |
| 9,073,649 B2 | 7/2015 | Norton et al. |
| 9,075,030 B2 | 7/2015 | Yamaguchi et al. |
| 9,075,031 B2 | 7/2015 | Jones et al. |
| 9,075,033 B2 | 7/2015 | Steinboeck et al. |
| 9,079,757 B2 | 7/2015 | Bjork |
| 9,084,996 B2 | 7/2015 | Chien et al. |
| 9,097,689 B2 | 8/2015 | Yamato et al. |
| 9,108,200 B2 | 8/2015 | Belz et al. |
| 9,108,832 B2 | 8/2015 | Akutsu et al. |
| 9,114,392 B2 | 8/2015 | Safar et al. |
| 9,116,093 B2 | 8/2015 | Abe et al. |
| 9,116,142 B2 | 8/2015 | Yu et al. |
| 9,121,851 B2 | 9/2015 | Burd et al. |
| 9,126,169 B2 | 9/2015 | Vann et al. |
| 9,128,069 B2 | 9/2015 | Oeltjen |
| 9,133,497 B2 | 9/2015 | Frei et al. |
| 9,134,203 B2 | 9/2015 | Smith et al. |
| 9,134,332 B2 | 9/2015 | Frey et al. |
| 9,140,632 B2 | 9/2015 | Furrer |
| 9,149,807 B2 | 10/2015 | Niggel et al. |
| 9,149,979 B2 | 10/2015 | Sattler et al. |
| 9,151,703 B2 | 10/2015 | Shiba et al. |
| 9,157,924 B2 | 10/2015 | Yamato et al. |
| 9,164,111 B2 | 10/2015 | Symonds et al. |
| 9,164,112 B2 | 10/2015 | Orihashi et al. |
| 9,194,866 B2 | 11/2015 | Kitagawa et al. |
| 9,199,755 B1 | 12/2015 | Cohen et al. |
| 9,200,315 B2 | 12/2015 | Jung et al. |
| 9,201,083 B2 | 12/2015 | Wakamiya |
| 9,217,712 B2 | 12/2015 | Mitsuyama et al. |
| 9,227,190 B2 | 1/2016 | Kondou et al. |
| 9,229,018 B2 | 1/2016 | Toyoshima et al. |
| 9,233,371 B2 | 1/2016 | Nakamura et al. |
| 9,243,993 B2 | 1/2016 | Nagai et al. |
| 9,244,086 B2 | 1/2016 | Yao et al. |
| 9,248,450 B2 | 2/2016 | Bauer |
| 9,248,451 B2 | 2/2016 | Kondou |
| 9,250,255 B2 | 2/2016 | Shibata et al. |
| 9,255,939 B2 | 2/2016 | Nishida et al. |
| 9,261,523 B2 | 2/2016 | Fritchie et al. |
| 9,266,706 B2 | 2/2016 | Forestelli et al. |
| 9,297,818 B2 | 3/2016 | Fujita |
| 9,297,820 B2 | 3/2016 | Iizumi et al. |
| 9,303,286 B2 | 4/2016 | Gibbons et al. |
| 9,308,508 B2 | 4/2016 | Peyvan |
| 9,328,381 B2 | 5/2016 | Zhou et al. |
| 9,329,172 B2 | 5/2016 | Kimura et al. |
| 9,329,194 B2 | 5/2016 | Fritchie et al. |
| 9,335,335 B2 | 5/2016 | Mimura et al. |
| 9,346,053 B2 | 5/2016 | Samuhel et al. |
| 9,372,199 B2 | 6/2016 | Fujino et al. |
| 9,381,524 B2 | 7/2016 | Bailey et al. |
| 9,389,228 B2 | 7/2016 | Jakubowicz et al. |
| 9,389,240 B2 | 7/2016 | Takahashi et al. |
| 9,395,379 B2 | 7/2016 | Kappelhoff et al. |
| 2002/0012611 A1 | 1/2002 | Stylli et al. |
| 2002/0015666 A1 | 2/2002 | Vann et al. |
| 2002/0114742 A1 | 8/2002 | Takahashi et al. |
| 2002/0131897 A1 | 9/2002 | Samsoondar |
| 2003/0092186 A1 | 5/2003 | Pressman et al. |
| 2003/0147778 A1 | 8/2003 | Takahashi |
| 2003/0157723 A1 | 8/2003 | Smith et al. |
| 2003/0180191 A1 | 9/2003 | Suzuki et al. |
| 2004/0005245 A1 | 1/2004 | Watson et al. |
| 2004/0022677 A1 | 2/2004 | Wohlstadter et al. |
| 2004/0037680 A1 | 2/2004 | Sato et al. |
| 2004/0096986 A1 | 5/2004 | Klein et al. |
| 2004/0134750 A1 | 7/2004 | Luoma, II |

(56) References Cited

U.S. PATENT DOCUMENTS

| | | |
|---|---|---|
| 2005/0013745 A1 | 1/2005 | Buchanan et al. |
| 2005/0032241 A1 | 2/2005 | Coassin et al. |
| 2005/0042138 A1 | 2/2005 | Ueda et al. |
| 2005/0063801 A1 | 3/2005 | Durand et al. |
| 2005/0112030 A1 | 5/2005 | Gaus |
| 2005/0142040 A1 | 6/2005 | Hanawa et al. |
| 2005/0158212 A1 | 7/2005 | Yavilevich |
| 2005/0214165 A1 | 9/2005 | Babel et al. |
| 2006/0120922 A1 | 6/2006 | Matsumoto |
| 2006/0159587 A1 | 7/2006 | Fechtner et al. |
| 2006/0263248 A1 | 11/2006 | Gomm et al. |
| 2006/0265133 A1 | 11/2006 | Cocks et al. |
| 2006/0286004 A1 | 12/2006 | Jacobs et al. |
| 2006/0292038 A1 | 12/2006 | Johansson et al. |
| 2007/0010019 A1 | 1/2007 | Luoma, II |
| 2007/0077173 A1 | 4/2007 | Melet |
| 2007/0104617 A1 | 5/2007 | Coulling et al. |
| 2007/0110624 A1 | 5/2007 | Lare et al. |
| 2007/0116600 A1 | 5/2007 | Kochar et al. |
| 2007/0134131 A1 | 6/2007 | Watson et al. |
| 2007/0166194 A1 | 7/2007 | Wakatake |
| 2007/0172396 A1 | 7/2007 | Neeper et al. |
| 2007/0215467 A1 | 9/2007 | Soma et al. |
| 2007/0253866 A1 | 11/2007 | Rousseau |
| 2007/0286771 A1 | 12/2007 | Nunes et al. |
| 2008/0020467 A1 | 1/2008 | Barnes et al. |
| 2008/0024301 A1 | 1/2008 | Fritchie et al. |
| 2008/0041956 A1 | 2/2008 | Neeper et al. |
| 2008/0044261 A1 | 2/2008 | Neeper et al. |
| 2008/0044263 A1 | 2/2008 | Neeper et al. |
| 2008/0044266 A1 | 2/2008 | Neeper et al. |
| 2008/0044912 A1 | 2/2008 | Yamamoto et al. |
| 2008/0056942 A1 | 3/2008 | Arima et al. |
| 2008/0145857 A1 | 6/2008 | Saito et al. |
| 2008/0171380 A1 | 7/2008 | Brown et al. |
| 2008/0219887 A1 | 9/2008 | Akutsu |
| 2008/0241937 A1 | 10/2008 | Wakamiya et al. |
| 2008/0253930 A1 | 10/2008 | Kartalov et al. |
| 2008/0269076 A1 | 10/2008 | Ermakov |
| 2008/0297314 A1 | 12/2008 | Kuwako et al. |
| 2008/0311678 A1 | 12/2008 | Ootani et al. |
| 2009/0003981 A1 | 1/2009 | Miller |
| 2009/0042256 A1 | 2/2009 | Hanafusa et al. |
| 2009/0104704 A1 | 4/2009 | Wang et al. |
| 2009/0114538 A1 | 5/2009 | Takayama et al. |
| 2009/0117044 A1 | 5/2009 | Hengerer et al. |
| 2009/0117620 A1 | 5/2009 | Fritchie et al. |
| 2009/0130679 A1 | 5/2009 | Wu et al. |
| 2009/0162247 A1 | 6/2009 | Tokieda et al. |
| 2009/0181359 A1 | 7/2009 | Lou et al. |
| 2009/0186776 A1 | 7/2009 | Webb et al. |
| 2009/0221090 A1 | 9/2009 | Kondou et al. |
| 2009/0224032 A1 | 9/2009 | Kondou et al. |
| 2009/0248318 A1 | 10/2009 | Nagai et al. |
| 2009/0269242 A1 | 10/2009 | Nozawa |
| 2009/0281930 A1 | 11/2009 | Sakagami |
| 2010/0028204 A1 | 2/2010 | Lee et al. |
| 2010/0062446 A1 | 3/2010 | Hanafusa |
| 2010/0104478 A1 | 4/2010 | Kondou |
| 2010/0105143 A1 | 4/2010 | Kawamura |
| 2010/0111765 A1 | 5/2010 | Gomm et al. |
| 2010/0114501 A1 | 5/2010 | Kondou et al. |
| 2010/0115463 A1 | 5/2010 | Kondou |
| 2010/0123551 A1 | 5/2010 | Fritchie |
| 2010/0230284 A1 | 9/2010 | Stephenson |
| 2010/0247379 A1 | 9/2010 | Schmidt |
| 2010/0248247 A1 | 9/2010 | Kataoka et al. |
| 2010/0290952 A1 | 11/2010 | Koike et al. |
| 2010/0303590 A1 | 12/2010 | Pedrazzini |
| 2010/0324722 A1 | 12/2010 | Fritchie et al. |
| 2011/0003286 A1 | 1/2011 | Hanafusa et al. |
| 2011/0064630 A1 | 3/2011 | Coulling et al. |
| 2011/0082648 A1 | 4/2011 | Matsumoto |
| 2011/0088517 A1 | 4/2011 | Tsujimura et al. |
| 2011/0143947 A1 | 6/2011 | Chamberlin et al. |
| 2011/0179859 A1 | 7/2011 | Hemmings et al. |
| 2011/0184570 A1 | 7/2011 | Nakanishi et al. |
| 2011/0223064 A1 | 9/2011 | Katsumi et al. |
| 2011/0229374 A1 | 9/2011 | Tokunaga |
| 2011/0232372 A1 | 9/2011 | Tokunaga |
| 2011/0244558 A1 | 10/2011 | Hamada et al. |
| 2011/0274584 A1 | 11/2011 | Kitamura et al. |
| 2011/0300620 A1 | 12/2011 | Belz et al. |
| 2011/0300621 A1 | 12/2011 | Belz et al. |
| 2011/0318845 A1 | 12/2011 | Kurono et al. |
| 2012/0003731 A1 | 1/2012 | Kuroda |
| 2012/0020838 A1 | 1/2012 | Mimura et al. |
| 2012/0058479 A1 | 3/2012 | Gisler et al. |
| 2012/0060514 A1 | 3/2012 | Warhurst et al. |
| 2012/0060520 A1 | 3/2012 | Collins et al. |
| 2012/0072027 A1 | 3/2012 | Evers et al. |
| 2012/0094869 A1 | 4/2012 | Talebpour et al. |
| 2012/0177536 A1 | 7/2012 | Sakai et al. |
| 2012/0240518 A1 | 9/2012 | Pairaud et al. |
| 2012/0244628 A1 | 9/2012 | Rueeck et al. |
| 2012/0252131 A1 | 10/2012 | Horii |
| 2012/0253693 A1 | 10/2012 | Inomata et al. |
| 2012/0282683 A1 | 11/2012 | Mototsu |
| 2012/0283867 A1 | 11/2012 | Gelbman et al. |
| 2012/0294764 A1 | 11/2012 | Tokieda et al. |
| 2012/0304597 A1 | 12/2012 | Mikhailov |
| 2012/0318302 A1 | 12/2012 | Nakayama |
| 2012/0321419 A1 | 12/2012 | Neeper et al. |
| 2013/0011298 A1 | 1/2013 | Itou et al. |
| 2013/0084647 A1 | 4/2013 | LaCourt |
| 2013/0122596 A1 | 5/2013 | Kamihara et al. |
| 2013/0132882 A1 | 5/2013 | Dussi et al. |
| 2013/0137093 A1 | 5/2013 | Fritchie et al. |
| 2013/0159135 A1 | 6/2013 | Jones et al. |
| 2013/0266484 A1 | 10/2013 | Kamihara et al. |
| 2013/0280129 A1 | 10/2013 | Watanabe et al. |
| 2013/0305846 A1 | 11/2013 | Yamagata et al. |
| 2014/0044611 A1 | 2/2014 | Uchihashi et al. |
| 2014/0051071 A1 | 2/2014 | Yoshida et al. |
| 2014/0087479 A1 | 3/2014 | Albuquerque et al. |
| 2014/0119994 A1 | 5/2014 | Ariyoshi et al. |
| 2014/0123774 A1 | 5/2014 | Tanoue et al. |
| 2014/0127818 A1 | 5/2014 | Fritchie et al. |
| 2014/0174028 A1 | 6/2014 | Yamagata et al. |
| 2014/0220705 A1 | 8/2014 | Yogi et al. |
| 2014/0242633 A1 | 8/2014 | Fukuda et al. |
| 2014/0255254 A1 | 9/2014 | Yamaguchi et al. |
| 2014/0273060 A1 | 9/2014 | Wu |
| 2014/0274809 A1 | 9/2014 | Harvey et al. |
| 2014/0286124 A1 | 9/2014 | Donohue et al. |
| 2014/0287523 A1 | 9/2014 | Donohue |
| 2014/0294673 A1 | 10/2014 | Matsuura et al. |
| 2014/0295453 A1 | 10/2014 | Hirata et al. |
| 2014/0295562 A1 | 10/2014 | Wakamiya et al. |
| 2014/0314623 A1 | 10/2014 | Yamagata et al. |
| 2014/0315228 A1 | 10/2014 | Yuan et al. |
| 2014/0333618 A1 | 11/2014 | Guggisberg et al. |
| 2014/0356895 A1 | 12/2014 | Tanaka et al. |
| 2014/0356964 A1 | 12/2014 | Makino et al. |
| 2014/0361022 A1 | 12/2014 | Finneran |
| 2014/0370609 A1 | 12/2014 | Frank et al. |
| 2014/0377132 A1 | 12/2014 | Shimase et al. |
| 2014/0377785 A1 | 12/2014 | Janetzko et al. |
| 2015/0010443 A1 | 1/2015 | Hasegawa |
| 2015/0037803 A1 | 2/2015 | Park et al. |
| 2015/0044096 A1 | 2/2015 | Nakasawa et al. |
| 2015/0064795 A1 | 3/2015 | Ariyoshi |
| 2015/0118706 A1 | 4/2015 | Tateyama et al. |
| 2015/0132185 A1 | 5/2015 | Khamu |
| 2015/0168436 A1 | 6/2015 | Kathe et al. |
| 2015/0175398 A1 | 6/2015 | Christensen et al. |
| 2015/0177110 A1 | 6/2015 | Cargill et al. |
| 2015/0182963 A1 | 7/2015 | Samper et al. |
| 2015/0204895 A1 | 7/2015 | Yasui et al. |
| 2015/0209786 A1 | 7/2015 | Hage et al. |
| 2015/0260743 A1 | 9/2015 | Huang et al. |
| 2015/0268259 A1 | 9/2015 | Gomm et al. |
| 2015/0273464 A1 | 10/2015 | Fukuju et al. |
| 2015/0273466 A1 | 10/2015 | Nagai et al. |

(56) References Cited

U.S. PATENT DOCUMENTS

| | | |
|---|---|---|
| 2015/0285793 A1 | 10/2015 | Chan et al. |
| 2015/0309025 A1 | 10/2015 | Van Praet et al. |
| 2015/0323557 A1 | 11/2015 | Tamezane et al. |
| 2015/0323776 A1 | 11/2015 | Dyson-Holland et al. |
| 2015/0362515 A1 | 12/2015 | Buse et al. |
| 2015/0369827 A1 | 12/2015 | Zimmerle et al. |
| 2016/0023211 A1 | 1/2016 | Knight |
| 2016/0025758 A1 | 1/2016 | Yogi et al. |
| 2016/0033487 A1 | 2/2016 | Zhang et al. |
| 2016/0033543 A1 | 2/2016 | Stankus et al. |
| 2016/0038942 A1 | 2/2016 | Roberts |
| 2016/0041180 A1 | 2/2016 | Nagamatsu et al. |
| 2016/0054222 A1 | 2/2016 | Tateyama et al. |
| 2016/0061714 A1 | 3/2016 | Matsuura |
| 2016/0061732 A1 | 3/2016 | Yamada et al. |
| 2016/0061821 A1 | 3/2016 | Tateyama et al. |
| 2016/0077118 A1 | 3/2016 | Silbert et al. |
| 2016/0083235 A1 | 3/2016 | Habura et al. |
| 2016/0084864 A1 | 3/2016 | Tokieda et al. |
| 2016/0097785 A1 | 4/2016 | Horstmann et al. |
| 2016/0139010 A1 | 5/2016 | Heras et al. |
| 2016/0144357 A1 | 5/2016 | Lin et al. |
| 2016/0144364 A1 | 5/2016 | Edwards |
| 2016/0161476 A1 | 6/2016 | Middleton-Davis et al. |
| 2016/0178594 A1 | 6/2016 | Jarvis et al. |
| 2016/0178651 A1 | 6/2016 | Shima et al. |
| 2016/0202246 A1 | 7/2016 | Tong et al. |
| 2016/0214114 A1 | 7/2016 | Tan et al. |
| 2016/0216289 A1 | 7/2016 | Augstein et al. |

FOREIGN PATENT DOCUMENTS

| | | |
|---|---|---|
| EP | 0632271 | 1/1995 |
| EP | 0908724 | 4/1999 |
| EP | 1254716 | 11/2002 |
| EP | 1391401 | 2/2004 |
| EP | 1757882 | 2/2007 |
| EP | 1923137 | 5/2008 |
| EP | 2282212 | 2/2011 |
| EP | 2333563 | 6/2011 |
| EP | 2367010 | 9/2011 |
| EP | 2367014 | 9/2011 |
| EP | 2463030 | 6/2012 |
| EP | 2677321 | 12/2013 |
| EP | 2728361 | 5/2014 |
| EP | 2728362 | 5/2014 |
| EP | 2784514 | 10/2014 |
| JP | H0268754 | 5/1990 |
| JP | H05164760 | 6/1993 |
| JP | H11316236 | 11/1999 |
| JP | 2000028620 | 1/2000 |
| JP | 2002142889 | 5/2002 |
| JP | 2004093365 | 3/2004 |
| JP | 2004233123 | 8/2004 |
| JP | 2005514291 | 5/2005 |
| JP | 2005148080 | 6/2005 |
| JP | 2005265717 | 9/2005 |
| JP | 2006204473 | 8/2006 |
| JP | 2007303882 | 11/2007 |
| JP | 2007315784 | 12/2007 |
| JP | 2007315949 | 12/2007 |
| JP | 2007333466 | 12/2007 |
| JP | 2008082777 | 4/2008 |
| JP | 2008180640 | 8/2008 |
| JP | 2008214098 | 9/2008 |
| JP | 2008249600 | 10/2008 |
| JP | 2008261753 | 10/2008 |
| JP | 2008292314 | 12/2008 |
| JP | 2009068992 | 4/2009 |
| JP | 2009085616 | 4/2009 |
| JP | 2009174997 | 8/2009 |
| JP | 2009244238 | 10/2009 |
| JP | 2009300152 | 12/2009 |
| JP | 2010117222 | 5/2010 |
| JP | 2010236926 | 10/2010 |
| JP | 2011112524 | 6/2011 |
| JP | 2011191148 | 9/2011 |
| JP | 2012053064 | 3/2012 |
| JP | 2012184982 | 9/2012 |
| JP | 2012225758 | 11/2012 |
| JP | 2012530899 | 12/2012 |
| JP | 2013007688 | 1/2013 |
| JP | 2013079926 | 5/2013 |
| JP | 2013079928 | 5/2013 |
| JP | 2013190446 | 9/2013 |
| JP | 2014020885 | 2/2014 |
| JP | 2015025687 | 2/2015 |
| JP | 2015102410 | 6/2015 |
| JP | 2015158410 | 9/2015 |
| JP | 2015172488 | 10/2015 |
| JP | 2015190828 | 11/2015 |
| WO | 9310454 | 5/1993 |
| WO | 9610035 | 4/1996 |
| WO | 9739327 | 10/1997 |
| WO | 9821595 | 5/1998 |
| WO | 9947261 | 9/1999 |
| WO | 9953121 | 10/1999 |
| WO | 03057599 | 7/2003 |
| WO | 2004088327 | 10/2004 |
| WO | 2006054964 | 5/2006 |
| WO | 2006119361 | 11/2006 |
| WO | 2009002358 | 12/2008 |
| WO | 2009002359 | 12/2008 |
| WO | 2010079630 | 7/2010 |
| WO | 2010147895 | 12/2010 |
| WO | 2011066269 | 6/2011 |
| WO | 2012024658 | 2/2012 |
| WO | 2013113054 | 8/2013 |
| WO | 2013151622 | 10/2013 |
| WO | 2013155966 | 10/2013 |
| WO | 2014144825 | 9/2014 |
| WO | 2015021228 | 2/2015 |
| WO | 2015039642 | 3/2015 |
| WO | 2015057877 | 4/2015 |
| WO | 2015126979 | 8/2015 |
| WO | 2015158818 | 10/2015 |
| WO | 2015183871 | 12/2015 |
| WO | 2015198097 | 12/2015 |
| WO | 2016001083 | 1/2016 |
| WO | 2016004171 | 1/2016 |
| WO | 2016018910 | 2/2016 |
| WO | 2016045835 | 3/2016 |
| WO | 2016046743 | 3/2016 |
| WO | 2015054113 | 4/2016 |

OTHER PUBLICATIONS

International Searching Authority, "International Search Report and Written Opinion," issued in connection with PCT application No. PCT/US2016/017827, dated Aug. 2, 2016, 17 pages.
Author Unknown, Architect System Operations Manual (PN 201837-106), Jan. 2009, sections 1-143-1-148, 6 pages.
Stewart, "Introduction to Real Time," Embedded Systems Design, Embededded.com, Nov. 1, 2001, 4 pages.
International Searching Authority, "Invitation to Pay Additional Fees and Where Applicable, Protest Fee," Issued in connection with Application No. PCT/US2016/017827, dated May 23, 2016, 7 pages.
International Searching Authority, "International Search Report and Written Opinion," issued in connection with Application No. PCT/US2016/017823, dated Jun. 6, 2016, 17 pages.
International Bureau, "International Preliminary Report on Patentability," issued in connection with International Patent Application No. PCT/US2016/017823, dated Aug. 24, 2017, 11 pages.
International Bureau, "International Preliminary Report on Patentability," issued in connection with International Patent Application No. PCT/US2016/017827, dated Aug. 24, 2017, 10 pages.

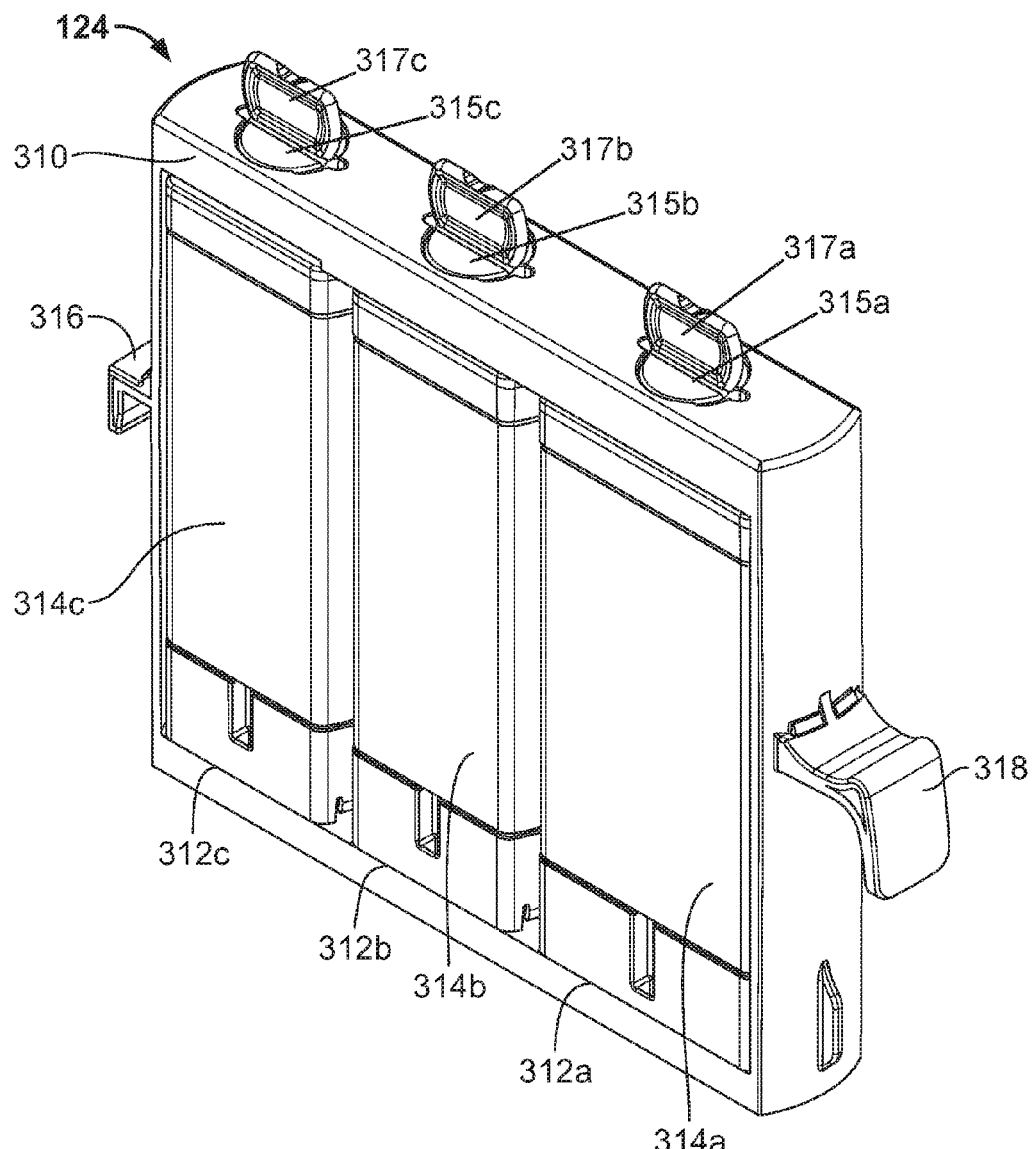
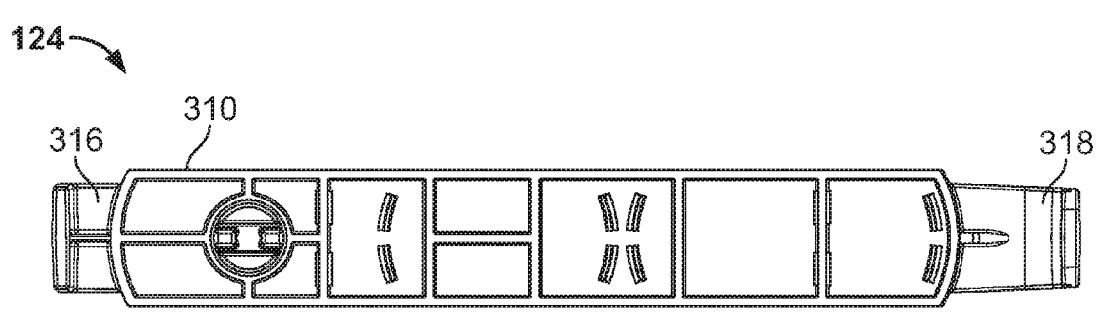

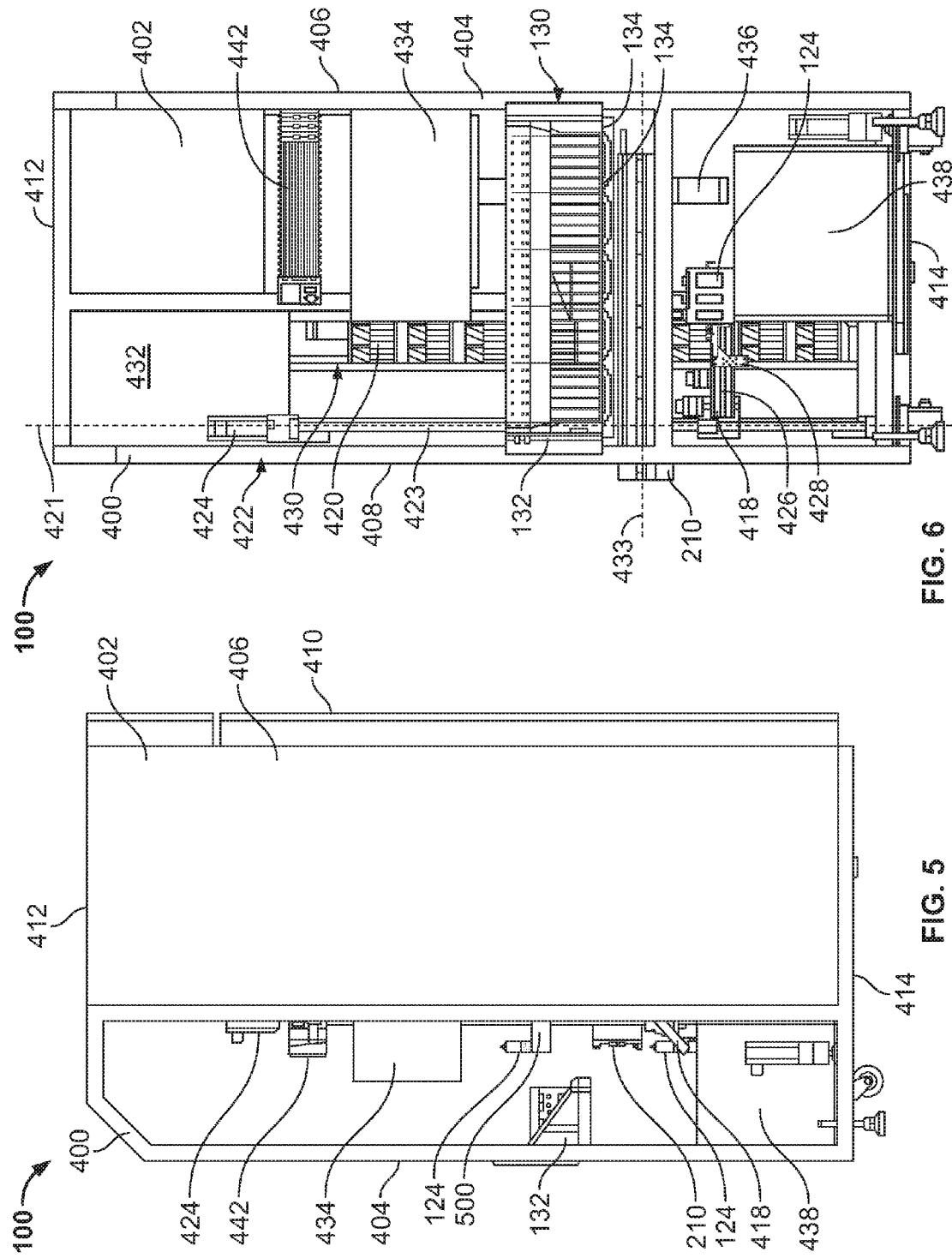

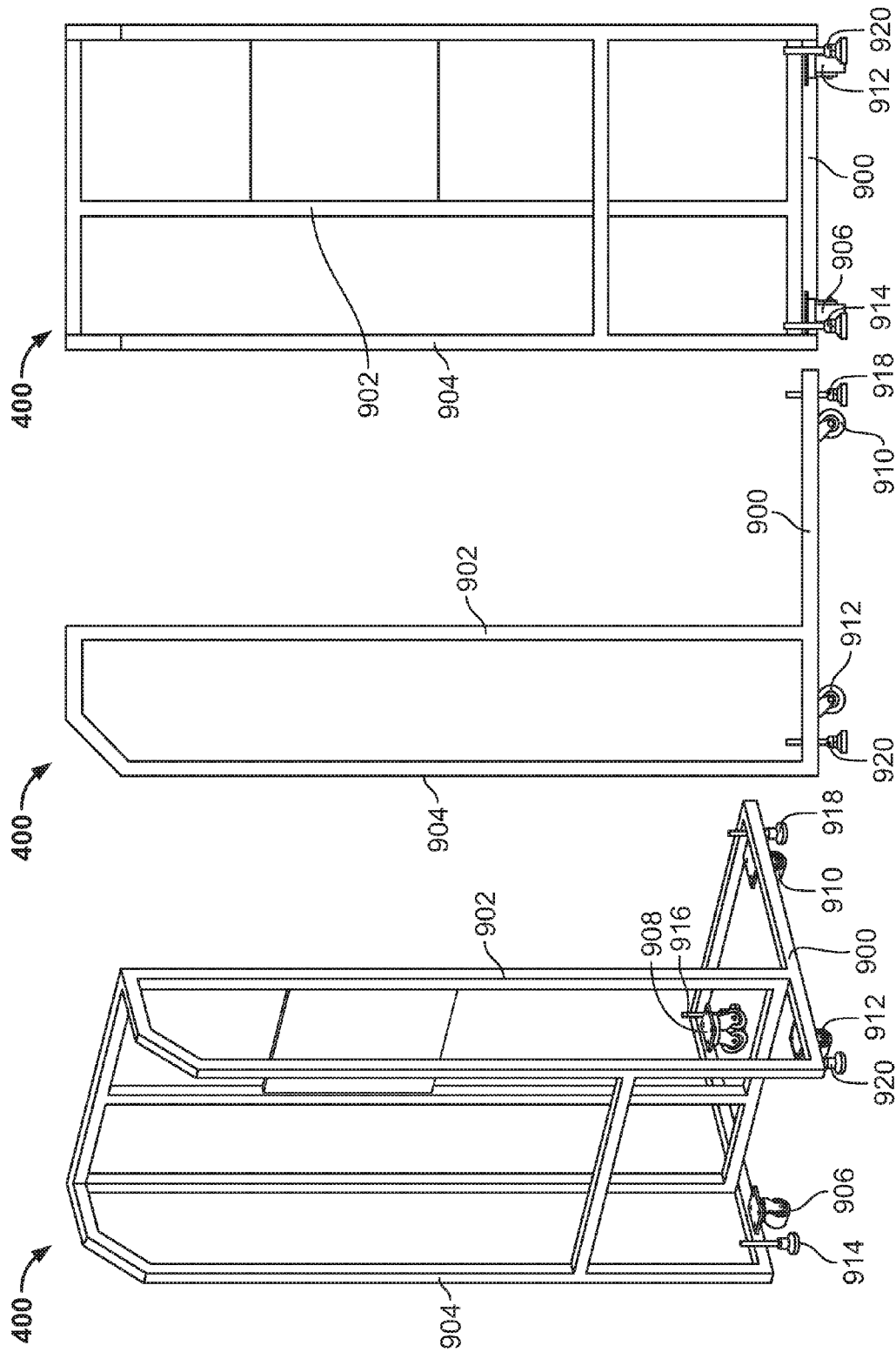

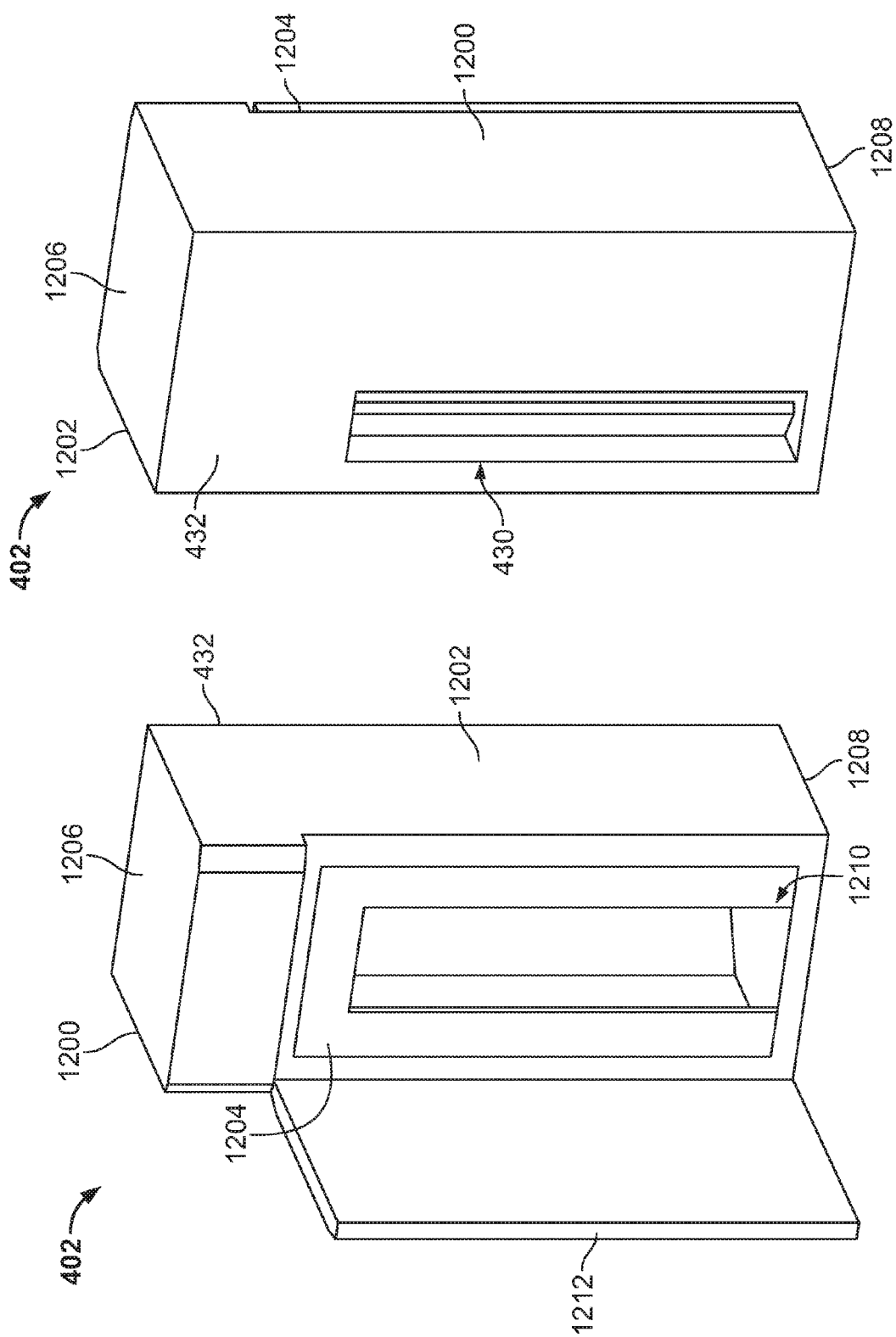

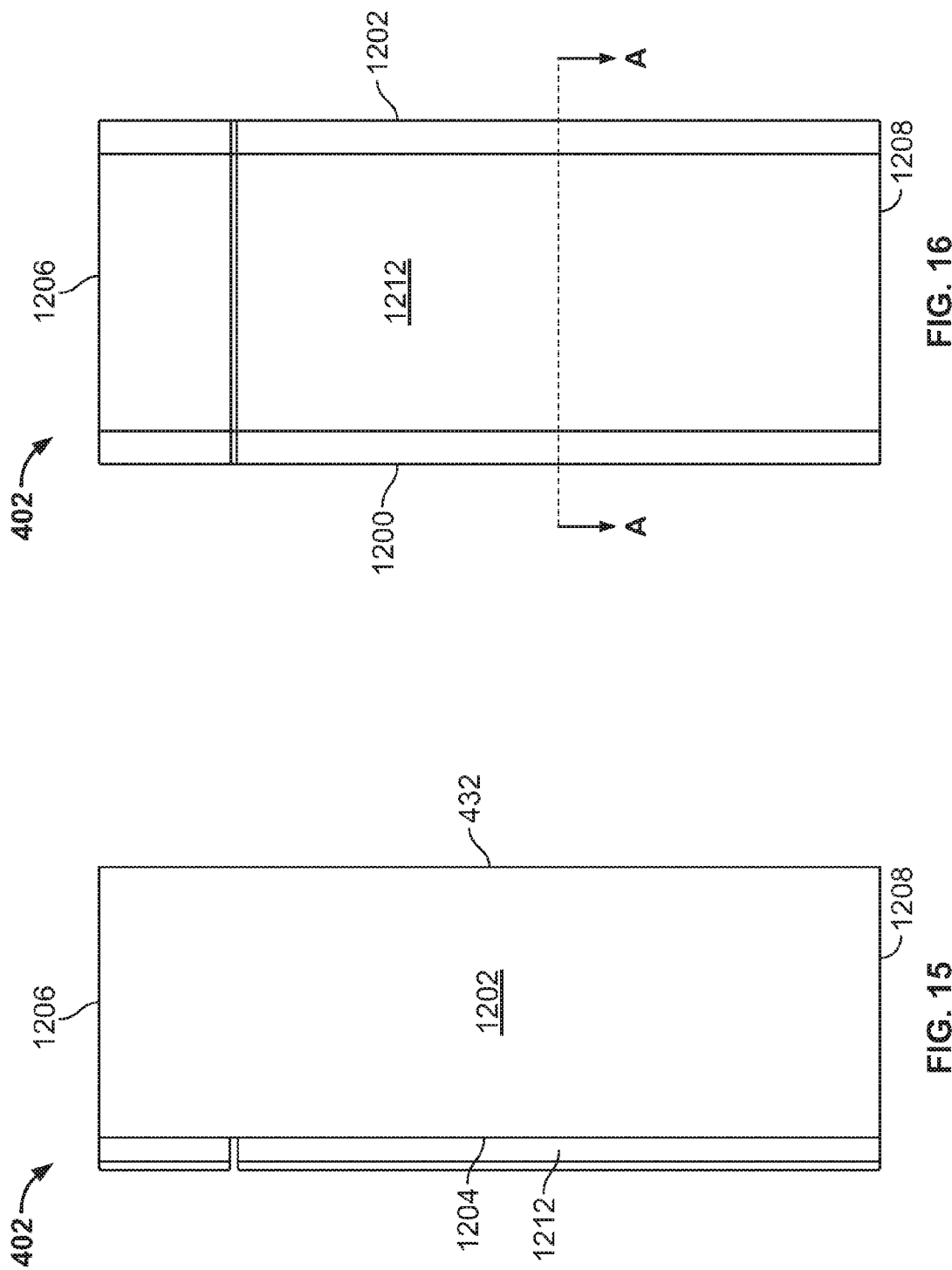

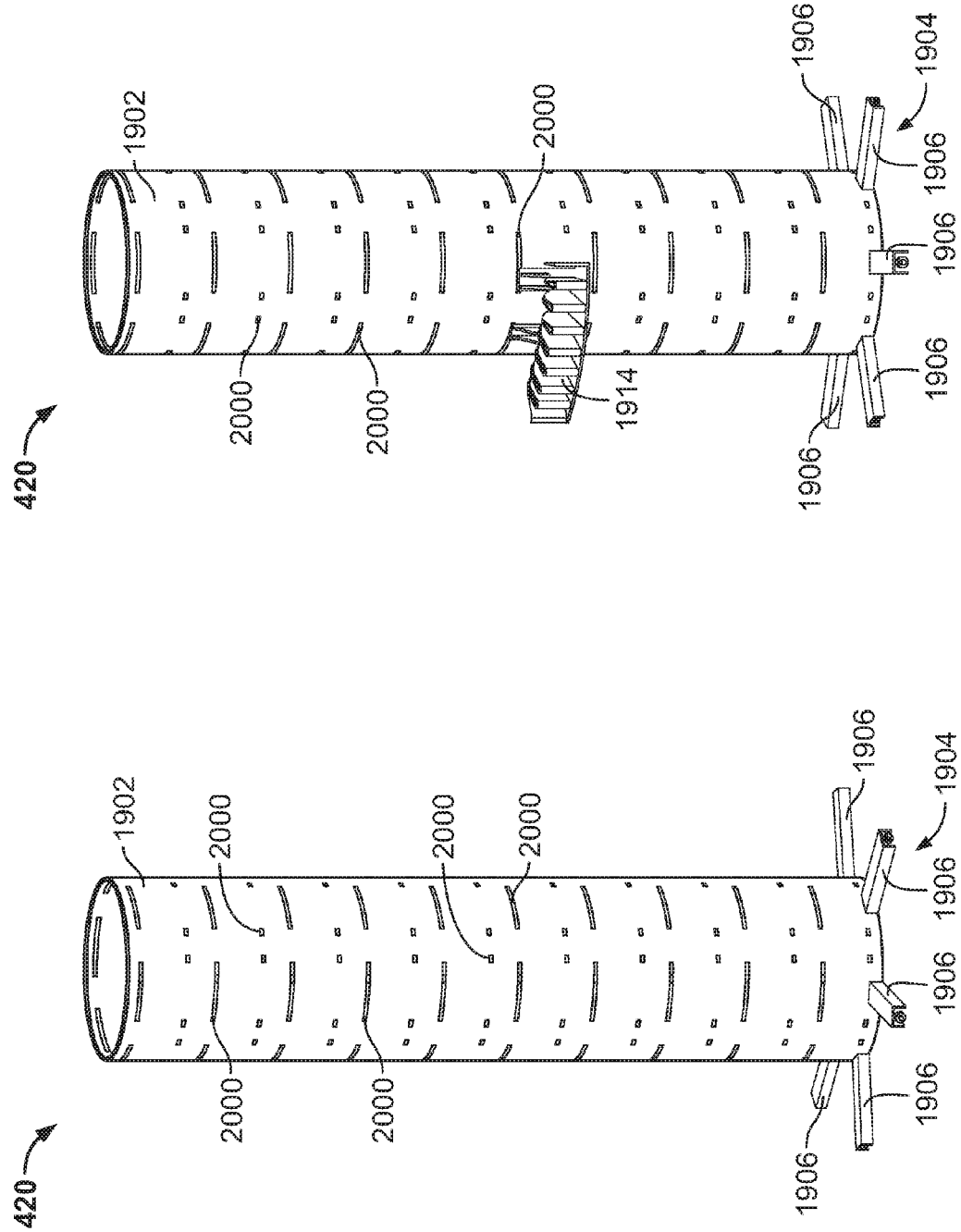

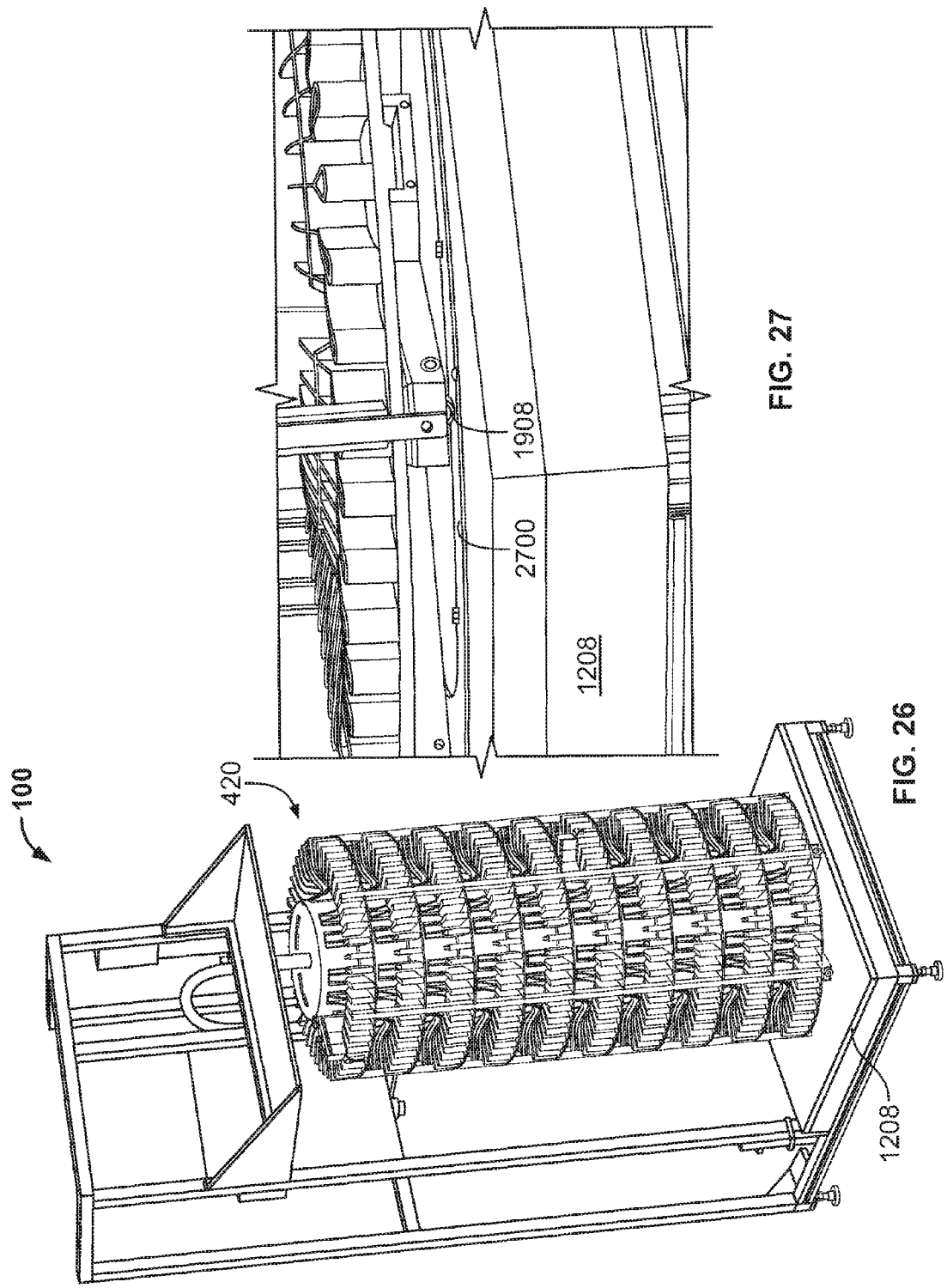

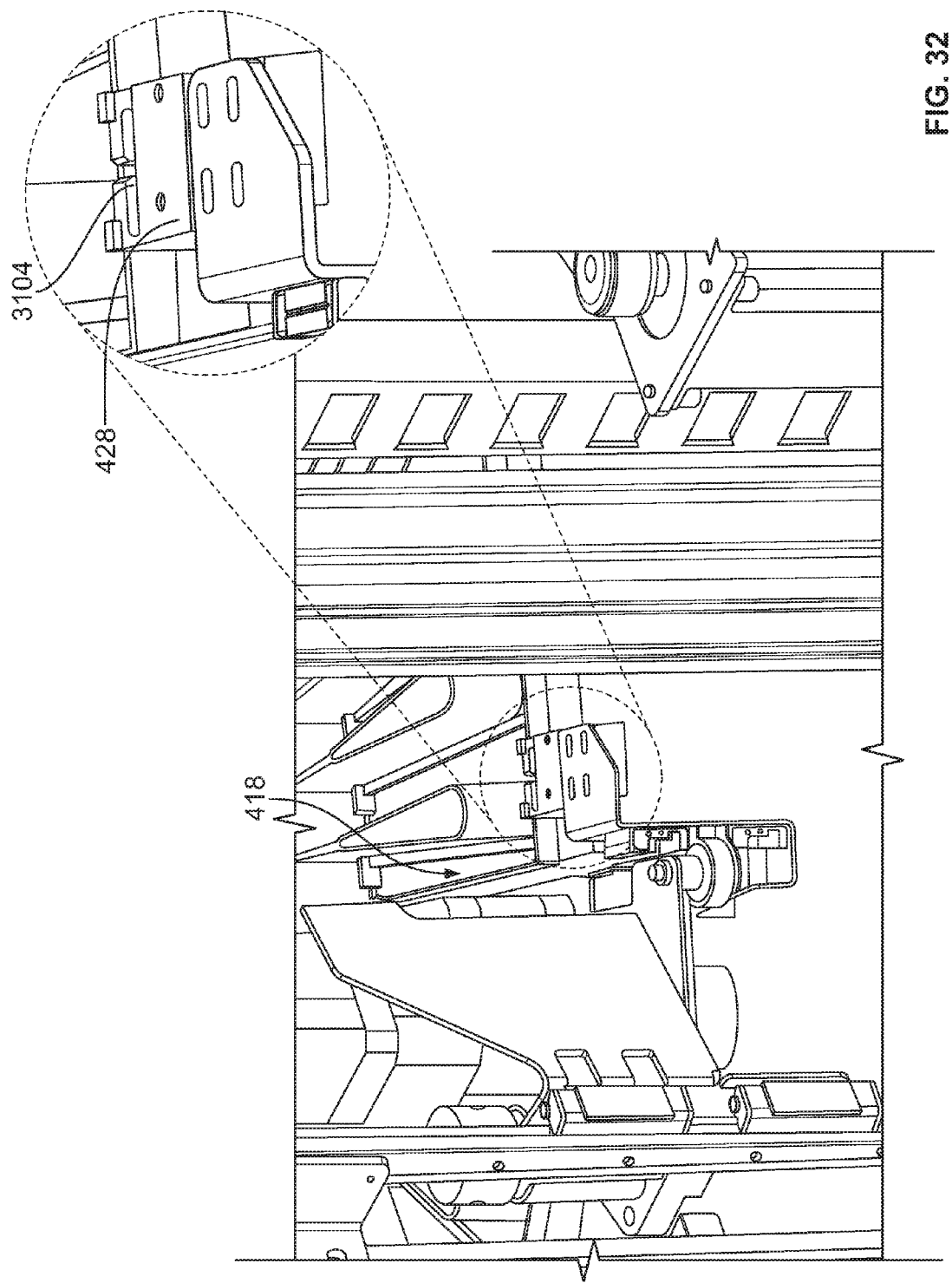

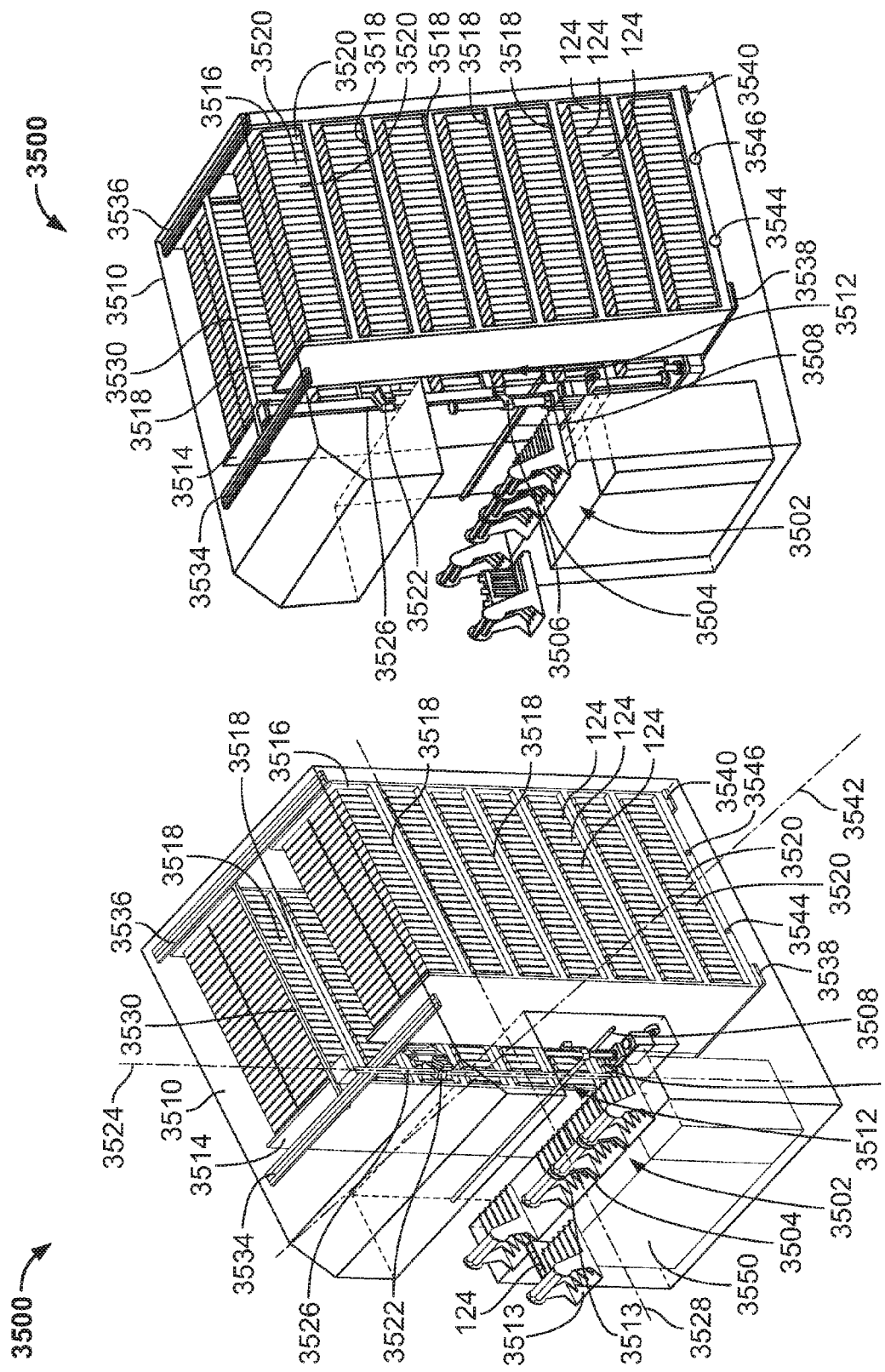

AUTOMATED STORAGE MODULES FOR DIAGNOSTIC ANALYZER LIQUIDS AND RELATED SYSTEMS AND METHODS

RELATED APPLICATIONS

This application claims the benefit under 35 U.S.C. §119 (e) to U.S. Provisional Application No. 62/115,959, titled "AUTOMATED STORAGE MODULES FOR DIAGNOSTIC ANALYZER LIQUIDS AND RELATED SYSTEMS AND METHODS," filed Feb. 13, 2015, and to U.S. Provisional Application No. 62/214,029, titled "AUTOMATED STORAGE MODULES FOR DIAGNOSTIC ANALYZER LIQUIDS AND RELATED SYSTEMS AND METHODS," filed Sep. 3, 2015. U.S. Provisional Application Nos. 62/115,959 and 62/214,029 are incorporated herein by this reference in their entireties.

FIELD OF THE DISCLOSURE

The present disclosure relates generally to storage modules and, more particularly, to automated storage modules for diagnostic analyzer liquids and related systems and methods.

BACKGROUND

Healthcare diagnostics laboratories use diagnostic instruments, such as diagnostic analyzers, for testing and analyzing samples. One or more sample tubes are typically placed into a rack or carrier and loaded into an analyzer by a technician or operator. Known diagnostic analyzers use various liquids, such as reagents, to perform the diagnostic analysis procedures. A reagent kit or carrier typically has one or more containers of reagents. The reagent carrier is also manually loaded into the analyzer by the technician or operator. When the reagent kit is empty, the operator unloads the reagent kit from the analyzer and loads another reagent kit into the analyzer. Known diagnostic analyzers also need to be calibrated and tested for accuracy. Calibration and/or control samples are similarly loaded into the analyzers and unloaded from the analyzers as needed.

BRIEF DESCRIPTION OF THE DRAWINGS

FIG. 3C illustrates an example immunoassay reagent carrier that may be implemented as one or more of the carriers in FIG. 1.

FIG. 3D is a bottom view of the example immunoassay reagent carrier of FIG. 3C.

FIG. 5 is a right side view of the example storage module of FIG. 4.

FIG. 6 is a front view of the example storage module of FIG. 4.

FIG. 9 is a front perspective view of an example frame of the example storage module of FIG. 4.

FIG. 10 is a right side view of the example frame of FIG. 9.

FIG. 11 is a front view of the example frame of FIG. 9.

FIG. 13 is a rear perspective view of the example storage housing of FIG. 12 with the other components of the example storage module removed for clarity.

FIG. 14 is a front perspective view of the example storage housing of FIG. 12 with the other components of the example storage module removed for clarity.

FIG. 15 is a left side view of the example storage housing of FIG. 12 with the other components of the example storage module removed for clarity.

FIG. 16 is a rear side view of the example storage housing of FIG. 12 with the other components of the example storage module removed for clarity.

FIG. 20 is a front perspective view of an example center support column of the example storage carousel in FIG. 19.

FIG. 21 is a rear perspective view of the example center support column of FIG. 21 illustrating one of the example cassettes with slots coupled to the example center support column.

FIG. 26 illustrates the example storage carousel of FIG. 19 supported on a bottom wall of the example storage housing of FIG. 12.

FIG. 27 is an enlarged view of the example storage carousel and the bottom wall of FIG. 26.

FIG. 32 shows an enlarged view of an example hand of the example carousel robot of FIG. 30.

FIG. 35 is a top perspective view of another example storage module having an alternative shelving unit configuration to store and transport carriers in accordance with the teachings of this disclosure.

FIG. 36 is side perspective view of the example storage module of FIG. 35.

FIG. 44 also shows an enlarged view of an example cap that is to be removed from a container of the example carrier.

FIG. 63 also shows an enlarged view of the example cap.

DETAILED DESCRIPTION

Figure 1:
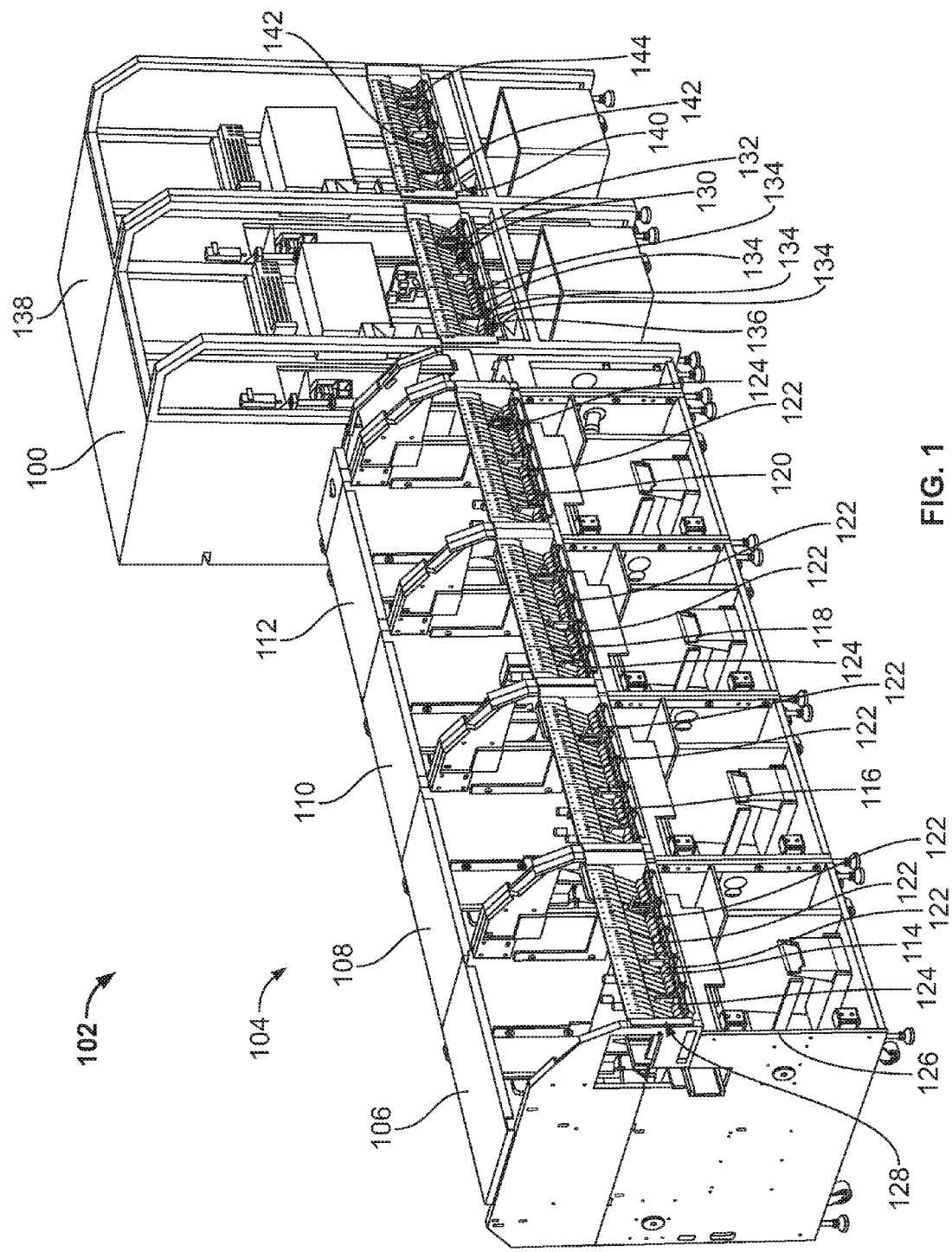
FIG. 1 is a perspective view of an example storage module, as part of a workcell having an array of analyzers, to provide automated storage and transportation of carriers of liquids to be used by the workcell in accordance with the teachings of this disclosure.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

Diagnostics laboratories employ diagnostic instruments such as those for testing and analyzing specimens or biological samples. A diagnostic instrument may be, for example, an immunoassay analyzer, a clinical chemistry assay analyzer, a hematology analyzer, a blood analyzer and/or any other diagnostic analyzer for analyzing a specimen. Specimens or biological samples are analyzed to, for example, check for the presence or absence of an item of interest including, for example, a specific region of DNA, mitochondrial DNA, a specific region of RNA, messenger RNA, transfer RNA, mitochondrial RNA, a fragment, a complement, a peptide, a polypeptide, an enzyme, a prion, a protein, an antibody, an antigen, an allergen, a part of a biological entity such as a cell or a viron, a surface protein, and/or functional equivalent(s) of the above. Specimens such as a patient's body fluids (e.g., serum, whole blood, urine, swabs, plasma, cerebra-spinal fluid, lymph fluids, tissue solids) can be analyzed using a number of different tests to provide information about the patient's health.

Generally, analysis of a test sample involves the reaction of the test sample with one or more reagents with respect to one or more analytes. The reaction mixture is analyzed by an apparatus for one or more characteristics such as, for example, the presence and/or concentration of a certain analyte in the test sample. Use of automated diagnostic analyzers improves the efficiency of the laboratory procedures as the technician (e.g., an operator) has fewer tasks to perform and, thus, the potential for operator or technician error is reduced. In addition, automated diagnostic analyzers also provide results much more rapidly and with increased accuracy and repeatability.

Automated diagnostic analyzers typically receive test samples in sample carriers, each having a plurality of test sample tubes. The analyzers employ robotic device(s) for moving the sample carriers throughout the analyzers to positions where the samples can be aspirated from the sample tubes. Sample carriers are manually loaded into the analyzers by an operator or technician. Additionally, reagent carriers, each having a plurality of reagent containers, are also loaded into the automated diagnostic analyzers by an operator and transported throughout the analyzers by robotic device(s) to positions where the reagents can be aspirated. The automated diagnostic analyzers use multiple pipettes to move liquids from the carriers to reactions vessels in which the samples are to be processed. For conducting additional tests, an operator can load more sample carriers into the automated diagnostic analyzers and unload the sample carriers that have been analyzed or are to be analyzed at a later time. When a reagent carrier is low or empty, for example, the operator can load another reagent carrier into the automated diagnostic analyzer and unload the empty reagent carrier.

Some known analyzers include a small onboard storage area (e.g., a reagent carousel) for storing reagent carriers. In such an example, the reagent carriers may be loaded into the diagnostic analyzer and transferred to the reagent storage area. Other analyzers are loaded with the reagents on an as-needed basis. In either case, these analyzers only have access to a limited supply of reagents, and the reagents must be replenished frequently by an operator when the regents are depleted.

Besides samples and reagents, automated diagnostic analyzers also frequently use calibrator samples and controls samples to calibrate and test the accuracy of the analyzers. Control tests and calibration tests may occur daily, weekly, monthly, etc. Calibration samples are samples that include a known concentration of an analyte. The calibration samples are tested or analyzed via routine testing in the analyzer and a calibration curve is generated so that the analyzer can be calibrated and so that the results of the actual test samples can be measured against the curve. Calibration procedures occur periodically (e.g., once or twice a month). Control samples, on the other hand, are run more frequently (e.g., daily), and are used ensure the analyzer is running correctly (e.g., as a control). Calibrator carriers and control carriers are also manually loaded into the automated diagnostic analyzers, when needed, by an operator or technician.

Therefore, many types of analyzer liquids are frequently loaded and unloaded from the automated diagnostic analyzers. The process of monitoring the levels of these liquids and loading/unloading often requires substantial operator time. Additionally, the known carriers for the different types of liquids have different sizes and shapes. As such, each of the different types of carriers are generally loaded into separate areas designated for the respective carriers, which also results in additional operator time. Further, because of the different carrier shapes and sizes, the known analyzers include separate robotic devices for interacting with the different carriers. Some known laboratory automation systems have a refrigerator for storing additional reagents. However, these known refrigerators only store reagents. Further, the refrigerators employ complex robotic doors for opening and closing the refrigerators for moving the reagents into and out of the refrigerators.

Additionally, the different containers of the carriers may have different types and/or sizes of caps. Some known storage modules have decappers for removing one specific type of cap. However, the known decappers are not able to remove different types of caps. Thus, multiple decappers are required for the known storage modules to remove the different types of caps. Also, some known storage modules use a capper to place a cap on a container. However, the capper is a different device than the decapper and is located in a different location than the decapper. As a result, the known storage modules require additional equipment to complete both capping and decapping operations. Further, the known storage modules generally take longer to complete decapping and capping operations because the carriers must be moved to different stations where the decapping and recapping can take place.

Disclosed herein are example storage modules that provide automated storage and transportation of carriers having analyzer liquids such as, for example, samples, reagents, calibrator and controls. In general, the example storage modules may operate in a stand-alone state or may be modularly coupled to one or more analyzers (e.g., as a workcell) and/or a laboratory automation system (LAS) and interact with the analyzers and/or the LAS to exchange the carriers therebetween. The example storage modules store multiple carriers such as, for example, samples carriers, reagent carriers, calibrator carriers and/or control carriers, and operate to provide the analyzer(s) and/or the LAS with the carriers when demanded.

For example, when an analyzer is low on a reagent, the storage module receives a request from the analyzer and the storage module provides the analyzer with a reagent carrier having the desired reagent(s). In a similar manner, the storage module may also supply the analyzer with additional sample(s), calibration material(s), control(s) and/or other analyzer liquid(s) as needed. Further, the example storage modules also receive carriers from the analyzer. The carriers may be automatically restored in the storage module (e.g., for later use) or disposed (e.g., when empty). As a result, relatively less time is spent by an operator loading and unloading the analyzer(s) with carriers of analyzer liquids. Additionally, the automatic replenishment of the analyzer liquids reduces the delays in test results caused by missing or insufficient onboard analyzer liquids and, thus, improves the efficiency and consistency of the laboratory workflow. The example storage modules provide a seamless and continuous flow of reagents, calibrators, controls, samples, etc. to the analyzer(s).

In some examples disclosed herein, the example storage modules utilize carriers having substantially the same form factor (e.g., footprint), which enables the resources (e.g., carrier transport devices, loading bays, etc.) of the example storage modules to operate with any type of carrier (e.g., a sample carrier, a reagent carrier, a calibrator carrier and/or a control carrier). For example, an example storage module disclosed herein can store multiple carriers having samples, reagents, calibrators and/or controls within the same storage housing and can transfer each of the carriers to and from an analyzer and/or a LAS using a common carrier transport system.

The example storage modules also include a loading bay having a plurality of slots to receive the carriers that are to be loaded into the storage housing. An operator may load the carriers into any of the slots of the loading bay, which are then transferred into the storage module. Thus, relatively less operator time is needed to load carriers into the storage module because all the carriers can be loaded into the storage module in one location.

In some examples disclosed herein, the storage modules include a refrigerated storage housing having a plurality of shelves with slots for accommodating the carriers. An opening is provided in the storage housing to enable the transfer of carriers into and out of the storage housing. Unlike other known refrigerators having complex door systems, the example storage modules enable faster and more efficient transfer of carriers into and out of the storage housing through the opening. To effectively cool the inside of the storage housing, some the example storage modules create an aircurtain across the opening of the storage housing to reduce airflow into and out of the storage housing and, thus, reduce heat transfer.

The example storage modules disclosed herein include a positioner that is movable along a track behind the loading bay. The track may be coupled to one or more analyzers (e.g., as a workcell) and/or an LAS. For example, the track may be coupled to a track of a positioner of an analyzer, which enables the positioner of the storage module and the positioner of the analyzer to exchange carriers between each other. In some examples, a transfer location is provided along the combined track where carriers can be exchange. For example, one or more slots in the loading bay of the storage module may be used as a transfer location. Because both positioners are movable along the combined track, both positioners can access the designated slots in the loading bay to exchange carriers. Therefore, the analyzers may perform diagnostic testing according to traditional protocols or schedules and may receive additional analyzer liquids (e.g., samples, reagents, calibrator and/or controls) via the transfer location without interrupting normal operations of the analyzers. Additionally, the modularity of the example storage modules allows more or fewer storage modules (e.g., two, four, ten, etc.) to be utilized depending on the demand (e.g., increased demand for immunoassay testing and/or clinical chemistry testing) of the laboratory or facility.

The example storage modules also include a carousel robot (e.g., a carrier transporter, a robotic transporter), which is movable along the storage housing to move carriers into and out of the storage housing. The carousel robot and the positioner exchange carriers at a transfer location such as, for example, a tray. The carousel robot and the positioner interact to transfer carriers between the loading bay, the storage housing and one or more analyzers and/or an LAS (via the transfer location).

In some examples, a rotatable storage carousel is disposed within the storage housing. The storage carousel has a plurality of shelves with slots to accommodate carriers. Each of the slots is capable of accepting a carrier having the common form factor. As a result, a plurality of carriers having different types of liquids may all be stored on storage carousel. Additionally, the example storage carousel is rotatable, which enables the storage carousel to accommodate relatively more carriers while still providing access to all of the carriers in the slots.

Also disclosed herein is an example capper/decapper that can remove different types of caps from the containers and can cap (e.g., recap) the containers with different types of caps. The example capper/decapper disclosed herein employs a gripper with first and second gripper hands that move together or apart. The gripper hands can be used to grip different types of caps including, for example, cylindrical caps and/or caps having tabs. Once a cap is gripped, the example gripper may be rotated to rotate the cap. Therefore, the example capper/decapper can be used to remove caps that are rotatably coupled to a container and/or can be used to cap a container with a cap that is to be rotatably coupled to the container. As a result, different decapping stations are not required for removing the different types of caps, which is an advantage over the known decapping systems. Further, because the capper/decapper can remove a cap from a container and can place a cap on a container, the same equipment can be employed for both operations. As such, the time spent performing these operations is relatively shorter than known capper or decapper systems.

An example apparatus disclosed herein includes a refrigerated storage module having a plurality of shelves to store a plurality of carriers having one or more containers of fluid for use in a diagnostic analysis and a loading bay disposed along a side of the storage module. The loading bay has an array of slots to receive one or more of the carriers. The loading bay is accessible by a user for manual loading or unloading of one or more of the carriers. The example apparatus includes a first carrier transporter coupled to the storage module. The first carrier transporter is to transfer one or more of the carriers between one or more of the shelves and a first transfer location. The example apparatus also include a track coupled to the storage module. The track is to connect the storage module to an automated diagnostic analyzer. The example apparatus includes a second carrier transporter movable along the track. The second carrier transporter is to transfer a first carrier between the first transfer location and a slot in the loading bay and transfer a second carrier between the first transfer location and a second transfer location accessible by the automated diagnostic analyzer.

In some examples, the shelves include vertically stacked carousels. In some examples, the storage module includes a vertical opening along a side of a storage housing to provide access to the carousels. In some such examples, the first carrier transporter is disposed outside of the storage housing, and the first carrier transporter includes a hand that is extendable through the vertical opening to access the carriers on the carousels.

In some examples, the storage module is to store carriers having reagents, calibrators, controls and samples for use in the automated diagnostic analyzer. In some such examples, the carriers containing the reagents, calibrators, controls and samples have substantially the same footprint. In some examples, the first carrier transporter is movable along a first axis and the second carrier transporter is movable along a second axis that is perpendicular to the vertical axis.

An example method disclosed herein includes storing a plurality of carriers on a plurality of shelves in a storage module. In the example method, the carriers have one or more containers of fluid for use in a diagnostic analysis. The example method includes transporting a first carrier, via a first carrier transporter, from a first shelf of the plurality of shelves to a transfer location and transporting the first carrier, via a second carrier transporter, from the transfer location to a slot in a loading bay disposed along a side of the storage module. The loading bay has an array of slots to receive one or more of the carriers. In the example method, the loading bay is accessible by a user for manual loading or unloading of one or more of the carriers. The example method also includes transporting a second carrier, via the first carrier transporter, from the first shelf to the transfer location and transporting the second carrier, via the second carrier transporter, from the transfer location to an automated diagnostic analyzer. The second carrier transporter is movable along a track coupled to the automated diagnostic analyzer.

In some examples, the shelves include vertically stacked carousels and the first shelf is a first carousel. In some examples, the method includes rotating the first carousel about a vertical axis to transfer the first carrier to a first location where the first carrier transporter is to retrieve the first carrier. In some such examples, the method further includes rotating the first carousel about the vertical axis to transfer the second carrier to the first location where the first carrier transporter is to retrieve the second carrier.

In some examples, transporting the first carrier from the first shelf to the transfer location includes moving the first carrier transporter vertically along a side of module storage housing in which the shelves are disposed. In some examples, transporting the first carrier from the first shelf to the transfer location includes retrieving, via the first carrier transporter, the first carrier from the first shelf by extending a hand of the first carrier transporter through a vertical opening in the storage housing to engage the first carrier on the first shelf.

Another example apparatus disclosed herein includes a housing, a refrigeration unit to reduce a temperature of air inside the housing and a plurality of vertically stacked carousels disposed within the housing. Each of the carousels has a plurality of slots to receive a plurality of carriers having one or more containers of fluid for use in a diagnostic analysis. The example apparatus also includes a loading bay disposed along a side of the housing. The loading bay has an array of slots to receive one or more of the carriers. The loading bay provides access to a user for manual loading and unloading of one or more of the carriers. The example apparatus also includes a carrier transport system to transfer a carrier between a slot in the loading bay and a slot in a carousel.

In some examples, the carrier transport system is to insert a carrier into a rear side of a slot in the loading bay. In some such examples, a user has access to the carrier through a front side of the slot in the loading bay.

In some examples, the carrier transport system includes a first carrier transporter and a second carrier transporter. The first carrier transporter is movable along a vertical track and the second carrier transporter is movable along a horizontal track. In some such examples, the first carrier transporter is to transfer a carrier between a slot in a carousel and a transfer location, and the second carrier transporter is to transfer a carrier between the transfer location and a slot in the loading bay. In some examples, the second carrier transporter is to transfer a carrier between the transfer location and an automated diagnostic analyzer coupled to the horizontal track. In some examples, the housing includes a vertical opening to provide access to the carousels. In some such examples, the first carrier transporter is disposed outside of the housing and the first carrier transporter includes a hand that is extendable through the vertical opening to access the carriers on the carousels.

In some examples, the carousels are rotatable about a vertical axis. In some examples, the housing includes a vertical opening to provide access to the carousels, and the refrigeration unit is to circulate air past the vertical opening. In some examples, the slots of the carousels are arranged annularly around each of the respective carousels. In some examples, the slots of the loading bay are vertical slots arranged in a horizontal array.

Another example apparatus is disclosed herein that includes a storage enclosure having a side wall with a vertical opening and a plurality of shelves stacked vertically within the storage enclosure. The shelves have a plurality of slots to support a plurality of carriers having one or more containers of fluid for use in a diagnostic analysis. The example apparatus includes an air circulation unit to direct refrigerated air vertically inside of the enclosure to reduce a temperature of air inside the enclosure, an exhaust to direct the circulated air past the vertical opening in the side wall of the enclosure and a carrier transporter disposed outside of the enclosure. The carrier transporter includes a hand that is extendable through the vertical opening to place a carrier in a slot of a shelf or retrieve a carrier from a slot of a shelf.

In some examples, the enclosure includes a plurality of channels to direct the refrigerated air and the warm exhaust air along a length of the enclosure. In some such examples, the channels to direct the refrigerated air are disposed along interior corners of the enclosure.

In some examples, the apparatus includes a transfer location. The carrier transporter is to transfer a carrier between the transfer location and a slot of a shelf. In some examples, the apparatus also includes a loading bay coupled to the enclosure. The loading bay has an array of slots to receive one or more of the carriers. The loading bay is to provide access to a user for manual loading and unloading of one or more of the carriers. In some such examples, the carrier transporter is a first carrier transporter, and the apparatus includes a second carrier transporter movable along a track coupled to the housing. The second carrier transporter is to transfer a carrier between the transfer location and a slot in the loading bay. In some examples, the second carrier transporter is to transfer a carrier between the transfer location and an automated diagnostic analyzer coupled to the track.

An example method disclosed herein includes transporting, via a carrier transporter, a first carrier having a first container to position the first container in a first location. The first container has liquid to be used in a diagnostic analyzer, and the first container has a first cap. The example method includes removing, via a cap gripper, the first cap from the first container while the first container is disposed in the first location and transporting, via the carrier transporter, a second carrier having a second container to position the second container in the first location. The second container has liquid to be used in a diagnostic analyzer, and the second container has a second cap being a different type of cap than the first cap. The example method also includes removing, via the cap gripper, the second cap from the second container while the second container is disposed in the first location.

In some examples, when the first container is disposed in the first location, the first carrier is in a first position, and when the second container is disposed in the first location, the second carrier is in a second position different than the first position. In some examples, removing the first cap from the first container includes gripping, via the cap gripper, the first cap and rotating, via the cap gripper, the first cap to release the first cap from the first container. In some such examples, removing the second cap from the second container includes gripping, via the cap gripper, the second cap and moving, via the cap gripper, the second cap vertically upward to release the second cap from the second container. In some such examples, when removing the second cap from the second container, the second cap is not rotated.

In some examples, the cap gripper includes a first gripper hand and a second gripper hand. In such an example, removing the first cap from the first container includes moving at least one of the first gripper hand or the second gripper hand to grip the first cap between the first gripping hand and the second gripping hand. In some such examples, the first cap includes a tab that extends vertically, and removing the first cap from the first container includes moving at least one of the first gripper hand and the second gripper hand to engage opposite sides of the tab. In some such examples, the second cap includes a circular rim, and removing the second cap from the second container includes moving at least one of the first gripper hand and the second gripper hand to grip the second cap within a cylinder defined between the first gripper hand the second gripper hand.

In some examples, the method further includes identifying, via a camera, that the first container has the first cap and the second container has the second cap.

In some examples, the first carrier includes a third container, and the method further includes transporting, via the carrier transporter, the first carrier to position the third container in the first location. The third container has a third cap. The example method includes removing, via the cap gripper, the third cap from the third container while the third container is disposed in the first location. In some examples, the third cap is a same type as the first cap. In some examples, when the third container is disposed in the first location, the first container is disposed in a second location different than the first location.

In some examples, the method further includes clamping, via a carrier clamp, the first carrier while the first cap is removed from the first container. In some examples, the method further includes clamping, via the carrier clamp, the second container while the second cap is removed from the second container. In some such examples, the carrier clamp includes a first set of clamp arms and a second set of clamp arms. The first set of clamp arms are to engage the first carrier when the first container is clamped and the second set of clamp arms are to engage the second container when the second container is clamped. In some examples, when the first set of clamp arms are engaged with the first carrier, the second set of clamp arms are not engaged with the first carrier, and when the second set of clamp arms are engaged with the second container, the first set of clamp arms are not engaged with the second container.

In some examples, the method further includes transporting, via the carrier transporter, a third carrier having a third container to position the third container in the first location. In such an example, the third container has no cap. The example method includes coupling, via the cap gripper, a third cap onto the third container while the third container is disposed in the first location. In some examples, the third cap is a different type than the first cap and the second cap.

An example apparatus disclosed herein includes a carrier transporter to transport a first carrier having a first container to position the first container in a first location. The first container is to have a first cap. The carrier transporter is also to transport a second carrier having a second container to position the second container in the first location. The second container is to have a second cap being a different type than the first cap. The example apparatus also includes a cap gripper to remove the first cap from the first container when the first container is disposed in the first location and remove the second cap from the second container when the second container is disposed in the first location. In some examples, when the first container is disposed in the first location, the first carrier is in a first position, and when the second container is disposed in the first location, the second carrier is in a second position different than the first position.

In some examples, the cap gripper includes a first gripper arm with a first gripper hand and a second gripper arm with a second gripper hand. In some such examples, the first and second gripper arms are pivotable to move the respective first and second gripper hands toward each other or away from each other. In some such examples, the first gripper arm and the second gripper arm pivot about a horizontal axis. In some examples, the first gripper arm includes a first slot and the second gripper arms includes a second slot. In some such examples, the apparatus further includes a pin disposed in the first slot and the second slot. The pin is movable upward and downward to pivot the first and second gripper arms. In some examples, the first gripper hand includes a first curved surface and the second gripper hand includes a second curved surface. In such an example, the first and second curved surfaces form a cylinder when the first and second gripper hands are moved together. In some such examples, to remove the first cap from the first container, at least one of the first gripper hand or the second gripper hand is to be moved toward the other of the first gripper hand or the second gripper hand to engage opposites sides of the first cap. In some examples, to remove the second cap from the second container, at least one of the first gripper hand or the second gripper hand is to be moved toward the other of the first gripper hand or the second gripper hand to grip the second cap within the cylinder formed between the first and second gripper hands.

In some examples, the first location is located vertically below the cap gripper. In some examples, the cap gripper is movable along a vertical axis. In some such examples, the cap gripper is rotatable about the vertical axis.

In some examples, the apparatus further includes a sensor to detect a type of cap on the first container. In some examples, the apparatus further includes a clamp having a first clamp arm and a second clamp arm. In such an example, the first clamp arm and the second clamp arm are to clamp the first carrier when the first cap is to be removed from the first container. In some such examples, the clamp includes a third clamp arm and a fourth clamp arm. In such an example, the third clamp arm and the fourth clamp arm are to clamp the second container when the second cap is to be removed from the second container.

Another example method disclosed herein includes transporting, via a carrier transporter, a first container for use in a diagnostic analyzer to a first location. The first container has a first cap. The example method includes removing, via a cap gripper, the first cap from the first container while the first container is disposed in the first location and coupling, via the cap gripper, a second cap to the first container while the first container is disposed in the first location.

In some examples, the second cap is a different type than the first cap. In some examples, removing the first cap from the first container includes gripping the first cap with the cap gripper. In some such examples, removing the first cap from the first container further includes rotating, via the cap gripper, the first cap to release the first cap from the first container. In some such examples, coupling the second cap to the first container includes moving, via the cap gripper, the second cap towards the first container and inserting the second cap into a mouth of the first container without rotating the second cap. In some examples, removing the first cap from the first container includes moving, via the cap gripper, the first cap vertically without rotating the first cap to release the first cap from the first container.

In some examples, the cap gripper includes a first gripper hand and a second gripper hand, and removing the first cap from the first container includes moving at least one of the first gripper hand or the second gripper hand to grip the first cap between the first and second gripping hands. In some such examples, coupling the second cap to the first container includes moving at least one of the first gripper hand or the second gripper hand to grip the second cap and moving, via the cap gripper, the second cap toward the first container to insert the second cap into a mouth of the first container.

In some examples, the first container is disposed in a carrier, and transporting the first container to the first location includes transporting the carrier to a first position in which the first container is disposed in the first location. In some examples, the carrier includes a second container. In such an example, the method includes transporting, via the carrier transporter, the carrier to a second position in which the second container is disposed in the first location. In some examples, the first container is disposed in a second location when the carrier is in the second position, the second location different than the first location. In some examples, the second container has a third cap. In such an example, the method includes removing, via the cap gripper, the third cap from the second container while the second container is disposed in the first location. In some examples, the third cap is a different type than the first cap. In some examples, the third cap is a same type as the second cap. In some examples, the second container does not have a cap. In such an example, the method includes coupling, via the cap gripper, a third cap to the second container while the second container is disposed in the first location. In some such examples, the third cap is a same type as the second cap. In some examples, the method includes detecting, via a sensor, a type of the first cap.

Another example apparatus disclosed herein includes a carrier transporter to transport a first container having a liquid to be used in a diagnostic analyzer to a first location. The first container to have a first cap. The example apparatus also includes a cap gripper to remove the first cap from the first container while the first container is disposed in the first location and couple a second cap to the first container while the first container is disposed in the first location.

In some examples, the second cap is a different type than the first cap. In some examples, the cap gripper includes a first gripper arm with a first gripper hand and a second gripper arm with a second gripper hand. In some such examples, the first and the second gripper arms are pivotable to move the respective first and second gripper hands toward each other or away from each other. In some examples, the first gripper arm and the second gripper arm are pivotable about a horizontal axis. In some examples, the first gripper arm includes a first slot and the second gripper arms includes a second slot. In some such examples, the method apparatus further includes a pin disposed in the first slot and the second slot. The pin is movable upward and downward to pivot the first and second gripper arms. In some examples, the first gripper hand includes a first curved surface and the second gripper hand includes a second curved surface. In such an example, the first and second curved surfaces form a cylinder when the first and second gripper hands are moved together. In some examples, to remove the first cap from the first container, at least one of the first gripper hand or the second gripper hand is moved toward the other of the first gripper hand or the second gripper hand to engage opposites sides of the first cap. In some examples, to couple the second cap onto the first container, at least one of the first gripper hand or the second gripper hand is moved to grip the second cap within the cylinder formed between the first and second gripper hands.

In some examples, the first location is located vertically below the cap gripper. In some such examples, the cap gripper is movable along a vertical axis. In some such examples, the cap gripper is rotatable about the vertical axis.

In some examples, the apparatus includes a sensor to detect a type of cap on the first container. In some examples, the apparatus includes a clamp having a first clamp arm and a second clamp arm. In such an example, the first and second clamp arms are to clamp the first container when the first cap is to be removed from the first container and when the second cap is to be coupled to the first container.

Figure 2:
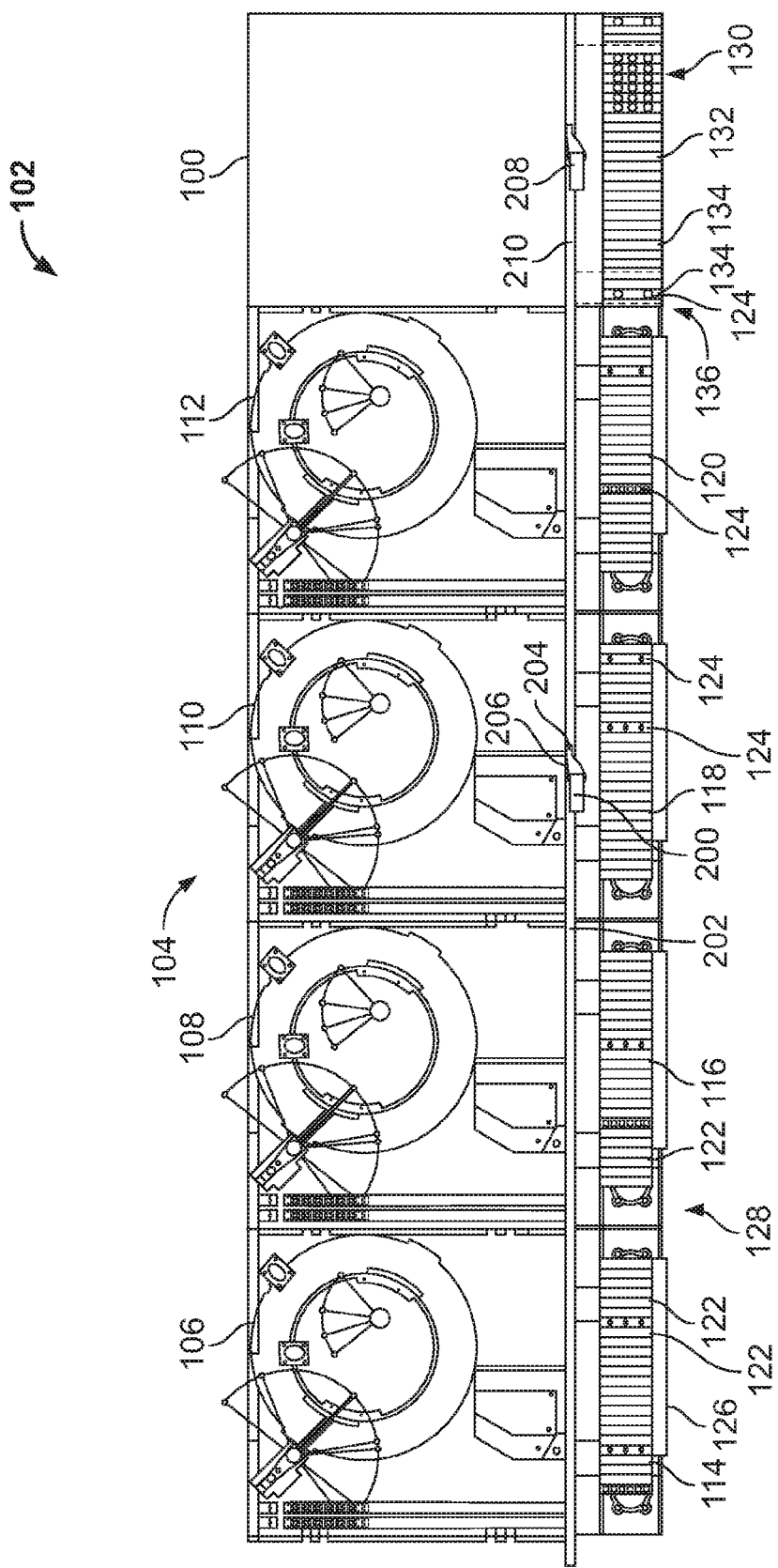
FIG. 2 is a top view of the example storage module and the workcell of FIG. 1.

Turning now to the figures, an example automated storage module 100 (e.g., a reagent automation module (RAM)) is illustrated in FIGS. 1 and 2. The storage module 100 may be connected to, for example, a laboratory automation system (LAS) and/or one or more analyzers. In the illustrated example, the storage module 100 is implemented as part of a workcell 102 having an array of analyzers 104. The example storage module 100 automatically loads, unloads, disposes, stores and/or exchanges one or more carriers of liquid to be used by the array of analyzers 104. In the illustrated example, the storage module 100 is coupled to (e.g., integrated with) the array of analyzers 104 to form the workcell 102. In other examples, the example storage module 100 may operate by itself as an independent storage module or may be coupled to the array of analyzers 104 via one or more track systems.

In the illustrated example, the array of analyzers 104 includes four analyzers: a first analyzer 106, a second analyzer 108, a third analyzer 110 and a fourth analyzer 112. In other examples, the array of analyzers 104 may include more or few analyzers. For example, the storage module 100 may be coupled to only one analyzer. The analyzers 106-112 may be, for example, any of an immunoassay analyzer, a clinical chemistry assay analyzer, a hematology analyzer, a blood sample analyzer and/or a molecular analyzer or any combination thereamong.

In the illustrated example, the first, second, third and fourth analyzers 106, 108, 110, 112 include respective first, second, third and fourth loading bays 114, 116, 118, 120. Each of the loading bays 114-120 has a plurality (e.g., an array) of slots 122 for receiving a plurality of carriers (e.g., racks) 124 and/or trays of the carriers 124. Each of the carriers 124 may hold one or more containers (e.g., a tube, a vessel, a vial, a cup, etc.) of a liquid, a suspension, and/or a plasma to be used by the analyzers 106-112 during testing. The one or more containers may hold, for example, a sample, a reagent, a calibration liquid and/or a control liquid. In the illustrated example of FIGS. 1 and 2, a plurality of carriers 124 are illustrated as disposed in the slots 122. As referred to herein, a "carrier" means any type of carrier having any type of liquid for use by the workcell 102 and/or an LAS (e.g., a sample carrier, a reagent carrier, a calibration carrier, a control liquid).

Figure 3A:
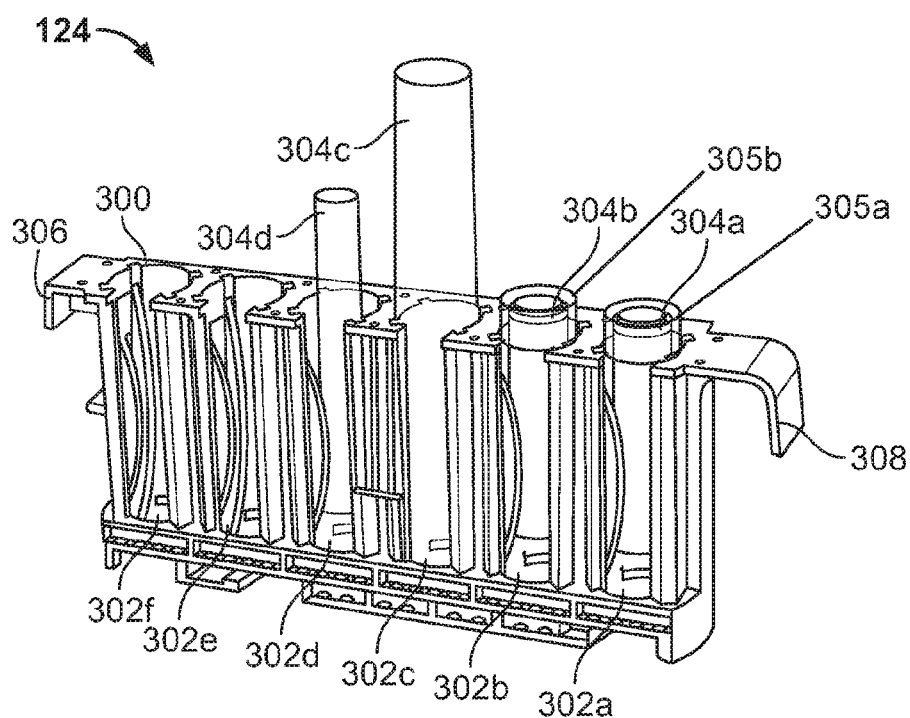
FIG. 3A illustrates an example sample carrier, calibrator carrier and/or control carrier that may be implemented as one or more of the carriers in FIG. 1.
Figure 3B:
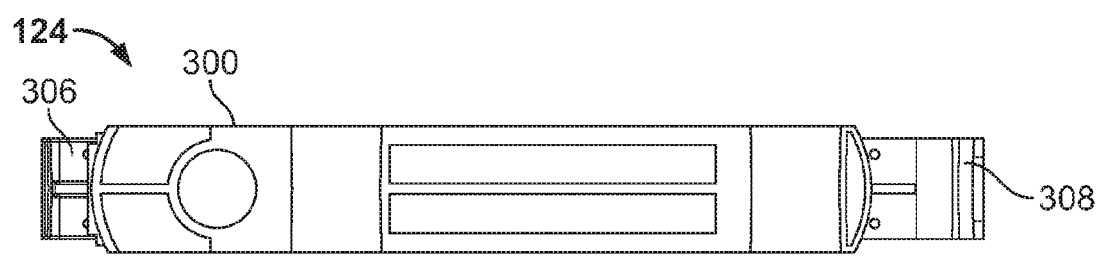
FIG. 3B is a bottom view of the example sample carrier, calibrator carrier and/or control carrier of FIG. 3A.

FIGS. 3A, 3B, 3C, 3D, 3E and 3F illustrate examples of various carriers that may be implemented as one or more of the carriers 124. For example, FIG. 3A is a perspective view of an example carrier 124, 300 and FIG. 3B is a bottom view of the example carrier 124, 300. In the illustrated example, the carrier 124, 300 has six holders 302a, 302b, 302c, 302d, 302e, 302f for holding up to six tubes (e.g., sample tubes). The carrier 124, 300 may be used as a sample carrier, for example, to hold up to six sample tubes. In other examples, the carrier 124, 300 may include more or fewer holders. In the illustrated example, four sample tubes 304a, 304b, 304c, 304d are disposed in the respective holders 302a, 302b, 302c, 302d. The sample tubes 304a-304d may include samples to be tested (e.g., by one or more of the analyzers 106-112). In the illustrated example, the first tube 304a has a first cap 305a. In the illustrated example, the first cap 305a is a cylindrical cap. In some examples, the first cap 305a is threaded onto the first tube 304a. Additionally or alternatively, the first cap 305a may be force fit (e.g., friction fit) onto the first tube 304a (e.g., without rotating the first cap 305a). In the illustrated example, the second tube 304b has a second cap 305b, which may be similar to the first cap 305a. The example carrier 124, 300 has an engagement tab 306 (e.g., a prong, a hook, a ledge, etc.) on one end and a finger tab 308 on the opposite end. The engagement tab 306 is used to couple the carrier 124, 300 to a transfer mechanism (disclosed in further detail herein). The finger tab 308 may be used by an operator to hold the carrier 124, 300 (e.g., by placing a finger under the finger tab 308).

The example carrier 124, 300 may also be used as a control carrier and/or a calibrator carrier. For example, one or more control tubes or bottles may be loaded into the holders 302a, 302b, 302c, 302d, 302e, 302 and, thus, the carrier 124, 300 may be implemented as a control carrier (e.g., a control kit). A control bottle may include a control liquid (e.g., a control sample) that is to be used to generate an analysis curve for a conducting diagnostic test. Similarly, one or more calibrator bottles may be loaded into the holders 302a, 302b, 302c, 302d, 302e, 302 and, thus, the carrier 124, 300 may be implemented as a calibrator carrier (e.g., a calibrator kit). A calibrator bottle may include a calibration liquid (e.g., a calibration sample) that is to be used to calibrate one or more of the analyzers 106-112, for example. In some examples, the sample tubes, the control bottles and/or the calibrator bottles may have different heights and/or different shapes. To accommodate different tubes and bottles, the carrier 124, 300 may include additional features to retain the tubes in the carrier 124, 300. For example, a spring may be included in one or more of the holders 302a, 302b, 302c, 302d, 302e, 302 to support a narrower tube, such as illustrated in FIG. 3A. Additionally or alternatively, a support or booster may be included in the bottom of one or more of the holders 302a, 302b, 302c, 302d, 302e, 302 to support shorter tube.

FIG. 3C is a perspective view of an example regent carrier 124, 310 (e.g., a reagent kit) and FIG. 3D is a bottom view of the example reagent carrier 124, 310. The reagent carrier 124, 310 is used to contain reagents for use in an immunoassay analysis. In the illustrated example, the reagent carrier 124, 310 has three holders 312a, 312b, 312c for holding up to three containers (e.g., reagent containers). In other examples, the sample carrier 124, 310 may include more or fewer holders. In the illustrated example, three containers 314a, 314b, 314c are disposed in the respective holders 312a, 312b, 312c. The containers 314a-314c may include reagents to be used for an immunoassay analysis. In the illustrated example, the first containers 314a has a first cap 315a. In the illustrated example, the first cap 315a is a butterfly cap, which includes a first tab 317a that extends vertically upward. The first cap 315a is rotatably coupled to the first container 314a. The first tab 317a may be used to twist the first cap 315a to remove the first cap 315a from the first container 314a and/or attach the first cap 315a onto the first container 314. In the illustrated example, the second container 314b has a second cap 315b with a second tab 317b and the third container 314c has a third cap 315c with a third tab 317c, which may be similar to the first cap 315a. The example reagent carrier 124, 310 has an engagement tab 316 on one end and a finger tab 318 on the opposite end, which may have similar structure to the engagement tab 306 and the finger tab 308 of the carrier 124, 300.

Figure 3E:
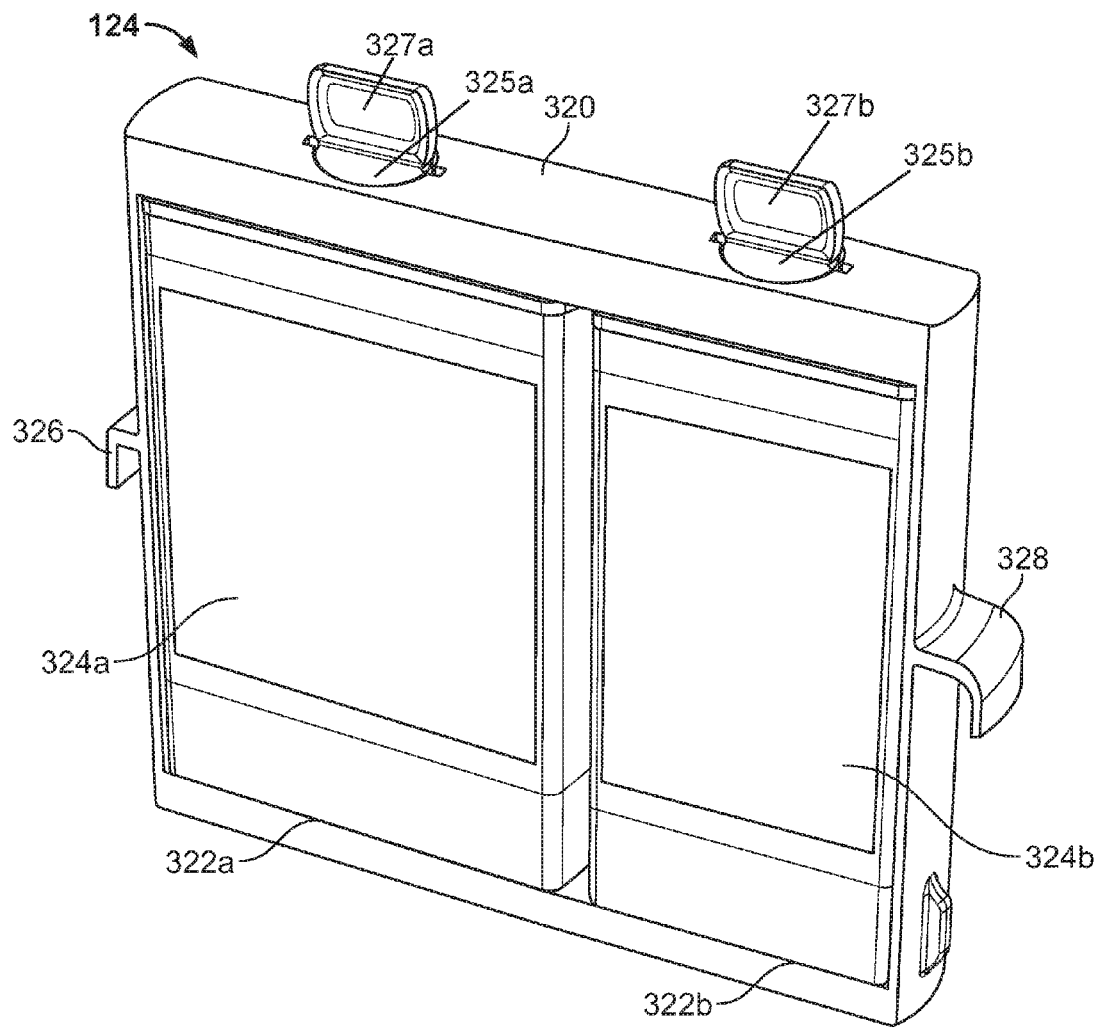
FIG. 3E illustrates an example clinical chemistry assay reagent carrier that may be implemented as one or more of the carriers in FIG. 1.
Figure 3F:
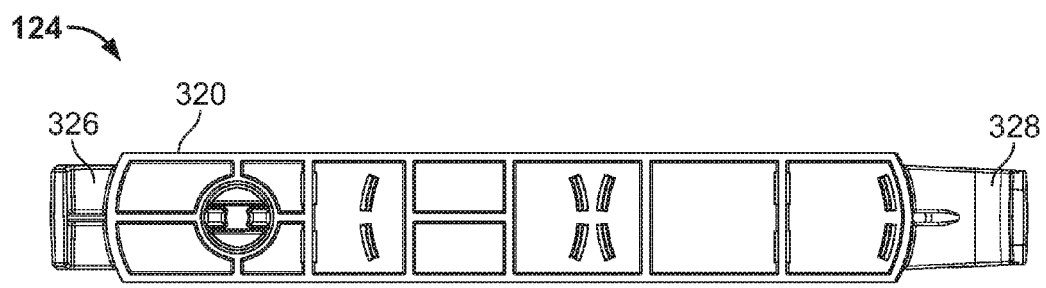
FIG. 3F is a bottom view of the example clinical chemistry assay reagent carrier of FIG. 3E.

FIG. 3E is a perspective view of an example regent carrier 124, 320 (e.g., a reagent kit) and FIG. 3F is a bottom view of the example reagent carrier 124, 320. The reagent carrier 124, 320 is used to contain reagents for use in a clinical chemistry assay analysis. In the illustrated example, the reagent carrier 124, 320 has two holders 322a, 322b for holding up to two containers (e.g., reagent containers). In other examples, the sample carrier 124, 320 may include more or fewer holders. In the illustrated example, three containers 324a, 324b are disposed in the respective holders 322a, 322b. The containers 324a, 324b include reagents to be used in a clinical chemistry assay analysis. In the illustrated example, the containers 324a, 324b include respective caps 325a, 325b. In the illustrated example, the caps 325a, 325b are butterfly caps, which include respective tabs 327a, 327b that may be used to twist the caps 325a, 325b onto the respective containers 324a, 324b. The example reagent carrier 124, 320 has an engagement tab 326 on one end and a finger tab 328 on the opposite end, which may have similar structure to the engagement tab 306 and the finger tab 308 of the carrier 124, 300.

To enable each of the carriers 124 to be transported, exchanged, stored etc. by the storage module 100 and/or the array of analyzers 104 (disclosed in further detail herein), each of the carriers 124 has substantially the same common form factor (e.g., the same footprint, the same base section, the same width). Further, each of the carriers 124 has similar engagement tabs 306, 316, 326 which enable carriers 124 to be transported using the same carrier transporter(s) (disclosed in further detail herein). In certain examples illustrated herein, certain ones of the carriers 124 (e.g., the immunoassay reagent carrier 124, 310) are illustrated. However, it is to be understood that the example carriers 124 can be any of the example carriers disclosed herein (e.g., the carrier 124, 300, which may be implemented as a sample carrier, a control carrier and/or a calibrator carrier, the immunoassay reagent carrier 124, 310, the clinical chemistry reagent carrier 124, 320, a carrier having eight containers, a carrier having five tubes, etc.).

In the illustrated example of FIGS. 1 and 2, an operator (e.g., a laboratory technician) may load/unload one or more of the carriers 124 into/from the slots 122 individually and/or in trays (e.g., batch loading/unloading). In some examples, the containers of the carriers 124 are to be uncapped prior to loading the carriers 124 into the slots 122. In other examples, as disclosed below, the carriers 124 are capped. To transport the carriers 124 between the slots 122 of the loading bays 114-120 and a position to be used in one or more of the analyzers 106-112 (e.g., to a sample aspiration position, to a device for transporting the carrier 124 to a sample aspiration position, to a side shuttle, to a reagent carousel, etc.), the array of analyzers 104 includes a positioner 200 (FIG. 2) (e.g., a carrier transporter, a robotic transporter, a robotic device). The positioner 200 is movable along a positioner track 202 (FIG. 2) disposed along a front side 126 of the analyzers 106-112 and behind the loading bays 114-120. In the illustrated example of FIGS. 1 and 2, the loading bays 114-120 and the positioner 200 define a random sample handler (RSH) 128 for the array of analyzers 104. In the illustrated example, one RSH 128 is implemented on the four analyzers 106-112. In other examples, each of the analyzers 106-112 may include a separate RSH 128 (e.g., a separate loading bay and positioner).

In the illustrated example, the positioner 200 has a hand 204 that is disposed on the end of an arm 206 that is rotatable about a vertical axis and movable along the vertical axis (disclosed in further detail herein). The hand 204 is employed to engage a tab (e.g., the engagement tab 306) on one of the carriers 124 and secure the carrier 124 to the positioner 200. Once engaged, the positioner 200 can remove the carrier 124 from its respective slot 122 and transport the carrier 124 to one or more locations along the positioner track 202. For example, the positioner 200 may retrieve one of the carriers 124 (e.g., the carrier 124, 300 having samples) from one of the slots 122 in the first loading bay 114 and transport the carrier 124 to position to be aspirated by a sample pipette of the first analyzer 106. In other examples, the first analyzer 106 may include one or more transportation devices to transport the carrier 124 from the positioner 200 to another location in the first analyzer 106 (e.g., to a sample aspiration position). The example positioner 200 may access any of the slots 122 in any of the loading bays 114-120 and may transfer any of the carriers 124 to any location along the front side 126 of the analyzers 106-112.

During testing, one or more of the analyzers 106-112 may need additional reagent(s), may need to be calibrated (e.g., with a calibration sample), may need to run a control (e.g., via a control sample), may have the capacity to analyze additional sample(s), etc. In previous systems, an operator or technician would be required to manually retrieve and prepare any of these liquids and load the respective carriers into the slots 122 of the loading bays 114-120. In some examples, the container(s) in the carriers 124 have cap and/or septums that need to be removed and/or installed. These processes require significant time and cost. In the examples disclosed herein, the example storage module 100 is implemented to automatically store, prepare (e.g., mix, remove caps, install septums, etc.) and/or transport carriers 124 of liquid to and from the array of analyzers 104. The storage module 100 can store a plurality of the carriers 124, which may include, for example, one or more of the carrier 124, 300 (which may be implemented as any of a sample carrier, a control carrier and/or a calibrator carrier), the immunoassay reagent carrier 124, 310 or the clinical chemistry assay reagent carrier 124, 320. When requested, the storage module 100 can automatically supply the array of analyzers 104 with the desired carriers 124. The storage module 100 may store a large quantity of carriers 124 and, as a result, significantly less technician time is needed operate the analyzers 106-112.

To load one or more of the carriers 124 into the storage module 100 (e.g., where the carriers 124 may be stored and/or transferred to/from the array of analyzers 104), the storage module 100 includes a random sample handler (RSH) 130 having a loading bay 132 (e.g., a loading platform, a rack). The loading bay 132 of the storage module 100 includes a plurality (e.g., an array) of slots 134 to receive a plurality of the carriers 124. The carriers 124 may be loaded individually into the slots 134 of the loading bay 126 and/or may be batch loaded using a tray, for example. The loading bay 126 of the storage module 100 may operate similar to the loading bays 114-120 of the analyzers 106-112. An operator or technician can manually load the carriers 124 into the front side of the loading bay 132 and manually unload the carriers from the front side of the loading bay 132. The example storage module 100 is capable of accepting carriers 124 having containers that are still capped (as discussed in further detail herein).

As illustrated in FIG. 2, the RSH 130 includes a positioner 208 that is movable along a track 210 behind the loading bay 132. The positioner 208 retrieves the carriers 124 from the slots 134 and/or deposits the carriers 124 in the slots 134 (e.g., through the rear side of the slots 134 in the loading bay 132). The carriers 124 may be transported, via the positioner 208, between the loading bay 132, the interior of the storage module 100 for storage (disclosed in further detail herein) and/or the array of analyzers 104.

To transfer a carrier 124 between the storage module 100 and the array of analyzers 104, a transfer location 136 (e.g., a hand-off location, a swap location, a transfer area) is disposed between the storage module 100 and the array of analyzers 104 that is accessible by both of the positioners 200, 208. In the illustrated example, the transfer location 136 is implemented as a plurality of the slots 134 of the loading bay 132 of the storage module 100. As illustrated, the track 202 of the analyzer RSH 128 and the track 210 of the storage module RSH 130 are coupled together (e.g., linked together). The loading bay 132 and track 202 of the storage module 100 form an RSH extension of the analyzer RSH 128. As a result, the positioner 200 of the analyzer RSH 128 is movable along the track 210 of the storage module RSH 130 into the storage module 100 to access the slots 134 that are designated as the transfer location 136 and, thus, any of the carriers 124 disposed in the slots 134 of the transfer location 136. For example, if the first analyzer 106 is low on a certain type of reagent, the storage module 100 receives a signal (e.g., a demand, a request message) from the array of analyzers 104 that the reagent is needed. The positioner 208 retrieves the carrier 124 (e.g., which may be implemented as one of the reagent carriers 124, 310, 124, 320), which was stored in the internal storage area of the storage module 100 (disclosed in further detail herein), and transfers the carrier 124 to one of the slots 134 of the transfer location 136. In the illustrated example, the positioner 208 inserts the carrier 124 into the slot 134 through the back side of the loading bay 132. Then, when the positioner 200 is free (e.g., because of scheduling constraints) to retrieve the carrier 124, the positioner 200 moves along the tracks 202, 210 and into the storage module 100 to retrieve the carrier 124 from the transfer location 136 (e.g., from the back side of the loading bay 132). In some examples, the positioner 200 operates under a relatively strict schedule (e.g., protocol) of moving carriers 124 throughout the analyzer 106-112. Therefore, having the transfer location 136 accessible by the positioner 200 enables the positioner 200 to retrieve the carrier when the positioner 200 is free to do so, rather than interfering with the scheduling of the positioner 200. The positioners 200, 208 may be programmed to avoid a collision. In some examples, the positioners 200, 208 are actuated using drive belts or linear actuators (e.g., linear ball screws). In such an example, the drive belts or linear actuators may be staggered or separated vertically from each other to avoid interference between the two positioners 200, 208.

The example storage module 100 operates to automatically supply any of the carriers 124 to any of the analyzers 106-114 based on, for example, a request message from, for example, one or more of the analyzers 106-112, an operator, a Laboratory Information System and/or Middleware. An LIS is an information system that clinical laboratories use to manage data and workflow (e.g., patient identification, test orders, results, etc.). Middleware is an informatics system that facilitates interfacing of one or more analyzers, an LAS and/or one or more laboratory devices with the LIS. In some instances, Middleware and/or the LIS is used for implementing reruns, retests, reflex test rules and/or for automatic and manual technical validation of the test results received from the analyzers. The request message may include, for example, a request for a reagent that is low or empty, an indication that one or more of the analyzers 106-112 has the capacity to analyze additional samples (e.g., which are stored in the storage module 100), a request for a calibration and/or control liquid, etc.

In the illustrated example, the transfer location 136 includes three slots 134 of the loading bay 132. However, in other examples, the transfer location 136 includes more or fewer slots 134 (e.g., one slot, ten slots, etc.). Additionally or alternatively, in some examples the transfer location 136 may include one or more slots 122 in one or more of the loading bays 114-120 of the analyzer RSH 128. In such an example, the positioner 208 may be movable along the track 210 into the RSH 128 (e.g., to deliver and/or retrieves one or more of the carriers 124 therefrom). In some examples, the transfer location 136 is implemented as a separate area (e.g., having one or more slots) between the storage module 100 and the array of analyzers 104 and is accessible by both the positioners 200, 208 along the combined tracks 202, 210 (e.g., the transfer location is outside the storage module 100). Additionally or alternatively, in some examples the positioners 200, 208 transfer the carriers 124 directly to each other. For example, the positioners 200, 208 may converge at a particular position and transfer one of the carriers 124 from one of the positioners 200, 208 to the other positioner 200, 208 (e.g., a direct hand-off). In other examples, only one positioner may be used in the example workcell 102. In such an example, the one positioner is movable along the entirety of the tracks 202, 210 to move the carriers 124 to the different positions along the tracks 202, 210.

In the illustrated example, the transfer location 136 is implemented as the first three slots 134 closest to the side of the storage module 100 adjacent the array of analyzers 104. However, in other examples, the transfer location 136 may include other slots 134 in the loading bay 132. For example, an LAS and/or one or more analyzers may be coupled to the other side of the storage module 100. In such an instance, another transfer location may be implemented on the other side of the loading bay 132 to accommodate a positioner of the LAS and/or the one or more analyzers.

Additionally or alternatively, more than one storage module may be implemented, as illustrated in FIG. 1. In the illustrated example, a second storage module 138 is coupled to the storage module 100 (e.g., a first storage module). The second storage module 138 may structurally and functionally similar to, for example, the storage module 100. In the illustrated example, the second storage module 138 is coupled to an opposite side of the storage module 100 as the array of analyzers 104. To transfer carriers 124 between the storage modules 100, 138, the track 210 of the storage module 100 may be coupled to a track of the second storage module 138, and the second storage module 138 may include a second transfer location 140 defined by one or more slots 142 in a second loading bay 144. The positioner 208 of the storage module 100 and a positioner of the second storage module 138 may exchange one or more of the carriers 124 between each other via the second transfer location 140. The positioner 208 of the storage module 100 may transfer one or more of the carriers between the first transfer location 136 and the second transfer location 140. In some examples, the track 210 of the storage module 100 extends into the second storage module 138 and the positioner 208 can access any of the slots 134 of the storage module 100 and any of the slots 142 of the second storage module 138. In such an example, the positioner 208 can transfer carriers 124 between the second storage module 138 (e.g., at one of the slots 142 and/or a tray such as, for example, tray 500 of FIG. 5, as disclosed in further detail herein) and the transfer location 136, where the carriers 124 can then be transferred to and from any one of the analyzers 106-114 and/or an LAS.

In the illustrated example of FIG. 1, the second storage module 138 is coupled to the side of the storage module 100. In other examples, the second storage module 138 may be coupled to the track 202 of the RSH 128 and/or a track of an LAS. For example, the second storage module 138 may be coupled to the side of the first analyzer 106. In such an example, the second transfer location 140 may be defined by one or more of the slots 142 adjacent the first analyzer 106 (e.g., opposite to the configuration illustrated in FIG. 1).

Figure 4:
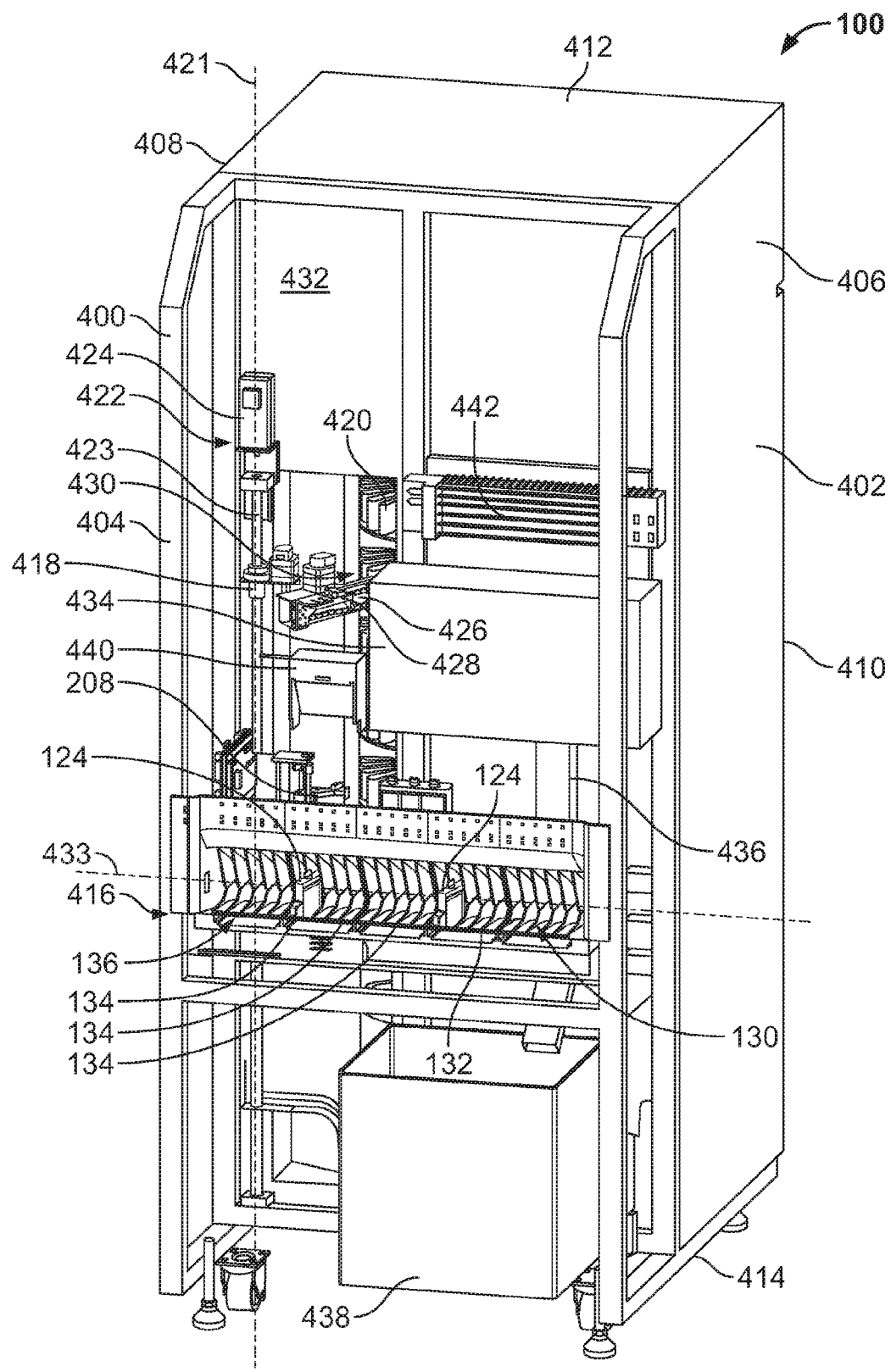
FIG. 4 is a front perspective view of the example storage module of FIG. 1.
Figure 7:
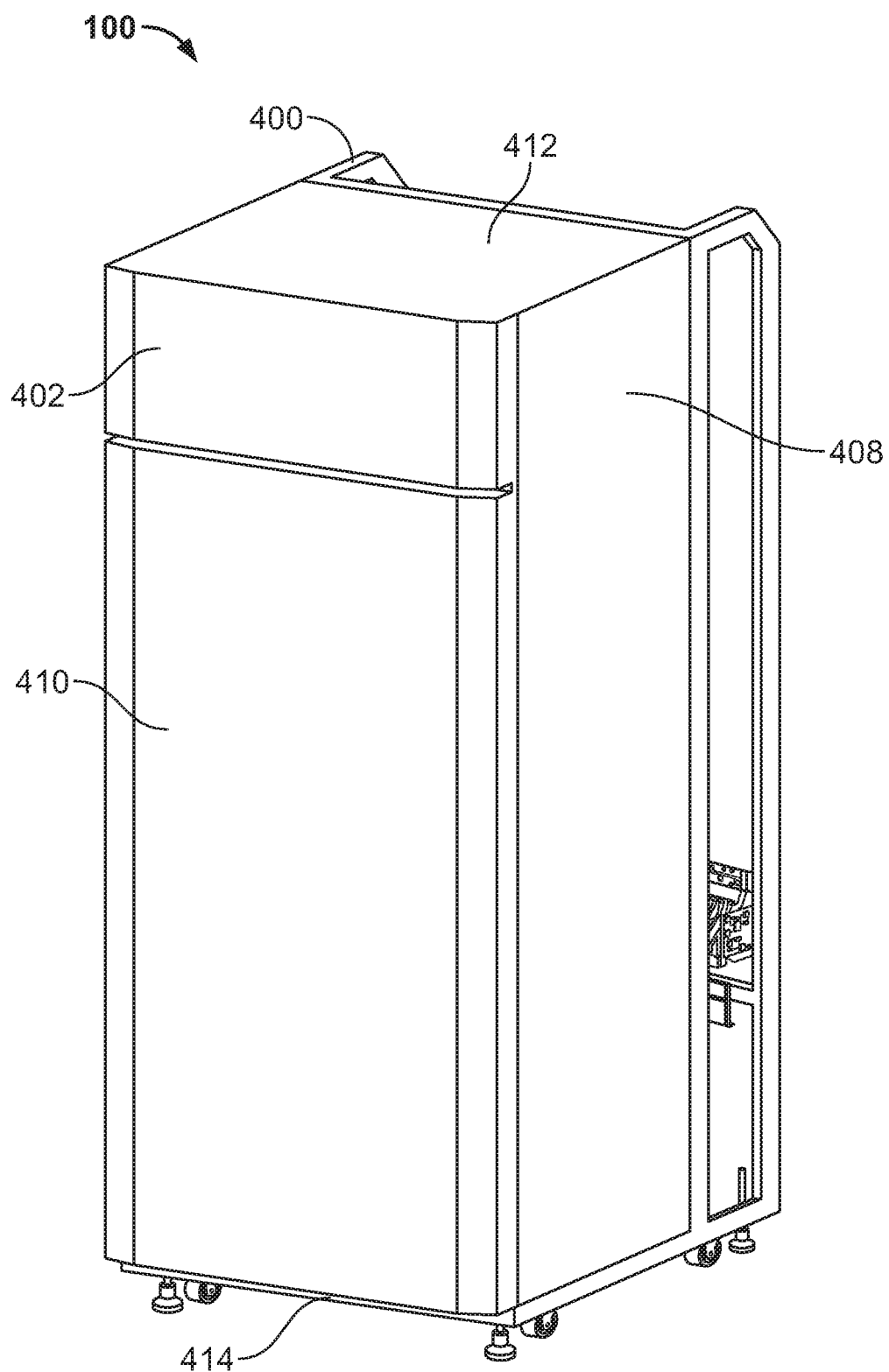
FIG. 7 is a rear perspective view of the example storage module of FIG. 4.

FIGS. 4-7 illustrate different views of the example storage module 100. Specifically, FIG. 4 shows a front perspective view of the storage module 100, FIG. 5 shows a right side view of the storage module 100, FIG. 6 shows a front side view of the storage module 100 and FIG. 7 shows a rear perspective view of the storage module 100. In the illustrated example, the storage module 100 includes a frame 400 and a storage housing 402 (e.g., an enclosure, a container, a vessel, a storage unit) supported by the frame 400. The storage housing 402 defines an area to store one or more of the carriers 124 and may be, for example, refrigerated. The storage module 100 has a front side 404, a right side 406, a left side 408, a rear side 410, a top side 412 and a bottom side 414.

To move a carrier between the storage housing 402, the transfer location 136 and/or any of the slots 134 in the loading bay 132, the example storage module 100 includes a carrier transport system 416. In the illustrated example, the carrier transport system 416 includes a carousel robot 418 (a first carrier transporter) (e.g., a positioner, a robotic transporter, etc.) and the positioner 208 (a second carrier transporter). The carousel robot 418 is provided to interface with a storage carousel 420 (e.g., a shelving unit with a plurality of shelves with slots) (disclosed in further detail herein) that is disposed within the storage housing 402 and stores one or more of the carriers 124. The carousel robot 418 is movable along a vertical axis 421 via, for example, a linear actuator 422. In the illustrated example, the linear actuator 422 includes a screw 423 that is driven by an actuator 424 (e.g., a DC servo motor, a stepper motor). In other examples, other electro-mechanical device(s) or other device(s) may be used to move the robot 418. The carousel robot 418 includes an arm 426 with a hand 428 (e.g., a gripper). The arm 426 is rotatable about the vertical axis 421 and the hand 428 (disclosed in further detail herein) is movable (e.g., extendable and retractable) along the arm 426. The carousel robot 418 uses the hand 428 to engage one of the carriers 124 (e.g., via a tab on the carrier 124), which secures the carrier 124 to the carousel robot 418 and enables the carousel robot 418 to transfer the carrier 124 from one location to another.

The carousel robot 418 translates up and down, along the screw 423 of the linear actuator 422, to access the carriers 124 stored on the carousel 420 (e.g., on vertically stacked shelves) in the storage housing 402 and moves the carriers 124 into and out of the storage housing 402. In the illustrated example, the carousel robot 418 is movable along a path that is disposed between the loading bay 132 and the storage housing 402 (e.g., outside of the storage housing 402). To move one of the carriers 124 into or out of the storage housing 402 (e.g., to be stored on the carousel 420), the storage housing 402 includes a vertical opening 430 along a front side wall 432 of the storage housing 402. The arm 426 of the carousel robot 418 is rotated to a position in which the hand 428 can be moved or extended into the opening 430 of the storage housing 402 to transport one of the carriers 124 into the storage housing 402 and retrieve one of the carriers 124 from the storage housing 402 (disclosed in further detail herein).

In the illustrated example, the positioner 208 is movable along a horizontal axis 433 (e.g., along the track 210) and the carousel robot 418 is movable along the vertical axis 421 (e.g., via the linear actuator 422), which is perpendicular to the horizontal axis 433. The positioner 208 has access to all of the slots 134 in the loading bay 132 and the carousel robot 418 has access to the storage carousel 420 (e.g., having a plurality of shelves with slots) disposed within the storage housing 402 that stores one or more of the carriers 124. The positioner 208 has been removed from FIG. 5 for clarity.

As disclosed herein, one or more of the carriers 124 may be loaded into the loading bay 132 and may be accessed by the positioner 208. To transfer one of the carriers 124 between the positioner 208 and the carousel robot 418, the storage module 100 includes a tray 500, as shown in FIG. 5, (e.g., a transfer location, a hand-off location, a swap location, a transfer area, a transfer position) that can support one or more of the carriers 124 and is accessible by both the positioner 208 and the carousel robot 418. In FIG. 5, the positioner 208 has been removed for clarity.

Figure 8:
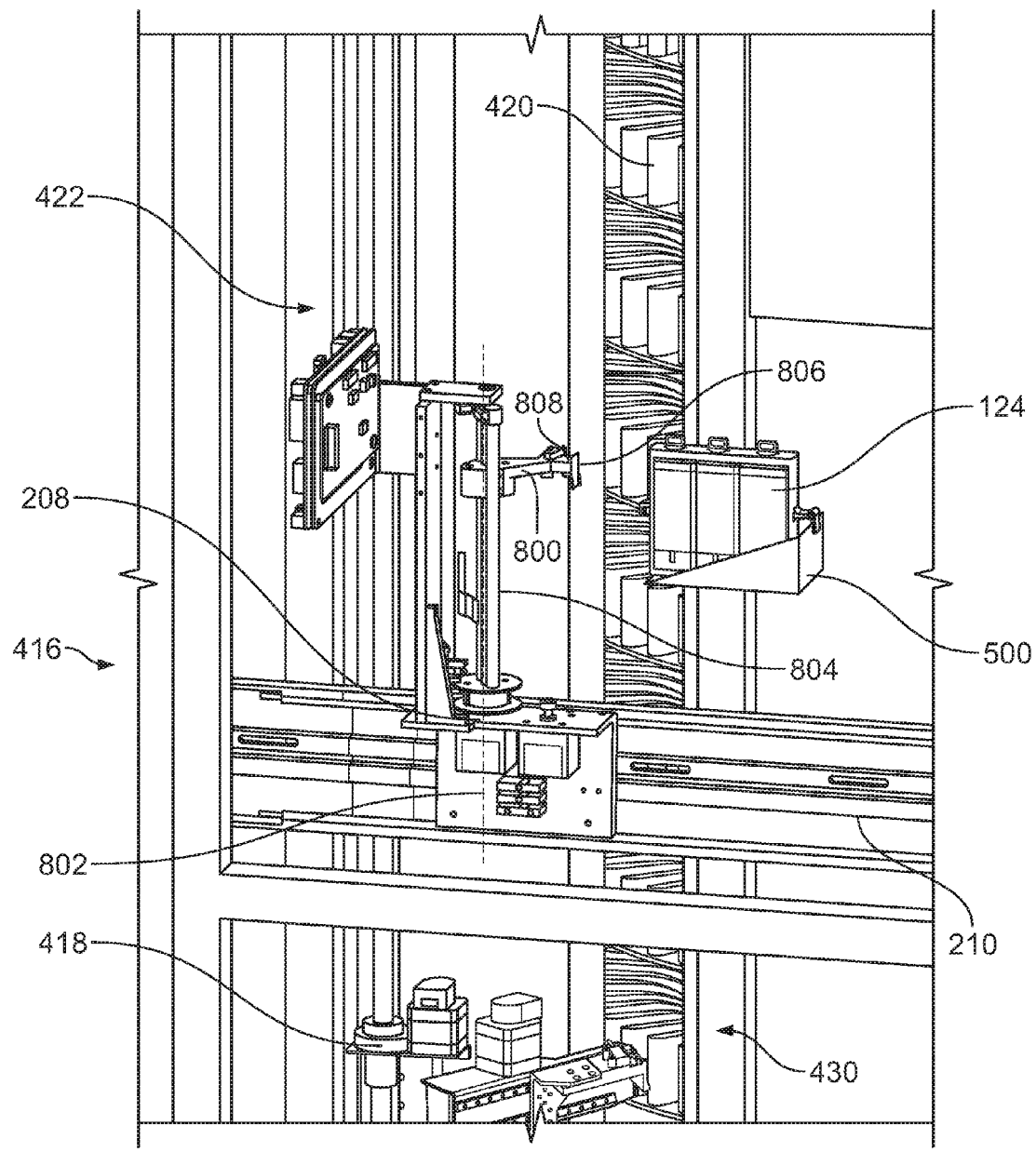
FIG. 8 illustrates an example carrier transport system of the example storage module of FIG. 4 having a positioner and a carousel robot for transporting one or more carriers.

FIG. 8 illustrates an enlarged view of the carrier transport system 416 with the loading bay 132 removed for clarity. In the illustrated example, the positioner 208 includes an arm 800, which is movable along a vertical axis 802 via, for example, a linear actuator 804 (e.g., a ball screw linear actuator) and rotatable (e.g., pivotable) about the vertical axis 802 (e.g., via an actuator). In other examples, other suitable device(s) may be used to move the positioner 208. The distal end of the arm includes a hand 806 having an opening 808 to receive a tab of one of the carriers 124 (e.g., the engagement tab 316 of the reagent carrier 124, 310). The positioner 208 may be structurally and functionally similar to, for example, the positioner 200 of the analyzer RSH 128 in FIGS. 1 and 2. In the illustrated example, the carrier transport system 416 includes two carrier transporters: the positioner 208 and the carousel robot 418. However in other examples, the carrier transport system 416 may include more or fewer carrier transporters that may be arranged in different configurations to transport carriers therebetween.

In an example process to transfer one of the carriers 124 from one of the slots 134 in the loading bay 132 to the storage housing 402 (e.g., for storage), the positioner 208 retrieves the carrier 124 from the slot 134 in the loading bay 132. After retrieving the carrier 124, the positioner 208 moves along the track 210 (e.g., along the horizontal axis 433) to a position adjacent the tray 500 and deposits the carrier 124 in the tray 500. The carousel robot 418 then moves along the vertical axis 421, via the linear actuator 422, to a position adjacent the tray 500 and retrieves the carrier 124. After retrieving the carrier 124, the carousel robot 418 moves upward or downward along the opening 430 and deposits the carrier 124 onto the carousel 420 in storage housing 402. This process may also be performed in reverse to remove one of the carriers 124 from the storage housing 402 and transfer the carrier 124 to the loading bay 132 and/or the transfer location 136. Further details of these operations are disclosed herein.

In the illustrated example, one transfer location (e.g., the tray 500) is implemented to transfer or hand-off carriers 124 between the positioner 208 and the carousel robot 418. However, in other examples, there may be multiple transfer locations (e.g., multiple trays) that may be implemented to transfer carriers 124 between the positioner 208 and the carousel robot 418. In such an example, the trays may be located adjacent each other. In other examples, the trays may be located at different heights, such as for example, with one above the other.

In some instances, one or more of the carriers 124 may have one or more containers having caps (e.g., lids), which are often utilized during shipping to prevent the liquid contents from spilling or becoming contaminated. The storage module 100 may store the carriers 124 with or without the cap(s) on the container(s). In some examples, prior to transporting one of the carriers 124 to an analyzer (e.g., the array of analyzers 104 of FIGS. 1 and 2), it may advantageous to remove the cap(s) of the container(s). Additionally, when returning one or more of the carriers 124 to the storage module 100 (e.g., after being used by an analyzer), it may be advantageous to cap (e.g., recap) the container(s) of the carrier 124 prior to placing the carrier 124 into the storage housing 402 for storage. As illustrated in FIGS. 4-6, the example storage module 100 includes a capper/decapper 434 to remove caps from containers in a carrier and/or place caps (or septums) onto the container of a carrier. In some examples, the storage module 100 includes a cap hopper that has a plurality of caps and transfers the caps to the capper/decapper 434 to be placed onto the containers of the carriers 124.

In some examples, the carousel robot 418 transfers one of the carriers 124 to the capper/decapper 434 and deposits the carrier 124 at the capper/decapper 434 where the capper/decapper 434 performs the related capping and/or decapping operations. Additionally or alternatively, in some examples the carousel robot 418 holds the carrier 124 in a position adjacent the capper/decapper 434 while the capper/decapper 434 performs the related capping and/or decapping operations on the carrier 124.

In the illustrated example, the storage module 100 includes a waste chute 436 that leads from the capper/decapper 434 to an onboard waste container 438. Caps that have been removed from the carriers 124 may be disposed of by transferring the caps to the waste container 438 via the chute 436. In some examples, one or more container(s) on a carrier and/or an entire carrier may be disposed of by depositing the container(s) and/or carrier in the waste container 438 (e.g., when the container and/or each of containers in a carrier is empty, defective, expired, etc.).

In some examples, the storage module 100 includes a mixer, which may be integrated with the capper/decapper 434, to mix or stir the liquids in the carriers 124 prior to storing the carriers in the storage housing or transferring the carriers 124 to the one or more analyzers 106-114 (FIG. 1) and/or an LAS. For example, some reagents contain microparticles that may settle at a bottom of a container. A mixer may be provided to mix (e.g., by vibrating) the carrier and/or the individual container to stir up the mixcroparticles within the reagent liquid.

To identify the carriers 124 and/or the individual containers in the carriers 124, the example storage module 100 includes a camera 440 (FIG. 4) or other type of reading device that can capture, scan, and/or otherwise read human-readable and/or machine-readable indicia. The camera 440 is located adjacent the linear actuator 422 (e.g., near the path of travel of the carousel robot 418, near the screw 423). After retrieving one of the carriers 124 from the tray 500 (FIGS. 5 and 8), the carousel robot 418 moves the carrier 124 to a position in front of the camera 440 to be read. The carriers 124 and/or the containers in the carriers 124 may have one or more bar codes, radio frequency identification (RFID) tags and/or any other type of identification indicia that is readable by a camera or reader (e.g., a Quick Read (QR) code). Additionally or alternatively, the camera 440 may be able to detect whether the containers of the carrier 124 have caps. In the illustrated example, the storage module 100 includes an electronics module 442, which may include one or more processing or computing components for controlling the operations of the storage module 100 and/or communicating with other instruments in a workcell and/or an LAS (e.g., the array of analyzers 104 of FIGS. 1 and 2).

The example frame 400 of the storage module 100 (FIG. 4) is illustrated in FIGS. 9-11. FIG. 9 is a front perspective view of the frame 400, FIG. 10 is a side view of the frame 400 and FIG. 11 is a front side view of the frame 400. The frame 400 includes a base frame 900, a first vertical support frame 902 and a second vertical support frame 904. The first and second vertical support frames 902, 904 are coupled to the base frame 900 at their respective bottoms and coupled to each other at their respective tops. In the illustrated example, a portion of the base frame 900 and the first vertical support frame 902 define an area to support the storage housing 402 (FIG. 4). The frame 400 also provides support for the various components of the storage module 100 (e.g., the positioner 208, the track 210, the carousel robot 418, the capper/decapper 434, etc.), which may be coupled, directly or indirectly, to the frame 400. In the illustrated example, a first wheel 906, a second wheel 908, a third wheel 910 and a fourth wheel 912 are coupled to the base frame 900 and enable the frame 400 (and, thus, the storage module 100) to be moved (e.g., across a floor of a laboratory). In some examples, one or more of the wheels are casters. Also, adjacent to the first, second, third and fourth wheels 906-912 are respective first, second, third and fourth stabilizers 914, 916, 918, 920 (e.g., feet), which are coupled to the frame base frame 900. The stabilizers 914-920 may be used to secure or stabilize the frame 400 on a supporting surface.

In the illustrated example, the frame 400 is constructed of a plurality of square or rectangular tubes or profiles coupled together. In other examples, the frame 400 may be constructed of tubes having other shapes. The tubes that define the frame 400 may coupled to each other using any suitable fastening techniques known to those skilled in the art (e.g., via welding, via mechanical fasteners, via adhesives, etc.). Additionally, more or fewer tubes may be used in the frame 400.

Figure 12:
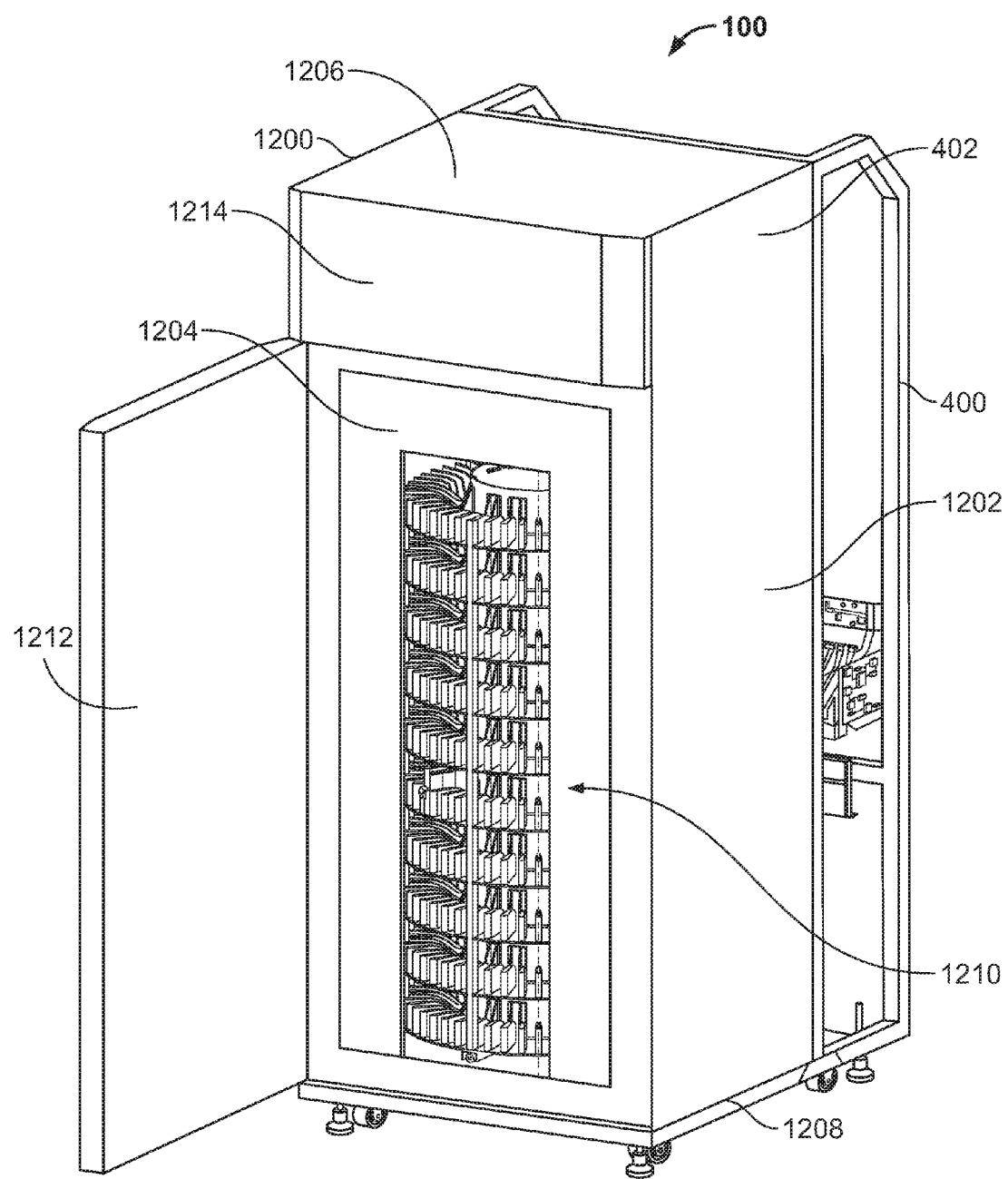
FIG. 12 is a rear perspective view of an example storage housing of the example storage module of FIG. 4 having an example door, illustrated in an open position, and an example refrigeration unit to cool the storage housing.

FIG. 12 shows a rear perspective view of the storage module 100. The storage housing 402, which is coupled to the frame 400, is defined by the front side wall 432 (FIG. 4.), a right side wall 1200, a left side wall 1202, a rear side wall 1204, a top wall 1206 and a bottom wall 1208. To provide access to the interior of the storage housing 402, the rear side wall 1204 includes an opening 1210 and a door 1212 that opens and closes over the opening 1210.

The storage module 100 includes a refrigeration unit 1214 to cool the inside of the storage housing 402. In some examples, the carriers 124 have liquids that are subject to deterioration. Cooling the inside of the storage housing 402 provides optimal stability for storing the carrier liquids (e.g., increases the lifespan). In the illustrated example, the refrigeration unit 1214 is disposed at a top of the storage housing 402. However, in other examples, the refrigeration unit 1214 may be disposed in other locations inside and/or outside the storage housing 402. For example, the refrigeration unit 1214 may be located beneath the loading bay 132 (FIG. 4) and the relatively cool air may be directed into the storage housing 402 via channels or ducts.

FIGS. 13-16 show different views of the example storage housing 402 (i.e., without any of the other components from the storage module 100) illustrating the front, right, left, right, rear, top and bottom side walls 432, 1200, 1202, 1204, 1206, 1208. FIG. 13 is a rear perspective view of the storage housing 402 with the door 1212 in an open position. The door 1212 opens to expose the opening 1210 in the rear side wall 1204. FIG. 14 is a front perspective view of the storage housing 402 and the vertical opening 430 in the front side wall 432. FIG. 15 shows a left side view of the storage housing 402 with the door 1212 in a closed position. FIG. 16 shows a rear side view of the storage housing 402 with the door 1212 in a closed position.

Figure 18:
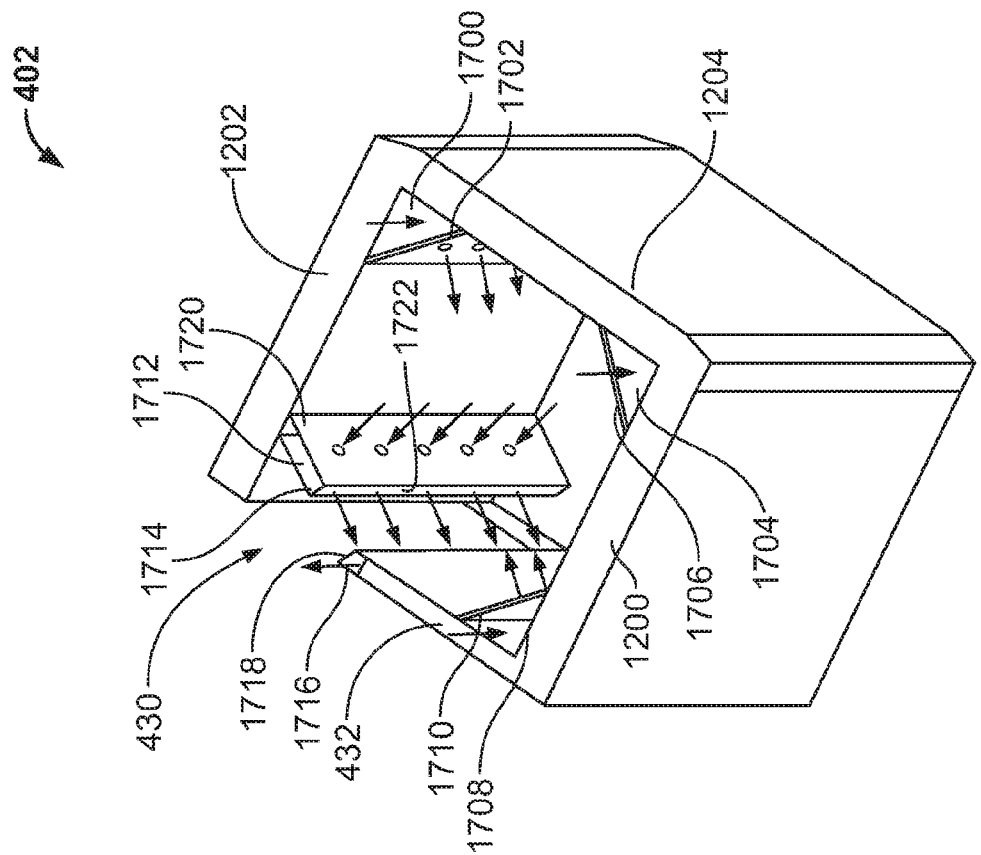
FIG. 18 is a perspective view of the example cross-sectioned storage housing of FIG. 17 illustrating example flow paths of air used to create an example aircurtain across an example opening in the example storage housing.
Figure 17:
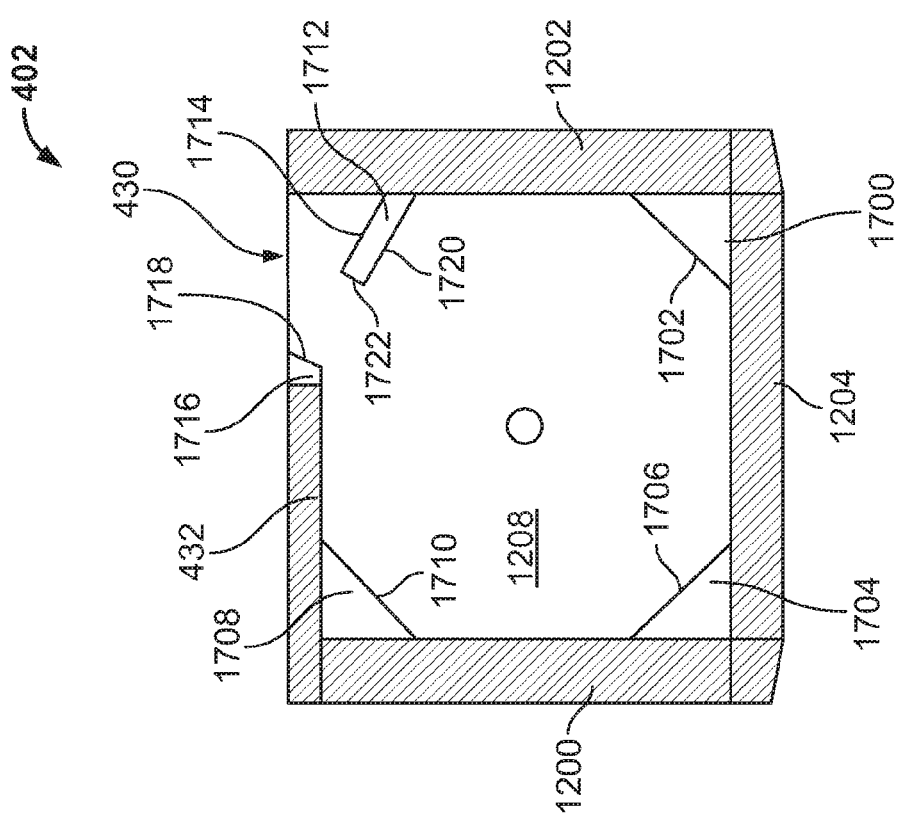
FIG. 17 is a cross-section view of the example storage housing taken along line A-A in FIG. 16.

FIG. 17 is a cross-sectional view of the storage housing 402 taken along line A-A in FIG. 16, and FIG. 18 is a perspective view of the cross-sectioned storage housing 402 in FIG. 17. To maintain a relatively lower air temperature inside the storage housing 402, an aircurtain (e.g., a wall of moving air) is generated across the opening 430 in the front side wall 432 of the storage housing 402, which reduces airflow into and out the storage housing 402 through the opening 430. In the illustrated example, relatively cooler air from the refrigeration unit 1214 (FIG. 12) is directed downward into the storage housing 402 and the relatively warmer exhaust air (e.g., return air) is blown across the opening 430 and directed upward back into the refrigeration unit 1214. The resulting curtain of moving air that is passing across the opening 430 reduces the ability for outside air to move into the storage housing 402 and displace the cooler internal air and vice versa.

As illustrated in FIGS. 17 and 18, the storage housing 402 includes a first channel 1700 (e.g., funnel) defined by a first duct plate 1702 and the corner of the left side wall 1202 and the rear side wall 1204. The first duct plate 1702 has a plurality of holes or apertures disposed along the height of the first duct plate 1702. The relatively cooler air generated by the refrigeration unit 1214 is ducted downward through the first channel 1700. As the relatively cooler air travels downward through the first channel 1700, the air is dispersed through the plurality of apertures in the first duct plate 1702 into the interior of the storage housing 402. In the illustrated example, a second channel 1704 is defined by a second duct plate 1706 and the corner of the rear side wall 1204 and the right side wall 1200, and a third channel 1708 is defined by a third duct plate 1710 in the corner defined by the right side wall 1200 and the front side wall 432. The second and third channels 1704, 1708 include a plurality of holes or apertures and operate similar to the first channel 1700.

To create the aircurtain, the storage housing 402 includes an aircurtain channel 1712 defined by an aircurtain duct 1714, which is disposed on the left side wall 1202 near one side of the opening 430, and a return channel 1716 defined by a return duct 1718 disposed on the front side wall 432 adjacent the other side of the opening 430. The aircurtain duct 1714 includes a plurality of apertures along the height of the aircurtain duct 1714 on an inlet side 1720 and an outlet side 1722. The return duct 1718 also includes a plurality of apertures along a height of the return duct 1718. The return channel 1716 is ducted to an intake (e.g., a return) of the refrigeration unit 1214, which creates a vacuum within the return channel 1716. A fan is disposed within the aircurtain channel 1712 and draws the relatively warmer exhaust air from inside the storage housing 402 into the aircurtain channel 1712, via the plurality of apertures in the inlet side 1720 of the aircurtain duct 1714, and directs the air out of the plurality of apertures in the outlet side 1722 toward the return duct 1718. In the illustrated example, the outlet side 1722 of the aircurtain duct 1714 is facing the return duct 1718. The warmer exhaust air is directed outward from the outlet side 1722 of the aircurtain duct 1714 and is drawn into the return channel 1716 through the plurality of apertures in the return duct 1718. As a result, a wall of return air (moving substantially horizontally) is created across the opening 430 and, thus, prevents the exchange of air across the aircurtain that would otherwise affect the temperature of the air inside of the storage housing 402. FIG. 18 shows example flow arrows illustrating the flow path of the air into and out of the first, second and third channels 1700, 1704, 1708, the aircurtain channel 1712 and the return channel 1716.

In the illustrated example, the storage housing 402 includes three channels (e.g., the first, second and third channels 1700, 1704, 1708) for directing cooler air into the storage housing 402. However, in other examples, more or fewer channels may be used and the channels may be disposed in other locations in the storage housing 402. Additionally, other example channel configurations may be implemented to create the aircurtain across the opening 430.

Figure 19:
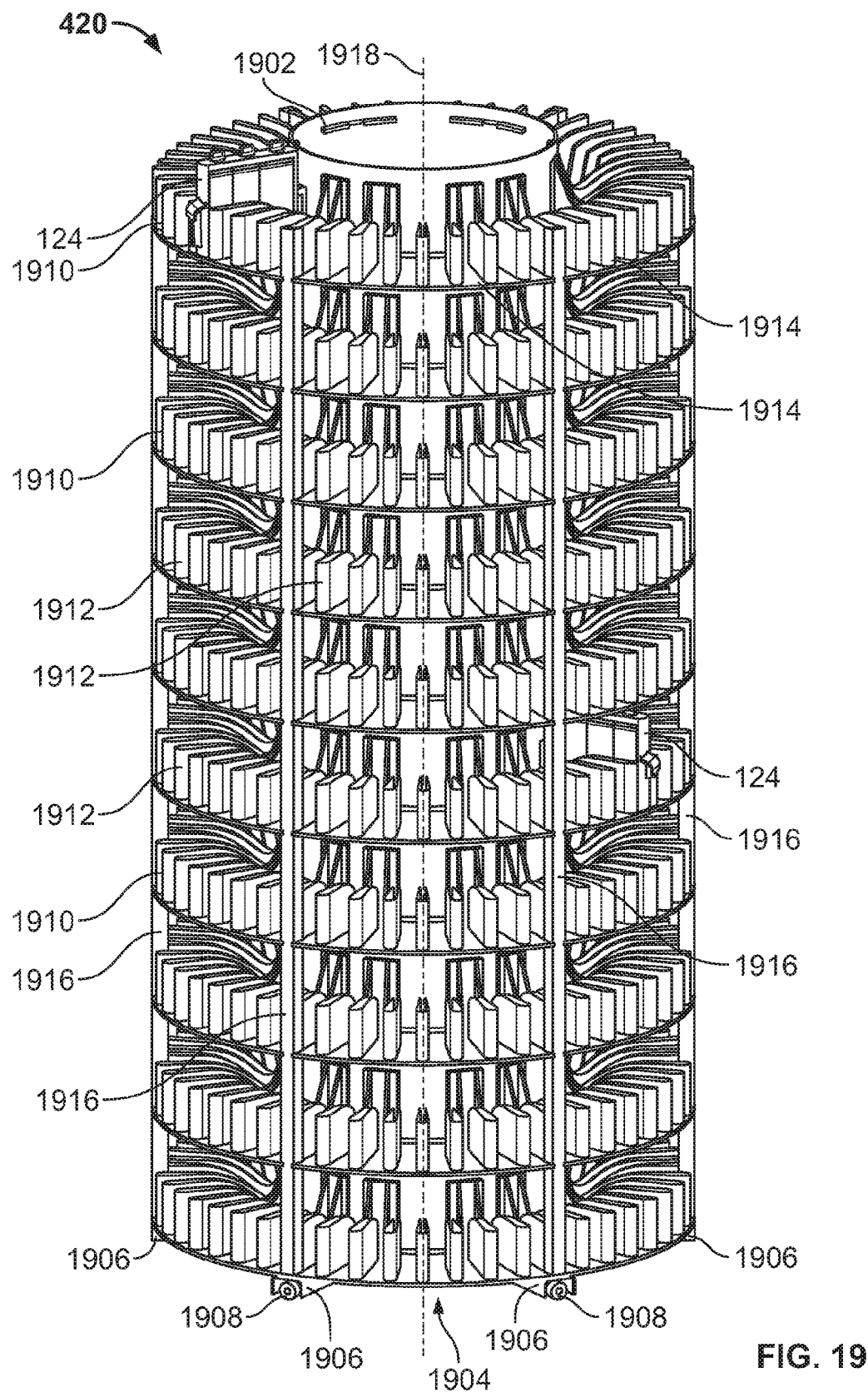
FIG. 19 illustrates an example storage carousel of the example storage module of FIG. 4 having a plurality of cassettes that form shelves with slots to store carriers.

The example storage carousel 420 is illustrated in FIG. 19. The carousel 420 includes a plurality of shelves to accommodate the carriers 124 inside of the storage housing 402 (FIG. 4). In the illustrated example, the carousel 420 has a center support column 1902 that is supported by a base 1904. The base 1904 includes a plurality of cross-bars 1906. Each of the cross-bars 1906 includes a wheel or bearing 1908 that enables the carousel 1900 to rotate. In the illustrated example, six cross-bars 1906 are used. However, in other examples, the carousel 420 may include more or fewer cross-bars 1906.

The carousel 420 includes a plurality of shelves 1910 (e.g., decks, carousels, etc.), and each of the shelves 1910 has a plurality of slots 1912 arranged annularly around the shelves 1910 to receive the carriers 124. In the illustrated example, the carousel 420 has ten shelves 1910, each with forty-eight (48) slots 1912, which totals 480 slots 1912. Therefore, the carousel 420 can accommodate 480 carriers 124. However, in other examples, the carousel 420 may include more or fewer shelves 1910 (e.g., two shelves, five shelves, thirty shelves) and each of the shelves 1910 may include more or slots 1912 (e.g., four slots, ten slots, fifty slots). In the illustrated example, each of the shelves 1910 is formed by a plurality of cassettes 1914. The cassettes 1914 are coupled to the center support column 1902 at different heights to form the respective shelves 1910. In the illustrated example, each of the shelves 1910 is formed by six of the cassettes 1914, and each of the cassettes 1914 has eight of the slots 1912. In other examples, more or fewer cassettes 1914 may be employed to form each of the shelves 1910 and each of the cassettes 1914 may include more or fewer slots 1912.

To further support or secure the cassettes 1914, the example carousel 420 includes a plurality of vertical support rails 1916 that couple two adjacent cassettes 1914 in each of the shelves 1910. In the illustrated example, there are six support rails 1916 that are coupled between adjacent ones of the cassettes 1914 to form the shelves 1910. The support rails 1916 are coupled at their respective bottoms to the cross-bars 1906. When disposed in the storage housing 402 (FIG. 4), the example storage carousel 420 is rotatable a vertical axis 1918.

FIGS. 20 and 21 show front and rear views, respectively, of the example carousel 420 without the shelves 1910 and the support rails 1916 (FIG. 19). In the illustrated example, the center support column 1902 is coupled to the base 1904, which includes the plurality of cross-bars 1906 extending outward from the center support column 1902. The center support column 1902 has a plurality of slots 2000 where the cassettes 1914 are coupled (e.g., clipped, hinged, hung).

Figure 22:
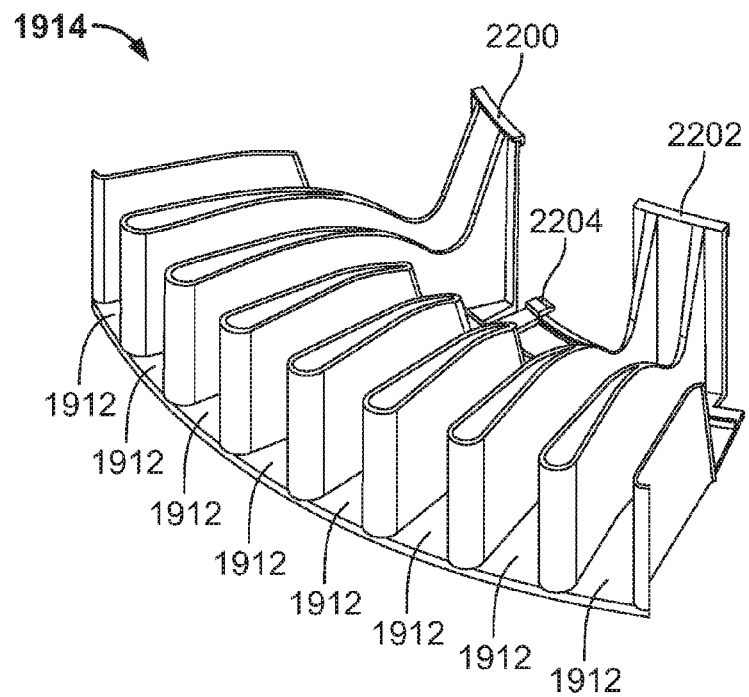
FIG. 22 is a front perspective view of one of the example cassettes of FIG. 19.
Figure 23:
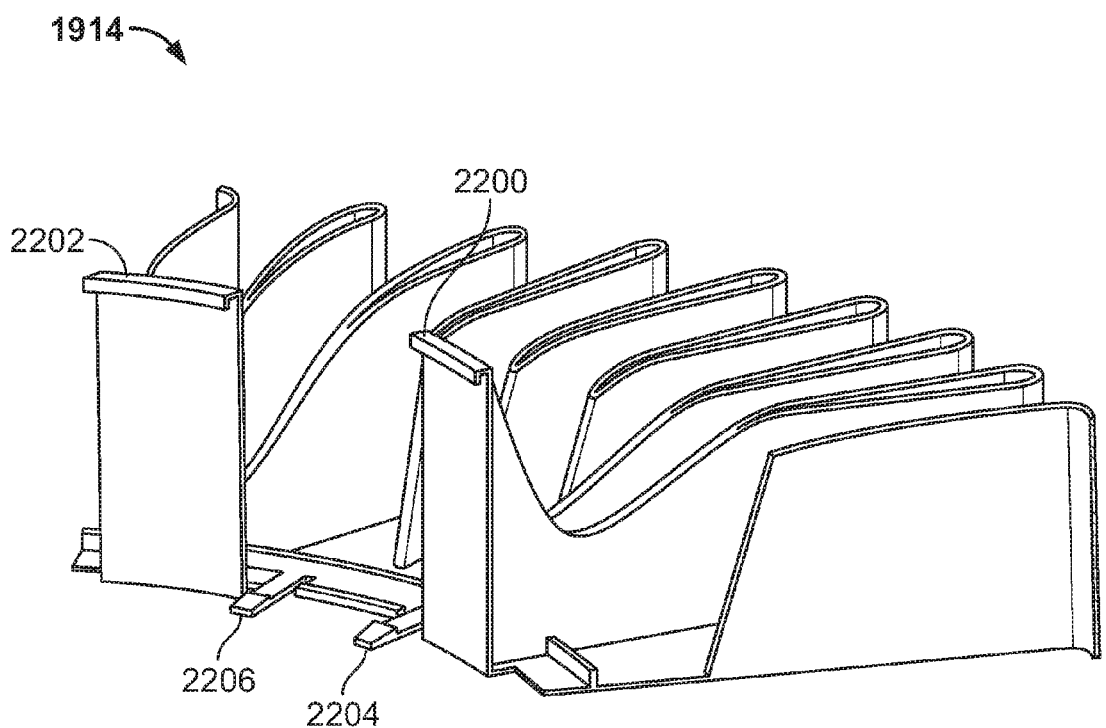
FIG. 23 is a rear perspective view of one of the example cassettes of FIG. 19.

One of the example cassettes 1914 is illustrated in FIGS. 22 and 23. As illustrated, the cassette 1914 includes eight of the slots 1912 to accommodate up to eight of the carriers 124. The example cassette 1914 has two clips 2200, 2202 and two tabs 2204, 2206, which enable the cassette 1914 to be removably coupled to the center support column 1902. An example of one of the cassettes 1914 coupled to the center support column 1902 is illustrated in FIG. 21. The clips 2200, 2202 and the tabs 2204, 2206 engage the slots 2000 in the center support column 1902. In other examples, the cassettes 1914 may be coupled to the center support column 1902 using other types of fastener(s).

Figure 25:
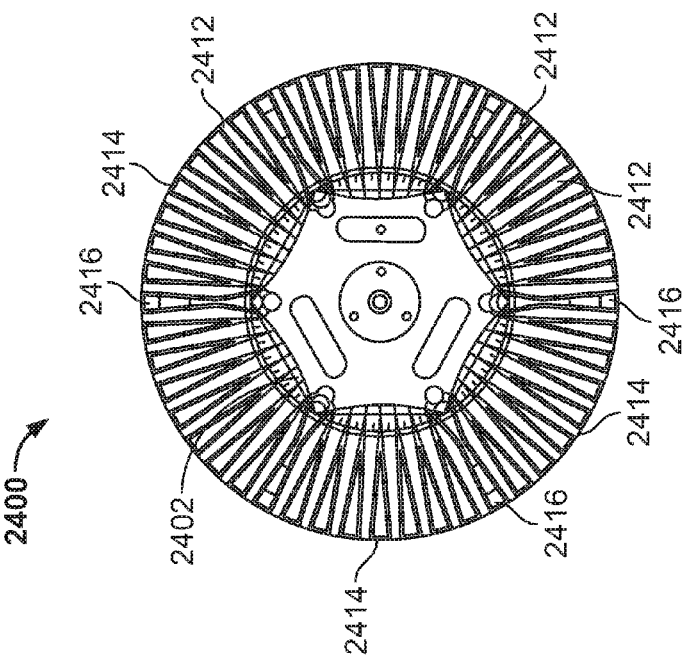
FIG. 25 is a top view of the example storage carousel of FIG. 24.
Figure 24:
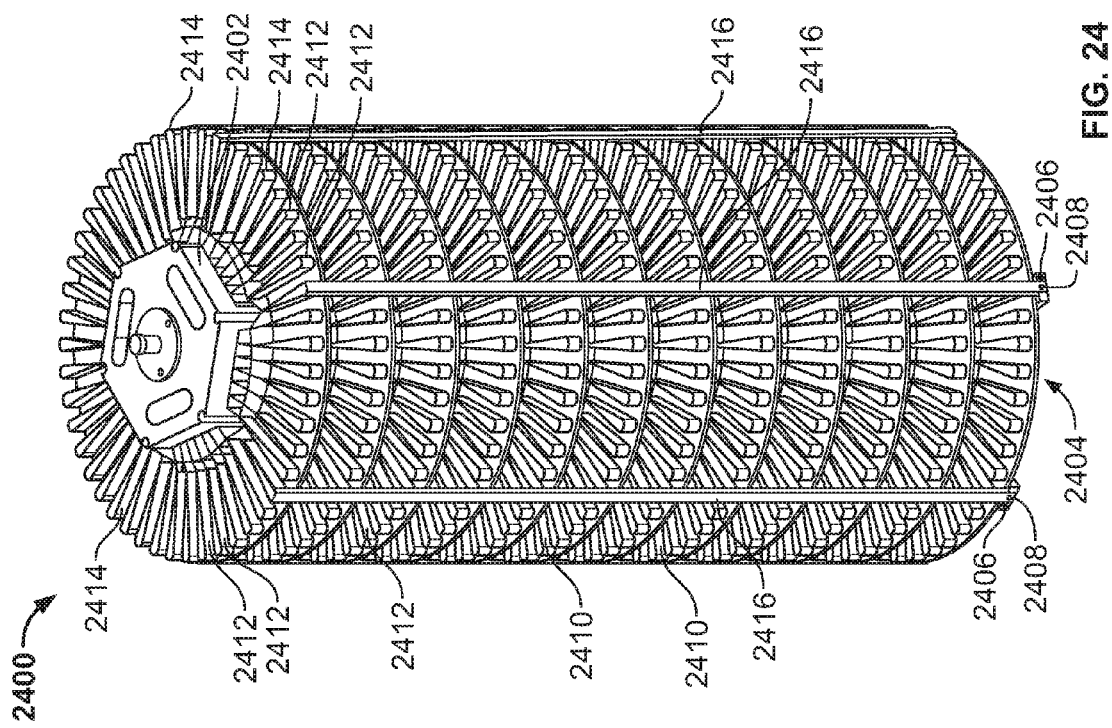
FIG. 24 illustrates an alternative storage carousel with an example hexagonal center support column that may be used in the example storage module of FIG. 4 to store carriers.

In the illustrated example of FIGS. 19-21, the center support column 1902 is circular in shape, and the cassettes 1914 are curved to match the circumferential arcs of the center support column 1902. However, in other examples, the center support column 1902 may have other shapes. For example, another example carousel 2400 is illustrated in FIGS. 24 and 25. The example carousel 2400 employs a center support column 2402 having six-sided or hexagon shape. The carousel 2400 includes a base 2404, a plurality of cross-bars 2406, wheels 2408, a plurality of shelves 2410, a plurality of slots 2412, a plurality of cassettes 2414 that form the shelves 2410, and a plurality of support rails 2416, which may be similar in structure and function to the respective components of the carousel 420 illustrated in FIG. 19. However, because the center support column 2402 of the example carousel 2400 has six flat sides instead of a smooth circular side like the center support column 1902 of the example carousel 420 (FIG. 19), the example cassettes 2414 are shaped to engage the flat sides. Specifically, the side of the cassettes 2414 that are to engage (e.g., but up against or otherwise be supported by) the center support column 2402 are flat instead of curved. In other examples, the center support column 2402 may have a different number of sides (e.g., three sides, five sides, ten sides) and the cassettes 2414 may be shaped to correspond accordingly. The example storage module 100 (FIG. 4) may employ any of the example carousels disclosed herein (e.g., the example carousel 420, the example carousel 2400, a carousel with a three-sided center support column, etc.).

To enable the carousel robot 418 (FIG. 4) to access any of the slots 1912 of the example carousel 420, the carousel 420 is rotatably disposed within the storage housing 402 (FIG. 4). FIG. 26 shows the example carousel 420 supported on the bottom wall 1208 of the storage housing 402 (FIG. 4). The other sides of the storage housing 402 and many of the other components of the storage module 100 have been removed for clarity. FIG. 27 is an enlarged view of the interface between the carousel 420 and the bottom wall 1208 of the storage housing 402. As illustrated, the wheels 1908 of the carousel 420 move along a guide plate 2700 coupled to the bottom wall 1208.

Figure 28:
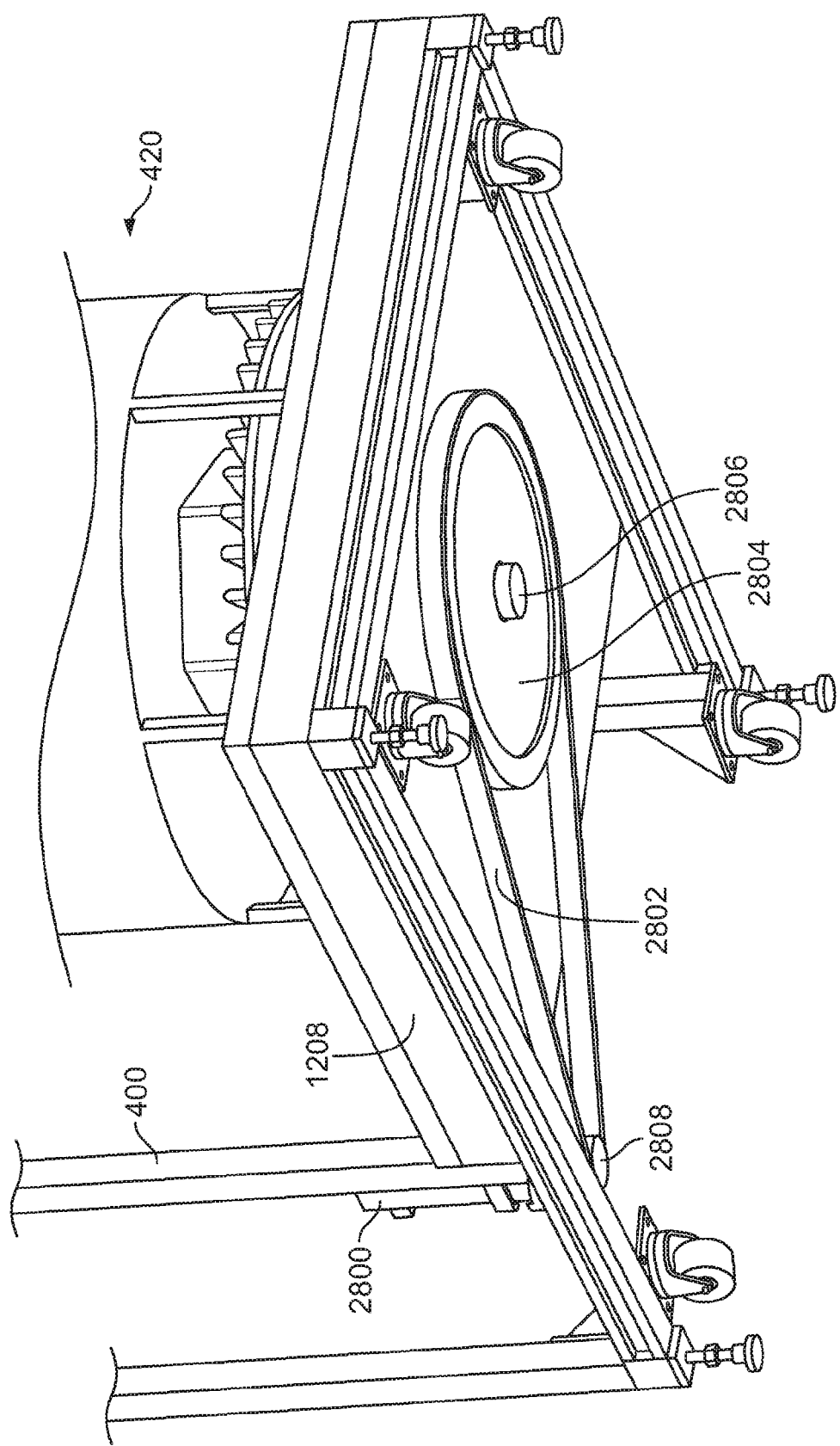
FIG. 28 is a bottom perspective view of the bottom wall in FIG. 14 illustrating an example actuator and pulley for rotating the example storage carousel.
Figure 29:
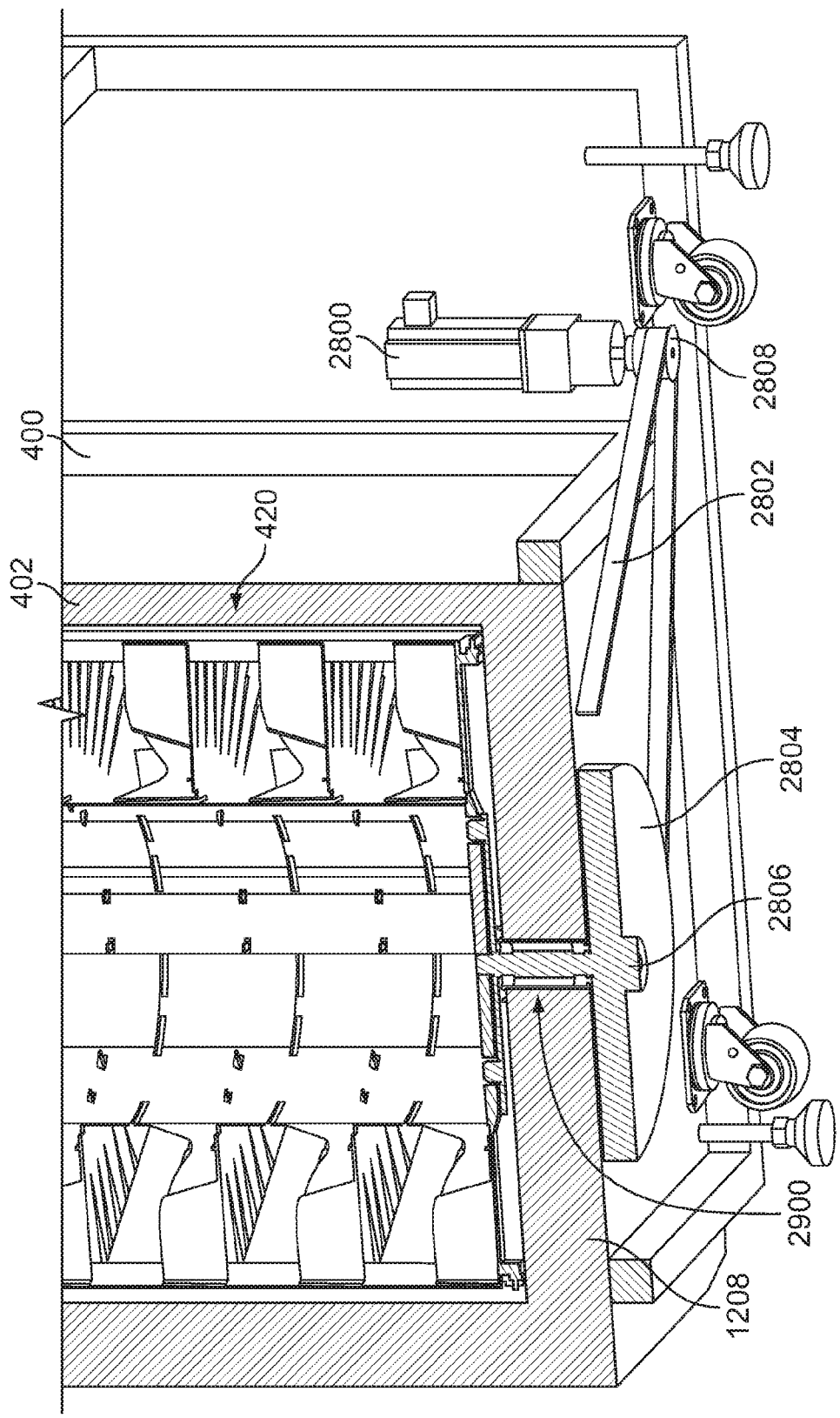
FIG. 29 is a cross-sectional view of the example storage carousel of FIG. 19 with the example storage housing of FIG. 12 illustrating the example actuator and pulley of FIG. 28.

FIG. 28 shows a bottom perspective view of the frame 400 and the bottom wall 1208 of the storage housing 402 (FIG. 4), and FIG. 29 shows a cross-sectional view of the storage housing 402 and the carousel 420. In the illustrated example, the storage module 100 includes an actuator 2800 (e.g., a motor, a DC servo motor, an electric motor) to drive the carousel 420. The actuator 2800 is disposed outside of the storage housing 402. The actuator 2800 drives the carousel 420 via a belt 2802 coupled to a pulley or gear 2804 disposed beneath the bottom wall 1208 of the storage housing 402. The carousel 420 is coupled to the pulley 2804 by an axle 2806 (e.g., a crankshaft). As illustrated in FIG. 29, the axle 2806 extends through an aperture 2900 in the bottom wall 1208 of the storage housing 402. The actuator 2800 rotates a gear 2808 (e.g., a planetary gear), which drives the belt 2802 to rotate the pulley 2804, which rotates the carousel 420 within the storage housing 402. In the illustrated example, the entire carousel 420 is rotated by the actuator 2800. However, in other examples, each of the shelves 1910 (FIG. 19) may operate independently of the other shelves 1910 and may rotate independently from each other. For example, each of the shelves 1910 may include an actuator and pulley arrangement to operate the respective shelves 1910.

Figure 30:
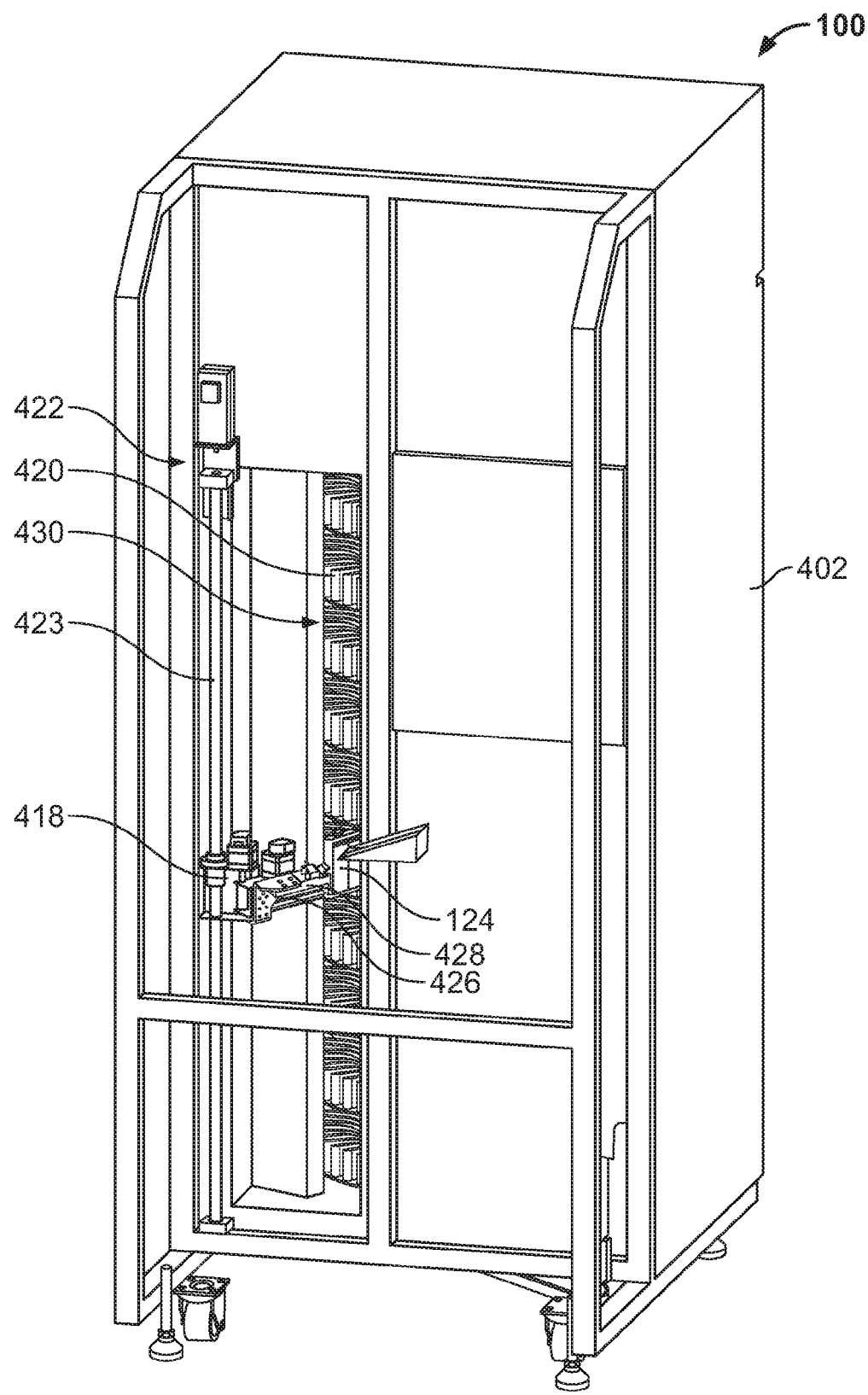
FIG. 30 is a front perspective view of the example storage module of FIG. 4 illustrating the example carousel robot of FIG. 8.
Figure 31:
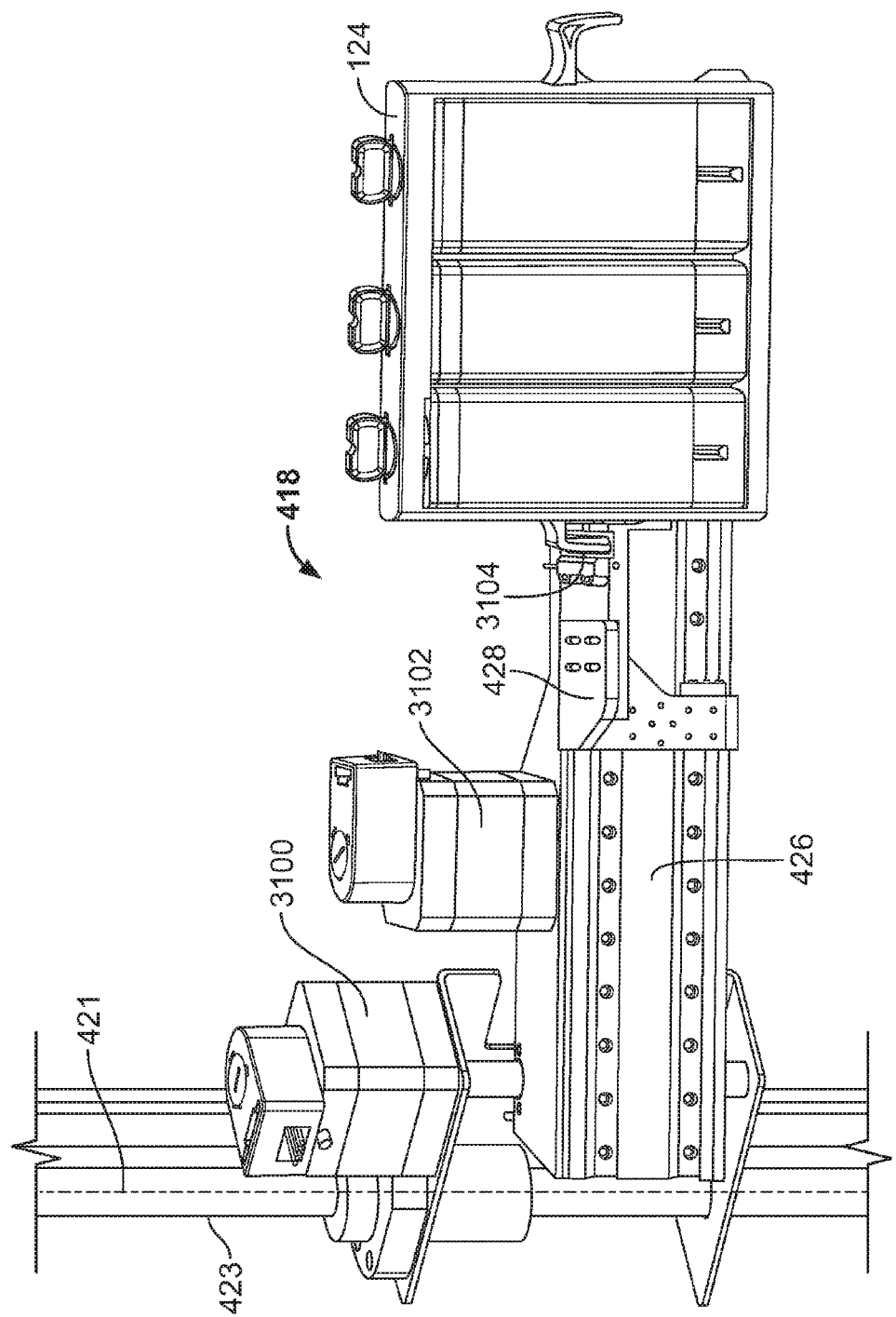
FIG. 31 is an enlarged view of the example carousel robot of FIG. 30 illustrating an example arm and an example hand that are movable via respective actuators.

FIG. 30 illustrates the carousel robot 418 engaged with one of the carriers 124 on the carousel 420. As disclosed herein, the carousel robot 418 is movable upward and downward via the linear actuator 422 outside of the storage housing 402. The carousel robot 418 can access one of the carriers 124 on the carousel 420 by rotating the arm 426 into the opening 430 and moving the hand 428 to a position to engage the carrier 124. An enlarged view of the example carousel robot 418 holding one of the carriers 124 is illustrated in FIG. 31. To rotate the arm 426 of the carousel robot 418, the carousel robot 418 includes a first actuator 3100 (e.g., a DC servo motor, a stepper motor (with a planetary gear), etc.). The first actuator 3100 causes the arm 426 to rotate about the vertical axis 421 (e.g., the axis defined by the screw 423 of the linear actuator 422). The hand 428 is extendable or movable along the arm 426 via a second actuator 3102 (e.g., a DC servo motor, a stepper motor, etc.). The hand 428 has an opening or slot 3104 to receive a tab on the carrier 124 (e.g., the engagement tab 316 of the reagent carrier 124, 310). An enlarged view of the example hand 428 and the slot 3104 of the carousel robot 418 are illustrated in FIG. 32. To engage a carrier 124, the carousel robot 418, for example, rotates the arm 426 (e.g., via the first actuator 3100) to a position aligned with the carrier 124 and moves the hand 428 radially (e.g., distally) outward to a position below the carrier tab such that the carrier tab is aligned vertically above the slot 3104 of the hand 428. Then, the carousel robot 418 moves upward, via the linear actuator 422, which causes the carrier tab to be inserted into the slot 3104 of the hand 428. The carousel robot 418 may then retract the hand 428 and/or rotate the arm 426 to clear the carrier 124 from any nearby objects before moving the carrier 124 to another position. This process can be performed in reverse to deposit one of the carriers 124 (e.g., to deposit the carrier 124 in one of the slots 1912 of the carousel 420 or the tray 500).

In the illustrated example, the carousel robot 418 engages one of the carriers 124 via the slot 3104 in the hand 428. However, in other examples, the carousel robot 418 may employ other mechanism(s) to engage the carrier 124 such as, for example, gripper(s).

Figure 33A:
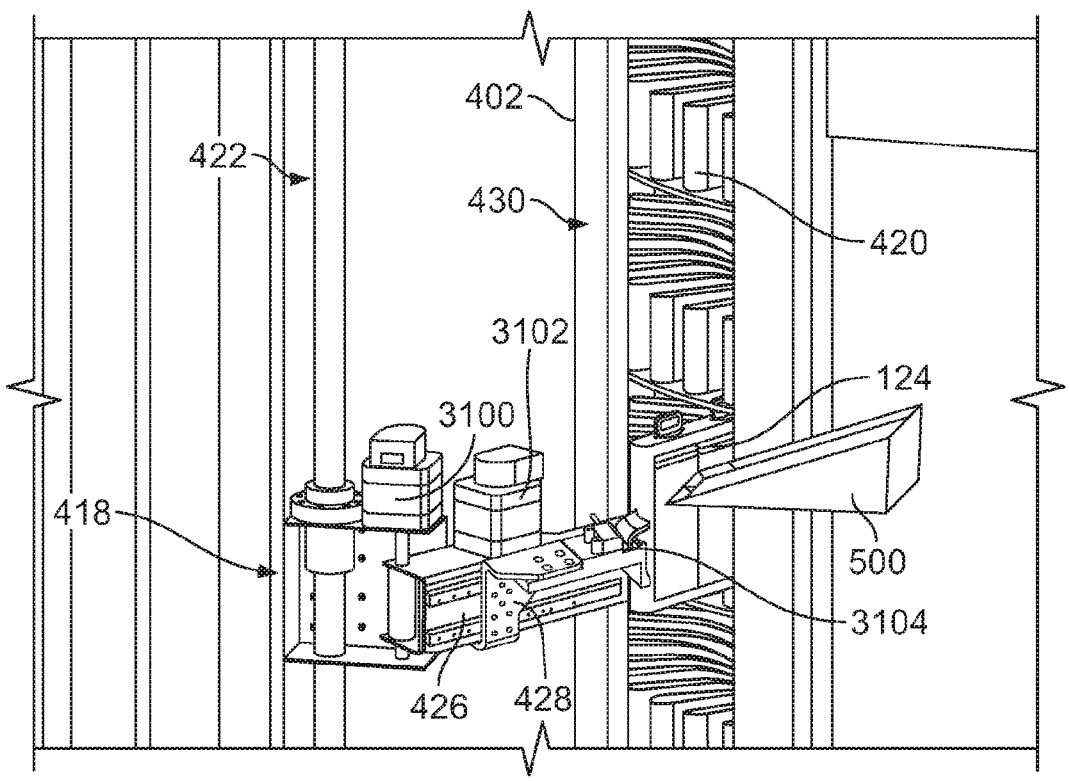
FIGS. 33A, 33B, 33C, 33D, 33E and 33F show an example sequence of the example carousel robot of FIG. 30 transporting a carrier from an example carousel to an example transfer location.
Figure 33B:
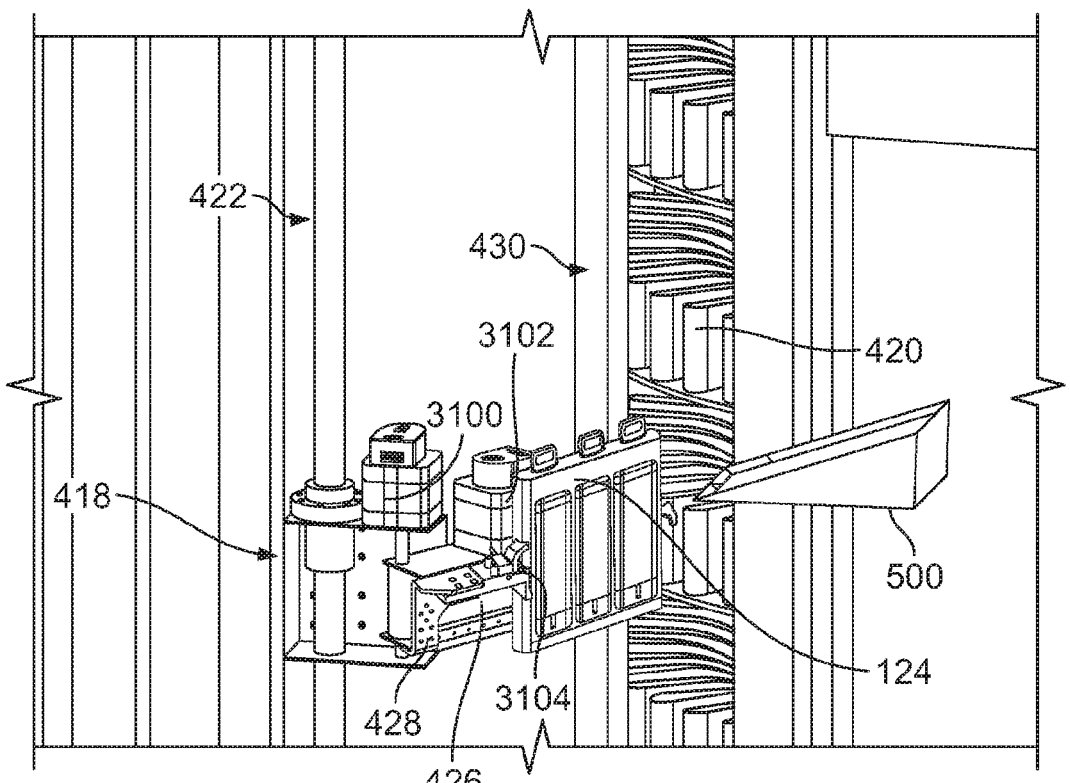

FIGS. 33A, 33B, 33C, 33D, 33E and 33F illustrate an example sequence of retrieving one of the carriers 124 from the carousel 420 and depositing the carrier 124 in the tray 500. As disclosed herein, to engage the carrier 124, the arm 426 of the carousel robot 418 is aligned with the carrier 124 (e.g., using the first actuator 3100) at a height that is below the carrier tab. The hand 428 is extended through the opening 430 of the storage housing 402, such the slot 3104 on the hand 428 is aligned vertically below the carrier tab. The carousel robot 418 is then moved upward (e.g., via the linear actuator 422) and the carrier tab is inserted into the slot 3104. Once engaged, the carousel robot 418 retracts the hand 428 radially inward along the arm 426 using the second actuator 3102, as illustrated in FIG. 33A. The hand 428 is retracted until the carrier 124 is clear from the carousel 420, as illustrated in FIG. 33B.

Figure 33C:
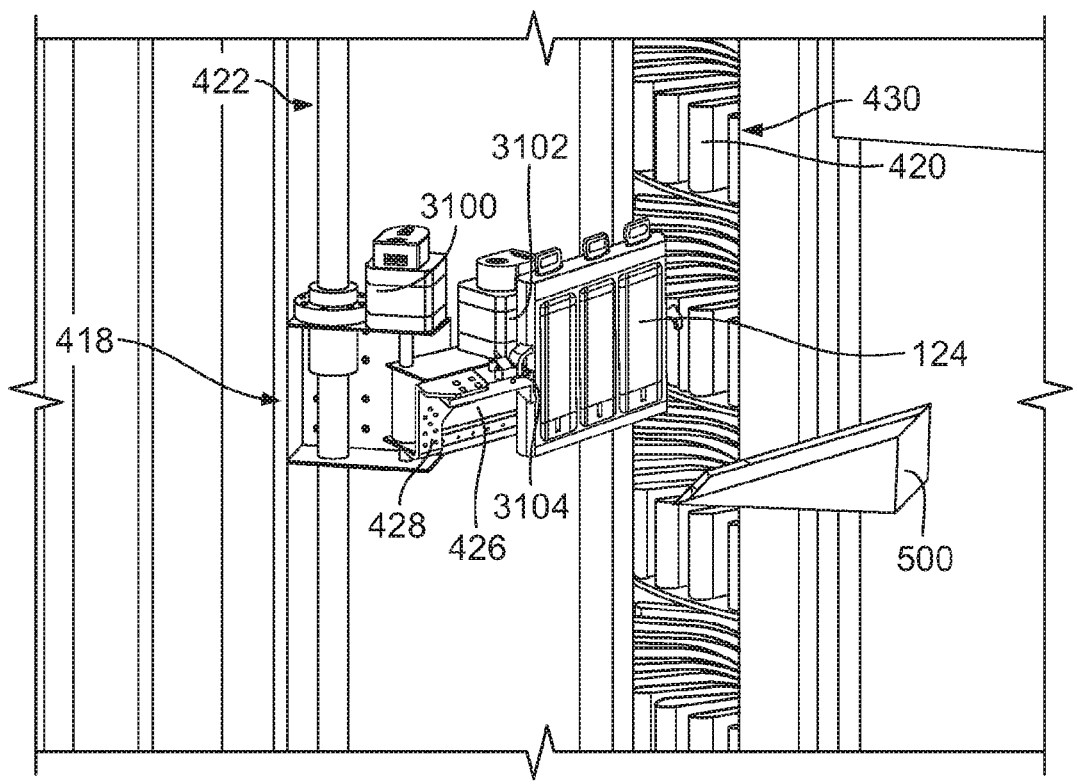
Figure 33D:
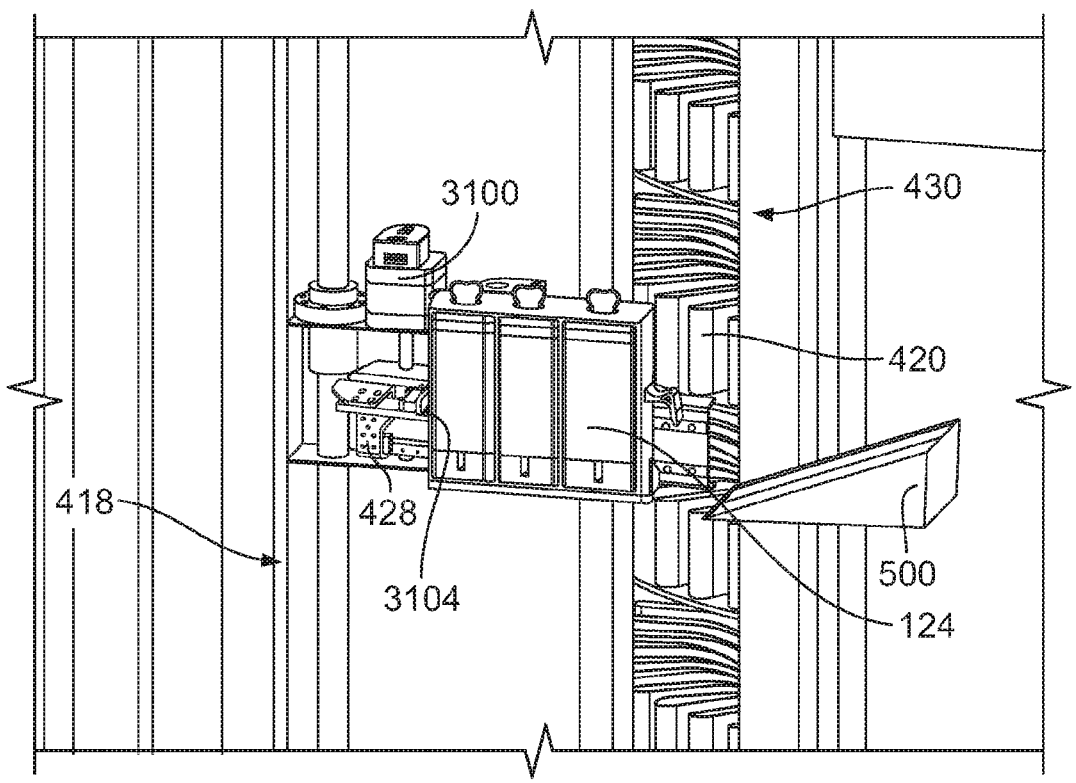

In the example operation, the carousel robot 418 moves upward or downward (depending the location of where the carrier 124 was retrieved) to position the carrier 124 at a height above the tray 500, as illustrated in FIG. 33C. The carousel robot 418 then rotates the carrier, by rotating the arm 426 via the first actuator 3100, to align the carrier 124 with the tray 500, as illustrated in FIG. 33D. The carousel robot 418 then extends the hand 428 (e.g., via the second actuator 3102) to move the carrier 124 radially outward toward the tray 500, as show in FIG. 33E. Once the carrier 124 is positioned above the tray 500, the carousel robot 418 moves downward (e.g., via linear actuator 422) to disengage the carrier tab from the opening 3104 in the hand 428. To retrieve one of the carriers 124 from the tray 500 (e.g., after one of the carriers 124 have been deposited in the tray 500 by the positioner 208), the example sequence may be performed in reverse.

Figure 34:
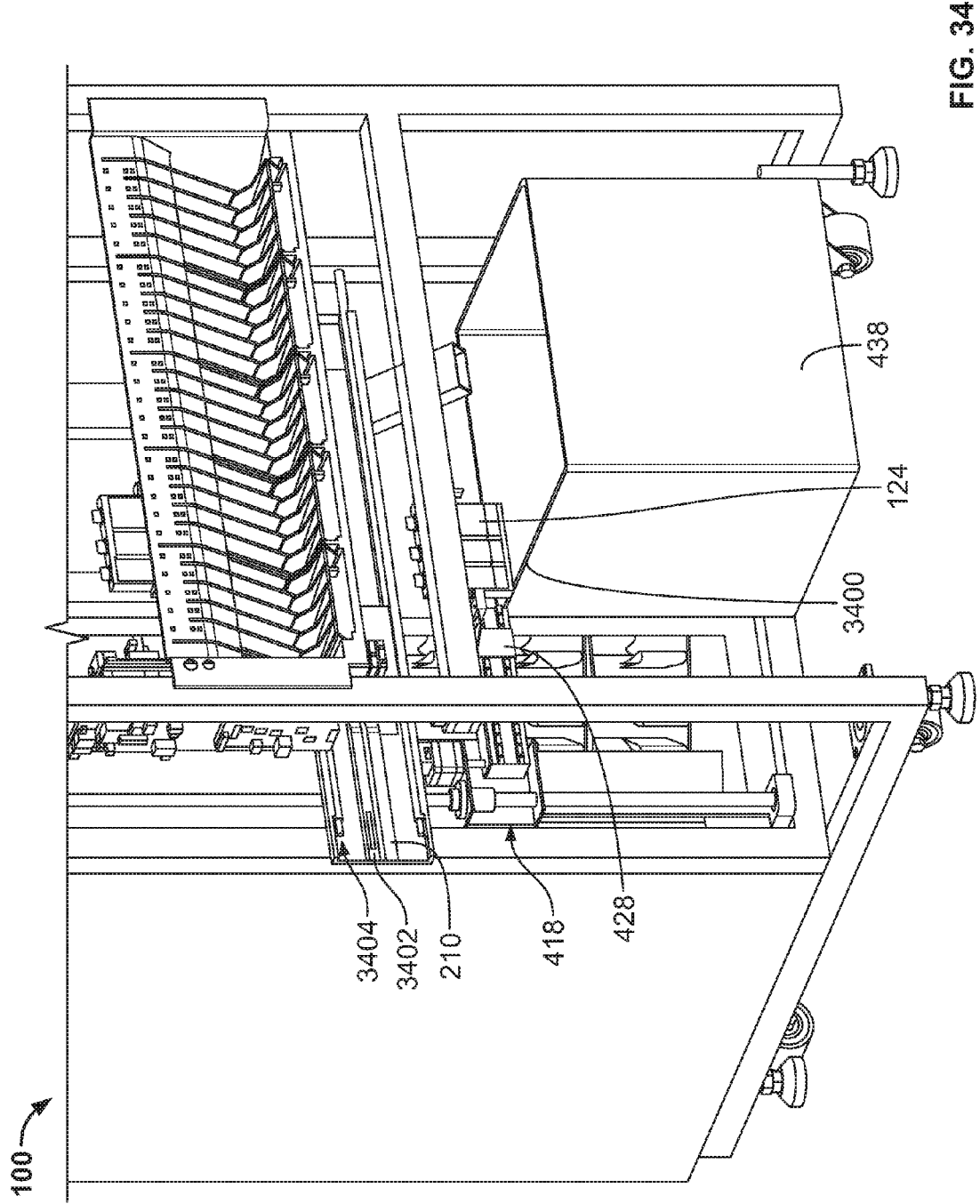
FIG. 34 is an enlarged side perspective view of the example storage module of FIG. 4 having an example track that may be coupled to an analyzer and having an example waste bin.

As disclosed herein, the example storage module 100 includes the waste bin 438. In some examples, the storage module 100 exposes of empty or defective carriers 124 by depositing the carrier 124 into the waste bin 438. FIG. 34 illustrates the example carousel robot 418 disposing of a carrier 124. The carousel robot 418 transfers the carrier 124 to a position where the edge of the carrier 124 is on a top edge 3400 of the waste bin 438. The carousel robot 418 then moves downward to disengage the carrier tab from the hand 428, which releases the carrier 124 into the waste bin 438.

Also illustrated in FIG. 34 is the example track 210 along which the positioner 208 (FIG. 2) travels. In the illustrated example, an end 3402 of the track 210 has a slot 3404 to receive an end of the track 202 (FIG. 2) of the RSH 128. The end of the track 202 has a counter or mating feature that engages the slot 3404. In some examples, the tracks 202, 210 are snapped or clipped together. Additionally or alternatively, the tracks 202, 210 may be coupled together via other mechanical fastener(s) (e.g., screws, bolts, etc.).

Figure 37:
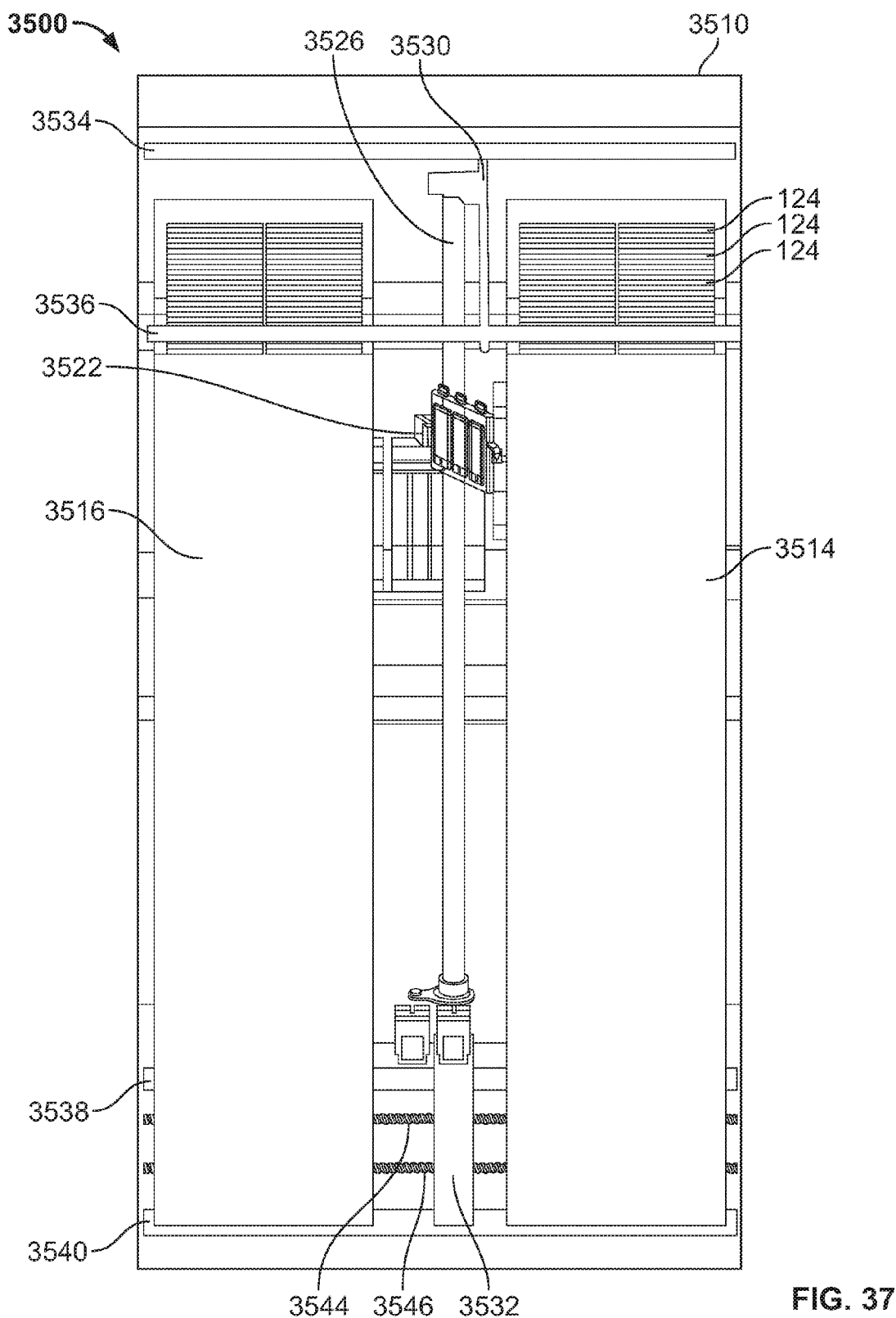
FIG. 37 is a rear view of the example storage module of FIG. 35.

FIGS. 35-37 illustrate another example storage module 3500 having an alternative shelving configuration. The example storage module 3500 has an RSH 3502 with a loading bay 3504 and a positioner 3506 movable along a track 3508, a storage housing 3510 and an opening 3512 in the storage housing 3410, all of which may be structurally and functionally similar to the corresponding components of the example storage module 100 (FIG. 4). The track 3508 may be coupled to one or more analyzers and/or an LAS similar to the storage module 100 disclosed herein. For example, the track 3508 may be coupled to the track 202 of the RSH 128 in FIG. 1. In FIGS. 35 and 36, a plurality of loading trays 3513 are illustrated in the loading bay 3504. The trays 3513 may be used to load one or more of the carriers 124 into the slots of the loading bay 3504 (e.g., for batch loading).

In the illustrated example, the storage module 3500 includes a first shelving unit 3514 and a second shelving unit 3516 disposed within the storage housing 3510. Each of the shelving units 3514, 3516 has a plurality of shelves 3518, each with a plurality of slots 3520 to store the carriers 124. In the illustrated example, the shelving units 3514, 3516 are rectangular and provide vertically arranged shelves 3518 to store the carriers 124. In the illustrated example, each of the shelving units 3514, 3516 includes seven shelves 3518, each of which includes two rows of slots 3520 (e.g., one row on each side of each of the shelves 3518). In the illustrated example, there are 756 slots 3520. However, in other examples, the shelving units 3514, 3516 may have more or fewer shelves, and each of the shelves may have more or fewer slots.

To move a carrier between the positioner 3506 (and/or a transfer location accessible by the one or more analyzers and/or the LAS) and the inside of the storage housing 3510, the example storage module 3500 includes a shelving robot 3522. In the illustrated example, the shelving robot 3522 is movable along a vertical axis 3524, via a linear actuator 3526, and along a first horizontal axis 3528 into the storage housing 3510, via a first track 3530 and a second track 3532. In the illustrated example, the linear actuator 3526 is implemented as a ball screw linear actuator. In other examples, other electro-mechanical device(s) or other device(s) may be used to move the shelving robot 3522. The first track 3530 is disposed along a top of the storage housing 3510 and the second track 3532 is disposed along a bottom of the storage housing 3510. The first and second tracks 3530, 3532 are parallel to each other. The linear actuator 3526 is movable along the first and second tracks 3530, 3532, which moves the shelving robot 3522 into the storage housing 3510. The first and second tracks 3530, 3532 are coupled to a first set of rails 3534, 3536 (e.g., which form the gantry for the shelving robot 3522). The first set of rails 3534, 3536 are disposed along a top of the storage housing 3510. The first and second tracks 3530, 3532 are movable along the first set of rails 3534, 3536 in a direction of a second horizontal axis 3542 (e.g., an 'X' axis). Thus, the shelving robot 3522 is movable along three axes (e.g., the vertical axis 3524 or 'Z' axis, the first horizontal axis 3528 or 'Y' axis, and the second horizontal axis 3542 or 'X' axis). In some examples, one or more rails or tracks may be provided along the bottom of the storage housing 3510 (e.g., parallel to the first set of rails 3534, 3536) to support the linear actuator 3526 from the bottom). The shelving robot 3522 may be structurally and functionally similar to the example carousel robot 418 (FIG. 4). In some examples, the shelving robot 3522 and the positioner 3506 exchange carriers directly between each other. In other examples, a transfer location (e.g., similar to the tray 500 of FIG. 5) may be provided that is accessible by both the shelving robot 3522 and the positioner 3506 to exchange carriers (e.g., by depositing and retrieving the carriers from the transfer location).

To enable the shelving robot 3522 to access to the slots 3520 on both sides of the shelving units 3514, 3516, the shelving units 3514, 3516 are movable along a second set of rails 3538, 3540. The second set of rails 3538, 3540 are disposed along a bottom of the storage housing 3510. Thus, the shelving units 3514, 3516 are movable along the second horizontal axis 3542 (e.g., the 'X' axis), which is parallel to the track 3508 of the positioner 3506. To move the shelving units 3514, 3516, a set of linear actuators 3544, 3546 is disposed beneath the shelving units 3514, 3516 and parallel to the second set of rails 3538, 3540. The linear actuators 3544, 3546 may include linear screws driven by, for example, a stepper motor. As the linear actuators 3544, 3546 move the shelving units 3514, 3516 forward or backward along the second set of rails 3538, 3540, which enables the shelving robot 3522 to access any of the slots 3520 on any of the shelves 3518. In some examples, one of the linear actuators 3544, 3546 operates to move one of the shelves 3514, 3516 and the other one of the linear actuators 3544, 3546 operates to move the other one of the shelves 3514, 3516. In other words, the shelves 3514, 3516 can be moved independent of each other.

For example, to access one of the carriers 124 on the outside of the first shelf 3514, the shelving robot 3522 retracts to a forward position along the first and second tracks 3530, 3532 (e.g., the position illustrated in FIG. 35). Then, the first shelf 3514 is moved (e.g., via one or both of the linear actuator 3544, 3546) toward the second shelf 3516. The shelving robot 3522 can then move along the second horizontal axis 3542 toward the side of the storage housing 3510 (e.g., along the first set of rails 3534, 3536). Then, the shelving robot 3522 can move back toward a rear of the storage housing 3510 (e.g., along the first horizontal axis 3528) to a position to retrieve or deposit the carrier 124.

In the illustrated example, the storage module 3500 includes a cooling or refrigeration unit 3550, which is disposed below the loading bay 3504, to provide relatively cool air to the storage housing 3510. In other examples, the refrigeration unit 3550 may be disposed in other locations in the storage module 3500. The electronics components of the example storage module 3500 may also be disposed below the loading bay 3504.

In the illustrated example, two shelving units (e.g., the first and second shelving units 3514, 3516) are provided to store the carriers 124. However, in other example, more or fewer shelving units may be utilized (e.g., four shelving units, eight shelving units, etc.) and may operate in a similar manner. Additionally, the example storage module 3500 may include any of the example components (e.g., the camera 440, the capper/decapper 434, the refrigeration unit 1214, etc.) of the storage module 100 of FIG. 4, and which may be structurally similar and operate in a similar manner.

Figure 38:
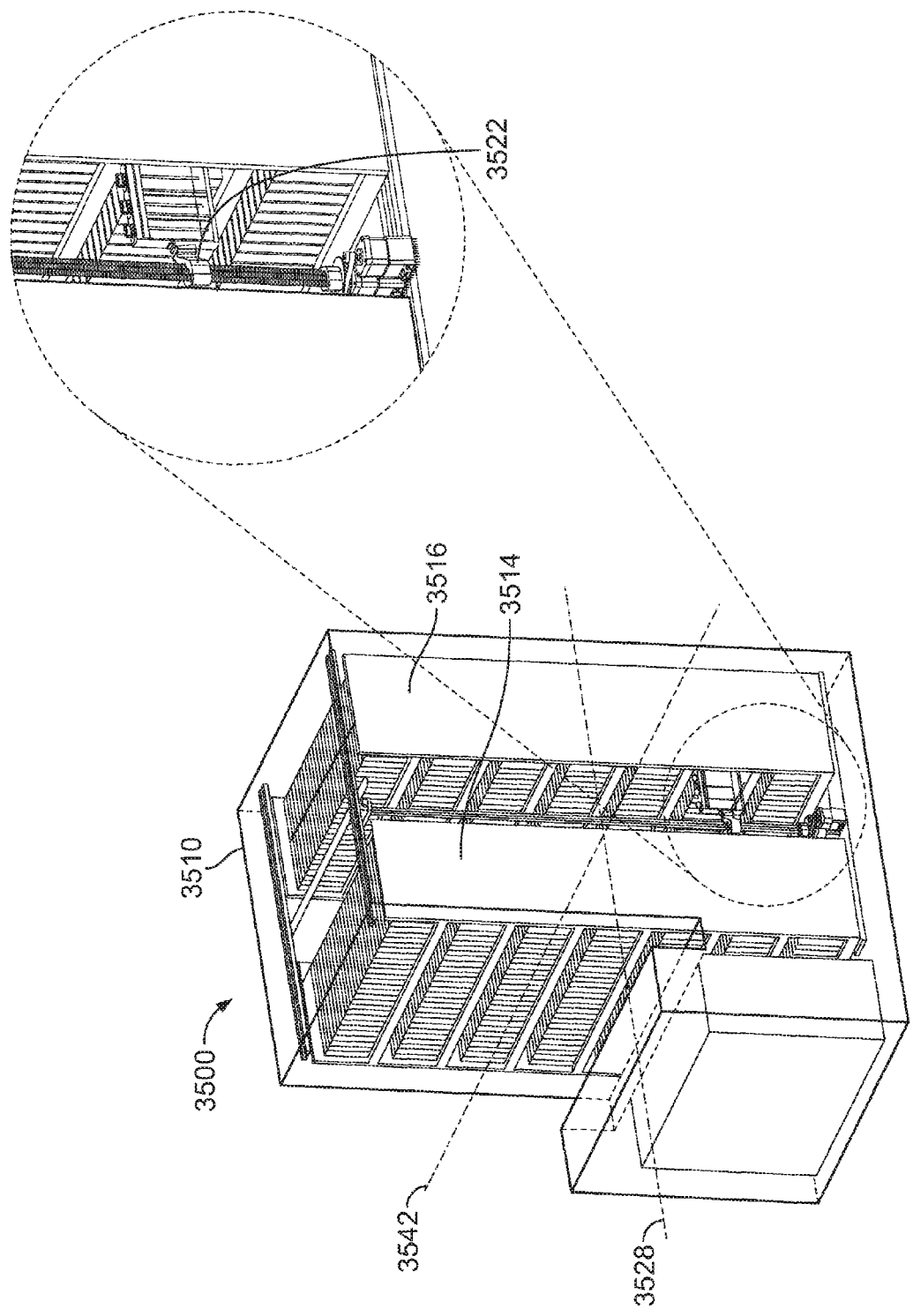
FIG. 38 shows the example storage module of FIG. 35 with example shelving units in an alternative orientation.
Figure 39:
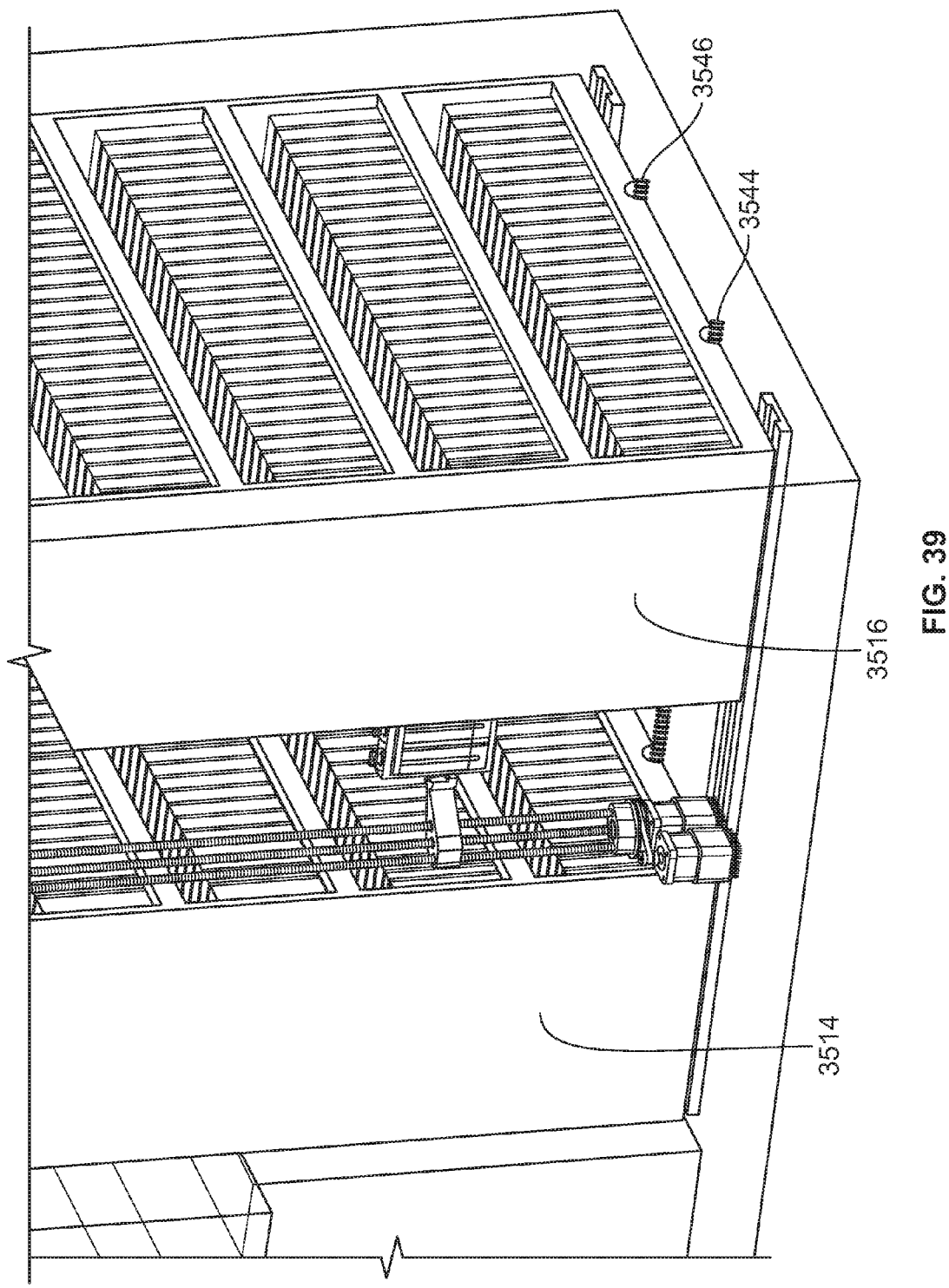
FIG. 39 is a rear perspective view of the example storage module of FIG. 38 with the example alternative shelving unit orientation.

FIGS. 38 and 39 illustrate the storage module 3500 with the shelving units 3514, 3516 arranged in an alternative orientation in the storage housing 3510. In particular, the shelving units 3514, 3516 in the example of FIGS. 38 and 39 move along the first horizontal axis 3528, which is perpendicular to the track 3508 of the positioner 3506 (FIG. 35). In the illustrated example, the position of the shelving robot 3522 has also changed. However, the shelving robot 3522 may still move in three axes as described herein. As illustrated in FIG. 39, the first and second actuators 3544, 3546 have also be reoriented to move the shelving units 3514, 3516 in along the first horizontal axis 3528. The shelving units 3514, 3516 and the shelving robot 3522 may operate similar to the description above.

To transfer one of the carriers 124 to the positioner 3506 (FIG. 35), the shelving robot 3522 moves over to the left or right and outside of the path of the shelving units 3514, 3516. For example, the first and second tracks 3530, 3532 (labeled in FIGS. 35-37) may be extended further past the ends of the shelving units 3514, 3516. The first shelving unit 3516 (e.g., the front most shelving unit) is then moved towards the second shelving unit 3516 (e.g., towards the rear of the storage module 3500), via the first and second actuators 3544, 3546. The shelving robot 3522 can then move toward the front of the storage housing 3510 (e.g., along the first set of rails 3534, 3536 as labeled in FIGS. 35-37) along the first horizontal axis 3528 and then back toward a center of the storage housing 3510 (e.g., along the first and second tracks 3530, 3532 as labeled in FIGS. 35-37) along the second horizontal axis 3542, where the shelving robot 3522 can transfer the carrier 124 to a transfer location or hand-off to be retrieved by the positioner 3506 (FIG. 35). This process can also be performed in reverse to transfer one of the carriers 124 from the positioner 3506 to the shelving robot 3522.

In the illustrated examples, the storage modules 100 and 3500 of FIGS. 4 and 35 include movable shelving units to accommodate the carriers 124. In the storage module 100, for example, the storage carousel 420 includes the plurality of circular shelves 1910 and is rotatable within the storage housing 402. In the storage module 3500, for example, the first and second shelving units 3514, 3516 are provided in the storage housing 3510 and are movable. However, in other examples, other types of shelving units may be utilized in the example storage modules 100, 3500 having other types robotic devices, conveyor belts, etc. to position and transfer the carriers into and out of the storage housings 402, 3510.

Figure 40:
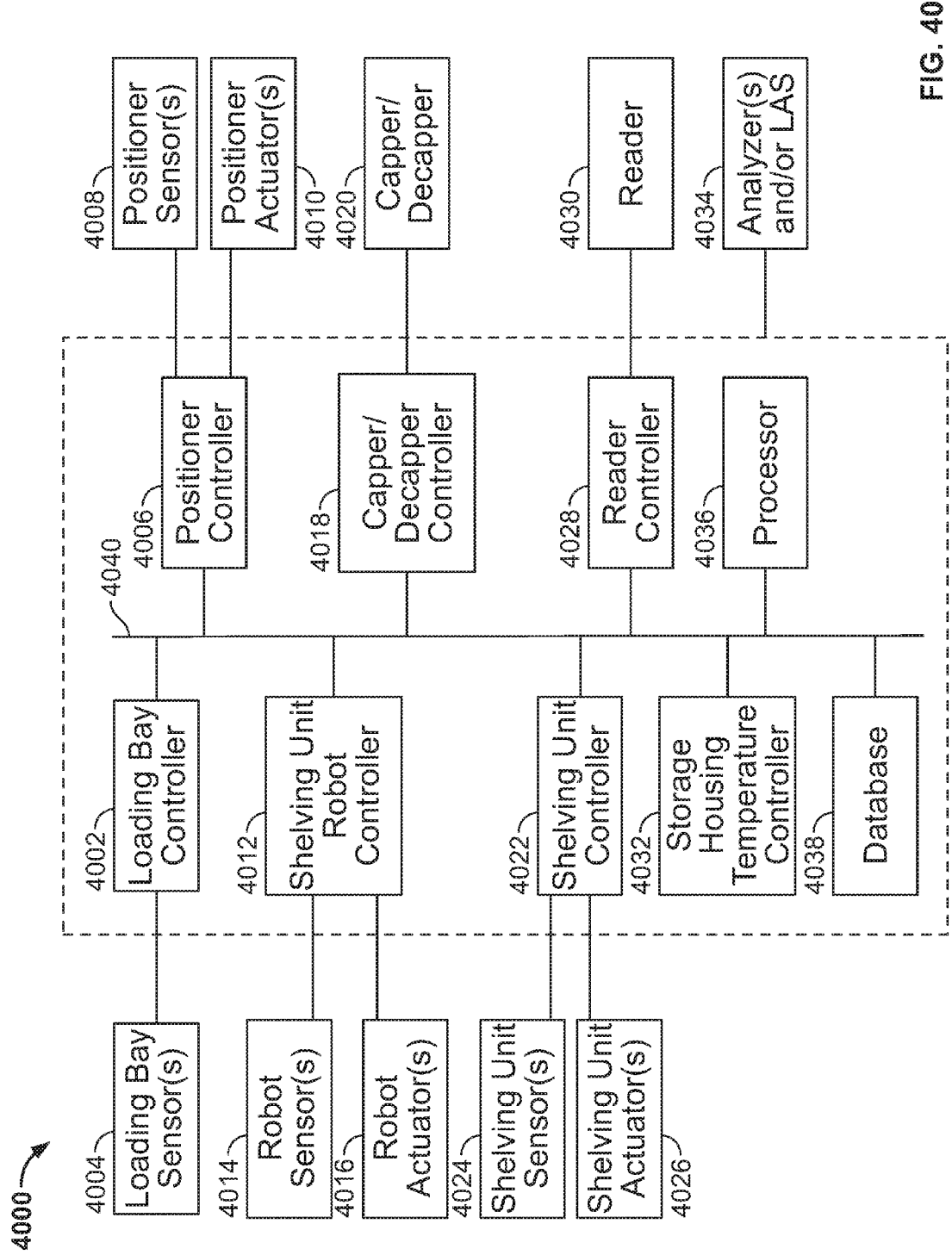
FIG. 40 is a block diagram of an example processing system for the example storage modules shown in FIGS. 4 and 35.

FIG. 40 is a block diagram of an example processing system 4000 that may be used with the example storage module 100 (FIGS. 1 and 4), the example storage module 3500 (FIG. 35) and/or the example workcell 102. The example processing system 4000 may be implemented by, for example, the electronics module 442 (FIG. 4). The example storage modules 100, 3500 disclosed herein may be coupled to one or more analyzer(s) and/or an LAS to provide automated storage and transportation of one or more carrier(s) to be used in the analyzer(s) and/or the LAS. Each of the carriers (e.g., the carriers 124) may include one or more containers of liquid to be used in the analyzer(s) such as, for example, a sample, a reagent, a control and/or a calibrator. The example processing system 4000 includes a loading bay controller 4002, which manages the loading bay and receives signal from one or more loading bay sensors 4004, to determine which slots in a loading bay are empty and which have carriers. For example, in the example storage module 100 shown in FIG. 4, the loading bay 132 includes the array of slots 134 to receive the carriers 124. When one of the carriers 124 is inserted into one of the slots 134, the loading bay controller determines which slot the carrier 124 is inserted.

The example processing system 4000 includes a positioner controller 4006 to control the operations of a positioner (e.g., a carrier transporter) to move carriers between the loading bay, a transfer location (e.g., to be transferred to the analyzer(s) and/or the LAS) and/or a location to be moved into the storage module. For example, the storage module 100 includes the positioner 208 to move the carriers 124 between the loading bay 132, the transfer location 136 and/or the tray 500. In the illustrated example, the positioner controller 4006 is communicatively coupled to one or more positioner sensors 4008 (e.g., an encoder), which detect a position or location of the positioner, and one or more positioner actuators 4010 (e.g., a motor, a DC servo motor) to move the positioner. For example, the positioner 208 is movable along the track 210 and includes the arm 800, which is movable along the vertical axis 802 and rotatably above the vertical axis 802. The positioner 208 includes one or more actuators to move the positioner 208 along the track 210, to move the arm 800 vertically and to rotate the arm 800. In some examples, one or more sensors (e.g., encoders) are included to detect the location of the positioner 208 and/or the arm 800 (e.g., the radial position of the arm 800). The example storage module 3500 also includes a positioner 3506 that is movable along the track 3508 and may operate similar to the positioner 208 of the storage module 100.

In the illustrated example, the processing system 4000 includes a shelving unit robot controller 4012 to control the operations of a shelving unit robot (e.g., a carrier transporter) to move carriers between a location that is accessible by the positioner and an inside of the storage module for storage. For example, the storage module 100 includes the carousel robot 418, which transfers the carriers 124 between the tray 500 and the carousel 420 inside of the storage housing 402. In another example, the storage module 3500 includes the shelving robot 3522, which transfers the carriers 124 into the storage housing 3510 to access the first and second shelving units 3514, 3516. In the illustrated example of FIG. 40, the shelving unit robot controller 4012 is communicatively coupled to one or more robot sensors 4014 (e.g., an encoder), which detect a position or location of the shelving unit robot, and one or more robot actuators 4016 (e.g., a motor, a DC servo motor), which move the shelving unit robot. In the storage module 100, for example, the linear actuator 422 is provided to move the carousel robot 418 along the vertical axis 421, the first actuator 3100 is provided to rotate the arm 426, and the second actuator 3102 is provided to move the hand 428 along the arm 426. In other examples, more or fewer actuators may be utilized to move the carousel robot 418, the arm 426 and/or the hand 428. Additionally, in some examples, a plurality of sensors (e.g., encoders) are included to detect the location of the carousel robot 418, the arm 426 and/or the hand 428.

The example processing system 4000 of FIG. 40 includes a capper/decapper controller 4018 to control the operations of a capper/decapper 4020. For example, in the storage module 100, the capper/decapper 434 is disposed along the travel path of the carousel robot 418 and removes caps from the containers in the carriers 124 (e.g., prior to being sent to the array of analyzers 104) and/or places caps onto the containers in the carriers 124 (e.g., prior to storage in the storage housing 402). The capper/decapper 4020 may be implemented as the example capper/decapper 4100 (see FIG. 41) disclosed in further details herein.

In the illustrated example of FIG. 40, the processing system 4000 includes a shelving unit control 4022 to control a shelving unit disposed within the storage housing. The shelving unit may be movable within the storage housing to position the shelving unit for retrieval of the carriers. For example, in the storage module 100, the carousel 420 (e.g., a shelving unit) is rotatable within the storage housing 402, so that the slots 1912 on the carousel 420 can be aligned with the opening 430 and accessed by the carousel robot 418. In another example, the storage module 3500 includes the first and second shelving units 3514, 3516, which are movable within the storage housing 3510 to allow the shelving robot 3522 to access the carriers 124 on the first and second shelving units 3514, 3516. In the illustrated example of FIG. 40, the shelving unit controller 4020 is communicatively coupled to one or more shelving unit sensors 4024 (e.g., an encoder), which detect the position (e.g., a radial position) of the shelving unit, and one or more shelving unit actuators 4026, which move the shelving unit. For example, in the storage module 100, the actuator 2800 is provided to rotate the pulley 2804 beneath the storage housing 402 to rotate the carousel 420 within the storage housing 402. The storage module 100 may include one or more sensor(s) (e.g., encoders) to detect a position of the carousel 420 (e.g., which column of slots 1912 is exposed at the opening 430). In the example storage module 3500, the linear actuators 3544, 3546 are provided to move the first and second storage units 3514, 3516.

To determine what types of liquids are in a carrier, the example processing system 4000 includes a reader control 4028. In some examples, a reader 4030 is included in the storage module to detect identification indicia on a carrier and/or the individual container(s) of a carrier. Additionally or alternatively, the reader 4030 may be implemented to detect if caps are present or absent on the containers before and/or after capping/decapping operations. For example, in the storage module 100, the camera 440 is disposed along the travel path of the carousel robot 418, such that the carriers 124 can be read as the carriers 124 pass in front of the camera 440. In other examples, the camera 440 may be disposed in other locations where the carriers 124 may be read.

The example processing system 4000 includes a storage housing temperature controller 4032 that controls the temperature within the storage housing and generates an air curtain across the opening of the storage housing. For example, in the storage module 100, the refrigeration unit 1214 produces relatively cooler air that is pumped into the channels 1700, 1704, 1708 inside of the storage housing 402. The storage housing 402 also includes the aircurtain channel 1712 (which may include a fan) and the return channel 1716 that directs the relatively warmer return air back to the refrigeration unit 1214. The aircurtain is produced across the opening 430 by the flow of the relatively warmer return air between the aircurtain channel 1712 and the return channel 1716. The illustrated storage housing temperature controller 4032 may operate to control the refrigeration unit 1214 and/or the fan inside of the aircurtain channel 1712 to produce the aircurtain.

The example processing system 4000 is communicatively coupled to one or more analyzers and/or an LAS 4034 to receive information from the one or more analyzers and/or the LAS 4034 regarding the analyzer liquids. For example, in the workcell 102 of FIG. 1, the storage module 100 interacts with the array of analyzers 104 to provide the carriers 124 to the array of analyzers 104 when desired. The example processing system 4000 also includes a processor 4036 and a database 4038. The processor 4036 interfaces with the controllers 4002, 4006, 4012, 4018, 4022, 4028, 4032 of the processing system 4000 to control the various operations of each of the components. The processor 4036 is programmable to operate in accordance with desired storage, transportation and/or testing protocol(s). The database 4038 may be used to store, for example, information regarding the contents of the carriers, positions of the carriers in the loading bay, positions of the carriers in the slots the shelving unit, which slots of the shelving unit are empty, how much liquid is left in the carriers, how many times the carriers have been used, the status of the caps on the containers of the carriers, the anticipated expiration date of the carriers (e.g., a reagent carrier), tests that have occurred, are to occur, and/or are occurring in the one or more analyzers 4034, testing protocol(s), positions of the positioner and/or the shelving unit robot, information regarding the temperatures to effectively store the carriers and/or any other information related to the operations of the storage module. By reading (e.g., via the camera 440) and storing information relating to the contents of the carriers and/or their locations within the storage module, the processing system 4000 can efficiently perform storage and exchange operations between the one or more analyzers and/or the LAS 4034. The processing system 4000 can quickly identify the location and/or status of any of the carriers to determine what operation should be performed on the carriers (e.g., store a carrier, transport a carrier to a slot in the loading bay to be unloaded, dispose of a carrier, transport a carrier to the transfer location to be retrieved by the one or more analyzers and/or the LAS 4034, etc.).

In the example shown, the processing system components 4002, 4006, 4012, 4018, 4022, 4028, 4032, 4036, 4038 are communicatively coupled to other components of the example system 4000 via communication links 4040. The communication links 4040 may be any type of wired connection (e.g., a databus, a USB connection, etc.) or a wireless communication mechanism (e.g., radio frequency, infrared, etc.) using any past, present or future communication protocol (e.g., Bluetooth, USB 2.0, USB 3.0, etc.). Also, the components of the example system 4000 may be integrated in one device or distributed over two or more devices.

Figure 41:
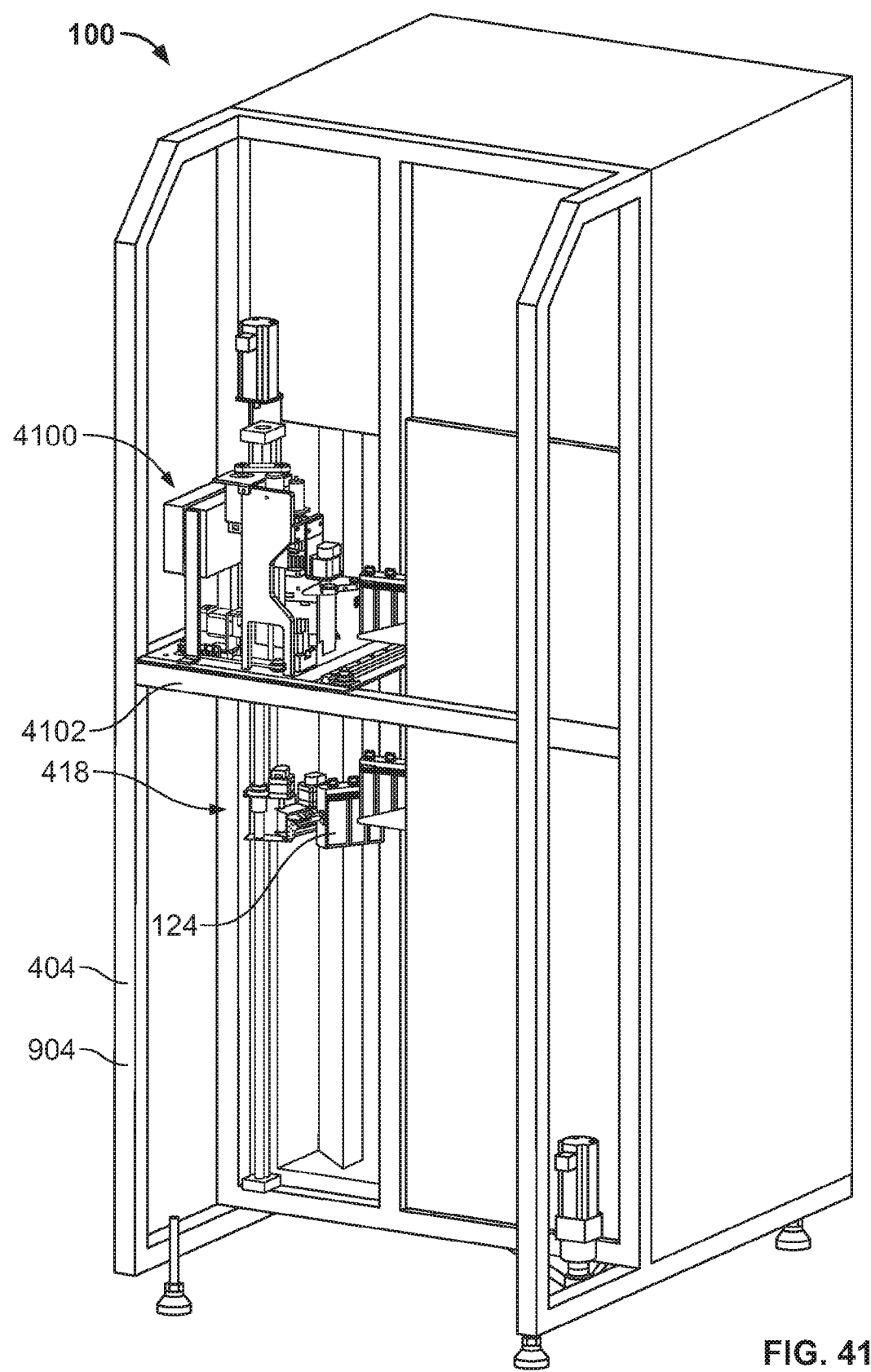
FIG. 41 is a front perspective view of the example storage module of FIG. 4 with an alternative example capper/decapper constructed in accordance with the teachings of this disclosure.

FIG. 41 illustrates an alternative example capper/decapper 4100 that may be used with the example storage module 100. In FIG. 41, many of the components of the storage module 100 have been removed to expose the example capper/decapper 4100. The example capper/decapper 4100 is used to remove a cap from a container of a carrier 124 and/or couple (e.g., insert, attach) a cap (e.g., a temporary cap, a plug, a septum) to a container of a carrier 124. In some examples, as disclosed herein, a container is to be uncapped prior to being sent to one or more of the analyzers 106-112 (FIG. 1). In some examples, prior to being loaded back into the storage housing 402 (FIG. 4), a container of a carrier 124 is to be capped and/or recapped. In some examples, when a carrier (e.g., a carrier that has not yet been sent to an analyzer) is to be transferred to the storage housing 402, the caps of the containers of the carrier 124 are removed and temporary caps (e.g., plugs) are placed on the containers, prior to loading the carrier 124 into the storage housing 402. The capper/decapper 4100 is referred to herein as a decapper 4100, although it is understood that the decapper 4100 is, alternatively or additionally, capable of capping a container.

Figure 63:
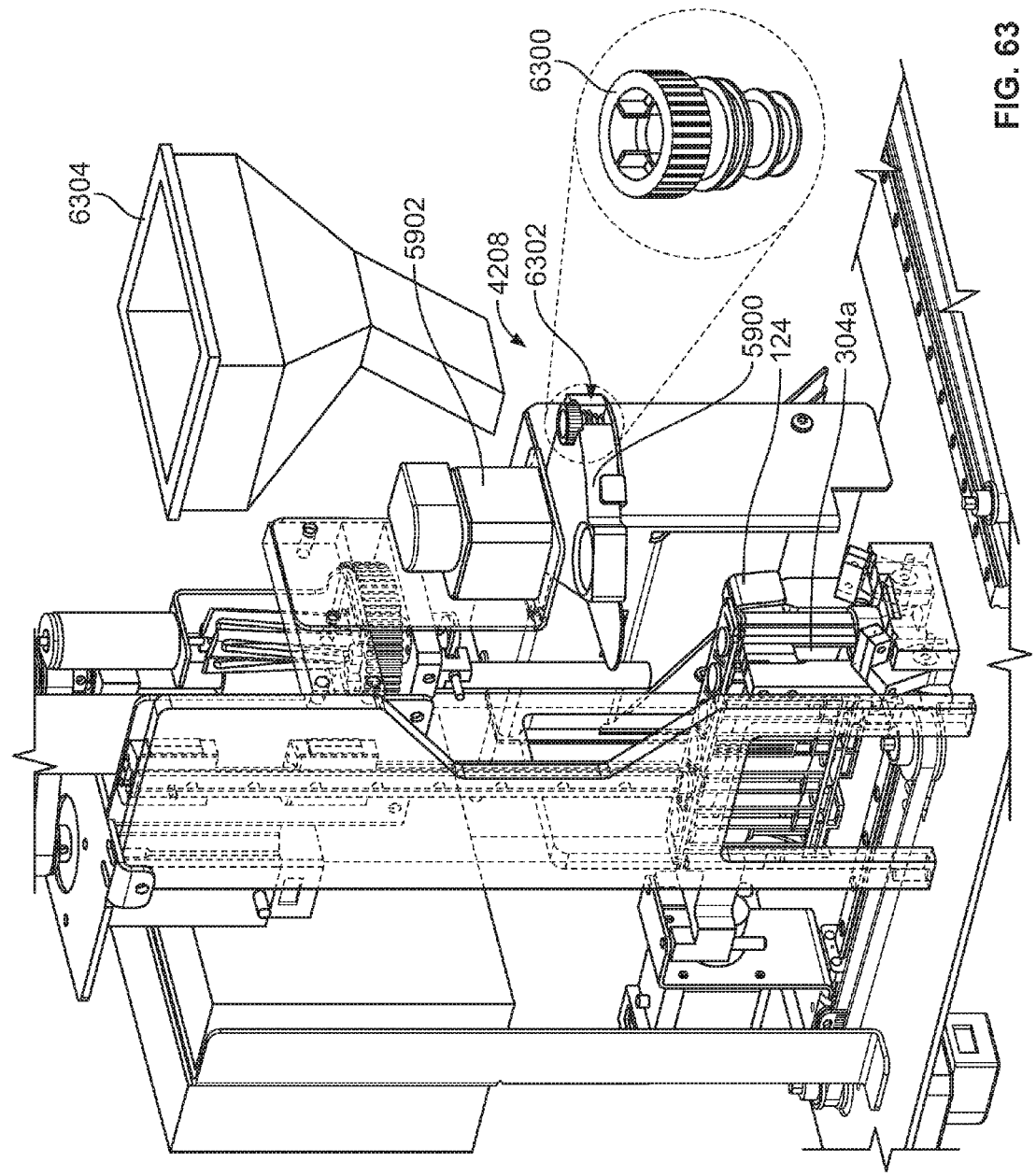
FIG. 63 shows the example cap handler tray of FIG. 59 having an example cap that is to be placed on a container of the example carrier of FIG. 62.

The containers of the different carriers (e.g., the carrier 124, 300, which may be implemented as a sample carrier, a control carrier and/or a calibrator carrier, the immunoassay reagent carrier 124, 310, the clinical chemistry reagent carrier 124, 320, a carrier having eight containers, a carrier having five tubes, etc.) may use different types of caps. For example, as illustrated in FIG. 3A, the first and second tubes 304a, 304b (which may be sample tubes, calibrator tubes, control tubes, etc.) include the respective caps 305a, 305b, which are cylindrical caps that may be threaded and/or force fit onto the respective tubes 304a, 304b. As illustrated in FIG. 3C, the containers 314a-314c of the immunoassay reagent carrier 124, 310 utilize butterfly caps 315a-315c, which are twisted onto the respective containers 314a-314c and include vertically extending tabs 317a-317c. The example decapper 4100 can remove different types of caps (e.g., the cylindrical cap 305*a*, the butterfly cap 315*a*, etc.) from a container and can couple a cap (e.g., the same type of cap or a different type of cap) to a container. In some examples, a plug type cap (e.g., the cap 6300 as illustrated in FIG. 63 and disclosed further herein) is used to recap the containers prior to moving the carrier 124 into the storage module 100. The plug type cap may fit into any of the example containers. For the sake of brevity, three types of example caps are disclosed herein to illustrate the example capping and decapping operations. However, it is understood that the example decapper 4100 could be utilized to cap and decap more types of caps.

In the illustrated example of FIG. 41, the decapper 4100 is disposed outside of the storage housing 402 (see FIG. 4), between the carousel robot 418 and the front side 404 of the storage module 100. The decapper 4100 is coupled to the second vertical support frame 604 via a cross-support bar 4102. The carousel robot 418 transfers carriers 124 to the decapper 4100, where one or more caps may be placed on the container(s) of a carrier 124 and/or one or more caps may be removed from the container(s) of a carrier 124. The carousel robot 418 also retrieves carriers 124 from the decapper 4100 (e.g., after one or more caps have been placed on the container(s) of a carrier 124 and/or one or more caps have been removed from the container(s) of a carrier 124).

Figure 42:
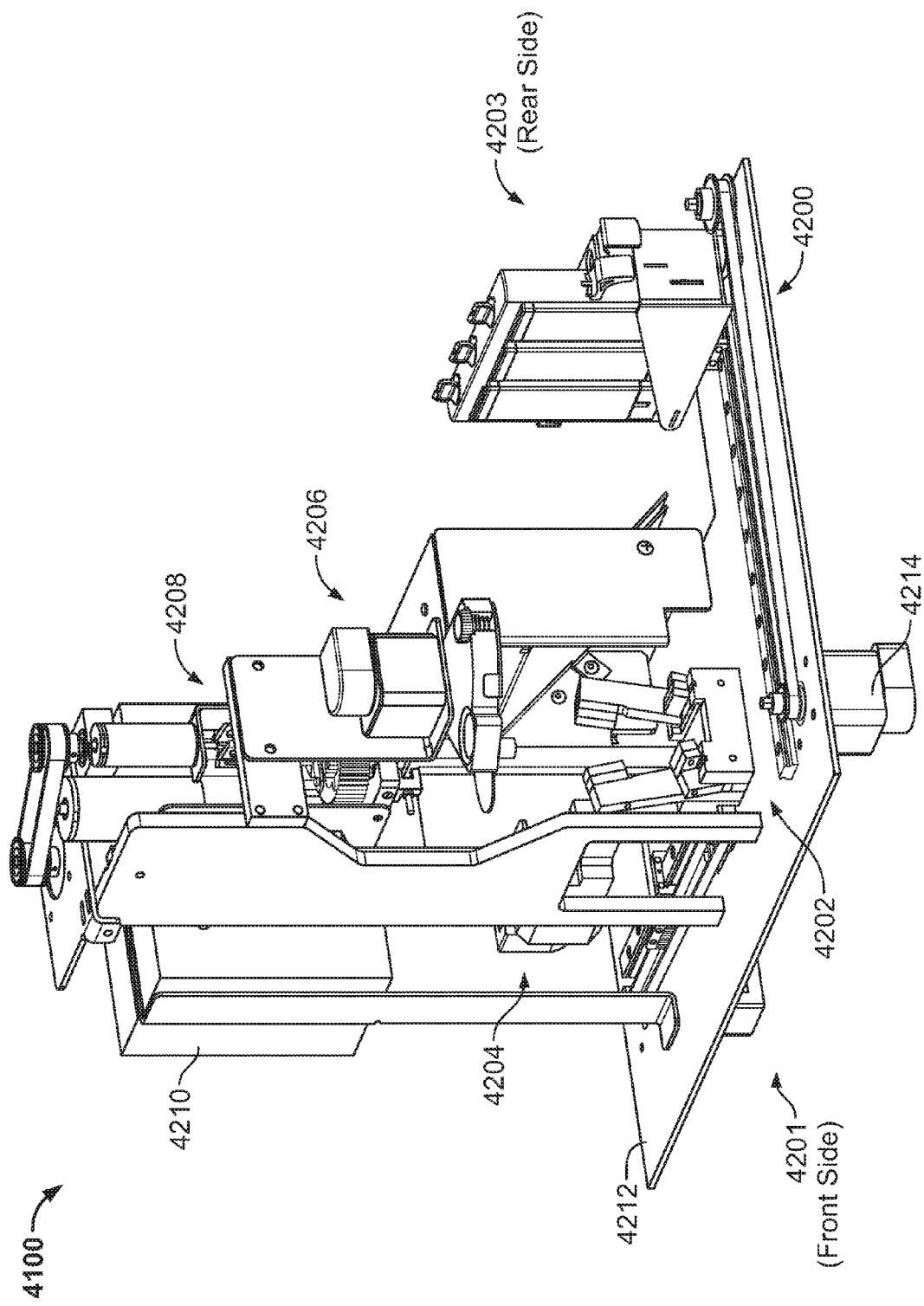
FIG. 42 is a front perspective view of the example capper/decapper of FIG. 41.
Figure 43:
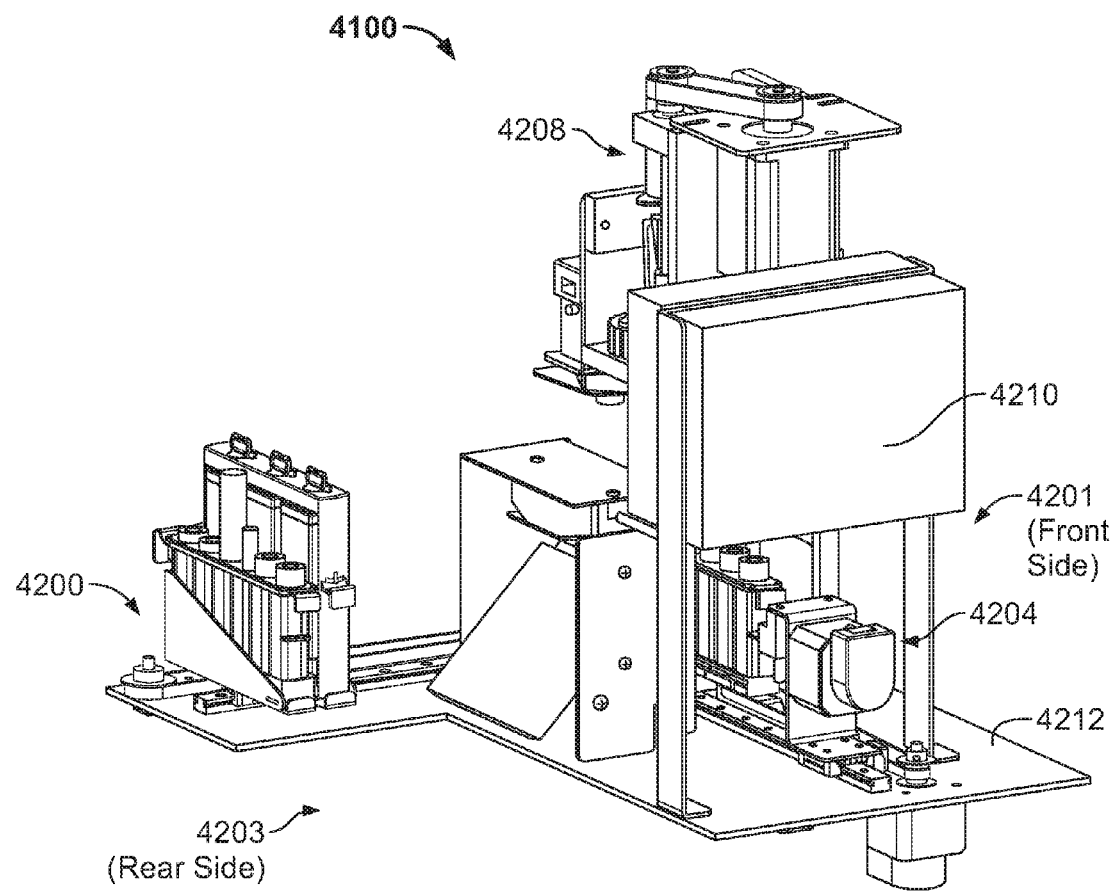
FIG. 43 is a rear perspective view of the example capper/decapper of FIG. 41.

FIG. 42 shows a front perspective view of the example decapper 4100 and FIG. 43 shows a rear perspective view of the example decapper 4100. When coupled to the storage module 100, a front side 4201 of the decapper 4100 faces the front of the storage module 100 and a rear side 4203 faces the rear of the storage module 100. The example decapper 4100 includes a shuttle 4200, a carrier clamp 4202, a carrier transporter 4204, a cap handler 4206, a cap gripper or gripper head 4208 and a control module 4210 that houses the electronics for controlling the decapper 4100 (e.g., which may correspond to the capper/decapper controller 4018 of FIG. 40). In the illustrated example, the shuttle 4200, the carrier clamp 4202, the carrier transporter 4204, the cap handler 4206, the gripper head 4208 and the control module 4210 are coupled to a support plate 4212.

An example decapping operation is illustrated in FIGS. 44-60 where a cap of a container on a carrier 124 is removed. In particular, the example sequence is illustrated on the example immunoassay reagent carrier 124, 310 (FIG. 3C) having the three containers 314*a*-314*c*. In the example decapping sequence, the first cap 315*a* of the first container 314*a* is removed. It is understood that a similar operation may be performed on any of the other containers 314*b*, 314*c* of the carrier 124 and/or on any of the other containers of the other types of carriers 124, 300, 124, 320 (FIGS. 3A and 3E), which may include more or fewer containers.

Figure 44:
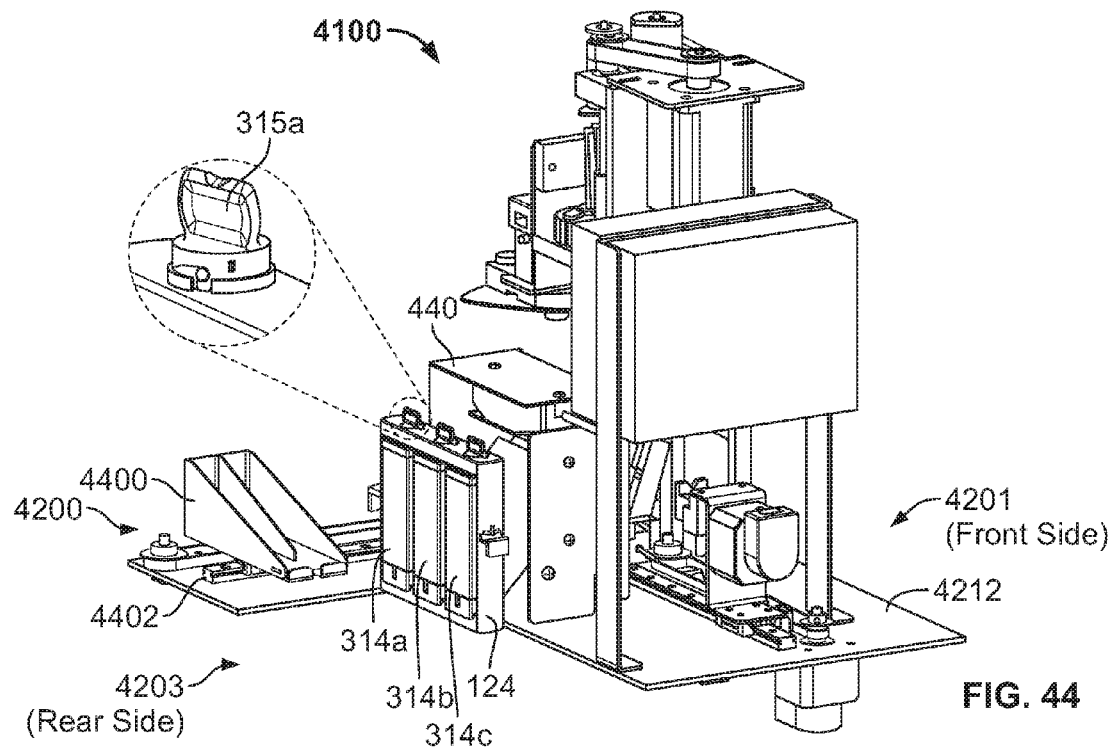
FIG. 44 shows an example carrier disposed in front of an example camera while being transferred to the example capper/decapper of FIG. 41 for a decapping operation.

To determine the type of container that is to be decapped (e.g., which may indicate the height at which the cap is disposed), the type of cap that is to be removed, and/or the position of the cap, the carousel robot 418 (FIG. 41) passes the carrier 124 in front of a sensor (e.g., a vision based sensor) such as the camera 440, as illustrated in FIG. 44. In the illustrated example, the camera 440 is coupled to the support plate 4212. However, in other examples, the camera 440 may be disposed in other locations. As disclosed herein, the camera 440 may read identification information (e.g., via a bar code, an RFID tag, etc.) from the carrier 124 and/or the container 314*a* to determine information about the carrier 124 and/or the container(s) of the carrier 124 (e.g., the type(s) of reagent(s) that are included in the carrier 124, the expiration date of the reagent(s), the volume of reagent in the container(s), etc.).

Figure 45:
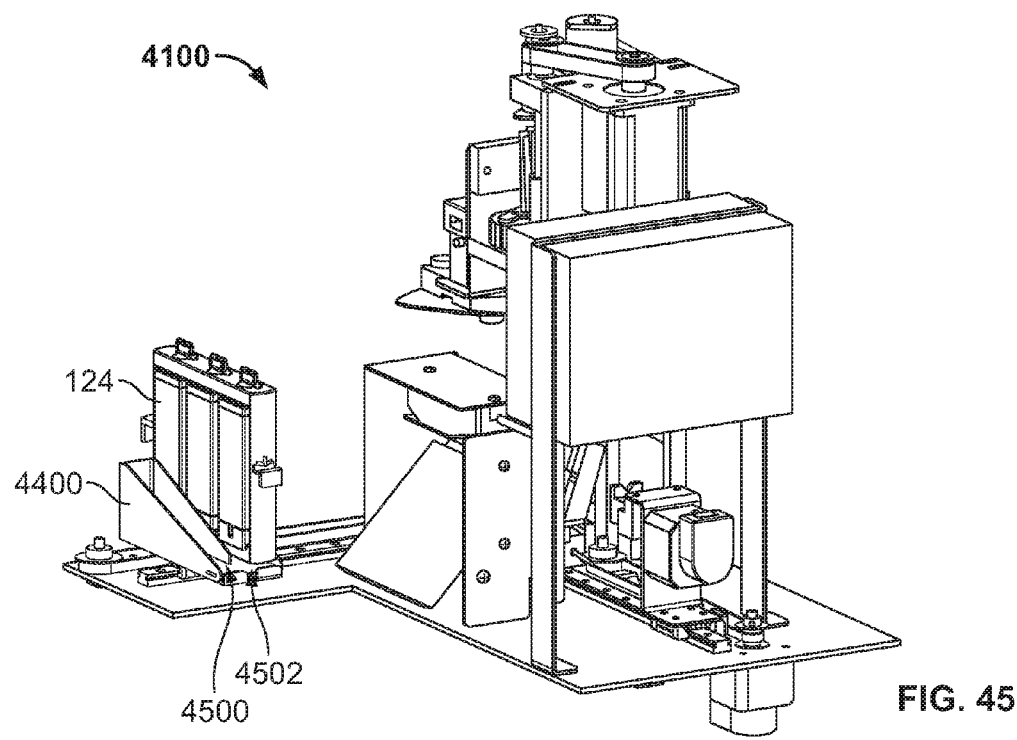
FIG. 45 shows the example carrier of FIG. 44 being placed in an example sled of the example capper/decapper.
Figure 46:
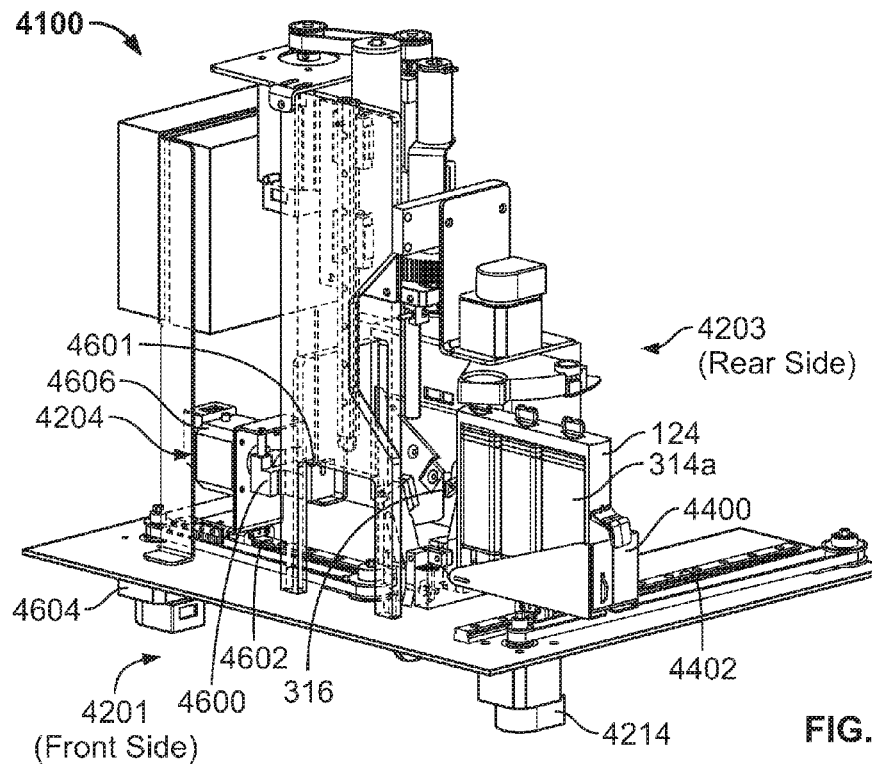
FIG. 46 shows the example carrier of FIG. 45 after being transported by the example sled of the example capper/decapper.

To move the carrier 124 between the rear side 4203 of the decapper 4100 to the front side 4301 of the decapper 4100, the decapper 4100 includes the shuttle 4200. The shuttle 4200 has a tray or sled 4400 that moves along a track 4402 via a sled actuator 4214 (FIG. 42). The carousel robot 418 deposits the carrier 124 onto the sled 4400, as illustrated in FIG. 45. In the illustrated example, the sled 4400 includes a first slot 4500 and a second slot 4502. The carrier 124 may be deposited into either slot 4500, 4502. Having two slots enables the carousel robot 418 to deposit one carrier 124 while retrieving another carrier from the other slot (e.g., after a capping and/or decapping operation has occurred on the other carrier). FIGS. 42 and 34 illustrate two carriers 124 in the sled 4400. However, in other examples, the sled 4400 may employ only one slot or position. The sled 4400 moves along the track 4402, via the shuttle actuator 4214, to transport the carrier 124 to the front side 4201 of the decapper 4100, as shown in FIG. 46.

Figure 47:
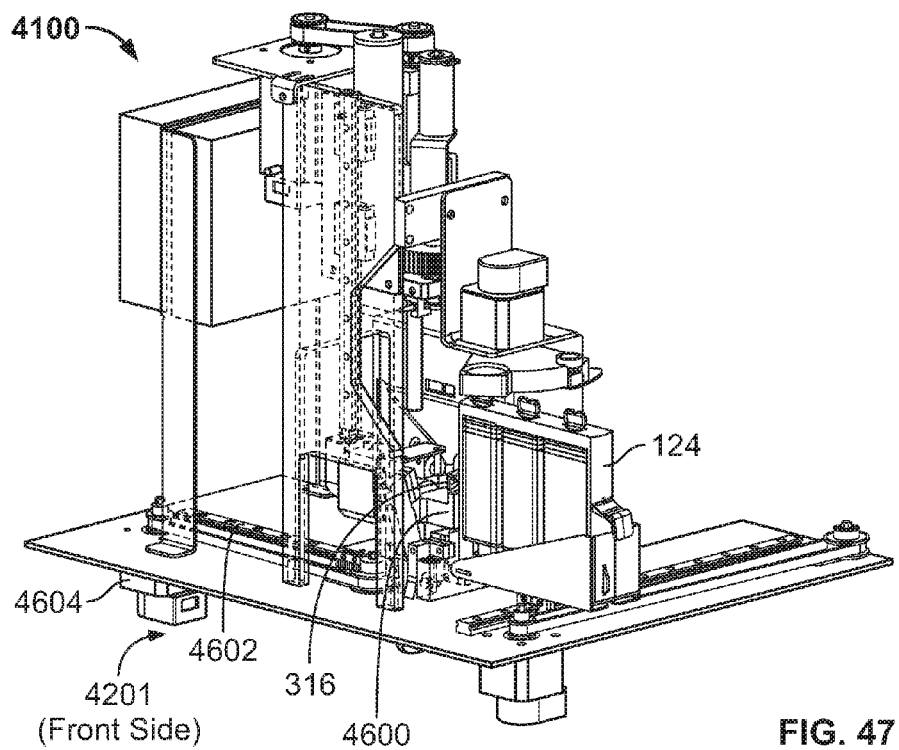
FIG. 47 shows an example carrier transporter of the example capper/decapper engaging the example carrier of FIG. 46.
Figure 48:
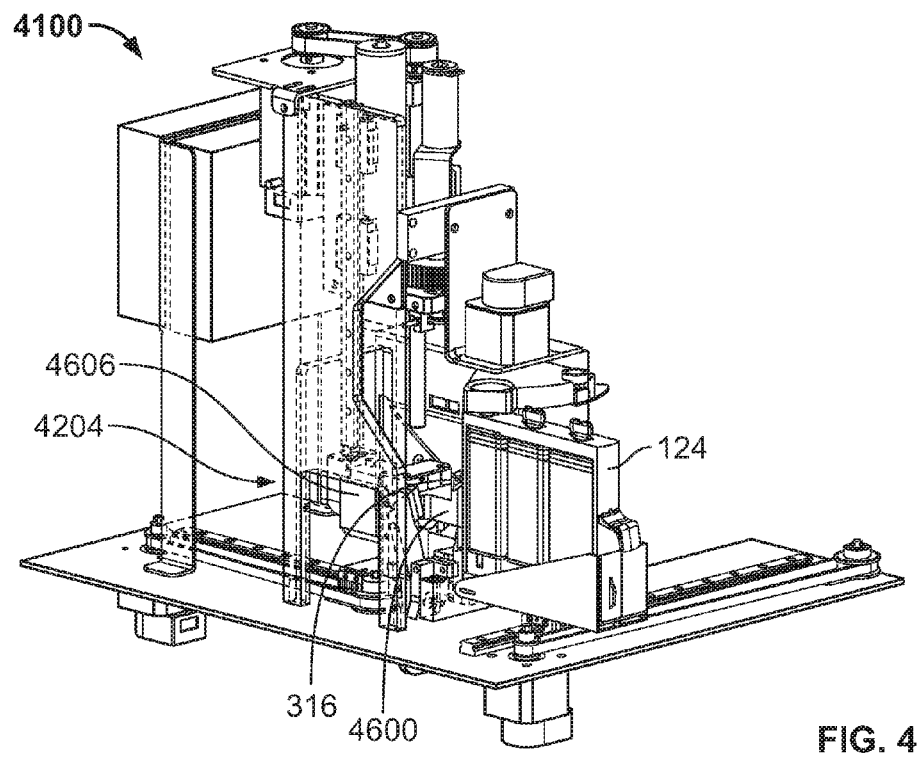
FIG. 48 shows the example carrier transporter lifting the example carrier out of the example sled of FIG. 47.

To position the carrier 124 in a location where the gripper head 4208 can access the container 314*a* (e.g., to remove the cap 315*a*), the decapper 4100 includes the carrier transporter 4204. The carrier transporter 4204 includes a hand 4600 having a slot 4601 to receive the tab 316 of the carrier. The hand 4600 is substantially similar to the hand 428 of the carousel robot 418, illustrated in FIG. 32, for example. The hand 4600 is movable along a track 4602, disposed along the front side 4201 of the decapper 4100, via a first carrier transporter actuator 4604. The hand 4600 is movable in the vertical direction via a second carrier transporter actuator 4606. To retrieve the carrier 124 from the sled 4400, the hand 4600 is moved (e.g., via the first carrier transporter actuator 4604) along the track 4602 to a position where the slot 4601 is aligned beneath the tab 316 of the carrier 124, as illustrated in FIG. 47. The hand 4600 is then moved vertically upward (e.g., via the second carrier transporter actuator 4606) to insert the tab 316 into the slot 4601 of the hand 4600, as illustrated in FIG. 48.

Figure 49:
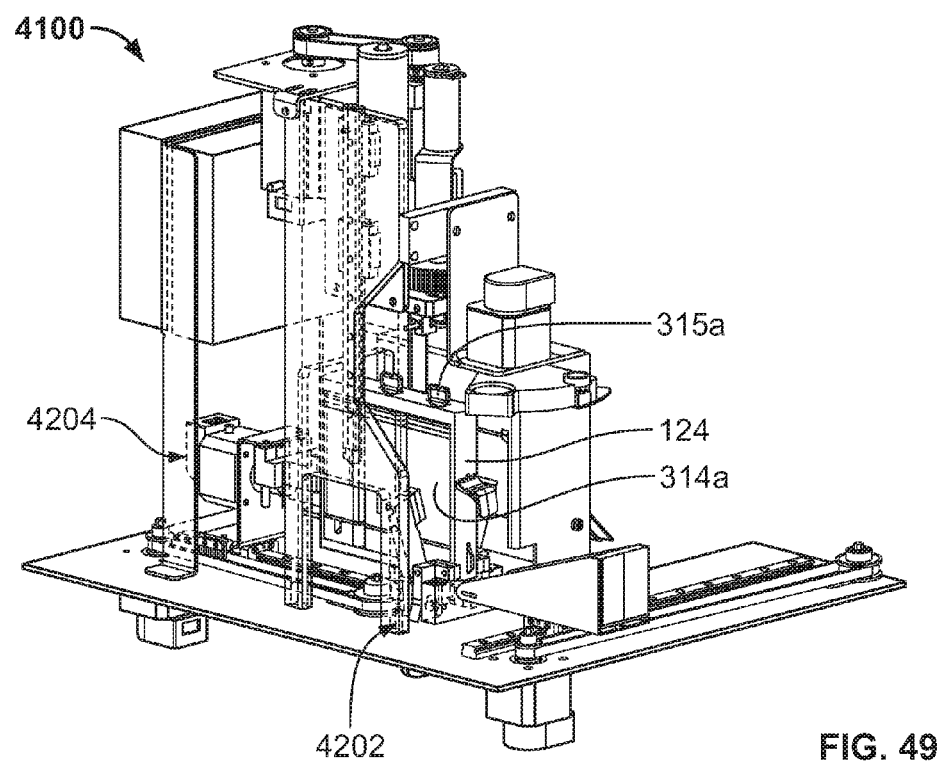
FIG. 49 shows the example carrier transporter moving the example carrier from the position in FIG. 48 to a position in which a container of the example carrier is disposed in a target location.

After the carrier 124 is obtained by the carrier transporter 4204, the carrier transporter 4204 transports the carrier 124 to a position where the container 314*a* is disposed in a target location, as illustrated in FIG. 49. The target location is where the cap 315*a* is located beneath the gripper 5200 (FIG. 52, disclosed in further detail herein) so that the gripper 5200 can access the cap 315*a* and remove the cap 315*a* from the container 314*a*.

Figure 50:
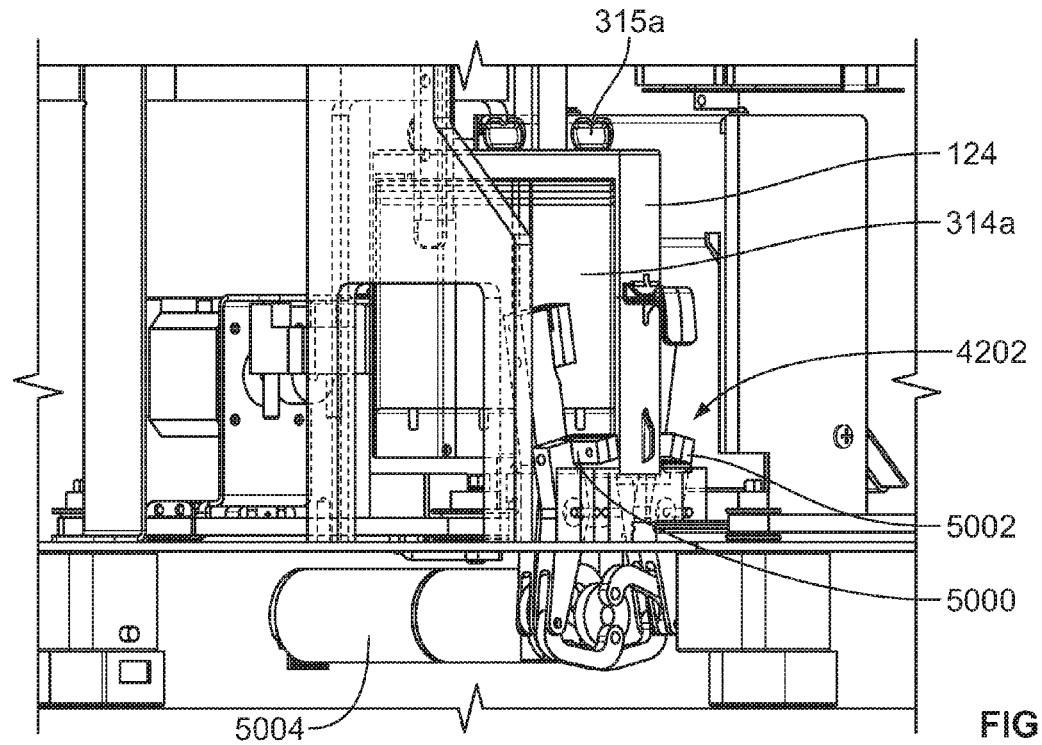
FIG. 50 illustrates an example clamp that may be used to secure the example carrier of FIG. 49.
Figure 51:
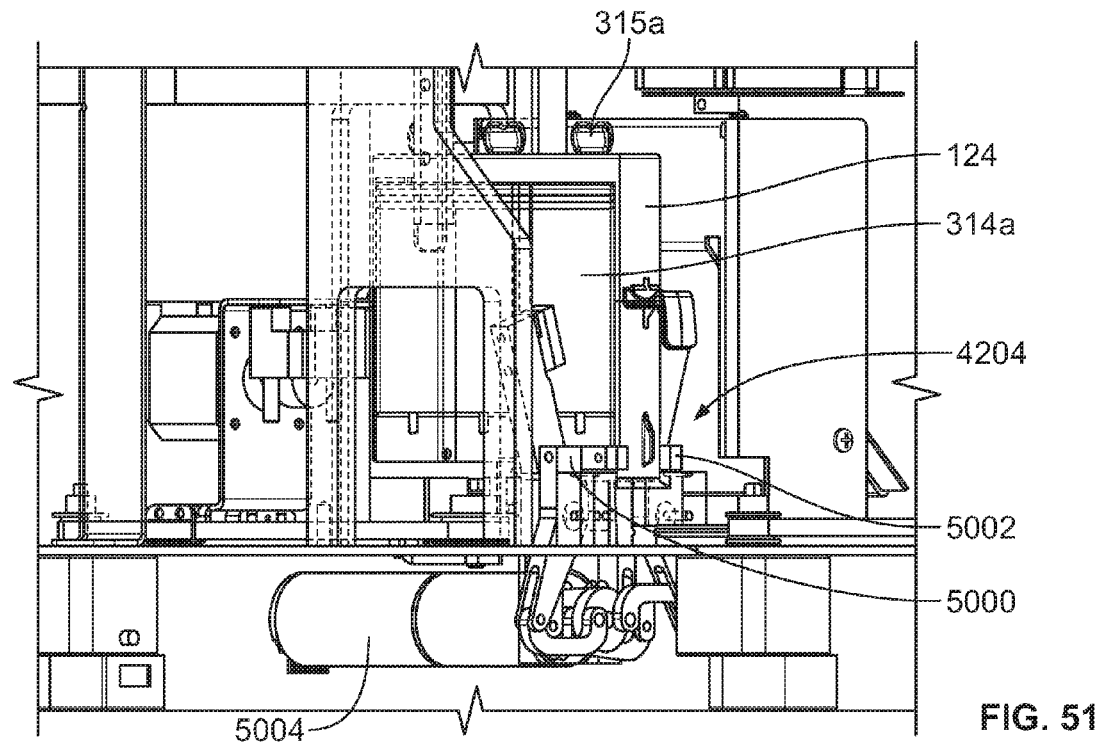
FIG. 51 shows the example clamp of FIG. 50 engaged with the example carrier to secure the example carrier in the illustrated position.

To secure the container 314*a* and/or the carrier 124 while the cap 315*a* is removed, the decapper 4100 includes the clamp 4202. FIGS. 50 and 51 show enlarged views of the clamp 4202. In the illustrated example, the clamp 4202 includes a first arm 5000 and a second arm 5002 that move toward and away from each other via a clamp actuator 5004. The first and second arms 5000, 5002 are moved together to engage the container 314*a* and the carrier 124, as illustrated in FIG. 51, to secure the container 314*a* and the carrier 124 while the cap 315*a* is being removed from the container 314*a*. In some examples, the container 314*a* is rotatable within the carrier 124. Therefore, the first and second arms 5000, 5002 clamp the container 314*a* (in addition to the carrier 124) to prevent the container 314*a* from rotating while the cap 315*a* is being removed (as disclosed in further detail herein). In other examples, only the container 314*a* or only the carrier 124 may be clamped. In the illustrated example, the first and second arms 5000, 5002 clamp the container 314*a* near a bottom of the container 314*a*. In some instances a container may be constructed of relatively thinner or softer material (e.g., polypropylene). To avoid deforming the side walls of the container, the first and second arms 5000, 5002 are positioned to clamp the container 314a near the bottom, where the material of the container 314a is relatively stronger. In the illustrated example, the clamp actuator 5004 is disposed beneath the support plate 4212. However, in other examples, the clamp actuator 5004 may be disposed in other locations.

Figure 52:
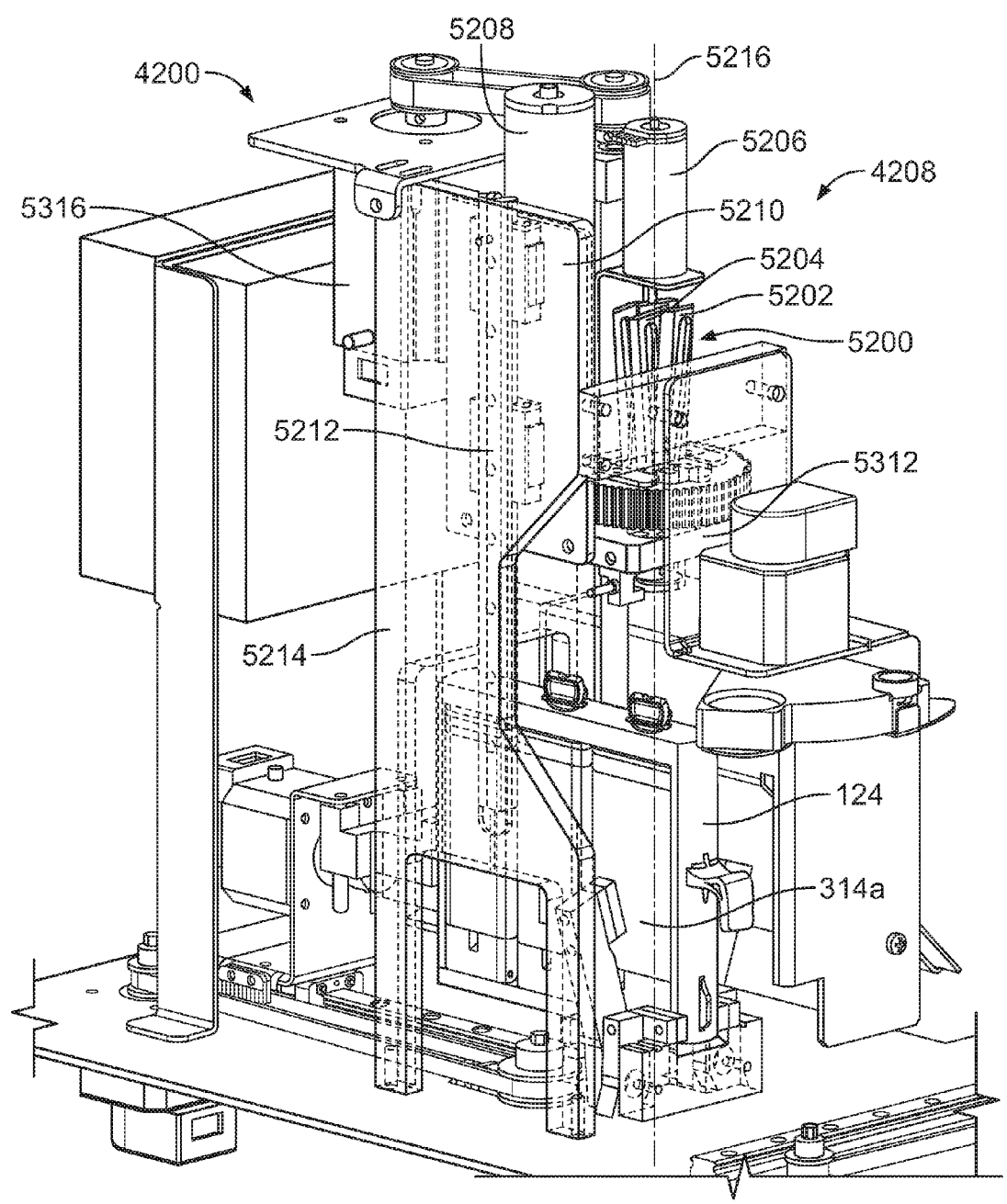
FIG. 52 is front perspective view of the example capper/decapper of FIG. 51 showing an example gripper head having an example gripper with an example first gripper arm and an example second gripper arm.
Figure 54:
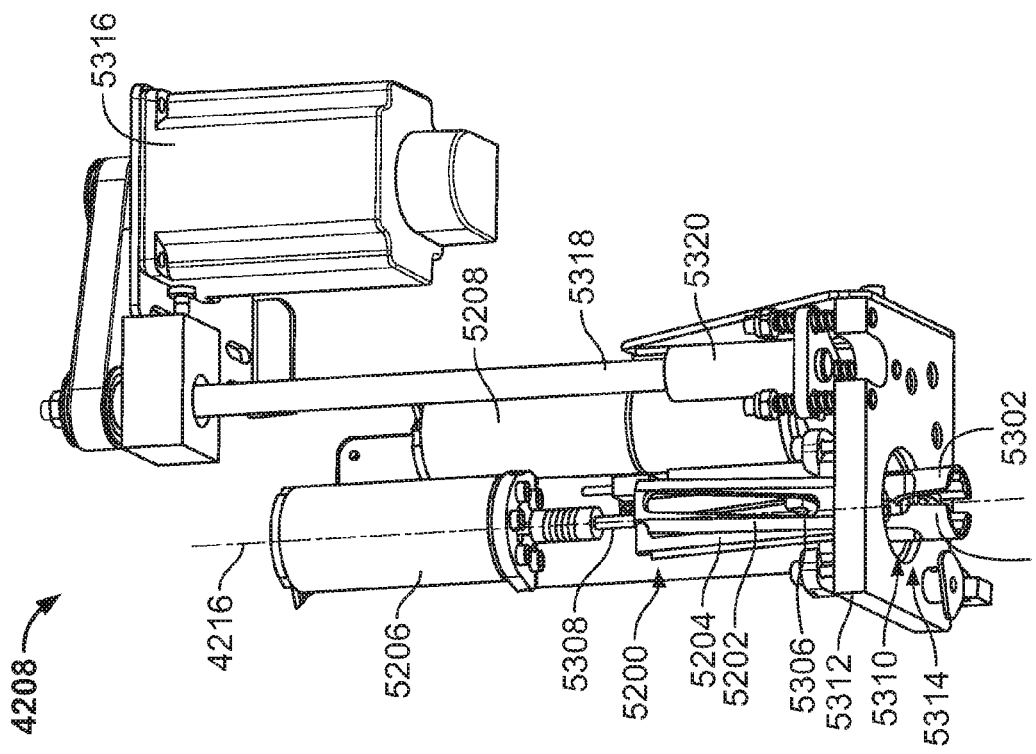
FIG. 54 is a bottom perspective view of the example gripper head of FIG. 52.
Figure 53:
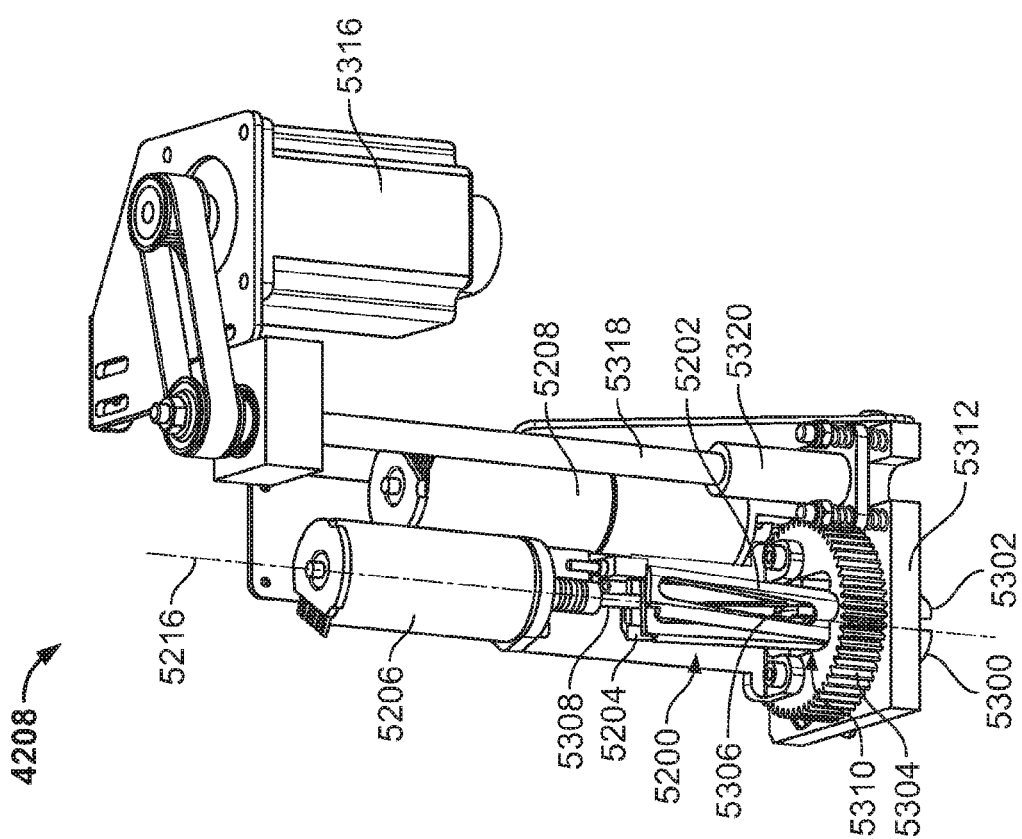
FIG. 53 is a top perspective view of the example gripper head of FIG. 52.
Figure 55:
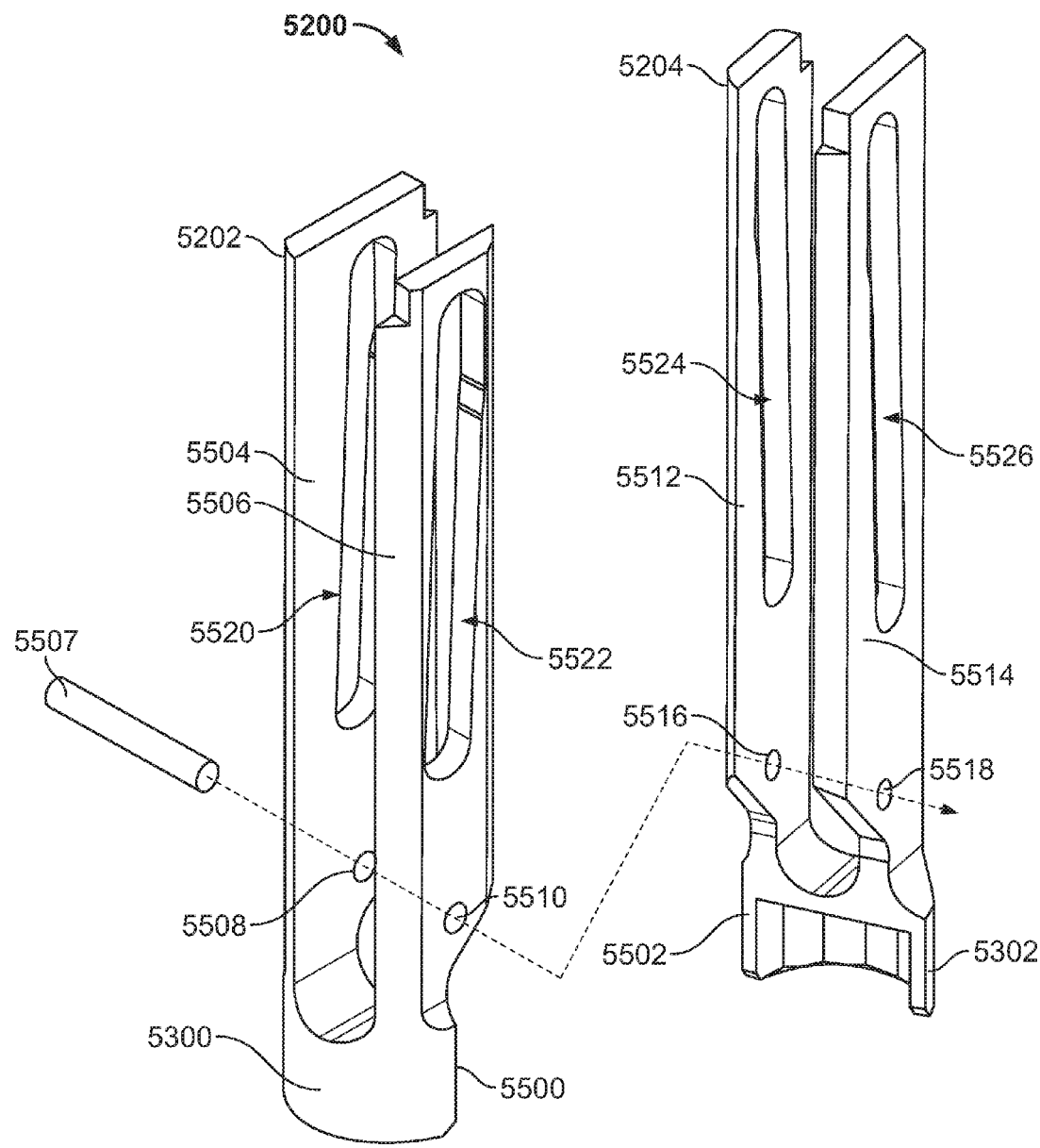
FIG. 55 is an exploded view of the example first and second gripper arms of FIG. 52.

As illustrated in FIG. 52, the carrier 124 and/or the container 314a are clamped in a position where the container 314a is disposed in the target location, beneath the gripper head 4208. FIG. 53 shows a top perspective view of the gripper head 4208, and FIG. 54 shows a bottom perspective view of the gripper head 4208, which are described in conjunction with FIG. 52. To grab or grasp the cap 315a, the gripper head 4208 includes a gripper 5200 having a first gripper arm 5202 and a second gripper arm 5204. FIG. 55 shows an exploded view of the gripper 5200. As illustrated in FIGS. 53-55, the first gripper arm 5202 includes a first gripper hand 5300 and the second gripper arm 5204 includes a second gripper hand 5302. The first and second gripper hands 5300, 5302 are movable toward each other to grip or grasp a cap, for example, and are movable away from each other to release a cap or to enable a cap to be inserted between the first and second gripper hands 5300, 5302. As illustrated in FIG. 55, the first and second gripper hands 5300, 5302 are curved. The first gripper hand 5300 has an inside surface or rim 5500 and the second gripper hand 5302 has an inner surface or rim 5502. When the first and second gripper hands 5300, 5302 are brought together, and inside surfaces 5500, 5502 are engaged, the first and second gripper hands 5300, 5302 form a cylindrical opening, which may be used to hold a cap therein (e.g., the first cap 305a illustrated in FIG. 3A). In another instance, a tab of a cap (e.g., such as the butterfly cap 315a) may be grasped between (e.g., pinched between) the inner surfaces 5500, 5502 of the first and second gripper hands 5300, 5302. Therefore, the gripper 5200 can be used to grasp different types of caps.

To enable the first and second gripper hands 5300, 5302 to move toward or away from each other, the first and second gripper arms 5202, 5204 are pivotable. As illustrated in FIG. 55, the first gripper arm 5202 includes a first wall 5504 and a second wall 5506 spaced apart from the first wall 5504. The first and second walls 5504, 5506 are coupled to the first gripper hand 5300. The first and second walls 5504, 5506 of the first gripper arm 5202 have respective apertures 5508, 5510, which receive a pin 5507 therethrough for enabling the first gripper arm 5202 to pivot. The apertures 5508, 5510 are aligned (e.g., concentric) and share the same axis. The second gripper are 5204 is similar to the first gripper arm 5202, and includes a first wall 5512, a second wall 5514 and respective apertures 5516, 5518. The first and second gripper arms 5202, 5204 are interleaved, such that the second wall 5514 of the second gripper arm 5204 is disposed between the first and second walls 5504, 5506 of the first gripper arm 5202, and the first wall 5504 of the first gripper arm 5202 is disposed between the first and second walls 5512, 5514 of the second gripper arm 5204. The apertures 5508, 551, 5516, 5518 are aligned and the pin 5507 is disposed therein, which enables the first and second gripper arms 5202, 5204 to pivot about the same axis. The pin 5507 is disposed within a gear 5304 (FIG. 53), disclosed in further detail herein.

To actuate the gripper 5200 and pivot the first and second gripper arms 5202, 5204 to move the first and second gripper hands 5300, 5302 toward or away from each other, the gripper head 4208 includes a first actuator 5206, which is illustrated in FIGS. 52, 53 and 54. The first actuator 5206 operates to move a pin 5306 (e.g., a closing pin), illustrated in FIGS. 53 and 54, via an output shaft 5308. As illustrated in FIG. 55, the first and second walls 5504, 5506 of the first gripper arm 5202 include respective slots 5520, 5222. The slots 5520, 5522 extended along the first and second walls 5504, 5506 and are angled with respect to a vertical orientation of the first gripper arm 5202. Similarly, the first and second walls 5512, 5514 of the second gripper arm 5204 include respective slots 5524, 5526 that are angled with respect to a vertical orientation of the second gripper arm 5204. As illustrated in FIGS. 53 and 54, the pin 5306 extends through the slots 5520, 5522, 5524, 5526 (labeled in FIG. 55) of the first and second gripper arms 5202, 5204. When the pin 5306 is at a downward position, as illustrated in the position in FIGS. 53 and 54, the first and second gripper arms 5300, 5302 are angled relative to each other, which causes the first and second gripper hands 5300, 5302 to be move away from each other. When the pin 5306 is moved upward, the angle of the slots 5520, 5522, 5524, 5526 causes the upper sections of the first and second gripper arms 5202, 5204 to move closer to a vertical axis, which causes the first and second gripper arms 5202, 5204 to rotate, thereby bringing the first and second gripper hands 5300, 5302 closer together.

In some examples, a cap may be threaded or rotatably coupled onto a container, and the cap is to be rotated to release the cap from the container. For example, the cap 315a is rotatably coupled to the container 314a. Therefore, in some examples, the gripper 5200 is to be rotated after the first and second gripper hands 5300, 5302 have been engaged with the cap 315a. To rotate the gripper 5200, the first and second gripper arms 5202, 5204 are disposed within an opening 5310 of the gear 5304. The first and second gripper arms 5202, 5204 are coupled to an inside of the opening 5310 of the gear 5304 via the pin 5507 (FIG. 55). The gear 5304 is rotatable on a platform 5312, which has an opening 5314. To rotate the gear 5304, the gripper head 4208 includes a second actuator 5208, which is illustrated in FIGS. 52, 53 and 54. The second actuator 5208 has an output gear that meshes with the gear 5304 to rotate the gear 5304 and, thus, the gripper 5200.

To move the gripper 5200 up and down, the gripper head 4208 includes a third actuator 5316, which is illustrated in FIGS. 53 and 54. The third actuator 5316 rotates a lead screw 5318, which is threaded through a mount 5320 on the platform 5312. As the lead screw 5318 rotates, the platform 5312 moves upward or downward, depending on the direction of rotation. As illustrated in FIG. 52, the platform 5312 is coupled to a backing plate 5210 that is slidable along a track 5212, which is coupled to a vertical mounting plate 5214. In the illustrated example, the third actuator 5316 is coupled to the vertical mounting plate 5214. The gripper 5200 moves along an axis 5216 via the third actuator 5316 and is rotatable about the axis 5216 via the second actuator 5208.

Figure 56:
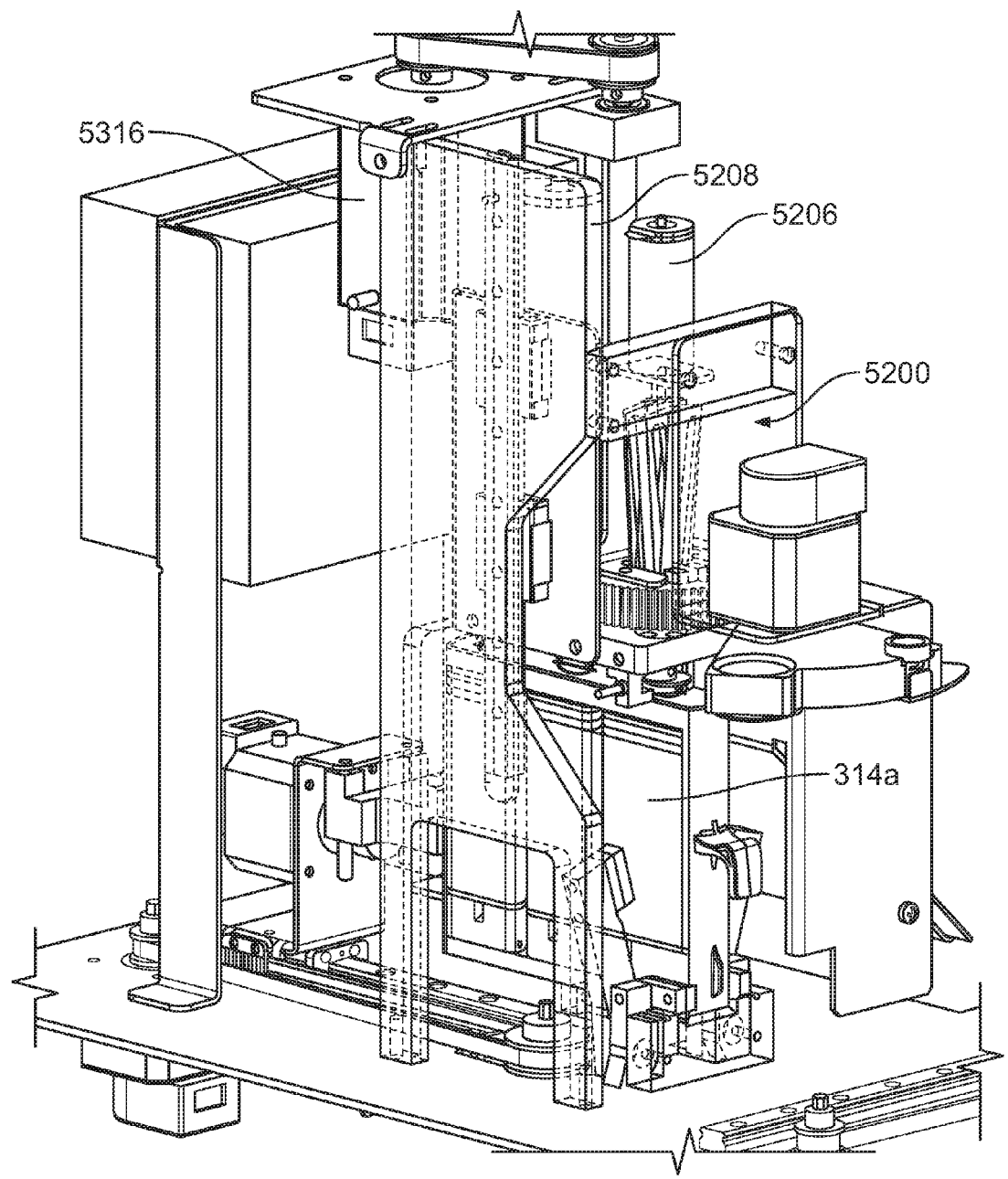
FIG. 56 shows the example gripper of FIG. 52 being moved toward the cap of the container disposed in the target location.
Figure 57:
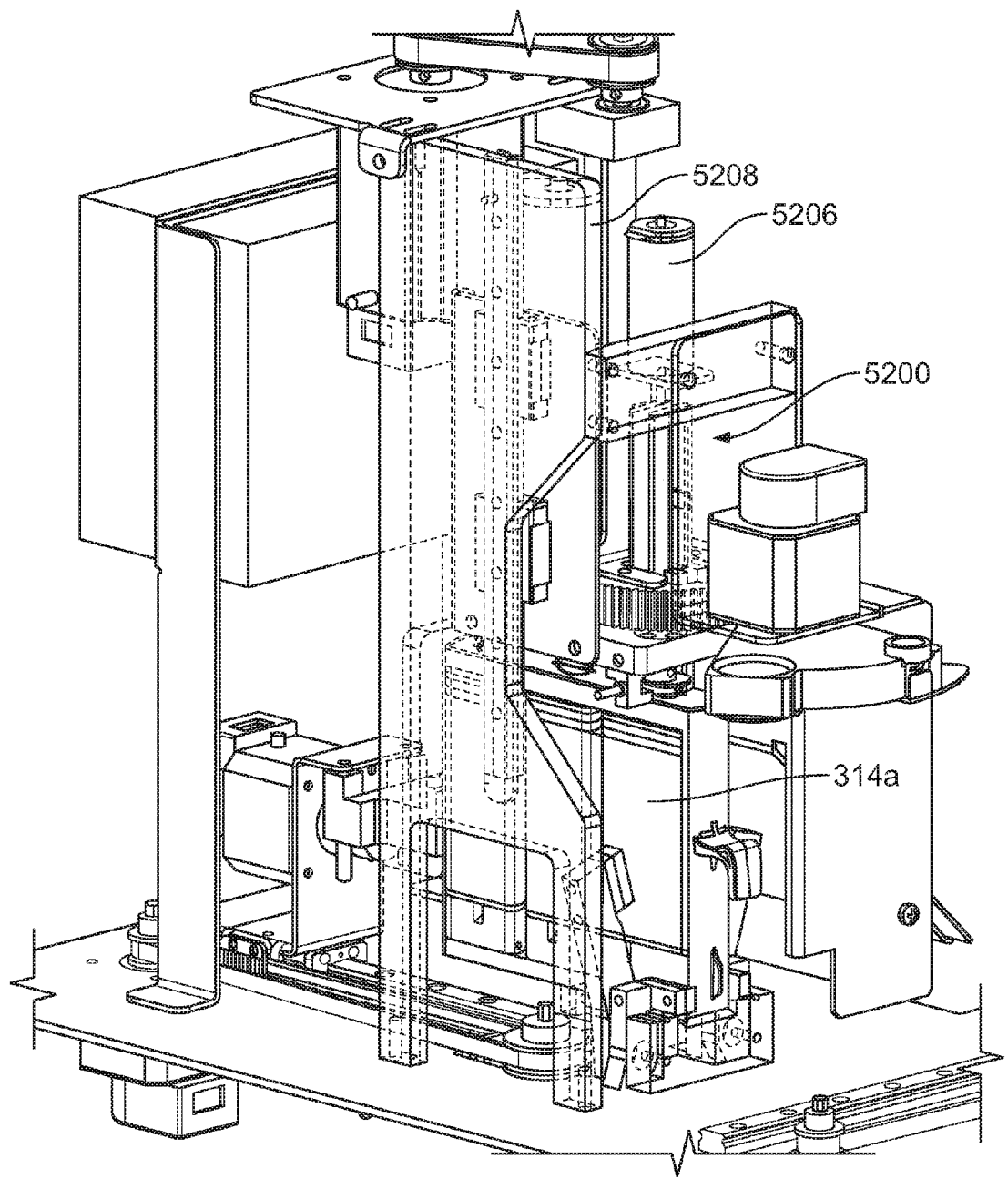
FIG. 57 shows the example gripper of FIG. 56 engaging the cap of the container.
Figure 58:
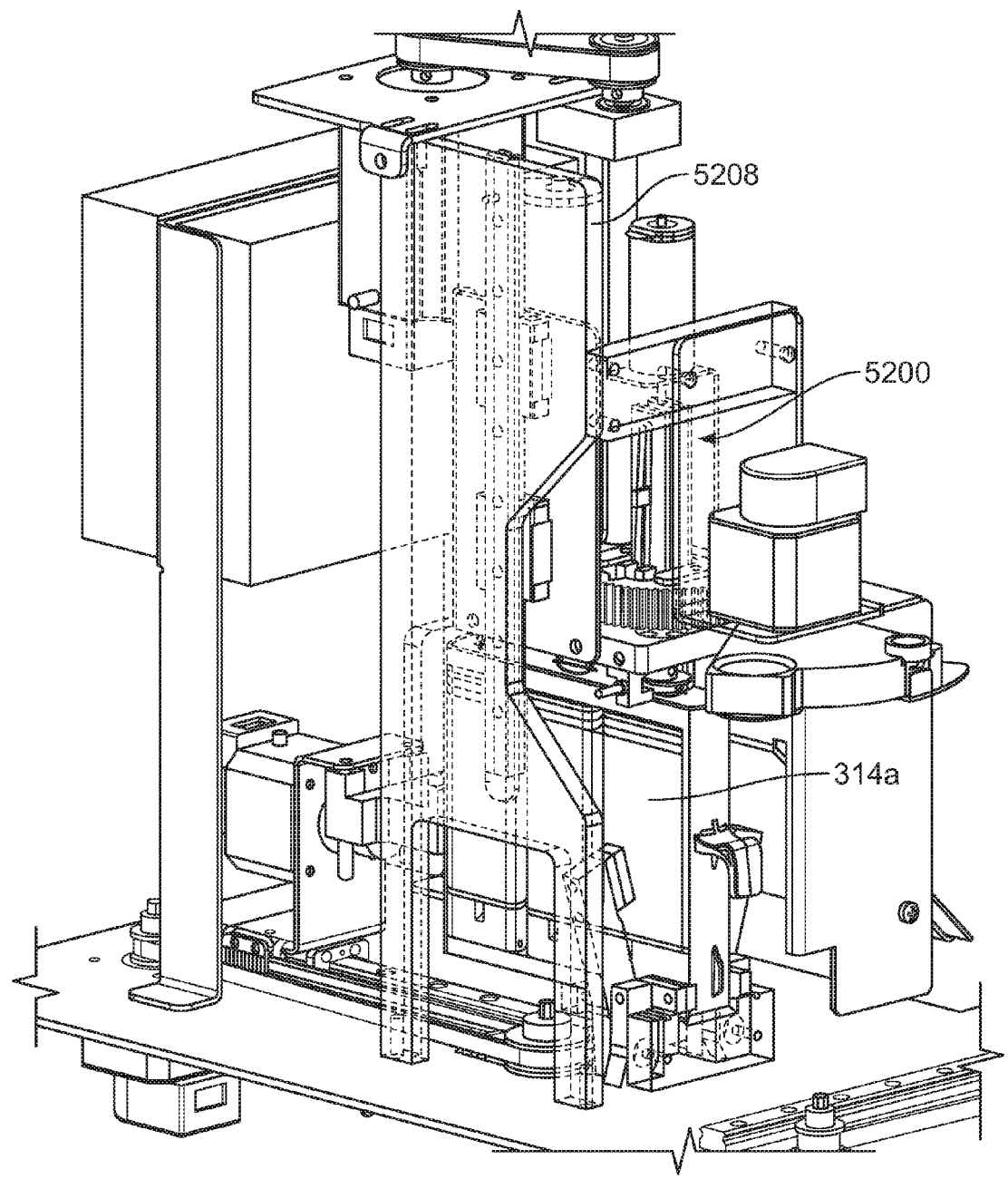
FIG. 58 shows the example gripper of FIG. 57 rotating to release the cap from the container.

Turning to FIG. 56, the gripper 5200 is moved downward, via the third actuator 5316, toward the cap 315a of the container 314a. The first and second gripper hands 5300, 5302 (FIG. 53) are opened so that the cap 315a can be receive between the gripper hands 5300, 5302. As illustrated in the enlarge view of FIG. 44, the cap 315a has a tab that extends vertically. The orientation of the cap 315a may be detected by the camera 440 as the carrier 124 originally passed the camera 440. Depending on the position of the tab, the gripper 5200 may be rotated, via the second actuator 5208, to align the tab between the first and second gripper hands 5300, 5302. In particular, the insides surfaces 5500, 5502 of the respective first and second gripper hands 5300, 5302 are to engage opposite sides of the tab (e.g., to pinch the tab between the inner surfaces 5500, 5502). Once the tab is disposed between the first and second gripper hands 5300, 5302, the first actuator 5206 moves the pin 5306 (FIG. 53) upward to pivot the first and second gripper arms 5202, 5204 and, thus, move the first and second gripper hands 5300, 5302 toward each other to engage the sides of the tab, as illustrated in FIG. 57. The gripper 5200 is then rotated, via the second actuator 5208 (e.g., clockwise or counter-clockwise), to release the cap 315*a* from the container 314*a*, as illustrated in FIG. 58.

Figure 59:
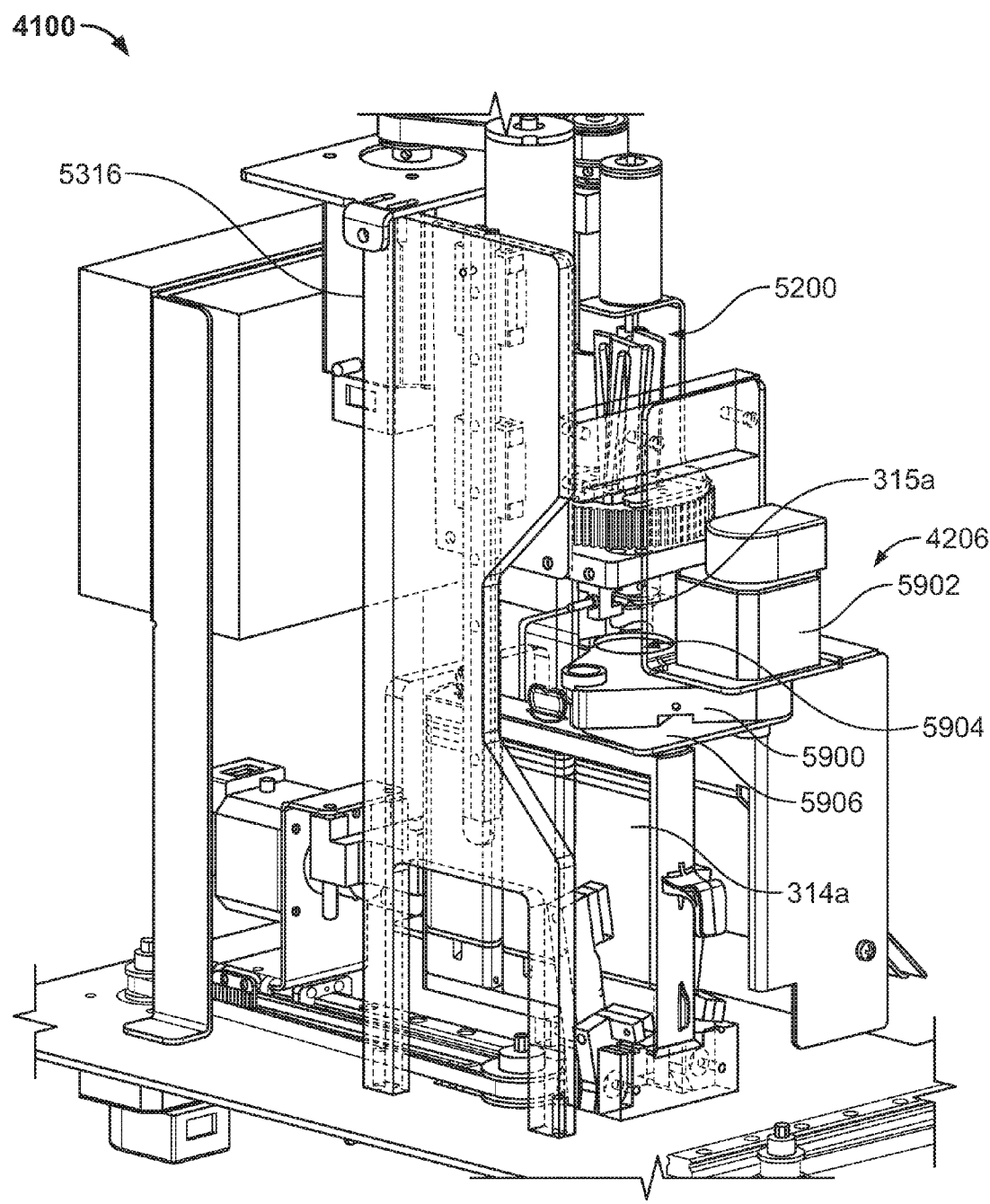
FIG. 59 shows the example gripper of FIG. 58 depositing the cap into an example cap handler tray.

After the cap 315*a* is released from the container 314*a*, the gripper 5200 is moved upward, via the third actuator 5316, as illustrated in FIG. 59. To dispose of the cap 315*a*, the decapper 4100 includes the cap handler 4206. In the illustrated example, the cap handler 4206 includes a tray 5900 that is pivotable via a cap handler actuator 5902. The tray 5900 has a first opening 5904 (e.g., a disposal opening). The tray 5900 is rotated until the first opening 5904 is located beneath the cap 315*a*. To release the cap 315*a* from the gripper 5200, the first actuator 5206 moves the pin 5306 (FIG. 53) downward to pivot the first and second gripper arms 5202, 5204 (FIG. 53) and, thus, move the first and second gripper hands 5300, 5302 away from each other. In some examples, the first opening 5904 is a through-hole. To prevent the cap 315*a* from falling through the first opening 5904 and back onto the container 314*a*, the cap handler 4206 includes a plate 5906 disposed below the tray 5900.

Figure 60:
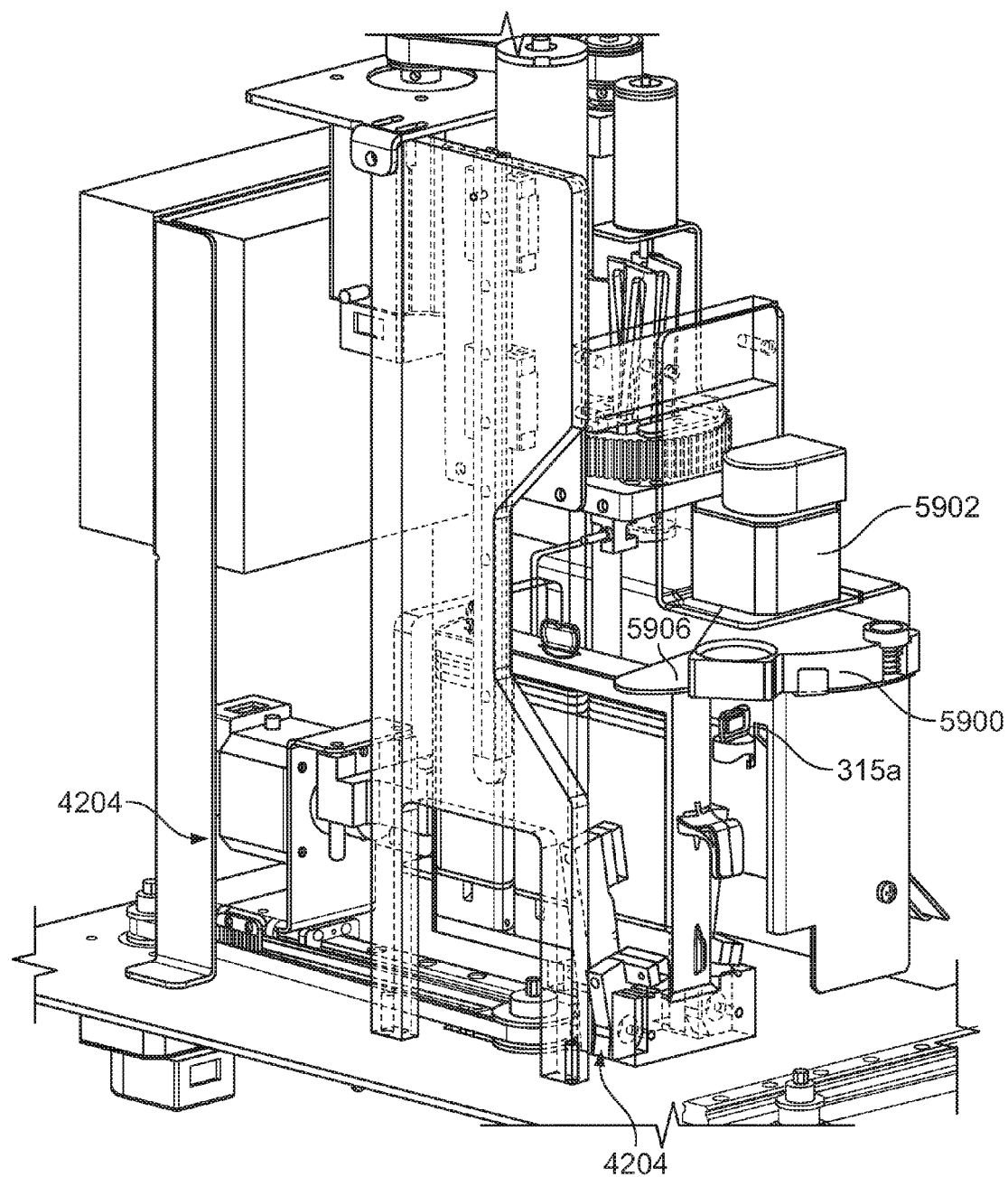
FIG. 60 shows the example cap handler tray of FIG. 59 disposing of the cap.

Once the cap is disposed in the first opening 5904 of the tray 5900, the cap handler actuator 5902 rotates the tray 5900. The plate 5906 is coupled to the tray 5900 via a spring. As the tray 5900 rotates (e.g., in the counter-clockwise direction looking down) the plate 5906 follows. The plate 5906 has a notch that allows the cap 315*a* to fall through the plate 5906 once the cap 315*a* is away from the container 314*a*, as illustrated in FIG. 60. In particular, a stop pin prevents the plate 5906 from continuing to rotate while the tray 5900 continues to rotate, at which point the first opening 5904 is moved over the notch in the plate 5906 and the cap 315*a* falls through the notch. The cap 315*a* is dropped into the chute 436 (FIG. 4) that leads to the onboard waste container 438 (FIG. 4).

If the second cap 315*b* of the second container 314*b* on the carrier 124 is also to be removed, the clamp 4202 releases the carrier 124 and/or the container 314*a* and the carrier transporter 4204 may move the carrier 124 along the track 4602 (e.g., to a second position) to dispose the second container 314*b* in the target location (e.g., along the axis 5216 beneath the gripper 5200). The second cap 315*b* of the second container 314*b* may then be removed by the gripper 5200, similar to the first cap 315*a*. The third cap 315*c* may also similarly be removed, if desired. This process may continue for as many containers are included in a carrier. For example, the carrier 124, 300 (FIG. 3A) includes six positions for containers. If no more caps are to be removed, the carrier transport 4204 may deposit the carrier 124 onto the sled 4400 (FIG. 44), which may then transfer the carrier 124 back to the rear side 4203 of the decapper 4100 where the carousel robot 418 can retrieve the carrier 124. Another carrier (e.g., a second carrier) may then be retrieved by the carrier transporter 4204 and transported to a position where a container on the subsequent carrier is in the target location.

The subsequent container may have the same or a different type of cap, and removal of the cap may occur as disclosed herein.

FIGS. 61-65 illustrate an example sequence of capping or recapping a container. In FIGS. 61-65, the example carrier 124 is illustrated as a control carrier 124, 300 (see FIG. 3A) having the six containers 304*a*-304*f*. In the example capping sequence, a cap is placed onto the first container 304*a*. It is understood that a similar operation may be performed on any of the other containers 304*b*-304*f* of the carrier 124 and/or on any of the other containers of the other types of carriers 124, 310, 124, 320 (FIGS. 3C, 3E).

Figure 61:
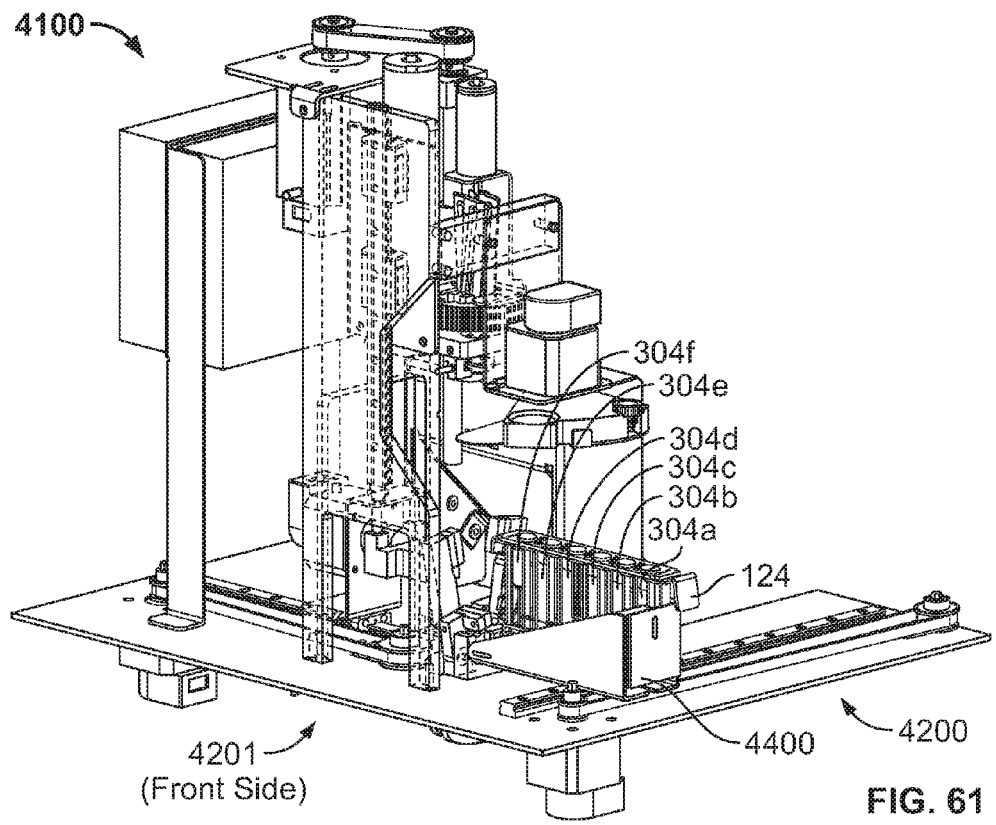
FIG. 61 shows an example carrier being transported to the example capper/decapper of FIG. 41 for an example capping operation.
Figure 62:
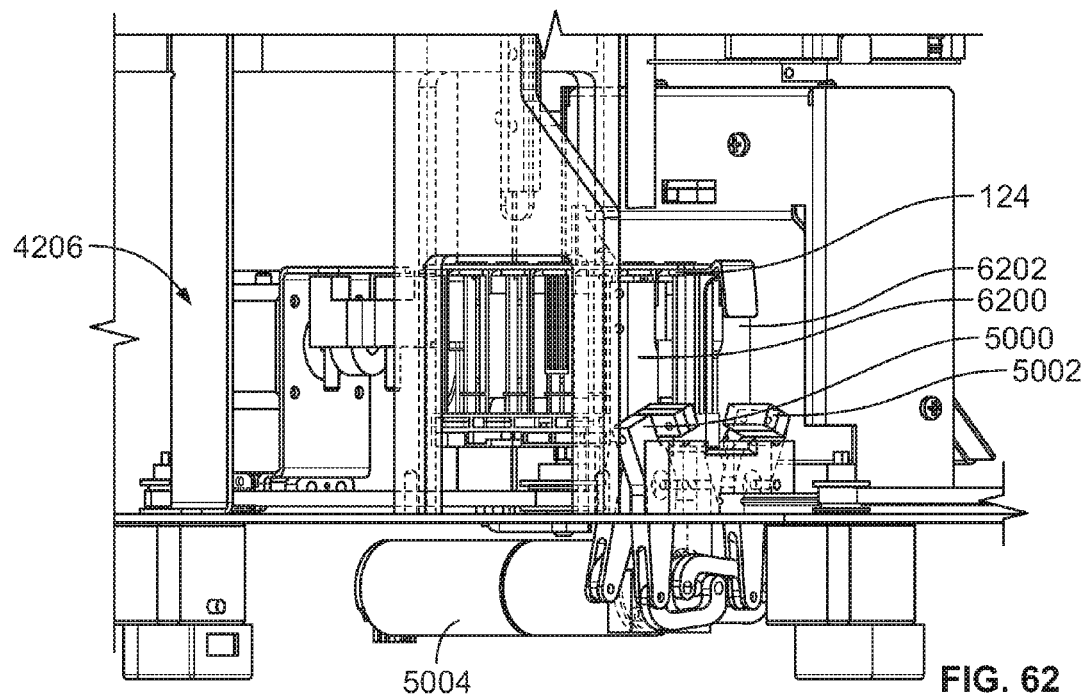
FIG. 62 shows an example container of example carrier of FIG. 61 being clamped to secure the example container while the container is in a target location.

In FIG. 61, the carrier 124 is transferred to the front side 4201 of the decapper 4100 by the sled 4400 of the shuttle 4200. The carrier transporter 4204 retrieves the carrier 124 from the sled 4400 and moves the carrier 124 to a position in which one of the container 304*a* is disposed in the target location (i.e., beneath the gripper 5200), as illustrated in FIG. 62. In the illustrated example, the clamp 4202 includes a third arm 6200 and a fourth arm 6202. The third and fourth arms 6200, 6202 are longer than the first and second arms 5000, 5002. The clamp actuator 5004 operates to move the third and fourth arms 6200, 6202 closer to each other or away from each other. In the illustrated example, the third and fourth arms 6200, 6202 engage the container 304*a* directly, rather than the first and second arms 5000, 5002, which are to engage the carrier 124 and/or the container located in the target position. In the illustrated example, the third and fourth arms 6200, 6202 operate opposite of the first and second arms 5000, 5002. In other words, when the first and second arms 5000, 5002 are fully open, the third and fourth arms 6200, 6202 are fully closed, and vice versa. The first and second arms 5000, 5002 and the third and fourth arms 6200, 6202 are coupled to the clamp actuator 5004 via a linkage system. When an output shaft of the clamp actuator 5004 rotates in one direction (e.g., counter-clockwise), the first and second arms 5000, 5002 open and the third and fourth arms 6200, 6202 close, and when the output shaft of the clamp actuator 5004 rotates in the other direction (e.g., clockwise), the first and second arms 5000, 5002 close and the third and fourth arms 6200, 6202 open. In the illustrated example, the third and fourth arms 6200, 6202 are longer than the first and second arms 5000, 5002, which enables the third and fourth arms 6200, 6202 to engage a relatively shorter container that is disposed within a carrier. For example, a shorter container may not reach all the way to the bottom of the 124. Therefore, the third and fourth arms 6200, 6202 are longer, thereby enabling them to grip a container closer to a top of the container.

Turning to FIG. 63, once the container 304*a* of the carrier 124 is secured, a cap 6300 is to be inserted into an opening of the container 304*a*. In the illustrated example, the cap 6300 is implemented as a rubber or silicon plug that may be force fit into an opening of the container 304*a*. However, in other examples, other types of caps may be used. The cap 6300 is deposited into a second opening 6302 of the tray 5900 of the cap handler 4206 via a cap hopper 6304. The cap hopper 6304 contains a plurality of the caps 6300, and the caps 6300 are delivered to the cap handler 4206 as needed.

Figure 64:
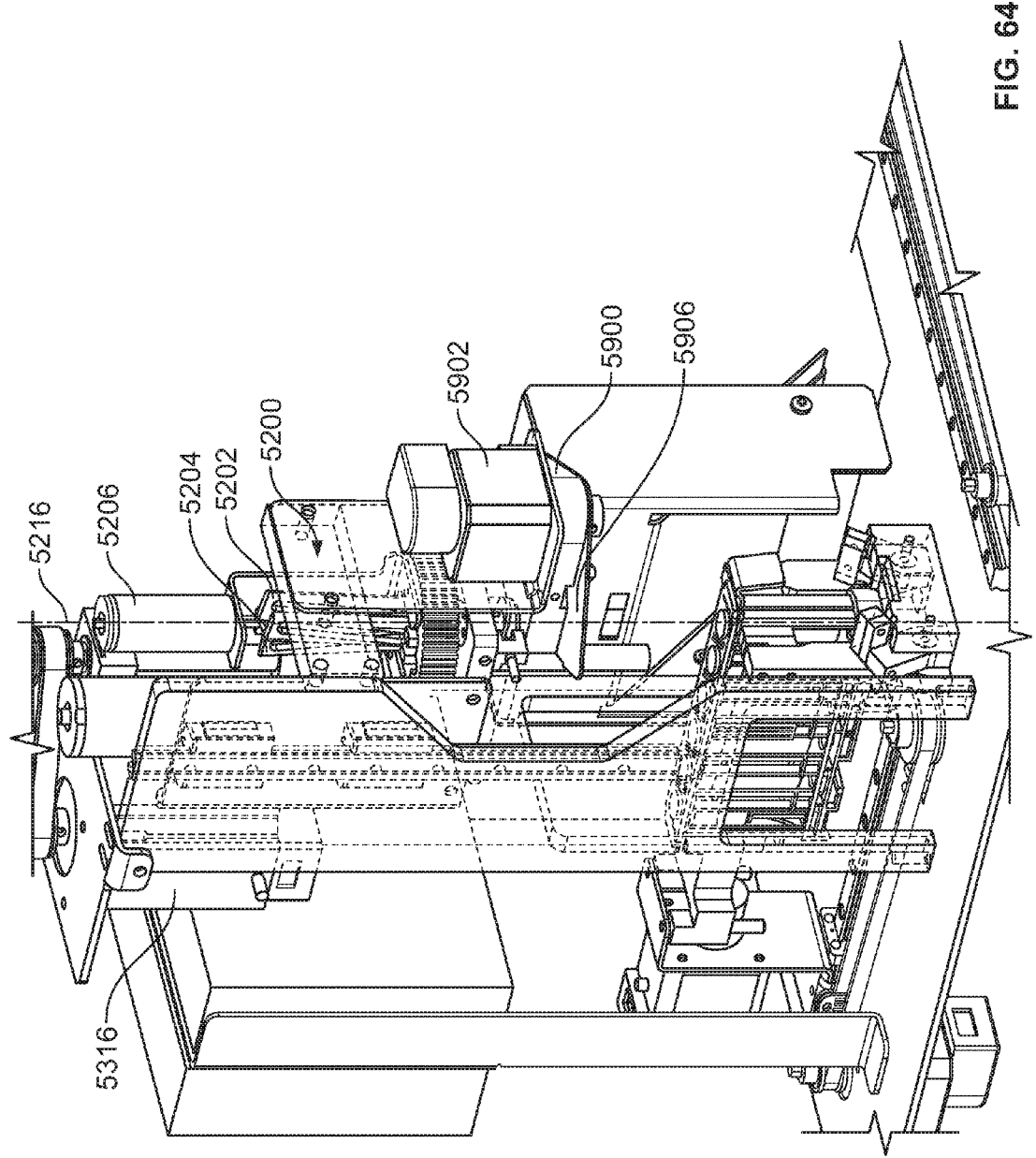
FIG. 64 shows the example gripper of FIG. 52 retrieving the example cap from the example cap handler tray of FIG. 63.

After the cap 6300 is deposited into the second opening 6302 of the tray 5900, the tray 5900 is rotated, via the cap handler actuator 5902, to position the cap 6300 along the axis 5216 beneath the gripper 5200, as illustrated in the position in FIG. 64. In some examples, the second opening 6302 is a through-hole. In such an example, the plate 5906 prevents the cap 6300 from falling through the tray 5900. In other examples, the second opening 6302 is a bore or cup that supports the cap 6300.

Figure 65:
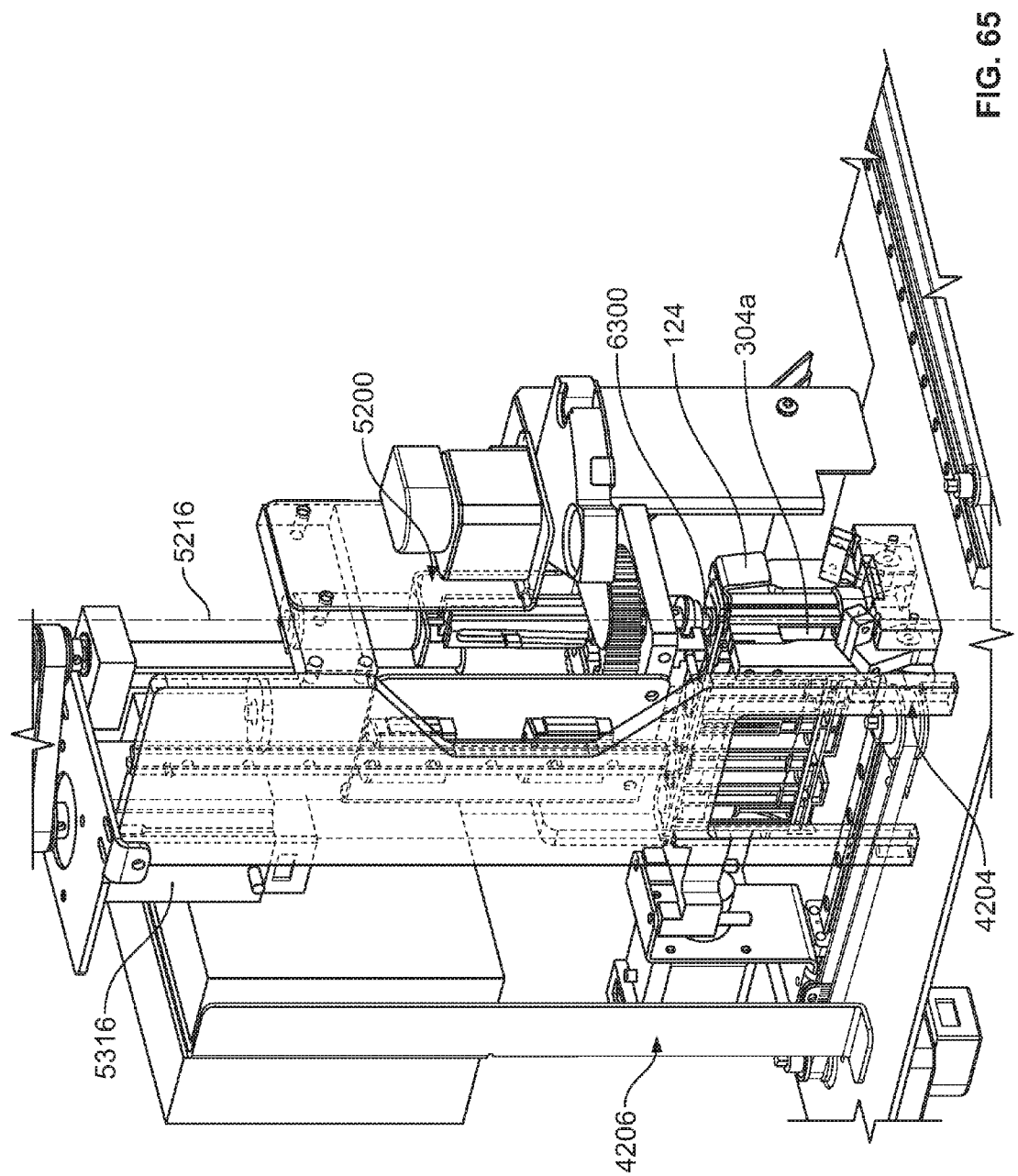
FIG. 65 shows the example gripper of FIG. 64 coupling the example cap onto the container.

Once the cap 6300 is positioned beneath the gripper 5200, the gripper 5200 is lowered, via the third actuator 5316, and the first and second gripper arms 5202, 5204 pivot (via the first actuator 5206) to move the first and second gripper hands 5300, 5302 (FIG. 53) toward each other to grasp the cap 6300. Once the cap 6300 is secure, the gripper 5200 may move upward and the tray 5900 is rotated out of the way (e.g., via the cap handler actuator 5902). The gripper 5200 is then moved downward along the axis 5216, via the third actuator 5316, to insert the cap 6300 into the opening of the container 304*a*, as illustrated in FIG. 65. In some examples, the gripper 5200 may also rotate while moving downward, which may reduce friction between the cap 6300 and the opening of the container 304*a*, thereby reducing the force needed to insert the cap 6300 into the opening.

If another container of the carrier 124 is to receive a cap, the clamp 4202 may release the container 304*a* and the carrier transporter 4204 may move the carrier 124 to another position (e.g., a second position) so that another container is disposed in the target location (e.g., along the axis 5216 beneath the gripper 5200). Another cap 6300 may be inserted into an opening of the second container, similar to the operation disclosed above. In other examples, a different type of cap may be inserted into another container (e.g., a butterfly type cap).

Figure 66:
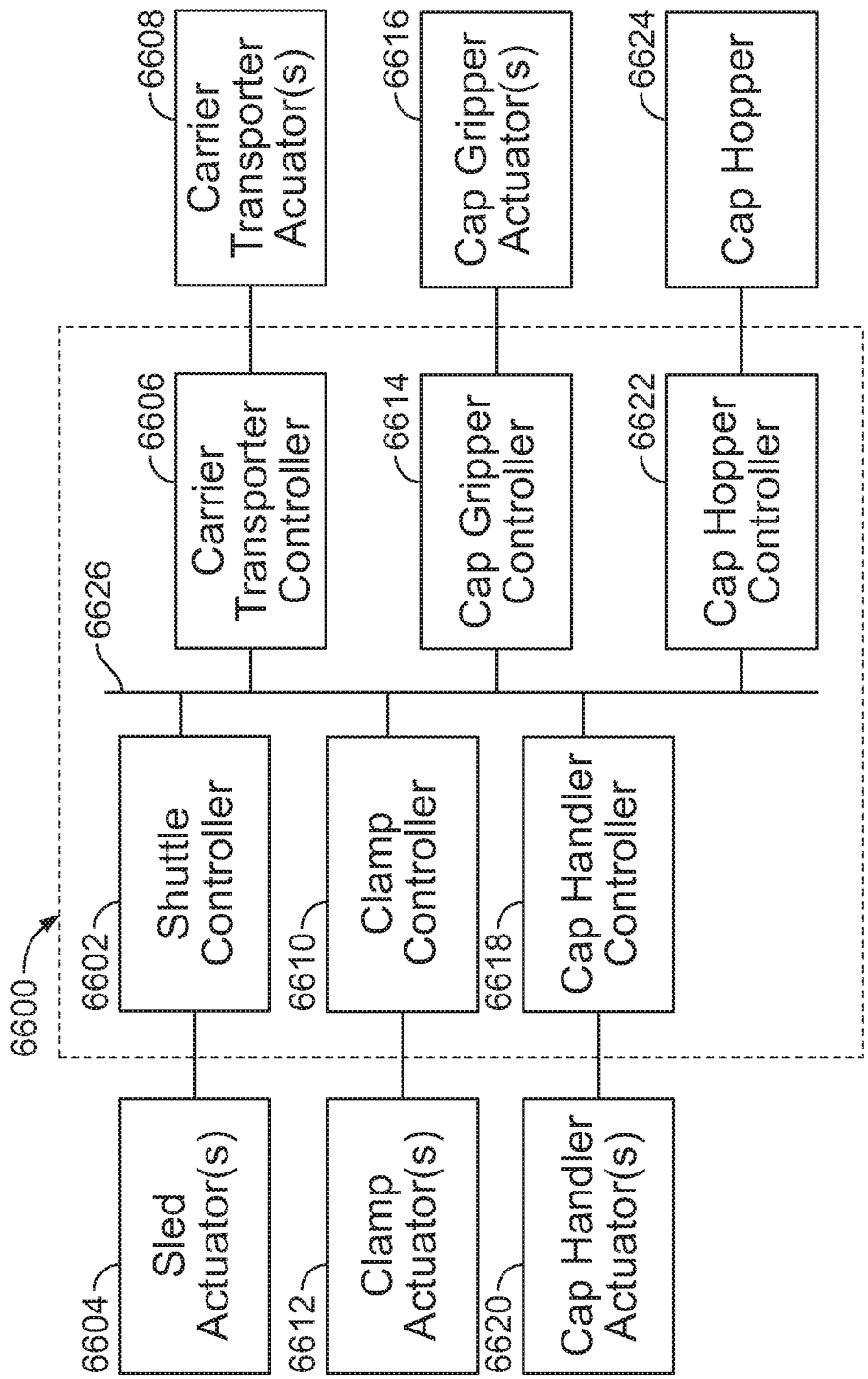
FIG. 66 is a block diagram of an example processing system for the example capper/decapper shown in FIG. 41.

FIG. 66 is a block diagram of an example processing system 6600 that may be used with the example decapper 4100 of FIG. 41. The example processing system 6600 may be implemented by, for example, the control module 4210. The example decapper 4100 disclosed herein may be used with a storage module, such as the storage module 100, to remove a cap from a container and/or couple a cap to a container. For example, the decapper 4100 may be used to remove the first cap 315*a* from the first container 314*a* of the immunoassay reagent carrier 124, 300 (FIG. 3C) before the carrier 124, 300 is stored in the storage module 100 and/or sent to an analyzer and/or an LAS for use therein. Additionally or attentively, the example decapper 4100 may be used to couple a cap (such as the cap 6300 of FIG. 63) to a container of a carrier 124 before the carrier 124 is stored in the storage module 100. The example processing system 6600 may correspond to the example capper/decapper controller 4018 as illustrated in FIG. 40, which is communicatively coupled to the processing system 4000 of a storage module.

The example processing system 6600 includes a shuttle controller 6602 to control a sled or shuttle to move one or more carriers between a first side of the decapper and a second side of the decapper. The shuttle controller 6602 is communicatively coupled to one or more sled actuators 6604. For example, as illustrated in FIGS. 42 and 44, the decapper 4100 includes the shuttle 4200 to move a carrier 124 between the rear side 4203 of the decapper 4100 and the front side 4201 of the decapper 4100. The shuttle 4200 includes the sled 4400, which is movable along the track 4402 via the shuttle actuator 4214.

In the illustrated example of FIG. 66, the processing system 6600 includes a carrier transporter controller 6606 to control a carrier transporter to move a carrier between the sled and desired position in which one of the containers of the carrier is disposed in a target location. In the illustrated example, the carrier transporter controller 6606 is communicatively coupled to one or more carrier transporter actuators 6608. For example, as illustrated in FIG. 46, the decapper 4100 includes the carrier transporter 4204 to move a carrier 124 between the sled 4400 and the target location (e.g., along the axis 5216 (FIG. 52) beneath the gripper 5200). The carrier transporter 4204 includes the hand 4600 that is movable along the track 4602 via the first carrier transporter actuator 4604. The hand 4600 is movable up and down via the second carrier transporter actuator 4606.

The example processing system 6600 of FIG. 66 includes a clamp controller 6610 to control a clamp that secures the carrier and/or a container of the carrier in a position to receive a cap or have a cap removed from the container. In the illustrated example, the clamp controller 6610 is communicatively coupled to one or more clamp actuators 6612. For example, as illustrated in FIG. 50, the example decapper 4100 includes the clamp 4202 to secure a carrier 124 and/or a container of the carrier 124. The example clamp 4202 includes the first and second arms 5000, 5002 that move together, via the clamp actuator 5004, to grasp onto a carrier 124 and/or a container in the carrier 124. Additionally, as illustrated in FIG. 62, the clamp 4202 includes the third and fourth arms 6200, 6202 that move together, via the clamp actuator 5004, to grasp onto a container in the carrier 124. The third and fourth arms 6200, 6202 operate opposite of the first and second arms 5000, 5002. For example, the clamp actuator 5004 may rotate or drive an output shaft in one direction to move the first and second arms 5000, 5002 toward each other and the third and fourth arms 6200, 6202 away from each other, and may rotate or drive the output shaft in the opposite direction to move the first and second arms 5000, 5002 away from each other and the third and fourth arms 6200, 6202 toward each other.

The example processing system 6600 of FIG. 66 includes a cap gripper controller 6614 that controls a gripper that may be used to grip a cap on a container to remove the cap from the container and/or to grip a cap and couple the cap onto a container (e.g., by inserting the cap into a mouth of the container). The cap gripper controller 6614 is communicatively coupled to one or more cap gripper actuators 6616. For example, as illustrated in FIG. 52, the example decapper 4100 includes the gripper head 4208, which includes the gripper 5200. The gripper 5200 includes the first and second gripper arms 5202, 5204 that pivot to move the first and second gripper hands 5300, 5302 (FIG. 53) toward or away from each other. The first and second gripper arms 5202, 5204 pivot via the first gripper actuator 5206, the gripper 5200 is rotatable via the second gripper actuator 5208, and the gripper 5200 is movable up and down via the third gripper actuator 5316. The first and second gripper hands 5300, 5302 may be used to grasp onto different types of caps (e.g., a butterfly type cap such as the cap 315*a* of FIG. 44, a plug type cap such as the cap 6300 of FIG. 63, a screw type cap such as the cap 305*a* of FIG. 3A, etc.).

To dispose of a cap that has been removed from a container and/or to transfer a cap to the gripper for placement on a container, the example processing system of FIG. 66 includes a cap handler controller 6618, which is communicatively coupled to one or more cap handler actuators 6620. For example, as illustrated in FIG. 59, the decapper 4100 includes the cap handler 4206. The cap handler 4206 includes the tray 5900 that rotates via the cap handler actuator 5902. After a cap has been removed from a container, the tray 5900 is rotated beneath the gripper 5200 and the cap is dropped into the first opening 5904 on the tray 5900. The tray 5900 is then rotated, via the cap handler actuator 5902 to a position where the cap can fall through the first opening 5904. Additionally or alternatively, the tray 5900 may be used to supply a cap to the gripper 5200 for placement on a container. For example, as illustrated in FIG. 63, a cap may be deposited into the second opening 6302 (e.g., via the cap hopper 6304), and may be rotated to a position where the cap is located under the gripper 5200 and can be retrieved by the gripper 5200.

To operate a cap hopper and provide caps to the cap handler, the example processing system 6600 of FIG. 66 includes a cap hopper controller 6622, which is communicatively coupled to a cap hopper 6624. The cap hopper 6624 may correspond to, for example, the cap hopper 6304 of FIG. 63. The cap hopper 6304 may contain a plurality of caps, such as the cap 6300, and may deposit the cap(s) 6300 into the second opening 6302 of the tray 5900 as desired.

In the illustrated example of FIG. 66, the processing system components 6602, 6606, 6610, 6614, 6618, 6622 are communicatively coupled to other components of the example system 6600 via communication links 6626. The communication links 6626 may be any type of wired connection (e.g., a databus, a USB connection, etc.) or a wireless communication mechanism (e.g., radio frequency, infrared, etc.) using any past, present or future communication protocol (e.g., Bluetooth, USB 2.0, USB 3.0, etc.). Also, the processing system components 6602, 6606, 6610, 6614, 6618, 6622 may be integrated in one device or distributed over two or more devices.

While an example manner of implementing the storage module 100 of FIG. 4 and/or the storage module 3500 of FIG. 35 is illustrated in FIG. 40, and an example manner of implementing the decapper 4100 of FIG. 41 is illustrated in FIG. 66, one or more of the elements, processes and/or devices illustrated in FIGS. 40 and 66 may be combined, divided, re-arranged, omitted, eliminated and/or implemented in any other way. Further, the example loading bay controller 4002, the example positioner controller 4006, the example shelving unit robot controller 4012, the example capper/decapper controller 4018, the example shelving unit controller 4022, the example reader controller 4028, the example storage housing temperature controller 4032, the example processor 4036, the example database 4038, the example shuttle controller 6602, the example carrier transporter controller 6606, the example clamp controller 6610, the example cap gripper controller 6614, the example cap handler controller 6618, the example cap hopper controller 6622, and/or, more generally, the example processing systems 4000, 6600 of FIGS. 40 and 66 may be implemented by hardware, software, firmware and/or any combination of hardware, software and/or firmware. Thus, for example, any of the example loading bay controller 4002, the example positioner controller 4006, the example shelving unit robot controller 4012, the example capper/decapper controller 4018, the example shelving unit controller 4022, the example reader controller 4028, the example storage housing temperature controller 4032, the example processor 4036, the example database 4038, the example shuttle controller 6602, the example carrier transporter controller 6606, the example clamp controller 6610, the example cap gripper controller 6614, the example cap handler controller 6618, the example cap hopper controller 6622 and/or, more generally, the example processing systems 4000, 6600 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example, loading bay controller 4002, the example positioner controller 4006, the example shelving unit robot controller 4012, the example capper/decapper controller 4018, the example shelving unit controller 4022, the example reader controller 4028, the example storage housing temperature controller 4032, the example processor 4036, the example database 4038, the example shuttle controller 6602, the example carrier transporter controller 6606, the example clamp controller 6610, the example cap gripper controller 6614, the example cap handler controller 6618 and/or the example cap hopper controller 6622 is/are hereby expressly defined to include a tangible computer readable storage device or storage disk such as a memory, a digital versatile disk (DVD), a compact disk (CD), a Blu-ray disk, etc. storing the software and/or firmware. Further still, the example processing systems 4000, 6600 of FIGS. 40 and 66 may include one or more elements, processes and/or devices in addition to, or instead of, those illustrated in FIGS. 40 and 66, and/or may include more than one of any or all of the illustrated elements, processes and devices.

Figure 67:
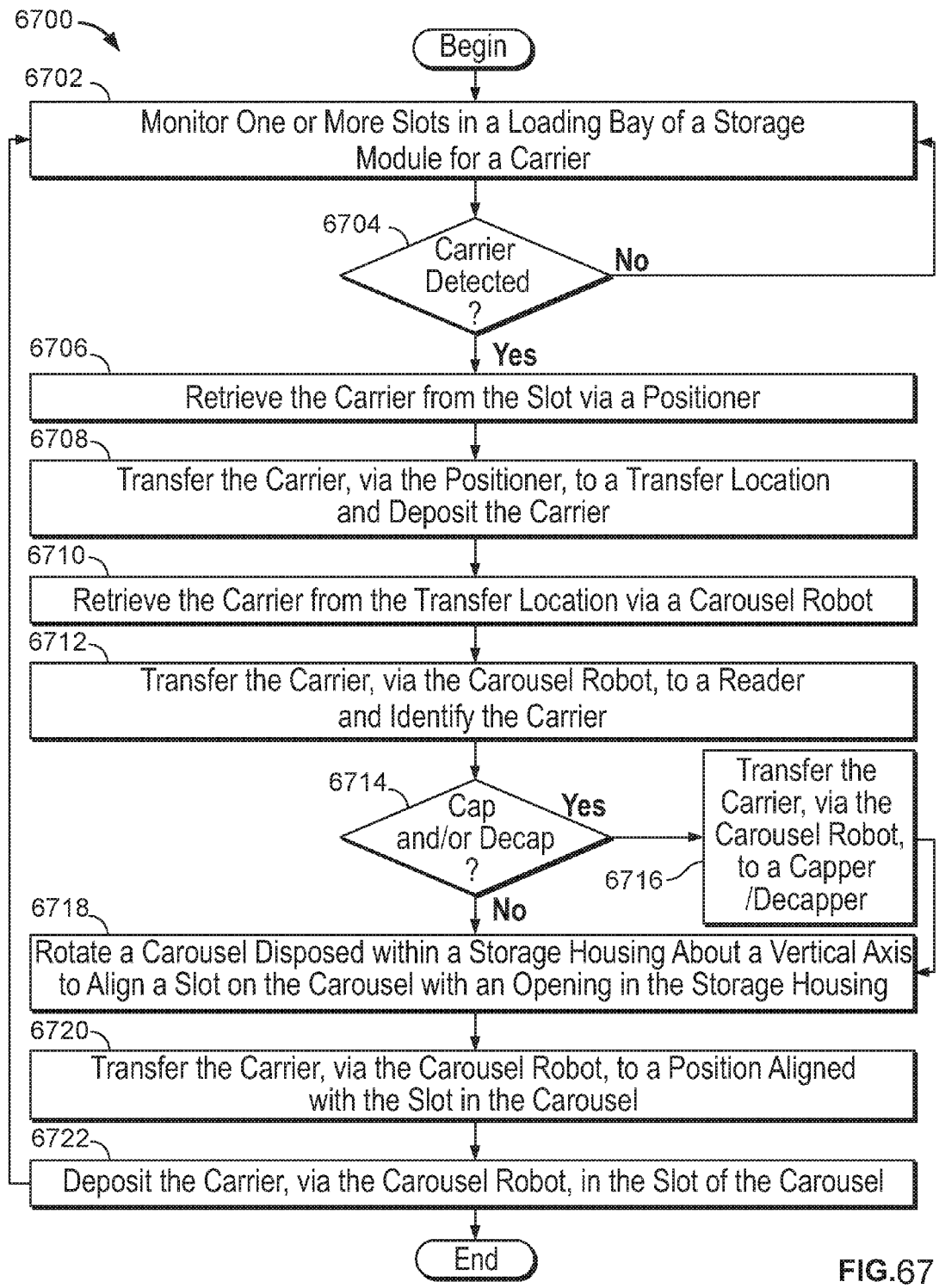
FIG. 67 is a flowchart illustrating an example process of transporting a carrier into an example storage module in accordance with the teachings of this disclosure.
Figure 68:
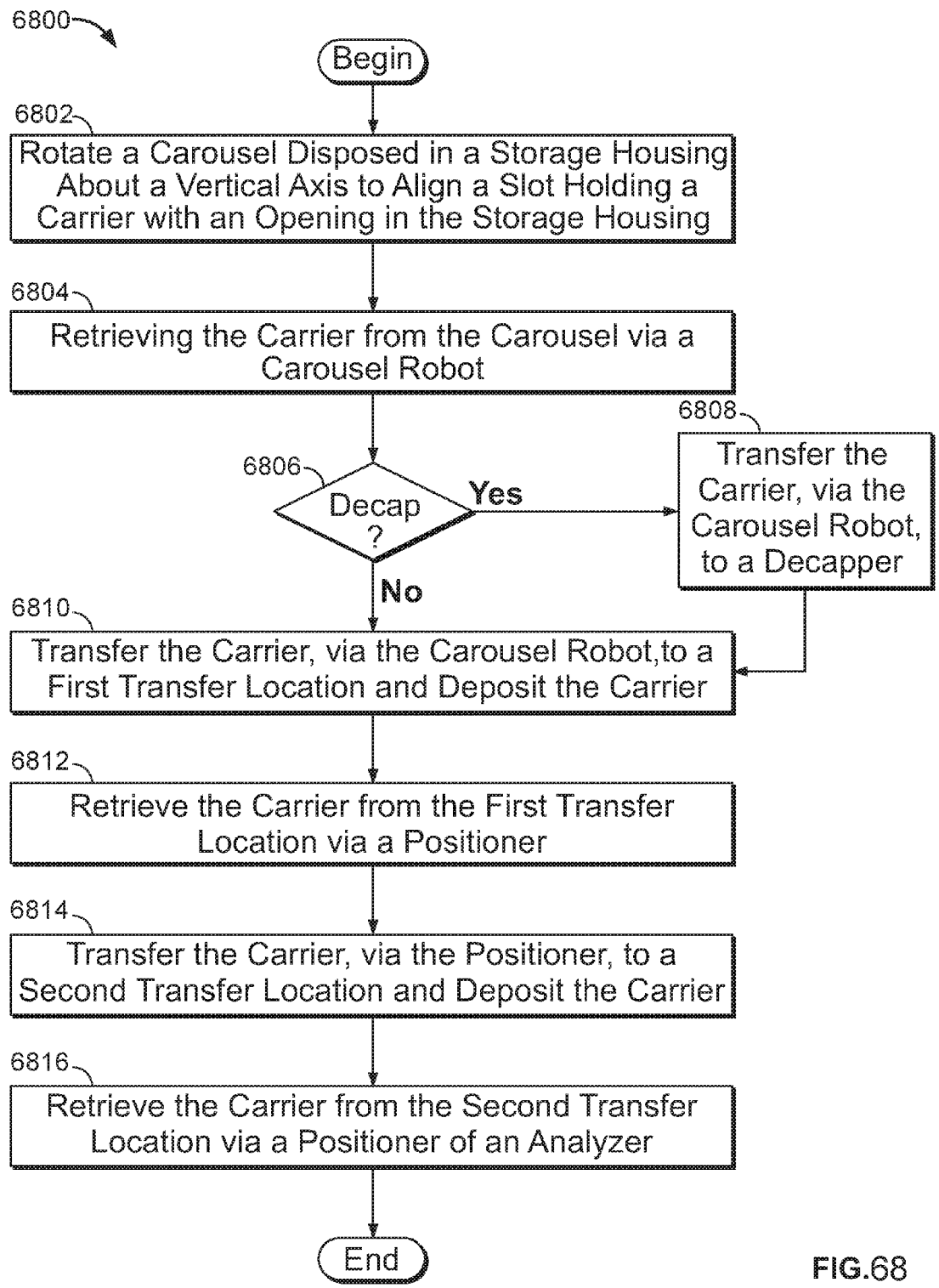
FIG. 68 is a flowchart illustrating an example process of transporting a carrier from an example storage module to an analyzer and/or a laboratory automation system in accordance with the teachings of this disclosure.
Figure 69:
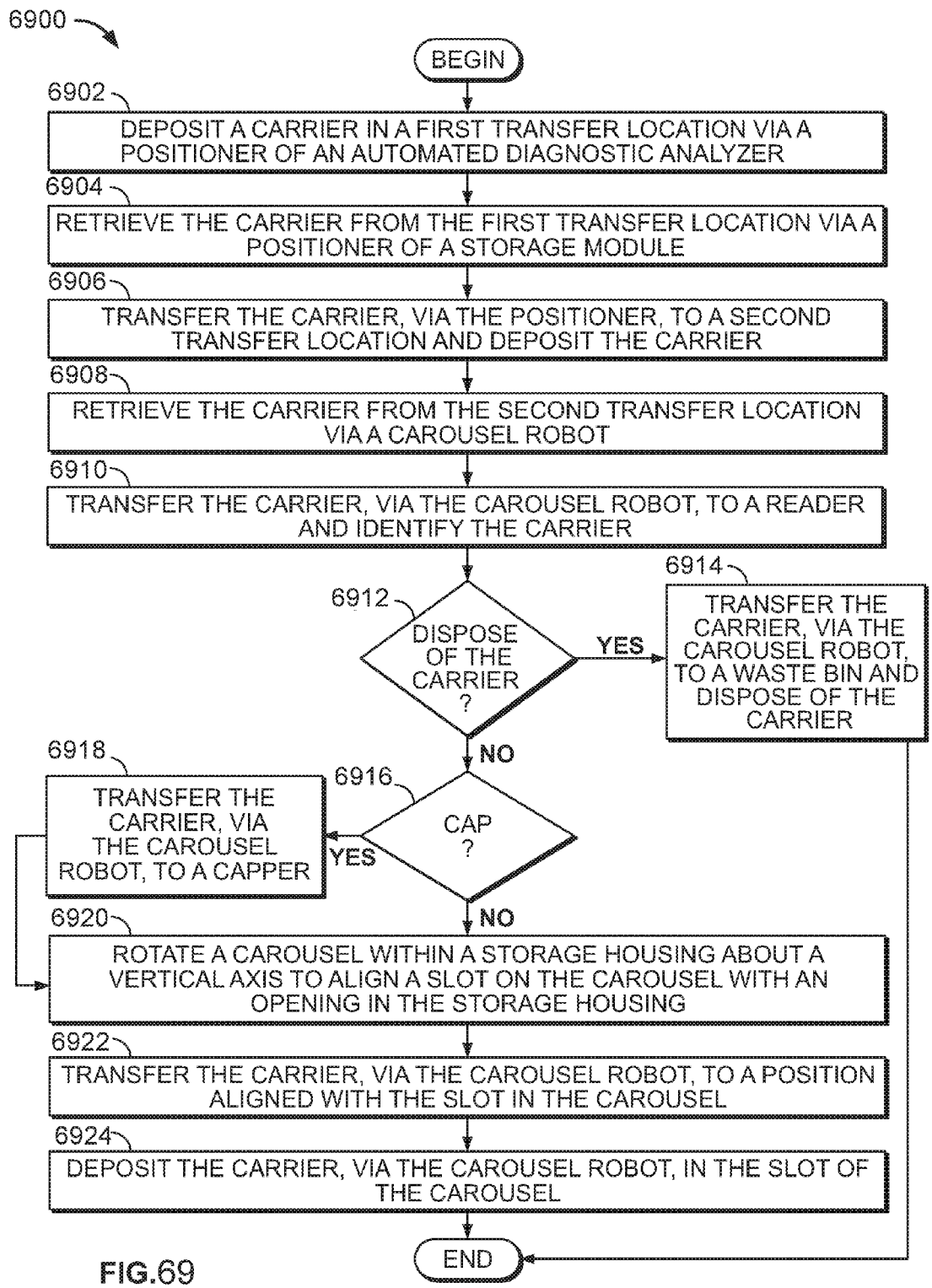
FIG. 69 is a flowchart illustrating an example process of transporting a carrier from an analyzer and/or a laboratory automation system into an example storage module in accordance with the teachings of this disclosure.
Figure 70:
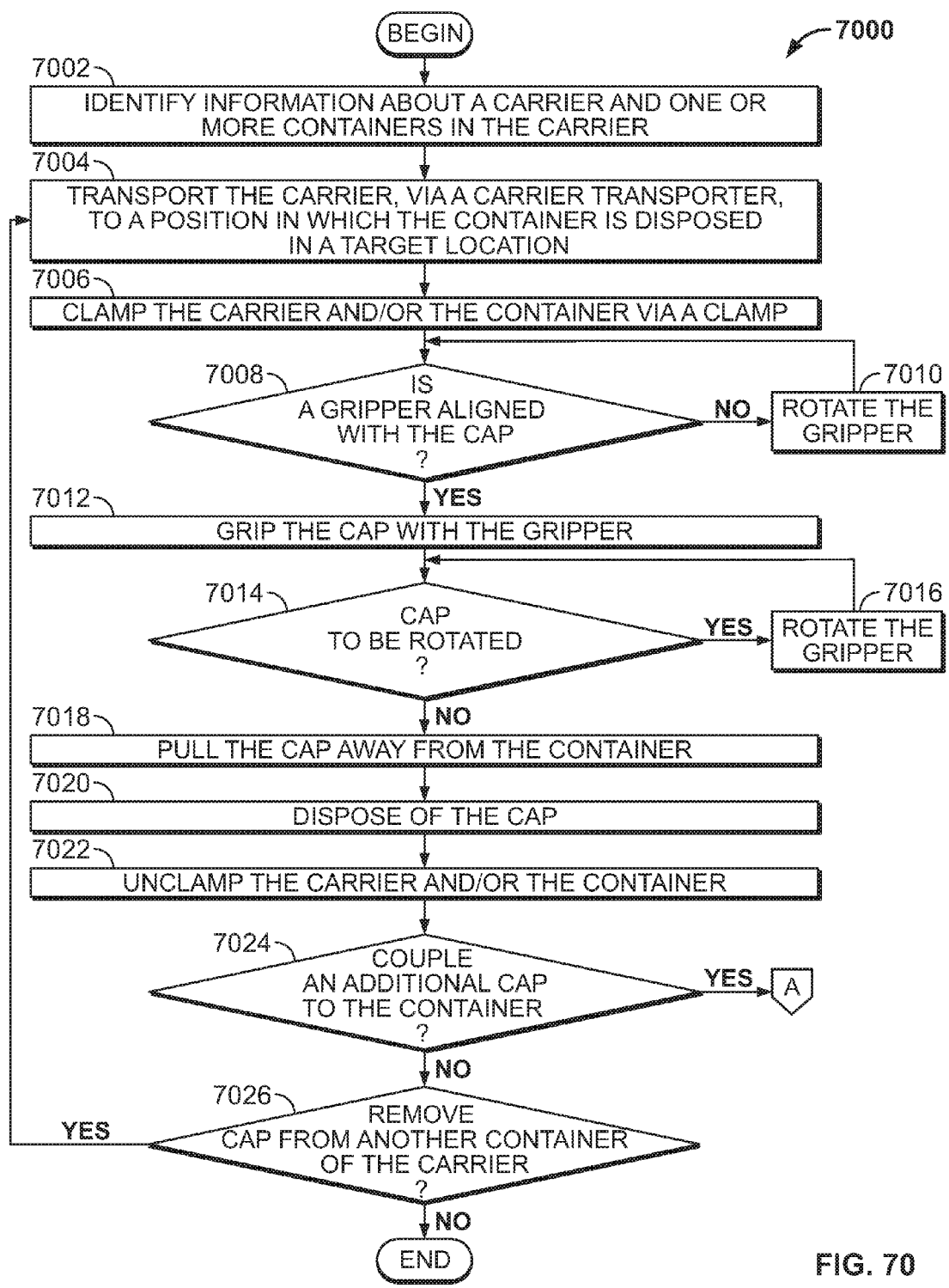
FIG. 70 is a flowchart illustrating an example process of removing a cap from a container of a carrier that may be implemented using the example capper/decapper of FIG. 41 in accordance with the teachings of this disclosure.
Figure 71:
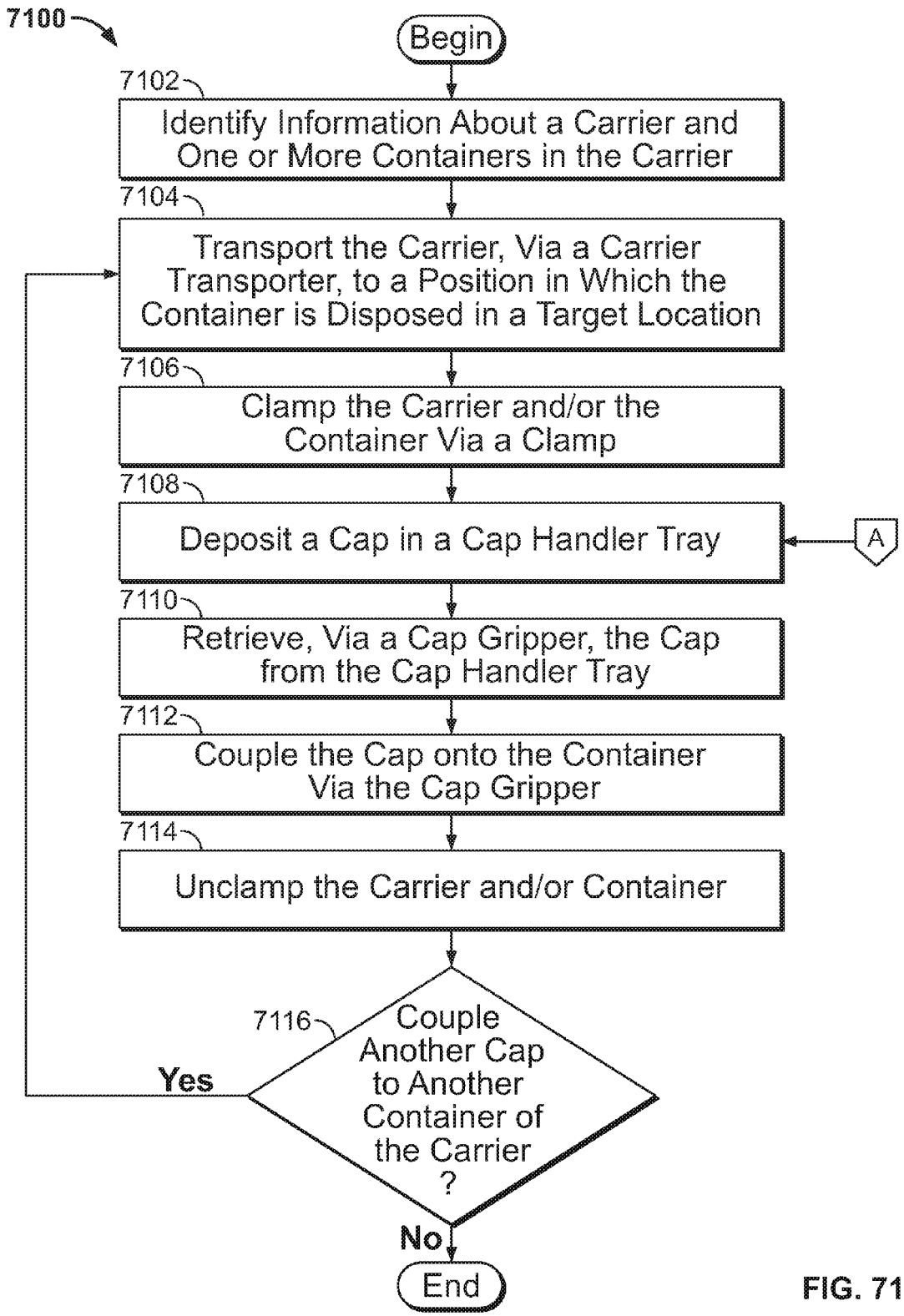
FIG. 71 is a flowchart illustrating an example process of capping a container of a carrier that may be implemented using the example capper/decapper of FIG. 41 in accordance with the teachings of this disclosure.

Flowcharts representative of example machine readable instructions for implementing the example processing system 4000 of FIG. 40 are shown in FIGS. 67-69 and the example processing system 6600 of FIG. 66 are shown in FIGS. 70 and 71. In this example, the machine readable instructions comprise a program for execution by a processor such as the processor 7212 shown in the example processor platform 7200 discussed below in connection with FIG. 72. The program may be embodied in software stored on a tangible computer readable storage medium such as a CD-ROM, a floppy disk, a hard drive, a digital versatile disk (DVD), a Blu-ray disk, or a memory associated with the processor 7212, but the entire program and/or parts thereof could alternatively be executed by a device other than the processor 7212 and/or embodied in firmware or dedicated hardware. Further, although the example program is described with reference to the flowcharts illustrated in FIGS. 67-71, many other methods of implementing the example processing systems 4000, 6600 of FIGS. 40 and 66 may alternatively be used. For example, the order of execution of the blocks may be changed, and/or some of the blocks described may be changed, eliminated, or combined.

As mentioned above, the example processes of FIGS. 67-71 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 67-71 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 67 depicts an example flow diagram representative of an example method 6700 for transporting a carrier into a storage module such as, for example, the storage module 100 and/or the storage module 3500 illustrated in FIGS. 4 and 35, and implemented by the processing system 4000 illustrated in FIG. 40. The example method 6700 includes monitoring one or more slots in a loading bay of a storage module for a carrier (block 6702). In some examples, the storage module includes an array of slots that may receive carriers from, for example, an operator, to be stored within the storage module. The storage module detects when a carrier has been inserted into a slot of the loading bay. The loading bay may correspond to, for example, the loading bay 132 of the storage module 100 and/or the loading bay 3504 of the storage module 3500, which may include a plurality of sensors to detect one or more of the carriers 124 in the slots. The loading bay 132 and/or the loading bay 3504 may be controlled by, for example, the loading bay controller 4002 of the example processing system 4000 in FIG. 40.

The example method 6700 includes determining if a carrier is detecting in one of the slots of the loading bay (block 6704). If a carrier is not detected, the example method 6700 continues to monitor the one or more slots (block 6702). If a carrier is detected, the example method 6700 includes retrieving the carrier from its respective slot in the loading bay via a positioner (block 6706). In some examples, a positioner (e.g., a carrier transporter) moves along a track disposed along a back side of the loading bay (e.g., along a horizontal axis) and retrieves a carrier from a slot in the loading bay and transfers the carrier to another location along the track. In some examples, the positioner includes an arm with a hand having a slot or opening that can engage a tab on the carrier to secure the carrier to the positioner. The arm, for example, may be movable along a vertical axis and/or rotatable the vertical axis. The positioner may correspond to, for example, the positioner 208 of the storage module 100 and/or the positioner 3506 of the storage module 3500. The example positioner 208, for example, includes the arm 800, which is rotatable about the vertical axis 802, and which is movable along the vertical axis 802 via the linear actuator 804. The hand 806 includes an opening to receive a carrier tab to secure the carrier to the positioner 208. The positioner 208 and/or the positioner 3506 may be controlled by, for example, the positioner controller 4006 of the example processing system 4000 in FIG. 40.

The example method 6700 includes transferring the carrier, via the positioner, to a transfer location and depositing the carrier (block 6708). In some examples, transferring the carrier includes moving the carrier along the horizontal axis on the track. The positioner may correspond to, for example, the positioner 208 of the storage module 100 and/or the positioner 3506 of the storage module 3500. The example positioner 208, for example, is movable along the horizontal axis 433 defined by the track 210 to deliver one of the carriers 124 to the tray 500 (e.g., a transfer location, a swap location, a hand-off location, etc.). The positioner 208 and/or the positioner 3506 may be controlled by, for example, the positioner controller 3506 of the example processing system 4000 in FIG. 40.

The example method 6700 includes retrieving the carrier from the transfer location via a carousel robot (block 6710). The carousel robot may correspond to, for example, the carousel robot 418 and/or the shelving robot 3422. The carousel robot 418 for example, includes the arm 426 and the hand 428 which includes the slot 3304 to receive a carrier tab (e.g., the engagement tab 316 of the reagent carrier 124, 310). The carousel robot 418 is movable along the vertical axis 421 (e.g., along the screw 423), via the linear actuator 422, and includes the arm 426, which is rotatable via the first actuator 3100, and the hand 428, which is movable along the arm 426, via the second actuator 3102. To retrieve one of the carriers 124 from the tray 500, a tab on the carrier 124 is inserted into the slot 3104, which secures the carrier 124 to the carousel robot 418. The carousel robot 418 and/or the shelving robot 3522 may be controlled by, for example, the shelving unit robot controller 4022 of the example processing system 4000 in FIG. 40.

The example method 6700 includes transferring the carrier, via the carousel robot, to a reader and identifying the carrier (block 6712). The reader may include, for example, a camera, an RFID tag reader, a bar reader, a QR code reader, and/or any other reader known to those of skill in the art for reading identification indicia. The identification indicia may be disposed on the carrier and/or one or more of the container(s) within the carrier. The reader reads the identification indicia to determine information about carrier and/or the container(s) (e.g., what type of liquid is in each of the container(s), expiration dates, patient information, storage temperature information, chain of custody information, etc.). The reader may correspond to, for example, the camera 440 of the storage module 100, which is disposed along the path of travel of the carousel robot 418. The camera 440 may be controlled by, for example, the reader controller 4030 of the example processing system 4000 in FIG. 40.

The example method 6700 includes determining whether the container(s) in the carrier need to be capped and/or decapped (block 6714) (which may be performed via the example methods 7000, 7100 of FIGS. 70 and 71, disclosed in further detail herein). For example, a reagent carrier may have caps on the respective reagents containers of the reagent carrier. Prior to placing the reagent carrier into the storage module for storage, the caps may be removed. In some examples, temporary caps may be attached to the containers, which reduce evaporation, dilution and/or contamination of the liquids in the carriers. In other examples, when returning a carrier to the storage module after use by an analyzer, for example, temporary caps may be placed on the container(s) before the carrier is stored in the storage module. If the container(s) of the carrier are to be capped and/or recapped, the example method 6700 includes transferring the carrier, via the carousel robot, to a capper/decapper (block 6716). The capper/decapper may correspond to, for example, the capper/decapper 434 of the storage module 100, which is disposed adjacent the path of travel of the carousel robot 418. The capper/decapper 434 may be controlled by, for example, the capper/decapper controller 4018 of the example processing system 4000 in FIG. 40.

The example method 6700 of FIG. 67 includes rotating a carousel about a vertical axis within a storage housing to align a slot on the carousel with an opening in the storage housing (block 6718). In some examples, the storage module includes a storage housing that has a carousel having a plurality of decks or shelves, each having a plurality of slots. To access the different slots disposed around the carousel, the carousel is rotatable within the storage housing. By employing a movable carousel, more slots for storing more carriers can be utilized in the example storage module. In some examples, the storage housing is temperature controlled via a refrigeration unit. The storage housing may generate an aircurtain across the opening to reduce the transfer of heat into the storage housing, such that the opening is always open (e.g., there is no door that opens and closes). The carousel may correspond to, for example, the carousel 420 of the storage module 100, which is rotatable about the vertical axis 1918. The carousel 420 is rotatable via the actuator 2800 and rotates within the storage housing 402. The example carousel 420 is rotated to align an empty slot 1912 with the opening 430 so that the carousel robot 418 can insert the carrier 124 through the opening 430 and into the corresponding slot 1912. In other examples, rotating (e.g., moving) a carousel (e.g., a shelving unit) within a storage housing (block 6718) includes moving one or more shelving units along horizontal and/or vertical axes in the storage housing. For example, in the storage module 3500, the first and second shelving units 3514, 3516 are movable along the first horizontal axis 3528 to enable the shelving robot to 3522 to access the slots 3520 on either one of the shelving units 3514, 3516. The carousel 420 and/or the shelving units 3514, 3516 may be controlled by, for example, the shelving unit controller 4022 of the example processing system 4000 in FIG. 40.

The example method 6700 includes transferring the carrier, via the carousel robot, to a position aligned with the slot in the carousel (block 6720). In some examples, transferring the carrier, via the carousel robot, includes moving the carrier along a vertical axis or axis that is perpendicular to the path of travel of the positioner. For example, the carousel robot 418 of the storage module 100 moves one of the carriers 124 along the vertical axis 421 (e.g., which is perpendicular to the horizontal axis 433 of the track 210), via the linear actuator 422, to align the carrier 124 with one of the slots 1912 on the carousel 420. In the storage module 3500, the shelving robot 3522 is movable along the vertical axis 3524 and along the horizontal axis 3528 into the storage housing 3510. The shelving robot 3522 moves along the two axes 3524, 3528 to align one the carriers 124 with one of the slots 3520 in one of the shelving units 3514, 3516, for example.

The example method 6700 includes depositing the carrier, via the carousel robot, in the slot of the carousel (block 6722). For example, the carousel robot 418 may extend the hand 428 outward (with the carrier 124 coupled thereto) to insert the carrier 124 into one of the slots 1912 on the carousel 420. To release the carrier from the carousel robot 418, the carousel robot 418 moves downward to disengage the tab of the carrier from the slot 3104 in the hand 428. The example method 6700 may end and/or may continue to monitor the one or more slots of the loading bay for another carrier (block 6702).

FIG. 68 depicts an example flow diagram representative of an example method 6800 for transporting a carrier from a storage module such as, for example, the storage module 100 and/or the storage module 3500 illustrated in FIGS. 4 and 35, to a transfer location to be retrieved by one or more analyzers and/or an LAS and implemented by the processing system 4000 illustrated in FIG. 40. The example method 6800 includes rotating a carousel disposed in a storage housing about a vertical axis to align a slot holding a carrier with an opening in the storage housing (block 6802). In some example storage modules, a carousel having a plurality of vertically stacked shelves or decks is disposed within a storage housing. Each of the shelves includes a plurality of slots to receive carriers. The storage housing may be at least partially enclosed and include a refrigeration unit to reduce the temperature inside of the storage housing. To align a particular slot (and, thus, a particular carrier) with an opening in the storage housing for retrieval, the carousel may be rotatable within the storage housing. For example, in the storage module 100, the carousel 420 is rotatable via the actuator 2800, which causes the carousel 420 to rotate within the storage housing 402. In other examples, rotating (e.g., moving) a carousel (e.g., a shelving unit) within a storage housing (block 6802) includes moving one or more shelving units along horizontal and/or vertical axes in the storage housing. For example, in the storage module 3500, the first and second shelving units 3514, 3516 are movable along the first horizontal axis 3528 to enable the shelving robot to 3522 to access the slots 3520 on either one of the shelving units 3514, 3516. The shelving robot 3522 is movable along the first horizontal axis 3528 into and out of the storage housing 3510 through the opening 3512. The carousel 420 and/or the shelving units 3514, 3516 may be controlled by, for example, the shelving unit controller 4022 of the example processing system 4000 in FIG. 40.

The example method 6800 includes retrieving the carrier from the carousel via a carousel robot (block 6804). The carousel robot may correspond to, for example, the carousel robot 418 and/or the shelving robot 3522. The carousel robot 418, for example, includes the arm 426 and the hand 428, which includes the slot 3104 to receive a carrier tab. The carousel robot 418 is movable along the vertical axis 421, via the linear actuator 422, and includes the arm 426, which is rotatable via the first actuator 3100, and the hand 428 is movable along the arm 426, via the second actuator 3102. To remove a carrier from the carousel 420, a tab of the carrier 124 is inserted into the slot 3104 of the hand 428, which secures the carrier 124 to the carousel robot 418. The hand 428 is then retracted to slide the carrier 124 out of the slot 1912 of the carousel 420. The carousel robot 418 and/or the shelving robot 3522 may be controlled by, for example, the shelving unit robot controller 4022 of the example processing system 4000 in FIG. 40.

The example method 6800 includes determining whether the container(s) in the carrier are to be decapped (block 6806) (which may be performed via the example method 7000 of FIG. 70, disclosed in further detail herein). For example, the carrier may be stored in the storage module with cap(s) on the container(s) to reduce evaporation, dilution and/or contamination. Prior to transporting the carrier to an analyzer to be used, the carrier is decapped to enable an aspirating/dispensing to be able access to the contents of the containers. If the container(s) of the carrier are to be decapped, the example method 6800 includes transferring the carrier, via the carousel robot, to a decapper (e.g., a capper/decapper). The decapper may correspond to, for example, the capper/decapper 434 of the storage module 100, which is disposed adjacent the path of travel of the carousel robot 418. The capper/decapper 434 may be controlled by, for example, the capper/decapper controller 4018 of the example processing system 4000 in FIG. 40.

The example method 6800 includes transferring the carrier, via the carousel robot, to a first transfer location and depositing the carrier (block 6810). In some examples, transferring the carrier includes moving the carrier along a vertical axis. The carousel robot, for example, may be movable along a vertical axis outside of the storage housing.

Figure 33E:
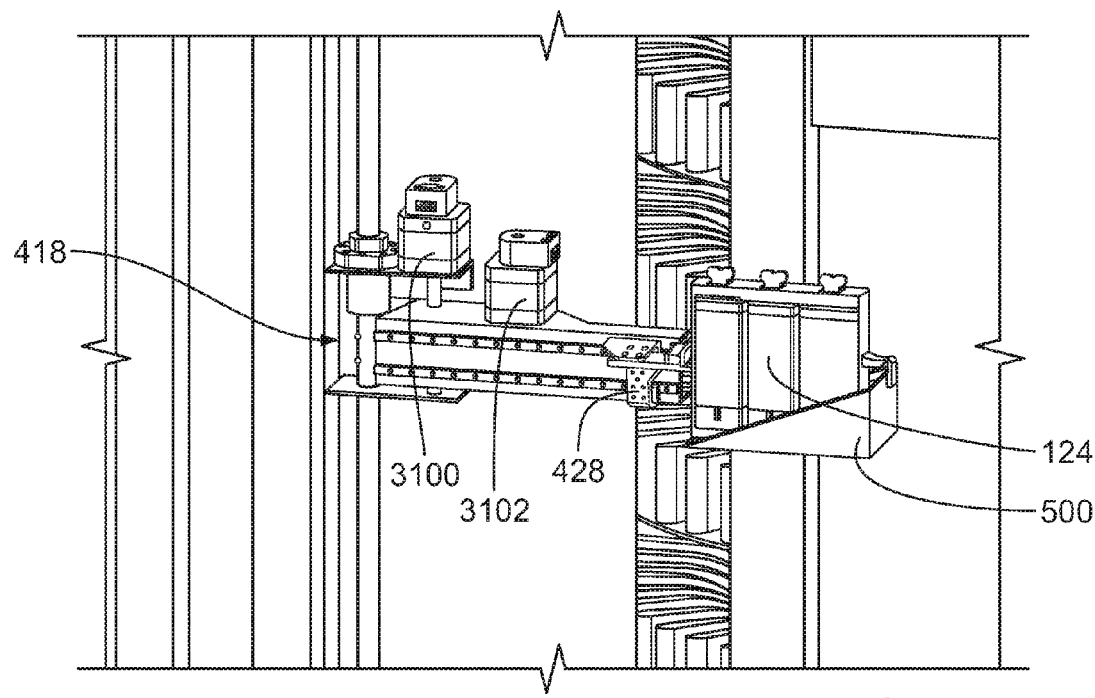
Figure 33F:
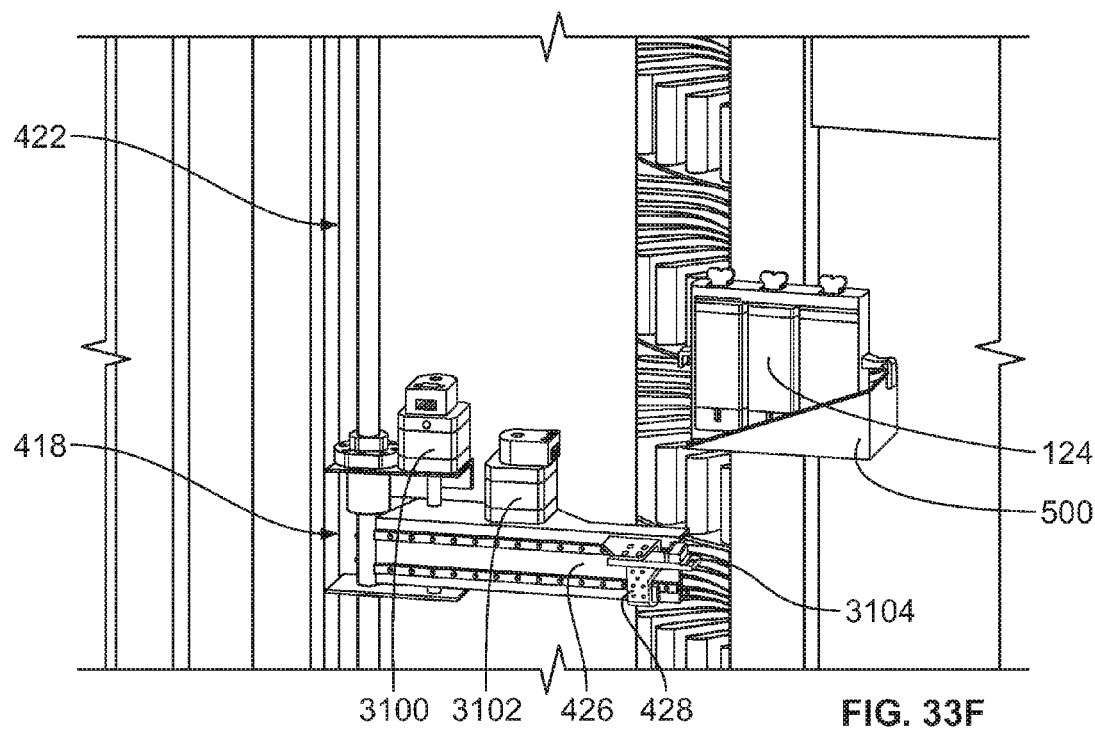

A tray (e.g., a first transfer location), for example, may be located adjacent the vertical axis such that the carousel robot may deposit the carrier in the tray. The first transfer location may correspond to, for example, the tray 500 of the storage module 100. In the example storage module 100, the tray 500 is disposed along the vertical travel path of the carousel robot 418. The carousel robot 418 deposits a carrier 124 into the tray 500 such as, for example, as illustrated in FIGS. 33D-33F.

The example method 6800 includes retrieving the carrier from the first transfer location via a positioner (block 6812). In some examples, a positioner (e.g., a carrier transporter) is movable along a track disposed (e.g., in a horizontal direction) along a front side of the storage module. In some examples, the positioner includes an arm with a hand having a slot or opening to receive a tab of the carrier. The arm, for example, may be movable along a vertical axis and/or rotatable the vertical axis. The positioner may correspond to, for example, the positioner 208 of the storage module 100 and/or the positioner 3506 of the storage module 3500. The example positioner 208, for example, includes the arm 800, which is rotatable about the vertical axis 802 and movable along the vertical axis 802. The hand 806 includes an opening to receive a tab of a carrier to secure the carrier 124 to the positioner 208. The positioner 208 is movable along the track 210 and has access to the slots 134 of the loading bay 132, the tray 500 and the transfer location 136. The positioner 208 and/or the positioner 3506 may be controlled by, for example, the positioner controller 4006 of the example processing system 4000 in FIG. 40.

The example method 6800 includes transferring the carrier, via the positioner, to a second transfer location and depositing the carrier (block 6814). In some examples, the storage module is used to automatically store and transport carriers to one or more analyzers and/or an LAS, which may be coupled to the storage module. The track of the positioner of the storage module, for example, may be coupled to a track and/or accessible by a positioner of the one or more analyzers. In such an example, the positioner of the storage module and the positioner of the analyzer(s) may be movable along the combined tracks. To pass a carrier from one positioner to another, a transfer location (e.g., a second transfer location) may be implemented. In some examples, therefore, transferring the carrier to the second transfer location includes moving the carrier along a horizontal axis. For example, the transfer location 136 of storage module 100 is accessible by the positioner 208. The transfer location 136 is a plurality of the slots 134 in the loading bay 132 of the storage module 100. In other examples, other types of transfer locations may be implemented (e.g., a plurality of slots outside of the storage module 100).

The example method 6800 includes retrieving the carrier from the second transfer location via a positioner of an analyzer (block 6816). For example, in the workcell 102, the positioner 200 (a third carrier transporter) is movable along the track 202 and operates to transfer carriers between the analyzers 106-112 and the loading bays 114-120. The track 202 is coupled to the track 210. Therefore, the positioner 200 is movable into the storage module 100 to access the transfer location 136 and any of the carriers 124 therein. Once one of the carriers 124 is retrieved from the transfer location 136, the carrier 124 may be transported, via the positioner 200, to one or more of the analyzers 106-112. The example method 6800 may end and/or may be implemented again to retrieve another carrier from another slot in the carousel (block 6802).

FIG. 69 depicts an example flow diagram representative of an example method 6900 for receiving a carrier from an analyzer and transporting the carrier into a storage module such as, for example, the storage module 100 and/or the storage module 3500 illustrated in FIGS. 4 and 35, and implemented by the processing system 4000 illustrated in FIG. 40. The example method 6900 includes depositing a carrier in a first transfer location via a positioner of an automated diagnostic analyzer (block 6902). The first transfer location may correspond to, for example, the transfer location 136 of the storage module 100. In the workcell 102 of FIG. 1, the array of analyzers 106-112 includes the positioner 200, which is movable along the combined tracks 202, 210 and into the storage module 100. The positioner 200 can access the transfer location 136, which is a plurality of the slots 134 in the loading bay 132, to deposit and/or retrieve the carriers 124 from the transfer location 136. One or more of the carriers 124 may be transferred to the transfer location 136, for example, after the carriers 124 have been used by one or more of the analyzers 106-112. In other examples, one of the carriers 124 may be inserted into one of the loading bays 114-120 and the workcell 102 may determine the carrier 124 should instead be stored in the storage module 100. As a result, the positioner 200 transfers the carrier 124 to the transfer location 136.

The example method 6900 includes retrieving the carrier from the first transfer location via a positioner of a storage module (block 6904). In some examples, a positioner (e.g., a carrier transporter) of a storage module is movable along a track (e.g., along a horizontal axis) disposed on a front side of the storage module. In some examples, the positioner includes an arm with a hand having a slot or opening that can receive a tab on the carrier (e.g., the engagement tab 316 of the reagent carrier 124, 310). The arm, for example, may be movable along a vertical axis and/or rotatable the vertical axis, and the positioner may be movable along a horizontal axis. The positioner may correspond to, for example, the positioner 208 of the storage module 100 and/or the positioner 3506 of the storage module 3500. The example positioner 208, for example, includes the arm 800, which is rotatable about the vertical axis 802 and movable along the vertical axis 802. The hand 806 includes an opening to receive a tab of the carrier 124 to secure the carrier 124 to the positioner 208. The positioner 208 is movable along the track 210 and has access to the slots 134 of the loading bay 132, the tray 500 and the transfer location 136 (e.g., the first transfer location). The positioner 208 moves along the same combined track 202, 210 as the positioner 200 of the analyzers 106-112. The positioner 208 and/or the positioner 3506 may be controlled by, for example, the positioner controller 4006 of the example processing system 4000 in FIG. 40.

The example method 6900 includes transferring the carrier, via the positioner of the storage module, to a second transfer location and depositing the carrier (block 6906). In some examples, the positioner of the storage module transfers the carrier along a track that is oriented along a horizontal axis. A tray (e.g., a second transfer location), for example, may be located adjacent the horizontal axis such that the positioner may deposit the carrier in the tray. The positioner may correspond to, for example, the positioner 208 of the storage module 100 and/or the positioner 3506 of the storage module 3500. The positioner 208, for example, is movable along the track 210 to deliver one of the carriers 124 to the tray 500 (e.g., a second transfer location).

The example method 6900 includes retrieving the carrier from the second transfer location via a carousel robot (block 6908). The carousel robot may correspond to, for example, the carousel robot 418 and/or the shelving robot 3522. The carousel robot 418, for example, includes the arm 426 and the hand 428, which includes the slot 3104 to receive a tab of the carrier 124. The carousel robot 418 is movable along the vertical axis 421, via linear actuator 422, and includes the arm 426, which is rotatable via the first actuator 3100, and the hand 428, is movable along the arm 426 via the second actuator 3102. To retrieve one of the carriers 124 from the tray 500, a tab of the carrier 124 is inserted into the slot 3104, which secures the carrier 124 to the carousel robot 418. The carousel robot 418 and/or the shelving robot 3522 may be controlled by, for example, the shelving unit robot controller 4022 of the example processing system 4000 in FIG. 40.

The example method 6900 includes transferring the carrier, via the carousel robot, to a reader and identifying the carrier and/or specific contents of the carrier (block 6910), which may be performed similar to block 6712 of FIG. 67. Besides the identification information and expiration date, the storage module may be able to determine how much liquid is left in the containers on the carrier based on input from the analyzer. The example method 6900 includes determining whether the carrier should be disposed of (block 6912) such as, for example, when the one or more of containers on the carrier is empty, expired and/or otherwise defective. If the carrier is to be disposed of, the example method 6900 includes transferring the carrier, via the carousel robot, to a waste bin and disposing of the carrier (block 6914). For example, in the storage module 100, the carousel robot 418 may transfer one of the carriers 124 to the waste bin 438 and dispose of the carrier 124, as illustrated in FIG. 33.

The example method 6900 includes determining whether the container(s) in the carrier are to be capped (block 6916) (which may be performed via the example method 7100 of FIG. 71, disclosed in further detail herein). For example, prior to placing a reagent carrier into the storage module for storage, the container(s) of the carrier may be capped to reduce evaporation, dilution and/or contamination of the liquid contents. In some examples, a temporary cap (e.g., the cap 6300 of FIG. 63) is used. If the container(s) of the carrier are to be capped or recapped, the example method 6900 includes transferring the carrier, via the carousel robot, to a capper (block 6918). The capper may correspond to, for example, the capper/decapper 434 of the storage module 100, which is disposed adjacent the path of travel of the carousel robot 418. The capper/decapper 434 may be controlled by, for example, the capper/decapper controller 4018 of the example processing system 4000 in FIG. 40.

The example method 6900 of FIG. 69 includes rotating a carousel within a storage housing about a vertical axis to align a slot on the carousel with an opening in the storage housing (block 6920), transferring the carrier, via the carousel robot, to a position aligned with the slot in the carousel (block 6922) and depositing the carrier, via the carousel robot, in the slot of the carousel (block 6924), which may be performed similar to blocks 6718, 6720, 6722 of FIG. 67.

FIG. 70 depicts an example flow diagram representative of an example method 7000 to remove a cap from a container using a decapper such as, for example, the decapper 4100 illustrated in FIG. 41, and implemented by the processing system 6600 illustrated in FIG. 66. The example method 7000 includes identifying information about a carrier and one or more containers in the carrier (block 7002). In some examples, the carrier and/or the one or more containers of the carrier have identifying indicia (e.g., a bar code). The information may be read by a sensor such as, for example, a bar code reader or a camera to identify a carrier type, a number of containers, a liquid type disposed in the container(s), a volume, etc. Additionally or alternatively, the camera may detect the presence of cap(s), cap types, the position of the caps, etc. For example, as illustrated in FIG. 44, a carrier 124 may be disposed in front of the camera 440 so that the camera 440 can read any identification indicia on the carrier 124 and/or on the one or more containers 314a-314c. The camera 440 may detect whether the containers 314a-314c have caps, the cap types, the cap positions, etc. The camera 440 may be controlled by, for example, the reader controller 4030 of the example processing system 4000 in FIG. 40.

The example method 7000 includes transporting the carrier, via a carrier transporter, to a position in which the container is disposed in a target location (block 7004). The carrier transporter may correspond to, for example, the carrier transporter 4204. The example carrier transporter 4204 includes the hand 4600 that has a slot to receive a tab of a carrier. The hand 4600 is movable along a horizontal axis via the first carrier transporter actuator 4604 and movable along a vertical axis via the second carrier transporter actuator 4606. The carrier transporter 4204 retrieves a carrier 124 from the sled 4400 and moves the carrier to a position in which a container is disposed in the target location (i.e., along the axis 5216 beneath the gripper 5200). In some examples, a shuttle is used to transport the carrier from one side of the decapper to another side of the decapper where the carrier transporter can retrieve the carrier. For example, as illustrated in FIG. 46, the shuttle 4200 includes the sled 4400 that moves along the track 4402 to move a carrier from the rear side 4203 of the decapper 4100 to the front side 4201 of the decapper. The carrier transporter 4204 may be controlled by, for example, the carrier transporter controller 6606 of the example processing system 6600 in FIG. 66.

The example method 7000 of FIG. 70 includes clamping the carrier and/or the container via a clamp. The clamp may be used to secure the container while a cap is removed from the container. The clamp may correspond to, for example, the clamp 4202. In the example of FIGS. 50 and 62, the clamp 4202 includes the first and second arms 5000, 5002, which may be used to clamp a carrier, and includes the third and fourth arms 6200, 6202, which may be used to clamp a container. The clamp 4202 may be controlled by, for example, the clamp controller 6610 of the example processing system 6600 in FIG. 66.

The example method 7000 includes determining whether a gripper is aligned with the cap (block 7008). If the gripper is not aligned with the cap, the example method 7000 includes rotating the gripper (block 7010). In some examples, the cap may not be cylindrical or otherwise not able to be grabbed from any direction. For example, as illustrated in FIG. 44, the cap 315a has a tab that is to be engaged by the gripper 5200. The gripper 5200 includes the first and second gripper hands 5300, 5302, and the tab is to be grasped between the first and second gripper hands 5300, 5302. Therefore, the gripper 5200 may be rotated in order to align the tab to be inserted between the first and second gripper hands 5300, 5302. The second gripper actuator 5208 may be used to rotate the gripper 5200. The second gripper actuator 5208 may be controlled by, for example, the cap gripper controller 6614 of the example processing system 6600 in FIG. 66. Some examples proceed without gripper rotation. For example, a cylindrical cap may fit into the first and second gripper hands 5300, 5302 at any angle.

The example method 7000 includes gripping the cap with the gripper (block 7012). In some examples, the gripper includes first and second gripper arms with respective first and second gripper hands that are moved together to grip the cap. For example, the gripper 5200 includes the first and second gripper hands 5300, 5302 on the respective first and second gripper arms 5202, 5204. The first and second gripper arms 5202, 5204 are pivotable to move the first and second gripper arms 5300, 5302 toward or away from each other. The third gripper actuator 5316 moves the gripper 5200 downward toward the cap and the first gripper actuator 5206 moves the pin 5306 to rotate the first and second gripper arms 5202, 5204 to close the first and second gripper hands 5300, 5302. The first gripper actuator 5206 and the third gripper actuator 5316 may be controlled by, for example, the cap gripper controller 6614 of the example processing system 6600 in FIG. 66.

The example method 7000 includes determining whether the cap is to be rotated to release the cap from the container (block 7014). In some examples, the cap is threadably or rotatably coupled to the container. For example, as illustrated in FIG. 44, the cap 315a is rotatably coupled to the container 314a, and the cap type is detected by the camera 440. If the cap is to be rotated, the example method 7000 includes rotating the gripper (block 7016). For example, the gripper 5200 may be rotated, via the second gripper actuator 5208. Some examples proceed without rotating the cap for release from the container. For example, with the cap 6300 illustrated in FIG. 63, the cap may be pulled out of the mouth of a container without rotating. In other examples, the cap 6300 may be rotated to reduce friction between the cap 6300 and the opening of the container.

The example method 7000 includes pulling the cap away from the container (block 7018). For example, as illustrated in FIG. 59, the gripper 5200 may be moved upward with the cap 315a. The gripper 5200 is moved vertically by the third gripper actuator 5316, which may be controlled by, for example, the cap gripper controller 6614 of the example processing system 6600 in FIG. 66.

The example method 7000 of FIG. 70 includes disposing of the cap (block 7020). In some examples, a tray is used to transfer the cap from the gripper to a waste chute. For example, as illustrated in FIG. 59, the decapper 4100 includes the cap handler 4206, which uses the tray 5900 to transfer the cap to a waste chute. The tray 5900 is rotatable via the cap gripper actuator 5902, which may be controlled by, for example, the cap handler controller 6618 of the example processing system 6600 in FIG. 66.

The example method 7000 includes determining whether an additional cap is to be coupled to the container (block 7024). In some examples, the original cap of the container is to be removed and another cap (e.g., a temporary cap such as the cap 6300) is to be coupled to the container prior to placement in the storage module. In some example, the original cap is to be coupled back to the container. If another cap is to be coupled to the container, the example method 7000 continues to block 7108 of FIG. 71, disclosed in further detail herein. The example method 7000 includes determining if another cap from another container on the carrier is to be removed (block 7026). If another cap on another container is to be removed, the example 7000 continues to block 7004 where the carrier is transported, via the carrier transporter, to a position (e.g., a second position) in which the next subsequent container is disposed in the target location. The method 7000 may repeat for each container on the carrier until the desired number of caps of the containers are removed. Once the cap of the container(s) is removed, the method 7000 ends. The method 7000 may similarly be performed on a subsequent container of another carrier.

FIG. 71 depicts an example flow diagram representative of an example method 7100 to couple a cap on a container using a decapper such as, for example, the decapper 4100 illustrated in FIG. 41, and implemented by the processing system 6600 illustrated in FIG. 66. The method 7100 may be performed, for example, to recap a container before transferring the container into a storage module. In the illustrated example, the method 7100 includes identifying information about a carrier and one or more containers in the carrier (block 7102), transporting the carrier, via a carrier transporter, to a position in which the container is disposed in a target location (block 7104) and clamping the carrier and/or the container via a clamp (block 7106), which may be performed similar to the respective blocks 7002, 7004, 7006 of FIG. 70.

The example method 7100 includes depositing a cap in a cap handler tray (block 7108). In some examples, a cap hopper having a plurality of caps deposits a cap in the cap handler tray. The cap handler tray may include an opening to receive the cap. The cap handler tray may be movable to bring the cap to a gripper where the gripper can be retrieve. The cap handler tray may correspond to, for example, the tray 5900 as illustrated in FIG. 63. The tray 5900 is rotatable via the cap handler actuator 5902. The cap hopper 6304 may deposit a cap into the second opening 6302 of the tray 5900. The tray 5900 may be rotate, with the cap, to a position where the gripper 5200 can retrieve the cap. The cap handler 4206 may be controlled by, for example, the cap handler controller 6618 of the example processing system 6600 in FIG. 66.

The example method 7100 includes retrieving, via a cap gripper, the cap from the cap handler tray (block 7110). In some examples, the gripper includes first and second gripper arms with respective first and second gripper hands that are moved together to grip the cap. For example, the gripper 5200 includes the first and second gripper hands 5300, 5302 on the respective first and second gripper arms 5202, 5204. The first and second gripper arms 5202, 5204 are pivotable to move the first and second gripper arms 5300, 5302 toward or away from each other. The third gripper actuator 5316 moves the gripper 5200 downward toward the cap and the first gripper actuator 5206 moves the pin 5306 to rotate the first and second gripper arms 5202, 5204 to close the first and second gripper hands 5300, 5302. The first gripper actuator 5206 and the third gripper actuator 5316 may be controlled by, for example, the cap gripper controller 6614 of the example processing system 6600 in FIG. 66.

The example method 7100 of FIG. 71 includes coupling the cap onto the container via the cap gripper (block 7112). For example, as illustrated in FIG. 65, the gripper 5200 is moved downward via the third gripper actuator 5317 to insert the cap 6300 into a mouth of the container 304a. In some examples, the cap may be rotatably coupled the container. In such an example, the method 7100 may include rotating the gripper with the cap to couple the cap to the container.

The example method 7100 includes unclamping the carrier and/or the container (block 7114). The example method 7100 includes determining whether another container cap is to be coupled to another container of the carrier (block 7116). If another container on the carrier is to receive a cap, the example method 7100 continues to block 7104, where the carrier is transported, via the carrier transporter, to a position (e.g., a second position) in which the subsequent container is disposed in the target location. The example method 7100 may continue for each container of the carrier. After the container(s) is capped, the example method 7100 ends.

Figure 72:
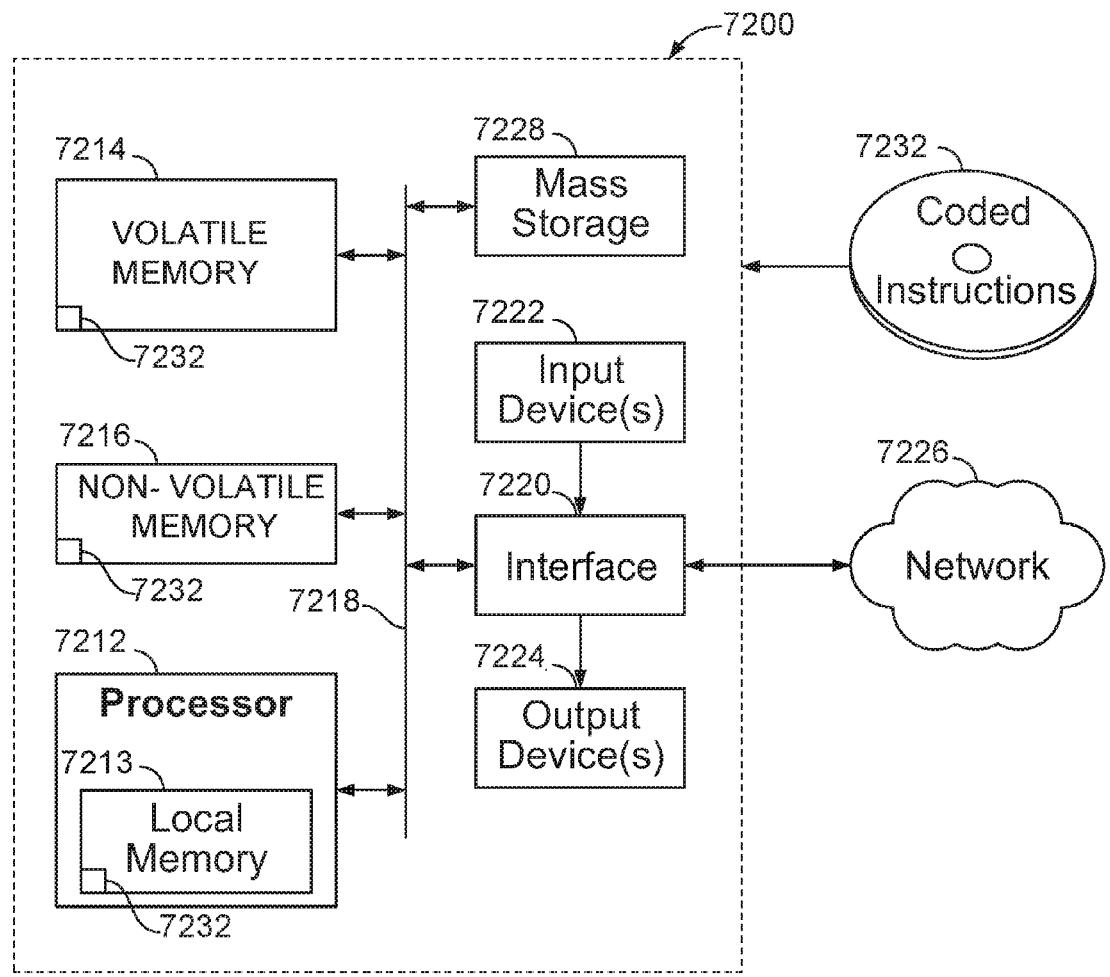
FIG. 72 is a diagram of a processor platform for use with the examples disclosed herein.

FIG. 72 is a block diagram of an example processor platform 7200 capable of executing the instructions of FIGS. 67-71 to implement the example processing systems 4000, 6000 of FIGS. 40 and 66. The processor platform 7200 can be, for example, a server, a personal computer, a mobile device (e.g., a cell phone, a smart phone, a tablet such as an iPad™), a personal digital assistant (PDA), an Internet appliance, a digital video recorder, a set top box, or any other type of computing device.

The processor platform 7200 of the illustrated example includes a processor 7212. The processor 7212 of the illustrated example is hardware. For example, the processor 7212 can be implemented by one or more integrated circuits, logic circuits, microprocessors or controllers from any desired family or manufacturer.

The processor 7212 of the illustrated example includes a local memory 7213 (e.g., a cache). The processor 7212 of the illustrated example is in communication with a main memory including a volatile memory 7214 and a non-volatile memory 7216 via a bus 7218. The volatile memory 7214 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 7216 may be implemented by flash memory and/or any other desired type of memory device. Access to the main memory 7214, 7216 is controlled by a memory controller.

The processor platform 7200 of the illustrated example also includes an interface circuit 7220. The interface circuit 7220 may be implemented by any type of interface standard, such as an Ethernet interface, a universal serial bus (USB), and/or a PCI express interface.

In the illustrated example, one or more input devices 7222 are connected to the interface circuit 7220. The input device(s) 7222 permit(s) a user to enter data and commands into the processor 7212. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 7224 are also connected to the interface circuit 7220 of the illustrated example. The output devices 7224 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 7220 of the illustrated example, thus, typically includes a graphics driver card, a graphics driver chip or a graphics driver processor.

The interface circuit 7220 of the illustrated example also includes a communication device such as a transmitter, a receiver, a transceiver, a modem and/or network interface card to facilitate exchange of data with external machines (e.g., computing devices of any kind) via a network 7226 (e.g., an Ethernet connection, a digital subscriber line (DSL), a telephone line, coaxial cable, a cellular telephone system, etc.).

The processor platform 7200 of the illustrated example also includes one or more mass storage devices 7228 for storing software and/or data. Examples of such mass storage devices 7228 include floppy disk drives, hard drive disks, compact disk drives, Blu-ray disk drives, RAID systems, and digital versatile disk (DVD) drives.

The coded instructions 7232 of FIGS. 67-71 may be stored in the mass storage device 7228, in the volatile memory 7214, in the non-volatile memory 7216, and/or on a removable tangible computer readable storage medium such as a CD or DVD.

From the foregoing, it will be appreciated that the above disclosed methods, apparatus and articles of manufacture provide automated storage and transportation of carriers of analyzer liquids between a storage module and one or more analyzers. As a result, significantly less operator time is required to supply and unloaded the various liquid carriers into the analyzers. Additionally, because the carriers have a common form factor, each of the carriers can be loaded, stored, exchanged and unloaded with the same systems of the storage module, thereby increasing efficiency.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
   a refrigerated storage module having a plurality of shelves to store a plurality of carriers having one or more containers of fluid for use in a diagnostic analysis;
   a loading bay disposed along a side of the storage module, the loading bay having an array of slots to receive one or more of the carriers, the loading bay accessible by a user for manual loading or unloading of one or more of the carriers;
   a first carrier transporter coupled to the storage module, the first carrier transporter to transfer one or more of the carriers between one or more of the shelves and a first transfer location;
   a first track disposed along the side of the storage module between the storage module and the loading bay;
   a second carrier transporter movable along the first track;
   a diagnostic analyzer disposed adjacent the storage module;
   a second track disposed along the diagnostic analyzer, the second track aligned with and coupled to the first track;
   a third carrier transporter movable along the second track; and
   a controller executing instructions to:
      control the second carrier transporter to transfer a first carrier between the first transfer location and a slot in the loading bay;
      control the second carrier transporter to transfer a second carrier between the first transfer location and a second transfer location; and
      control the third carrier transporter to transfer the second carrier between the second transfer location and a position to be used in the diagnostic analyzer.

2. The apparatus of claim 1, wherein the shelves include vertically stacked carousels.

3. The apparatus of claim 2, wherein the storage module includes a storage housing in which the carousels are disposed, and wherein the storage housing includes a vertical opening along a side of the storage housing to provide access to the carousels.

4. The apparatus of claim 2, wherein the carousels are rotatable about a vertical axis.

5. The apparatus of claim 2, wherein each of the carousels include a plurality of slots arranged annularly around the respective carousel.

6. The apparatus of claim 3, wherein the first carrier transporter is disposed outside of the storage housing, and the first carrier transporter includes a hand extendable through the vertical opening to access the carriers on the carousels.

7. The apparatus of claim 1, wherein the second carrier transporter is to insert the first carrier into a rear side of the slot in the loading bay.

8. The apparatus of claim 7, wherein the first carrier is accessible through a front side of the slot in the loading bay.

9. The apparatus of claim 1, wherein the slots of the loading bay are vertical slots arranged in a horizontal array.

10. The apparatus of claim 1, wherein the second transfer location is one of the slots of the loading bay.

11. The apparatus of claim 1, wherein the storage module is to store carriers having reagents, calibrators, controls and samples for use in the diagnostic analyzer.

12. The apparatus of claim 11, wherein the carriers containing the reagents, calibrators, controls and samples have substantially the same footprint.

13. The apparatus of claim 1, wherein the first carrier transporter is movable along a first axis and the second carrier transporter is movable along a second axis, perpendicular to the first axis.

14. A method comprising:
storing a plurality of carriers on a plurality of shelves in a storage module, the carriers having one or more containers of fluid for use in a diagnostic analysis;
transporting a first carrier, via a first carrier transporter, from a first shelf of the plurality of shelves to a first transfer location;
transporting the first carrier, via a second carrier transporter, from the first transfer location to a slot in a loading bay disposed along a first side of the storage module, the second carrier transporter movable along a first track disposed along the first side of the storage module between the storage module and the loading bay, the loading bay having an array of slots to receive one or more of the carriers, the loading bay accessible by a user for manual loading or unloading of one or more of the carriers;
transporting a second carrier, via the first carrier transporter, from the first shelf to the first transfer location;
transporting the second carrier, via the second carrier transporter, from the first transfer location to a second transfer location disposed between the storage module and an automated diagnostic analyzer, the diagnostic analyzer disposed adjacent the storage module, a first side of the diagnostic analyzer facing a same direction as the first side of the storage module; and
transporting the second carrier, via a third carrier transporter, from the second transfer location to a position to be used in the diagnostic analyzer, the third carrier transporter movable along a second track disposed along the first side of the diagnostic analyzer.

15. The method of claim 14, wherein the shelves include vertically stacked carousels, the first shelf being a first carousel.

16. The method of claim 15 further including rotating the first carousel about a vertical axis to transfer the first carrier to a first location where the first carrier transporter is to retrieve the first carrier.

17. The method of claim 16 further including rotating the first carousel about the vertical axis to transfer the second carrier to the first location where the first carrier transporter is to retrieve the second carrier.

18. The method of claim 14, wherein the storage module includes a storage housing in which the shelves are disposed, and wherein transporting the first carrier from the first shelf to the first transfer location includes moving the first carrier transporter vertically along a side of the storage housing.

19. The method of claim 18, wherein transporting the first carrier from the first shelf to the first transfer location includes retrieving, via the first carrier transporter, the first carrier from the first shelf by extending a hand of the first carrier transporter through a vertical opening in the storage housing to engage the first carrier on the first shelf.

* * * * *